United States Patent
Owusu Danquah et al.

(10) Patent No.: US 9,908,935 B2
(45) Date of Patent: Mar. 6, 2018

(54) P2X7 RECEPTOR ANTAGONISTS AND AGONISTS

(71) Applicant: Ablynx N.V., Zwijnaarde (BE)

(72) Inventors: Welbeck Owusu Danquah, Hamburg (DE); Friedrich Nolte, Hamburg (DE); Catelijne Stortelers, Ghent (BE); Toon Laeremans, Dworp-Beersel (BE)

(73) Assignees: Ablynx N.V., Ghent-Zwijnaarde (BE); University Medical Center Hamburg-Eppendorf, Hamburg (DE)

( * ) Notice: Subject to any disclaimer, the term of this patent is extended or adjusted under 35 U.S.C. 154(b) by 201 days.

(21) Appl. No.: 14/403,754

(22) PCT Filed: May 31, 2013

(86) PCT No.: PCT/EP2013/061257
§ 371 (c)(1),
(2) Date: Nov. 25, 2014

(87) PCT Pub. No.: WO2013/178783
PCT Pub. Date: Dec. 5, 2013

(65) Prior Publication Data
US 2015/0133637 A1    May 14, 2015

Related U.S. Application Data

(60) Provisional application No. 61/654,417, filed on Jun. 1, 2012.

(51) Int. Cl.
| | |
|---|---|
| *C07K 16/28* | (2006.01) |
| *C12N 5/10* | (2006.01) |
| *C07K 14/705* | (2006.01) |
| *A61K 39/00* | (2006.01) |

(52) U.S. Cl.
CPC ........ *C07K 16/28* (2013.01); *A61K 2039/505* (2013.01); *C07K 14/705* (2013.01); *C07K 2317/21* (2013.01); *C07K 2317/22* (2013.01); *C07K 2317/565* (2013.01); *C07K 2317/569* (2013.01); *C07K 2317/64* (2013.01); *C07K 2317/76* (2013.01)

(58) Field of Classification Search
None
See application file for complete search history.

(56) References Cited

U.S. PATENT DOCUMENTS

| | | |
|---|---|---|
| 2010/0173799 A1 | 7/2010 | Laeremans et al. |
| 2012/0035350 A1 | 2/2012 | Franco et al. |

FOREIGN PATENT DOCUMENTS

| | | |
|---|---|---|
| WO | WO 2004/090097 | 10/2004 |
| WO | WO 2010/070145 | 6/2010 |

OTHER PUBLICATIONS

MacCallum et al. (1996). J. Mol. Biol. 262:732-745.*
De Pascalis et al. (2002). Journal of Immunology. 169:3076-3084.*
Casset et al. (2003). Biochemical and Biophysical Reseaerch Communications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*
[No Author Listed] Antibody LS-C138155. LifeSpan BioSciences, Inc. Jan. 1, 2012.
Adriouch et al., Probing the expression and function of the P2X7 purinoceptor with antibodies raised by genetic immunization. Cell Immunol. Jul.-Aug. 2005;236(1-2):72-7. Epub Sep. 12, 2005.
Matute et al., P2X(7) receptor blockade prevents ATP excitotoxicity in oligodendrocytes and ameliorates experimental autoimmune encephalomyelitis. J Neurosci. Aug. 29, 2007;27(35):9525-33.
Seman et al., NAD-induced T cell death: ADP-ribosylation of cell surface proteins by ART2 activates the cytolytic P2X7 purinoceptor. Immunity. Oct. 2003;19(4):571-82.
Skaper et al., The P2X7 purinergic receptor: from physiology to neurological disorders. FASEB J. Feb. 2010;24(2):337-45. doi: 10.1096/fj.09-138883. Epub Oct. 7, 2009.

* cited by examiner

*Primary Examiner* — Christine J Saoud
*Assistant Examiner* — Jon M Lockard
(74) *Attorney, Agent, or Firm* — Wolf, Greenfield & Sacks, P.C.

(57) ABSTRACT

The present invention relates to biological materials against P2X7 and more in particular to polypeptides, nucleic acids encoding such polypeptides; to methods for preparing such polypeptides; to host cells expressing or capable of expressing such polypeptides; to compositions and in particular to pharmaceutical compositions that comprise such polypeptides, for prophylactic, therapeutic or diagnostic purposes. In particular, the biological materials of the present invention inhibit the biological activity of the P2X7 receptor, such as activation by ATP.

16 Claims, 30 Drawing Sheets

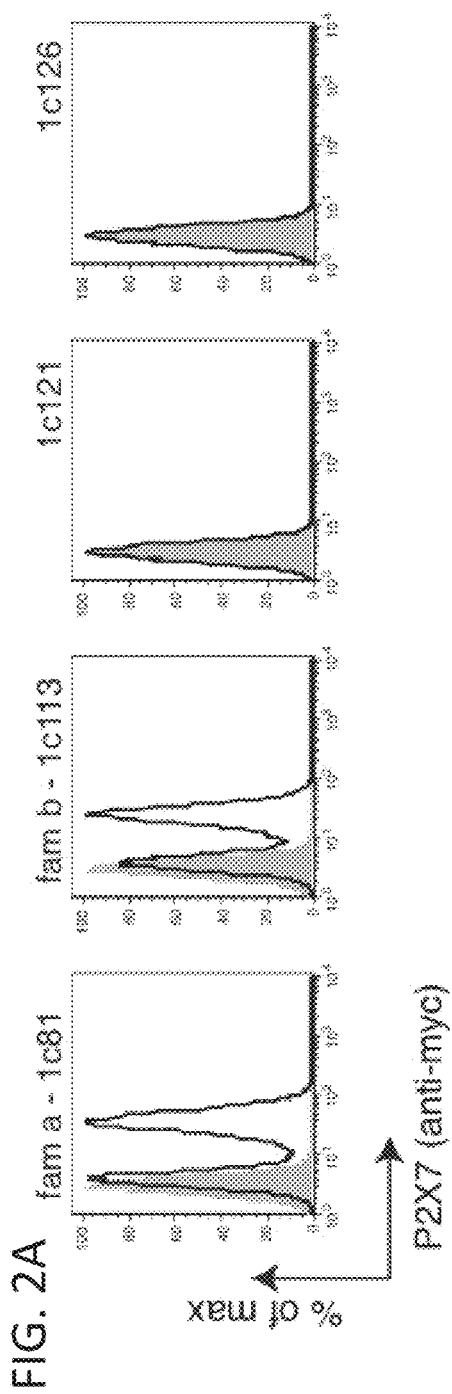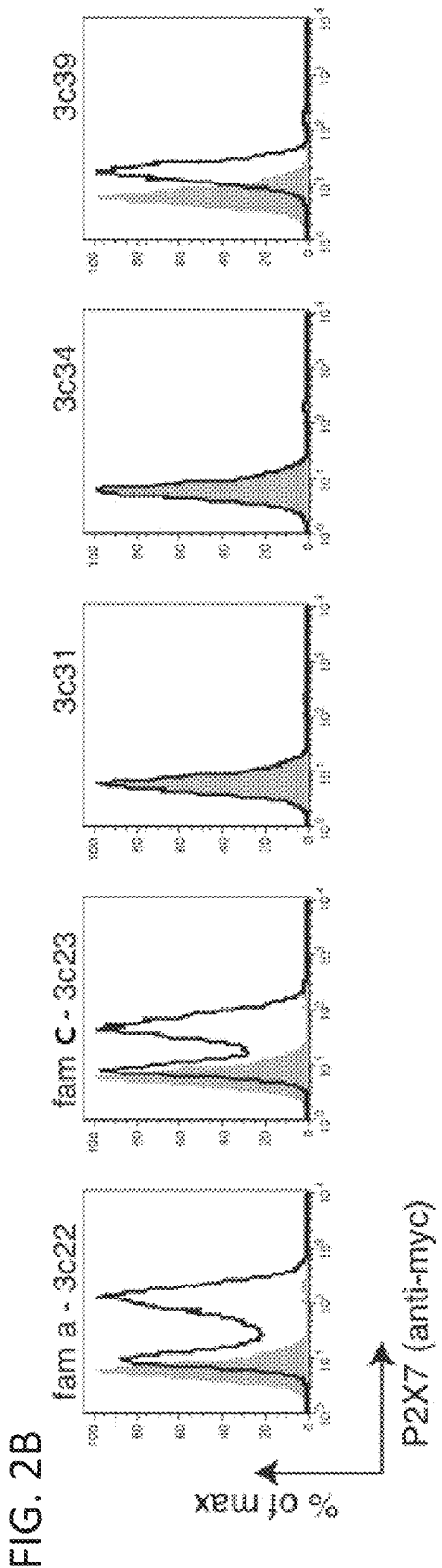

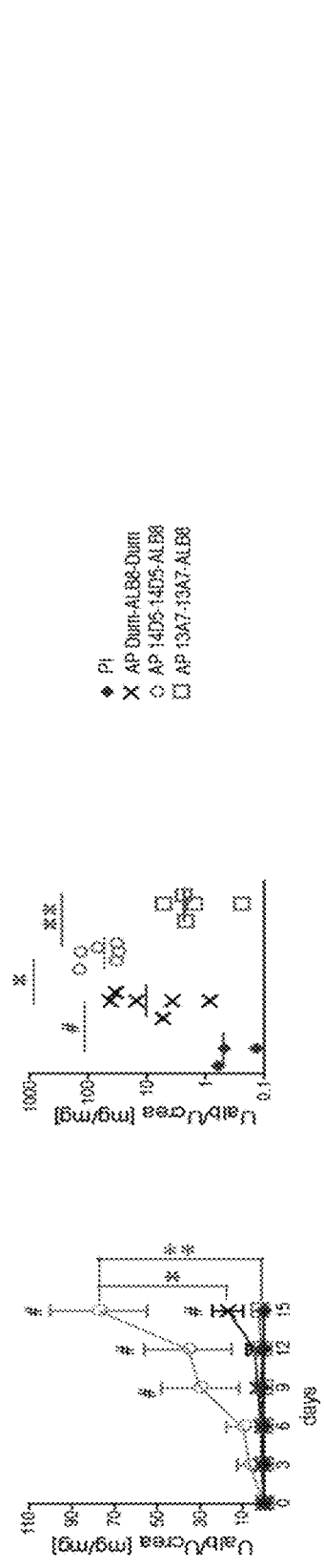
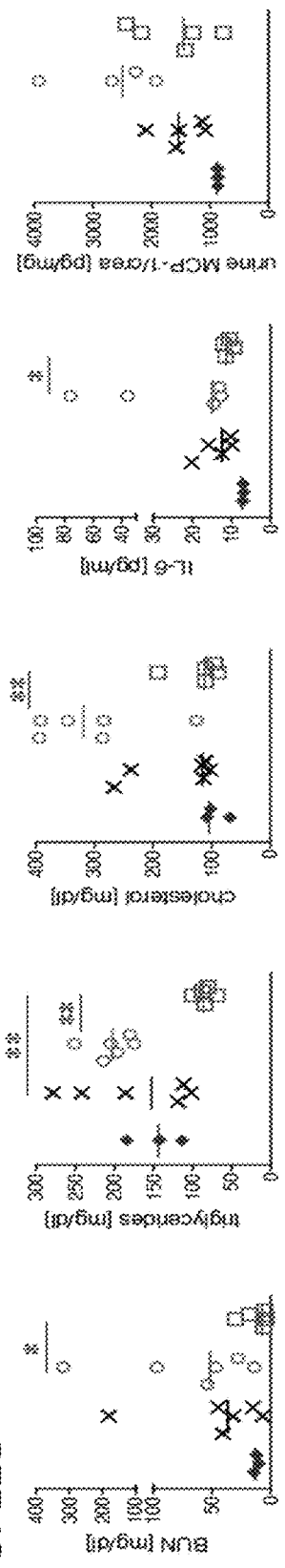
FIG. 12A
FIG. 12B

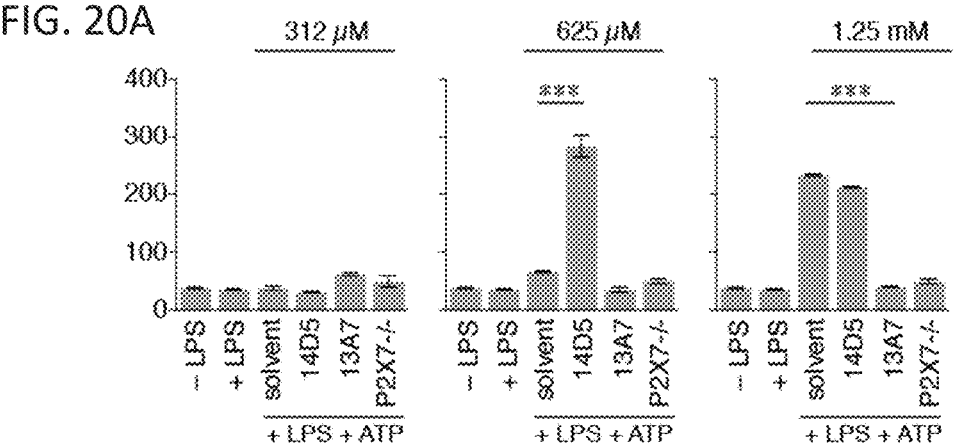
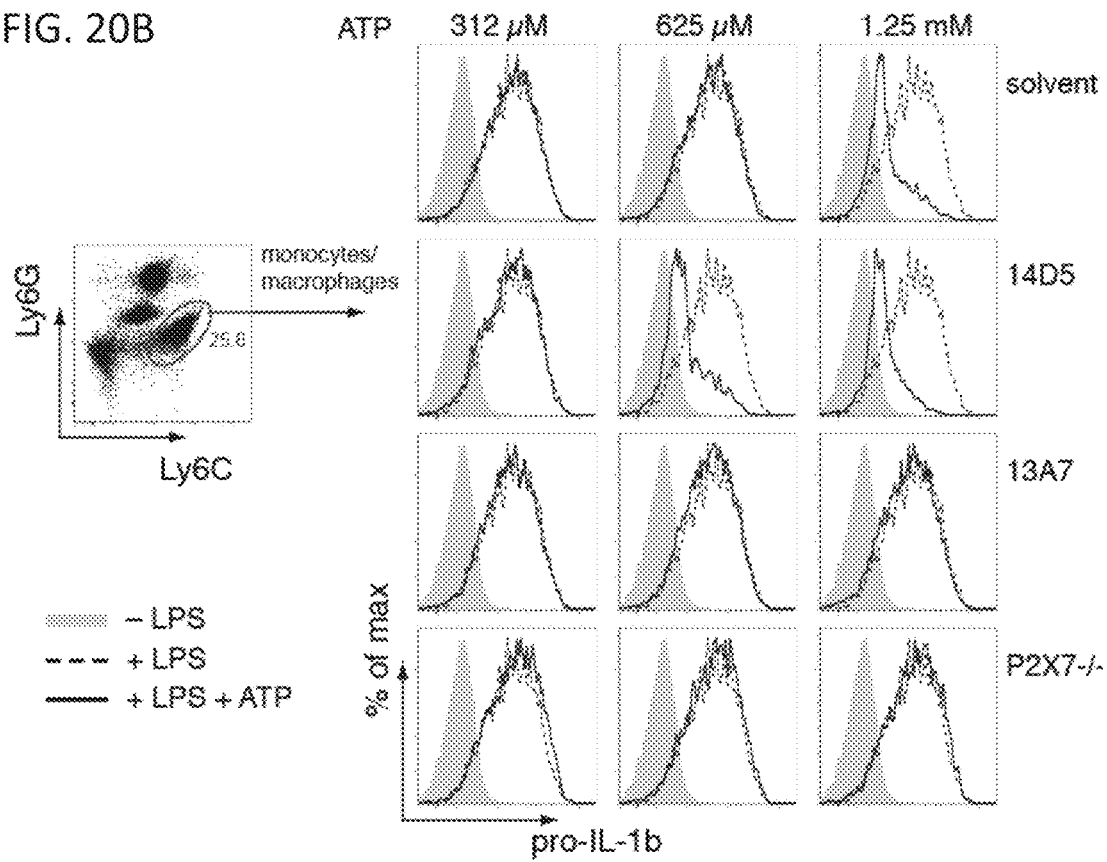

SEQUENCE LISTING

<160> NUMBER OF SEQ ID NOS: 138

<210> SEQ ID NO 1

<211> LENGTH: 595
<212> TYPE: PRT
<213> ORGANISM: Homo sapiens

<400> SEQUENCE: 1

Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
            20                  25                  30

Phe His Val Ile Ile Phe Ser Tyr Val Cys Phe Ala Leu Val Ser Asp
        35                  40                  45

Lys Leu Tyr Gln Arg Lys Glu Pro Val Ile Ser Ser Val His Thr Lys
    50                  55                  60

Val Lys Gly Ile Ala Glu Val Lys Glu Glu Ile Val Glu Asn Gly Val
65                  70                  75                  80

Lys Lys Leu Val His Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
            100                 105                 110

Gly Gln Glu Gln Arg Leu Cys Pro Glu Tyr Pro Thr Arg Arg Thr Leu
        115                 120                 125

Cys Ser Ser Asp Arg Gly Cys Lys Lys Gly Trp Met Asp Pro Gln Ser
    130                 135                 140

Lys Gly Ile Gln Thr Gly Arg Cys Val Val Tyr Glu Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Leu Ile
            180                 185                 190

Lys Asn Asn Ile Asp Phe Pro Gly His Asn Tyr Thr Thr Arg Asn Ile
        195                 200                 205

Leu Pro Gly Leu Asn Ile Thr Cys Thr Phe His Lys Thr Gln Asn Pro
    210                 215                 220

Gln Cys Pro Ile Phe Arg Leu Gly Asp Ile Phe Arg Glu Thr Gly Asp
225                 230                 235                 240

Asn Phe Ser Asp Val Ala Ile Gln Gly Gly Ile Met Gly Ile Glu Ile
                245                 250                 255

Tyr Trp Asp Cys Asn Leu Asp Arg Trp Phe His His Cys Arg Pro Lys
            260                 265                 270

Tyr Ser Phe Arg Arg Leu Asp Asp Lys Thr Thr Asn Val Ser Leu Tyr
        275                 280                 285

Pro Gly Tyr Asn Phe Arg Tyr Ala Lys Tyr Tyr Lys Glu Asn Asn Val
    290                 295                 300

Glu Lys Arg Thr Leu Ile Lys Val Phe Gly Ile Arg Phe Asp Ile Leu
305                 310                 315                 320

Val Phe Gly Thr Gly Gly Lys Phe Asp Ile Ile Gln Leu Val Val Tyr
                325                 330                 335

Ile Gly Ser Thr Leu Ser Tyr Phe Gly Leu Ala Ala Val Phe Ile Asp
            340                 345                 350

Phe Leu Ile Asp Thr Tyr Ser Ser Asn Cys Cys Arg Ser His Ile Tyr
        355                 360                 365

Pro Trp Cys Lys Cys Cys Gln Pro Cys Val Val Asn Glu Tyr Tyr Tyr
    370                 375                 380

Arg Lys Lys Cys Glu Ser Ile Val Glu Pro Lys Pro Thr Leu Lys Tyr

```
                385                 390                 395                 400
        Val Ser Phe Val Asp Glu Ser His Ile Arg Met Val Asn Gln Gln Leu
                            405                 410                 415

Leu Gly Arg Ser Leu Gln Asp Val Lys Gly Gln Glu Val Pro Arg Pro
                        420                 425                 430

Ala Met Asp Phe Thr Asp Leu Ser Arg Leu Pro Leu Ala Leu His Asp
                        435                 440                 445

Thr Pro Pro Ile Pro Gly Gln Pro Glu Glu Ile Gln Leu Leu Arg Lys
        450                 455                 460

Glu Ala Thr Pro Arg Ser Arg Asp Ser Pro Val Trp Cys Gln Cys Gly
        465                 470                 475                 480

Ser Cys Leu Pro Ser Gln Leu Pro Glu Ser His Arg Cys Leu Glu Glu
                        485                 490                 495

Leu Cys Cys Arg Lys Lys Pro Gly Ala Cys Ile Thr Thr Ser Glu Leu
                        500                 505                 510

Phe Arg Lys Leu Val Leu Ser Arg His Val Leu Gln Phe Leu Leu Leu
                        515                 520                 525

Tyr Gln Glu Pro Leu Leu Ala Leu Asp Val Asp Ser Thr Asn Ser Arg
                        530                 535                 540

Leu Arg His Cys Ala Tyr Arg Cys Tyr Ala Thr Trp Arg Phe Gly Ser
        545                 550                 555                 560

Gln Asp Met Ala Asp Phe Ala Ile Leu Pro Ser Cys Cys Arg Trp Arg
                        565                 570                 575

Ile Arg Lys Glu Phe Pro Lys Ser Glu Gly Tyr Ser Gly Phe Lys
                        580                 585                 590

Ser Pro Tyr
                        595

<210> SEQ ID NO 2
<211> LENGTH: 595
<212> TYPE: PRT
<213> ORGANISM: Homo sapiens

<400> SEQUENCE: 2

Met Pro Ala Cys Cys Ser Cys Ser Asp Val Phe Gln Tyr Glu Thr Asn
        1               5                   10                  15

Lys Val Thr Arg Ile Gln Ser Met Asn Tyr Gly Thr Ile Lys Trp Phe
                        20                  25                  30

Phe His Val Ile Ile Phe Ser Tyr Val Cys Phe Ala Leu Val Ser Asp
                        35                  40                  45

Lys Leu Tyr Gln Arg Lys Glu Pro Val Ile Ser Ser Val His Thr Lys
                50                  55                  60

Val Lys Gly Ile Ala Glu Val Lys Glu Glu Ile Val Glu Asn Gly Val
        65                  70                  75                  80

Lys Lys Leu Val His Ser Val Phe Asp Thr Ala Asp Tyr Thr Phe Pro
                        85                  90                  95

Leu Gln Gly Asn Ser Phe Phe Val Met Thr Asn Phe Leu Lys Thr Glu
                        100                 105                 110

Gly Gln Glu Gln Arg Leu Cys Pro Glu Tyr Pro Thr Arg Arg Thr Leu
                        115                 120                 125

Cys Ser Ser Asp Arg Gly Cys Lys Lys Gly Trp Met Asp Pro Gln Ser
                130                 135                 140

Lys Gly Ile Gln Thr Gly Arg Cys Val Val His Glu Gly Asn Gln Lys
        145                 150                 155                 160
```

```
Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Leu Ile
            180                 185                 190

Lys Asn Asn Ile Asp Phe Pro Gly His Asn Tyr Thr Thr Arg Asn Ile
        195                 200                 205

Leu Pro Gly Leu Asn Ile Thr Cys Thr Phe His Lys Thr Gln Asn Pro
    210                 215                 220

Gln Cys Pro Ile Phe Arg Leu Gly Asp Ile Phe Arg Glu Thr Gly Asp
225                 230                 235                 240

Asn Phe Ser Asp Val Ala Ile Gln Gly Gly Ile Met Gly Ile Glu Ile
                245                 250                 255

Tyr Trp Asp Cys Asn Leu Asp Arg Trp Phe His His Cys His Pro Lys
            260                 265                 270

Tyr Ser Phe Arg Arg Leu Asp Asp Lys Thr Thr Asn Val Ser Leu Tyr
        275                 280                 285

Pro Gly Tyr Asn Phe Arg Tyr Ala Lys Tyr Tyr Lys Glu Asn Asn Val
    290                 295                 300

Glu Lys Arg Thr Leu Ile Lys Val Phe Gly Ile Arg Phe Asp Ile Leu
305                 310                 315                 320

Val Phe Gly Thr Gly Gly Lys Phe Asp Ile Ile Gln Leu Val Val Tyr
                325                 330                 335

Ile Gly Ser Thr Leu Ser Tyr Phe Gly Leu Ala Ala Val Phe Ile Asp
            340                 345                 350

Phe Leu Ile Asp Thr Tyr Ser Ser Asn Cys Cys Arg Ser His Ile Tyr
        355                 360                 365

Pro Trp Cys Lys Cys Gln Pro Cys Val Val Asn Glu Tyr Tyr Tyr
    370                 375                 380

Arg Lys Lys Cys Glu Ser Ile Val Glu Pro Lys Pro Thr Leu Lys Tyr
385                 390                 395                 400

Val Ser Phe Val Asp Glu Ser His Ile Arg Met Val Asn Gln Gln Leu
                405                 410                 415

Leu Gly Arg Ser Leu Gln Asp Val Lys Gly Gln Glu Val Pro Arg Pro
            420                 425                 430

Ala Met Asp Phe Thr Asp Leu Ser Arg Leu Pro Leu Ala Leu His Asp
        435                 440                 445

Thr Pro Pro Ile Pro Gly Gln Pro Glu Glu Ile Gln Leu Leu Arg Lys
    450                 455                 460

Glu Ala Thr Pro Arg Ser Arg Asp Ser Pro Val Trp Cys Gln Cys Gly
465                 470                 475                 480

Ser Cys Leu Pro Ser Gln Leu Pro Glu Ser His Arg Cys Leu Glu Glu
                485                 490                 495

Leu Cys Cys Arg Lys Lys Pro Gly Ala Cys Ile Thr Thr Ser Glu Leu
            500                 505                 510

Phe Arg Lys Leu Val Leu Ser Arg His Val Leu Gln Phe Leu Leu Leu
        515                 520                 525

Tyr Gln Glu Pro Leu Leu Ala Leu Asp Val Asp Ser Thr Asn Ser Arg
    530                 535                 540

Leu Arg His Cys Ala Tyr Arg Cys Tyr Ala Thr Trp Arg Phe Gly Ser
545                 550                 555                 560

Gln Asp Met Ala Asp Phe Ala Ile Leu Pro Ser Cys Cys Arg Trp Arg
                565                 570                 575

Ile Arg Lys Glu Phe Pro Lys Ser Glu Gly Gln Tyr Ser Gly Phe Lys
```

-continued

```
                580                 585                 590
Ser Pro Tyr
        595

<210> SEQ ID NO 3
<211> LENGTH: 595
<212> TYPE: PRT
<213> ORGANISM: Homo sapiens

<400> SEQUENCE: 3

Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
            20                  25                  30

Phe His Val Ile Ile Phe Ser Tyr Val Cys Phe Ala Leu Val Ser Asp
        35                  40                  45

Lys Leu Tyr Gln Arg Lys Glu Pro Val Ile Ser Ser Val His Thr Lys
    50                  55                  60

Val Lys Gly Ile Ala Glu Val Lys Glu Glu Ile Val Glu Asn Gly Val
65                  70                  75                  80

Lys Lys Leu Val His Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
            100                 105                 110

Gly Gln Glu Gln Arg Leu Cys Pro Glu Tyr Pro Thr Arg Arg Thr Leu
        115                 120                 125

Cys Ser Ser Asp Arg Gly Cys Lys Lys Gly Trp Met Asp Pro Gln Ser
130                 135                 140

Lys Gly Ile Gln Thr Gly Arg Cys Val Val Tyr Glu Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Leu Ile
            180                 185                 190

Lys Asn Asn Ile Asp Phe Pro Gly His Asn Tyr Thr Thr Arg Asn Ile
        195                 200                 205

Leu Pro Gly Leu Asn Ile Thr Cys Thr Phe His Lys Thr Gln Asn Pro
    210                 215                 220

Gln Cys Pro Ile Phe Arg Leu Gly Asp Ile Phe Arg Glu Thr Gly Asp
225                 230                 235                 240

Asn Phe Ser Asp Val Ala Ile Gln Gly Gly Ile Met Gly Ile Glu Ile
                245                 250                 255

Tyr Trp Asp Cys Asn Leu Asp Arg Trp Phe His His Cys His Pro Lys
            260                 265                 270

Tyr Ser Phe Arg Arg Leu Asp Asp Lys Thr Thr Asn Val Ser Leu Tyr
        275                 280                 285

Pro Gly Tyr Asn Phe Arg Tyr Ala Lys Tyr Tyr Lys Glu Asn Asn Val
    290                 295                 300

Glu Lys Arg Thr Leu Ile Lys Val Phe Gly Ile Arg Phe Asp Ile Leu
305                 310                 315                 320

Val Phe Gly Thr Gly Gly Lys Phe Asp Ile Ile Gln Leu Val Val Tyr
                325                 330                 335

Ile Gly Ser Thr Leu Ser Tyr Phe Gly Leu Ala Thr Val Phe Ile Asp
            340                 345                 350
```

Phe Leu Ile Asp Thr Tyr Ser Ser Asn Cys Cys Arg Ser His Ile Tyr
            355                 360                 365

Pro Trp Cys Lys Cys Gln Pro Cys Val Val Asn Glu Tyr Tyr
    370                 375                 380

Arg Lys Lys Cys Glu Ser Ile Val Glu Pro Lys Pro Thr Leu Lys Tyr
385                 390                 395                 400

Val Ser Phe Val Asp Glu Ser His Ile Arg Met Val Asn Gln Gln Leu
                405                 410                 415

Leu Gly Arg Ser Leu Gln Asp Val Lys Gly Gln Glu Val Pro Arg Pro
            420                 425                 430

Ala Met Asp Phe Thr Asp Leu Ser Arg Leu Pro Leu Ala Leu His Asp
            435                 440                 445

Thr Pro Pro Ile Pro Gly Gln Pro Glu Glu Ile Gln Leu Leu Arg Lys
    450                 455                 460

Glu Ala Thr Pro Arg Ser Arg Asp Ser Pro Val Trp Cys Gln Cys Gly
465                 470                 475                 480

Ser Cys Leu Pro Ser Gln Leu Pro Glu Ser His Arg Cys Leu Glu Glu
                485                 490                 495

Leu Cys Cys Arg Lys Lys Pro Gly Ala Cys Ile Thr Thr Ser Glu Leu
            500                 505                 510

Phe Arg Lys Leu Val Leu Ser Arg His Val Leu Gln Phe Leu Leu Leu
    515                 520                 525

Tyr Gln Glu Pro Leu Leu Ala Leu Asp Val Asp Ser Thr Asn Ser Arg
            530                 535                 540

Leu Arg His Cys Ala Tyr Arg Cys Tyr Ala Thr Trp Arg Phe Gly Ser
545                 550                 555                 560

Gln Asp Met Ala Asp Phe Ala Ile Leu Pro Ser Cys Cys Arg Trp Arg
                565                 570                 575

Ile Arg Lys Glu Phe Pro Lys Ser Glu Gly Gln Tyr Ser Gly Phe Lys
            580                 585                 590

Ser Pro Tyr
    595

<210> SEQ ID NO 4
<211> LENGTH: 595
<212> TYPE: PRT
<213> ORGANISM: Mus musculus

<400> SEQUENCE: 4

Met Pro Ala Cys Cys Ser Trp Asn Asp Val Phe Gln Tyr Glu Thr Asn
1               5                   10                  15

Lys Val Thr Arg Ile Gln Ser Thr Asn Tyr Gly Thr Val Lys Trp Val
            20                  25                  30

Leu His Met Ile Val Phe Ser Tyr Ile Ser Phe Ala Leu Val Ser Asp
        35                  40                  45

Lys Leu Tyr Gln Arg Lys Glu Pro Val Ile Ser Ser Val His Thr Lys
    50                  55                  60

Val Lys Gly Ile Ala Glu Val Thr Glu Asn Val Thr Glu Gly Gly Val
65                  70                  75                  80

Thr Lys Leu Gly His Ser Ile Phe Asp Thr Ala Asp Tyr Thr Phe Pro
                85                  90                  95

Leu Gln Gly Asn Ser Phe Phe Val Met Thr Asn Tyr Val Lys Ser Glu
            100                 105                 110

Gly Gln Val Gln Thr Leu Cys Pro Glu Tyr Pro Arg Arg Gly Ala Gln
        115                 120                 125

```
Cys Ser Ser Asp Arg Arg Cys Lys Lys Gly Trp Met Asp Pro Gln Ser
    130                 135                 140
Lys Gly Ile Gln Thr Gly Arg Cys Val Pro Tyr Asp Lys Thr Arg Lys
145                 150                 155                 160
Thr Cys Glu Val Ser Ala Trp Cys Pro Thr Glu Glu Lys Glu Ala
            165                 170                 175
Pro Arg Pro Ala Leu Leu Arg Ser Ala Glu Asn Phe Thr Val Leu Ile
            180                 185                 190
Lys Asn Asn Ile His Phe Pro Gly His Asn Tyr Thr Thr Arg Asn Ile
        195                 200                 205
Leu Pro Thr Met Asn Gly Ser Cys Thr Phe His Lys Ala Trp Asp Pro
210                 215                 220
Gln Cys Ser Ile Phe Arg Leu Gly Asp Ile Phe Gln Glu Ala Gly Glu
225                 230                 235                 240
Asn Phe Thr Glu Val Ala Val Gln Gly Gly Ile Met Gly Ile Glu Ile
                245                 250                 255
Tyr Trp Asp Cys Asn Leu Asp Ser Trp Ser His His Cys Arg Pro Arg
            260                 265                 270
Tyr Ser Phe Arg Arg Leu Asp Asp Lys Asn Met Asp Glu Ser Phe Val
        275                 280                 285
Pro Gly Tyr Asn Phe Arg Tyr Ala Lys Tyr Tyr Lys Glu Asn Asn Val
290                 295                 300
Glu Lys Arg Thr Leu Ile Lys Ala Phe Gly Ile Arg Phe Asp Ile Leu
305                 310                 315                 320
Val Phe Gly Thr Gly Gly Lys Phe Asp Ile Ile Gln Leu Val Val Tyr
                325                 330                 335
Ile Gly Ser Thr Leu Ser Tyr Phe Gly Leu Ala Thr Val Cys Ile Asp
            340                 345                 350
Leu Leu Ile Asn Thr Tyr Ser Ser Ala Phe Cys Arg Ser Gly Val Tyr
        355                 360                 365
Pro Tyr Cys Lys Cys Cys Glu Pro Cys Thr Val Asn Glu Tyr Tyr Tyr
370                 375                 380
Arg Lys Lys Cys Glu Ser Ile Met Glu Pro Lys Pro Thr Leu Lys Tyr
385                 390                 395                 400
Val Ser Phe Val Asp Glu Pro His Ile Arg Met Val Asp Gln Gln Leu
                405                 410                 415
Leu Gly Lys Ser Leu Gln Val Val Lys Gly Gln Glu Val Pro Arg Pro
            420                 425                 430
Gln Met Asp Phe Ser Asp Leu Ser Arg Leu Ser Leu Ser Leu His Asp
        435                 440                 445
Ser Pro Leu Thr Pro Gly Gln Ser Glu Glu Ile Gln Leu Leu His Glu
450                 455                 460
Glu Val Ala Pro Lys Ser Gly Asp Ser Pro Ser Trp Cys Gln Cys Gly
465                 470                 475                 480
Asn Cys Leu Pro Ser Arg Leu Pro Glu Gln Arg Arg Ala Leu Glu Glu
                485                 490                 495
Leu Cys Cys Arg Arg Lys Pro Gly Arg Cys Ile Thr Thr Ser Lys Leu
            500                 505                 510
Phe His Lys Leu Val Leu Ser Arg Asp Thr Leu Gln Leu Leu Leu Leu
        515                 520                 525
Tyr Gln Asp Pro Leu Leu Val Leu Gly Glu Glu Ala Thr Asn Ser Arg
530                 535                 540
```

```
Leu Arg His Arg Ala Tyr Arg Cys Tyr Ala Thr Trp Arg Phe Gly Ser
545                 550                 555                 560

Gln Asp Met Ala Asp Phe Ala Ile Leu Pro Ser Cys Cys Arg Trp Arg
                565                 570                 575

Ile Arg Lys Glu Phe Pro Lys Thr Glu Gly Gln Tyr Ser Gly Phe Lys
            580                 585                 590

Tyr Pro Tyr
        595

<210> SEQ ID NO 5
<211> LENGTH: 595
<212> TYPE: PRT
<213> ORGANISM: Rattus norvegicus

<400> SEQUENCE: 5

Met Pro Ala Cys Cys Ser Trp Asn Asp Val Phe Gln Tyr Glu Thr Asn
1               5                   10                  15

Lys Val Thr Arg Ile Gln Ser Val Asn Tyr Gly Thr Ile Lys Trp Ile
            20                  25                  30

Leu His Met Thr Val Phe Ser Tyr Val Ser Phe Ala Leu Met Ser Asp
                35                  40                  45

Lys Leu Tyr Gln Arg Lys Glu Pro Leu Ile Ser Ser Val His Thr Lys
50                  55                  60

Val Lys Gly Val Ala Glu Val Thr Glu Asn Val Thr Glu Gly Gly Val
65                  70                  75                  80

Thr Lys Leu Val His Gly Ile Phe Asp Thr Ala Asp Tyr Thr Leu Pro
                85                  90                  95

Leu Gln Gly Asn Ser Phe Phe Val Met Thr Asn Tyr Leu Lys Ser Glu
                100                 105                 110

Gly Gln Glu Gln Lys Leu Cys Pro Glu Tyr Pro Ser Arg Gly Lys Gln
            115                 120                 125

Cys His Ser Asp Gln Gly Cys Ile Lys Gly Trp Met Asp Pro Gln Ser
130                 135                 140

Lys Gly Ile Gln Thr Gly Arg Cys Ile Pro Tyr Asp Gln Lys Arg Lys
145                 150                 155                 160

Thr Cys Glu Ile Phe Ala Trp Cys Pro Ala Glu Glu Gly Lys Glu Ala
                165                 170                 175

Pro Arg Pro Ala Leu Leu Arg Ser Ala Glu Asn Phe Thr Val Leu Ile
            180                 185                 190

Lys Asn Asn Ile Asp Phe Pro Gly His Asn Tyr Thr Thr Arg Asn Ile
            195                 200                 205

Leu Pro Gly Met Asn Ile Ser Cys Thr Phe His Lys Thr Trp Asn Pro
210                 215                 220

Gln Cys Pro Ile Phe Arg Leu Gly Asp Ile Phe Gln Glu Ile Gly Glu
225                 230                 235                 240

Asn Phe Thr Glu Val Ala Val Gln Gly Gly Ile Met Gly Ile Glu Ile
                245                 250                 255

Tyr Trp Asp Cys Asn Leu Asp Ser Trp Ser His Arg Cys Gln Pro Lys
            260                 265                 270

Tyr Ser Phe Arg Arg Leu Asp Asp Lys Tyr Thr Asn Glu Ser Leu Phe
        275                 280                 285

Pro Gly Tyr Asn Phe Arg Tyr Ala Lys Tyr Tyr Lys Glu Asn Gly Met
    290                 295                 300

Glu Lys Arg Thr Leu Ile Lys Ala Phe Gly Val Arg Phe Asp Ile Leu
305                 310                 315                 320
```

```
Val Phe Gly Thr Gly Gly Lys Phe Asp Ile Ile Gln Leu Val Val Tyr
                325                 330                 335

Ile Gly Ser Thr Leu Ser Tyr Phe Gly Leu Ala Thr Val Cys Ile Asp
                340                 345                 350

Leu Ile Ile Asn Thr Tyr Ala Ser Thr Cys Cys Arg Ser Arg Val Tyr
                355                 360                 365

Pro Ser Cys Lys Cys Glu Pro Cys Ala Val Asn Glu Tyr Tyr Tyr
370                 375                 380

Arg Lys Lys Cys Glu Pro Ile Val Glu Pro Lys Pro Thr Leu Lys Tyr
385                 390                 395                 400

Val Ser Phe Val Asp Glu Pro His Ile Trp Met Val Asp Gln Gln Leu
                405                 410                 415

Leu Gly Lys Ser Leu Gln Asp Val Lys Gly Gln Glu Val Pro Arg Pro
                420                 425                 430

Gln Thr Asp Phe Leu Glu Leu Ser Arg Leu Ser Leu Ser Leu His His
                435                 440                 445

Ser Pro Pro Ile Pro Gly Gln Pro Glu Glu Met Gln Leu Leu Gln Ile
                450                 455                 460

Glu Ala Val Pro Arg Ser Arg Asp Ser Pro Asp Trp Cys Gln Cys Gly
465                 470                 475                 480

Asn Cys Leu Pro Ser Gln Leu Pro Glu Asn Arg Arg Ala Leu Glu Glu
                485                 490                 495

Leu Cys Cys Arg Arg Lys Pro Gly Gln Cys Ile Thr Thr Ser Glu Leu
                500                 505                 510

Phe Ser Lys Ile Val Leu Ser Arg Glu Ala Leu Gln Leu Leu Leu Leu
                515                 520                 525

Tyr Gln Glu Pro Leu Leu Ala Leu Glu Gly Glu Ala Ile Asn Ser Lys
                530                 535                 540

Leu Arg His Cys Ala Tyr Arg Ser Tyr Ala Thr Trp Arg Phe Val Ser
545                 550                 555                 560

Gln Asp Met Ala Asp Phe Ala Ile Leu Pro Ser Cys Cys Arg Trp Lys
                565                 570                 575

Ile Arg Lys Glu Phe Pro Lys Thr Gln Gly Gln Tyr Ser Gly Phe Lys
                580                 585                 590

Tyr Pro Tyr
        595

<210> SEQ ID NO 6
<211> LENGTH: 131
<212> TYPE: PRT
<213> ORGANISM: Artificial Sequence
<220> FEATURE:
<223> OTHER INFORMATION: Nanobody sequence

<400> SEQUENCE: 6

Glu Val Gln Leu Val Glu Ser Gly Gly Lys Leu Val Gln Ala Gly Gly
1               5                   10                  15

Ser Leu Arg Leu Ser Cys Ser Ala Ser Gly Arg Thr Phe Ser Phe Ser
                20                  25                  30

Thr Ser Met Gly Trp Phe Arg Gln Ala Pro Gly Lys Glu Leu Glu
            35                  40                  45

Phe Val Ala Ala Ile Asp Trp Ser Asp Phe Asn Thr Tyr Tyr Ala Asp
            50                  55                  60

Ser Val Lys Gly Arg Phe Thr Ile Ser Arg His Asn Pro Arg Asn Ser
65              70                  75                  80
```

```
Val Tyr Leu Gln Leu Asn Ser Leu Lys Pro Glu Asp Thr Ala Val Tyr
             85                  90                  95

Tyr Cys Ala Ala His Ser Glu Thr Arg Gly Thr Arg Tyr Phe Asp
            100                 105                 110

Arg Pro Ser Leu Tyr Asn Tyr Trp Gly Gln Gly Thr Gln Val Thr Val
            115                 120                 125

Ser Ser Ala
        130

<210> SEQ ID NO 7
<211> LENGTH: 119
<212> TYPE: PRT
<213> ORGANISM: Artificial Sequence
<220> FEATURE:
<223> OTHER INFORMATION: nanobody sequence

<400> SEQUENCE: 7

Glu Val Gln Leu Val Glu Ser Gly Gly Gly Leu Val Gln Pro Gly Gly
1               5                   10                  15

Ser Leu Thr Leu Ser Cys Ala Ala Ser Gly Ile Ala Phe Asn Tyr Tyr
            20                  25                  30

Ser Met Ser Trp His Arg Gln Ala Pro Gly Lys Gln Arg Thr Leu Val
        35                  40                  45

Ala Asp Ile Ser Pro Gly Gly His Thr Glu Tyr Glu Asp Ser Val Lys
50                  55                  60

Gly Arg Phe Thr Ile Ser Arg Asp Asn Phe Lys Asn Thr Met Thr Leu
65                  70                  75                  80

His Met Asn Ser Leu Lys Pro Glu Asp Thr Ala Val Tyr Phe Cys Ala
                85                  90                  95

Ala Arg Leu Arg Phe Glu Val Ser Asn Tyr Trp Gly Gln Gly Thr
            100                 105                 110

Gln Val Thr Val Ser Ser Ala
            115

<210> SEQ ID NO 8
<211> LENGTH: 117
<212> TYPE: PRT
<213> ORGANISM: Artificial Sequence
<220> FEATURE:
<223> OTHER INFORMATION: nanobody sequence

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

Asp Met Ser Trp Val Arg Gln Ala Pro Gly Lys Gly Pro Glu Trp Val
        35                  40                  45

Ser Tyr Met Asn Ser Gly Gly Gly Thr Ala Tyr Ala Asp Ser Val
    50                  55                  60

Lys Gly Arg Phe Thr Ile Ser Arg Asp Asn Ala Lys Asn Thr Leu Cys
65                  70                  75                  80

Leu Gln Met Asn Ser Leu Lys Pro Glu Asp Thr Ala Val Tyr Tyr Cys
                85                  90                  95

Ala Thr Glu Lys Pro Leu Gly Gly Ala Trp Gly Gln Gly Thr Gln Val
            100                 105                 110

Thr Val Ser Ser Ala
```

```
<210> SEQ ID NO 9
<211> LENGTH: 119
<212> TYPE: PRT
<213> ORGANISM: Artificial Sequence
<220> FEATURE:
<223> OTHER INFORMATION: nanobody sequence

<400> SEQUENCE: 9

Arg Gly Ala Ala Gly Gly Val Trp Gly Arg Leu Gly Ala Gly Trp Gly
1               5                   10                  15

Ser Leu Ser Leu Ser Cys Ala Ala Ser Gly Ser Thr Phe Asn Asn Ser
            20                  25                  30

Val Met Gly Trp Tyr Arg Gln Ala Pro Gly Lys Gln Arg Glu Leu Val
        35                  40                  45

Ala Asp Ile Ser Gly Gly Val Thr Asn Tyr Ala Asp Ser Val Lys
    50                  55                  60

Gly Arg Phe Thr Ile Ser Arg Asp Asn Ala Lys Asn Met Val Tyr Leu
65                  70                  75                  80

Gln Met His Ile Leu Lys Pro Glu Asp Thr Ala Val Tyr Tyr Cys Asn
                85                  90                  95

Val Lys Arg Arg Phe Pro Ile Trp Arg Asp Tyr Trp Gly Lys Gly Thr
            100                 105                 110

Leu Val Thr Val Ser Ser Ala
            115

<210> SEQ ID NO 10
<211> LENGTH: 131
<212> TYPE: PRT
<213> ORGANISM: Artificial Sequence
<220> FEATURE:
<223> OTHER INFORMATION: nanobody sequence

<400> SEQUENCE: 10

Glu Val Gln Leu Val Glu Ser Gly Gly Lys Leu Val Gln Ala Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Thr Ile Ser Arg His Asn Pro Arg Asn Ser
65                  70                  75                  80

Val Tyr Leu Gln Leu Asn Ser Leu Lys Pro Glu Asp Thr Ala Val Tyr
                85                  90                  95

Tyr Cys Ala Ala His Ser Glu Thr Arg Asp Gly Thr Arg Thr Phe Asp
            100                 105                 110

Arg Pro Ser Leu Tyr Asn Tyr Trp Gly Gln Gly Thr Gln Val Thr Val
            115                 120                 125

Ser Ser Ala
    130

<210> SEQ ID NO 11
<211> LENGTH: 131
<212> TYPE: PRT
<213> ORGANISM: Artificial Sequence
<220> FEATURE:
```

<223> OTHER INFORMATION: nanobody sequence

<400> SEQUENCE: 11

Glu Val Gln Leu Val Glu Ser Gly Gly Lys Leu Val Gln Ala Gly Gly
1               5                   10                  15

Ser Leu Arg Leu Ser Cys Ser Ala Ser Gly Arg Thr Phe Ser Phe Ser
            20                  25                  30

Thr Ser Thr Met Gly Trp Phe Arg Gln Ala Pro Gly Lys Glu Leu Glu
        35                  40                  45

Phe Val Ala Ala Ile Asp Trp Ser Asp Phe Asn Thr Tyr Tyr Ala Asp
    50                  55                  60

Ser Val Lys Gly Arg Phe Ile Ile Ser Arg His Asn Pro Arg Asn Ser
65                  70                  75                  80

Val Tyr Leu Gln Leu Asn Ser Leu Lys Pro Glu Asp Thr Ala Val Tyr
                85                  90                  95

Tyr Cys Ala Ala His Ser Glu Thr Arg Gly Gly Thr Arg Tyr Phe Asp
            100                 105                 110

Arg Pro Ser Leu Tyr Asn Tyr Trp Gly Gln Gly Thr Gln Val Thr Val
        115                 120                 125

Ser Ser Ala
    130

<210> SEQ ID NO 12
<211> LENGTH: 130
<212> TYPE: PRT
<213> ORGANISM: Artificial Sequence
<220> FEATURE:
<223> OTHER INFORMATION: nanobody sequence

<400> SEQUENCE: 12

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Arg His Tyr
            20                  25                  30

Ala Met Gly Trp Phe Arg Gln Ala Pro Gly Lys Glu Arg Glu Phe Val
        35                  40                  45

Ala Ala Ile Ser Ser Tyr Gly Ser Thr Asp Tyr Gly Asp Ser Val Lys
    50                  55                  60

Gly Arg Phe Thr Ile Ser Arg Asp Asp Ala Lys Asn Thr Val Pro Leu
65                  70                  75                  80

Gln Met Asn Ser Leu Lys Pro Glu Asp Thr Ala Val Tyr Tyr Cys Ala
                85                  90                  95

Ala Ala Asp Glu Thr Leu Gly Ala Val Pro Asn Phe Arg Leu His Glu
            100                 105                 110

Lys Tyr Glu Tyr Glu Tyr Trp Gly Gln Gly Thr Gln Val Thr Val Ser
        115                 120                 125

Ser Ala
    130

<210> SEQ ID NO 13
<211> LENGTH: 130
<212> TYPE: PRT
<213> ORGANISM: Artificial Sequence
<220> FEATURE:
<223> OTHER INFORMATION: nanobody sequence

<400> SEQUENCE: 13

Glu Met Gln Leu Val Glu Ser Gly Gly Gly Leu Val Gln Ala Gly Gly

-continued

```
                1               5                  10                  15
            Ser Leu Arg Leu Ser Cys Ala Ala Ser Gly Arg Thr Phe Arg His Tyr
                           20                  25                  30

Ala Met Gly Trp Phe Arg Gln Ala Pro Gly Lys Glu Arg Glu Phe Val
                       35                  40                  45

Ala Ala Ile Ser Ser Tyr Gly Ser Thr Asp Tyr Gly Asp Ser Val Lys
                   50                  55                  60

Gly Arg Phe Thr Ile Ser Arg Asp Asp Ala Lys Asn Thr Val Pro Leu
            65                  70                  75                  80

Gln Met Asn Ser Leu Lys Pro Glu Asp Thr Ala Val Tyr Tyr Cys Ala
                           85                  90                  95

Ala Ala Asp Glu Thr Leu Gly Ala Val Pro Asn Phe Arg Leu His Glu
                       100                 105                 110

Lys Tyr Glu Tyr Glu Tyr Trp Gly Gln Gly Thr Gln Val Thr Val Ser
                       115                 120                 125

Ser Ala
                130
```

<210> SEQ ID NO 14
<211> LENGTH: 125
<212> TYPE: PRT
<213> ORGANISM: Artificial Sequence
<220> FEATURE:
<223> OTHER INFORMATION: nanobody sequence

<400> SEQUENCE: 14

```
            Glu Val Gln Leu Val Glu Ser Gly Gly Gly Leu Val Gln Pro Gly Gly
            1               5                  10                  15

Ser Leu Arg Leu Ser Cys Val Val Ser Gly Phe Thr Val Asp Asp Tyr
                           20                  25                  30

Ala Ile Gly Trp Phe Arg Gln Ala Pro Gly Lys Glu Arg Glu Gly Ile
                       35                  40                  45

Ser Cys Ile Thr Ser Ser Asp Gly Asn Thr Tyr Tyr Ala Leu Ser Val
                   50                  55                  60

Lys Gly Arg Phe Thr Ala Ser Ser Asp Asn Ala Lys Asn Thr Val Tyr
            65                  70                  75                  80

Leu Gln Met Asn Ser Leu Asn Pro Glu Asp Thr Ala Val Tyr Tyr Cys
                           85                  90                  95

Ala Ala Asp Pro Val Arg Arg Gly Trp Gly Cys Arg Asp His Tyr Lys
                       100                 105                 110

Tyr Trp Gly Gln Gly Thr Gln Val Thr Val Ser Ser Ala
                       115                 120                 125
```

<210> SEQ ID NO 15
<211> LENGTH: 116
<212> TYPE: PRT
<213> ORGANISM: Artificial Sequence
<220> FEATURE:
<223> OTHER INFORMATION: nanobody sequence

<400> SEQUENCE: 15

```
            Glu Val Gln Leu Val Glu Ser Gly Gly Gly Leu Val Gln Pro Gly Gly
            1               5                  10                  15

Ser Leu Glu Leu Ser Cys Thr Val Ser Gly Ser Ile Phe Ser Thr Ser
                           20                  25                  30

Ala Met Ala Trp Tyr Arg Gln Val Pro Gly Lys Pro Arg Trp Leu Val
                       35                  40                  45
```

```
Ala Thr Ile Thr Arg Asp Gly Thr Thr Asn Tyr Ile Asp Ser Val Gln
        50                  55                  60

Gly Arg Phe Thr Ile Ser Arg Asp Asn Ala Lys Asn Met Ile Tyr Leu
 65                  70                  75                  80

Arg Met Asn Ser Leu Lys Pro Glu Asp Thr Ala Val Tyr Tyr Cys Val
                85                  90                  95

Thr Ile Leu Ser Gly Lys Lys Thr Trp Gly Gln Gly Thr Gln Val Thr
            100                 105                 110

Val Ser Ser Ala
        115

<210> SEQ ID NO 16
<211> LENGTH: 117
<212> TYPE: PRT
<213> ORGANISM: Artificial Sequence
<220> FEATURE:
<223> OTHER INFORMATION: nanobody sequence

<400> SEQUENCE: 16

Glu Val Gln Leu Val Glu Ser Gly Gly Gly Leu Val Gln Ala Gly Gly
 1               5                  10                  15

Ser Leu Arg Leu Ser Cys Ala Ala Ser Gly Ile Thr Phe Ser Ser Tyr
            20                  25                  30

Ala Met Gly Trp Tyr Arg Gln Ala Pro Gly Lys Gln Arg Glu Leu Val
        35                  40                  45

Ala Glu Ile Ser Asp Gly Gly Thr Tyr Ser Ala Asp Ser Val Lys
    50                  55                  60

Gly Arg Phe Thr Ile Ser Arg Asp Asn Ala Lys Asn Thr Val Tyr Leu
 65                  70                  75                  80

Gln Met Thr Ser Leu Arg Pro Glu Asp Thr Ala Val Tyr Tyr Cys Asn
                85                  90                  95

Ala Leu Phe Thr Ser Asp Trp Phe Gly Trp Gly Gln Gly Thr Gln Val
            100                 105                 110

Thr Val Ser Ser Ala
        115

<210> SEQ ID NO 17
<211> LENGTH: 120
<212> TYPE: PRT
<213> ORGANISM: Artificial Sequence
<220> FEATURE:
<223> OTHER INFORMATION: nanobody sequence

<400> SEQUENCE: 17

Ala Val Gln Leu Val Glu Ser Gly Gly Gly Leu Val Gln Ala Gly Gly
 1               5                  10                  15

Ser Leu Arg Leu Ser Cys Ala Ala Ser Gly Asn Phe Phe Arg Val Asn
            20                  25                  30

Thr Met Ala Trp Tyr Arg Gln Ala Pro Gly Lys Gln Arg Glu Leu Val
        35                  40                  45

Ala Asp Ile Thr Arg Gly Asp Arg Thr Asn Tyr Ala Asp Thr Val Asn
    50                  55                  60

Gly Arg Phe Thr Ile Ser Arg Asp Asn Val Arg Asn Thr Val Tyr Leu
 65                  70                  75                  80

Gln Met Asn Gly Leu Arg Pro Glu Asp Thr Ala Ala Tyr Tyr Cys Tyr
                85                  90                  95

Ala Val Ile Glu Leu Gly Val Leu Glu Pro Arg Asp Tyr Trp Gly Gln
            100                 105                 110
```

```
Gly Thr Gln Val Thr Val Ser Ser
        115             120
```

<210> SEQ ID NO 18
<211> LENGTH: 114
<212> TYPE: PRT
<213> ORGANISM: Artificial Sequence
<220> FEATURE:
<223> OTHER INFORMATION: nanobody sequence

<400> SEQUENCE: 18

```
Lys Val Gln Leu Val Glu Ser Gly Gly Gly Leu Val Gln Ala Gly Gly
1               5                   10                  15

Ser Leu Arg Leu Ser Cys Ala Ala Ser Gly Ser Pro Ile Ser Ser Tyr
            20                  25                  30

Ala Met Gly Trp Tyr Arg Gln Ala Pro Gly Lys Pro Arg Glu Leu Val
        35                  40                  45

Ala Arg Ile Tyr Thr Gly Gly Thr Ala Trp Tyr Glu Asp Ser Val Lys
    50                  55                  60

Gly Arg Phe Thr Ile Ser Arg Asp Asn Ala Gln Asn Thr Val Tyr Leu
65                  70                  75                  80

Gln Met Asn Ser Leu Lys Ser Glu Asp Thr Ala Val Tyr Tyr Cys His
                85                  90                  95

Gly Arg Val Arg Tyr Asp Tyr Trp Gly Gln Gly Thr Gln Val Thr Val
            100                 105                 110

Ser Ser
```

<210> SEQ ID NO 19
<211> LENGTH: 127
<212> TYPE: PRT
<213> ORGANISM: Artificial Sequence
<220> FEATURE:
<223> OTHER INFORMATION: nanobody sequence

<400> SEQUENCE: 19

```
Glu Val Gln Leu Val Glu Ser Gly Gly Gly Leu Val Gln Pro Gly Glu
1               5                   10                  15

Ser Leu Arg Leu Ser Cys Thr Ala Ser Arg Phe Met Leu Asp Tyr Tyr
            20                  25                  30

Asp Ile Gly Trp Phe Arg Gln Ala Pro Gly Lys Glu Arg Glu Gly Val
        35                  40                  45

Ser Cys Arg Phe Thr Asn Asp Gly Ser Thr Ala Tyr Ala Asp Ser Val
    50                  55                  60

Lys Gly Arg Phe Thr Ile Ser Arg Asp Ile Val Lys His Thr Val Tyr
65                  70                  75                  80

Leu Gln Met Asn Ser Leu Gln Pro Glu Asp Thr Ala Val Tyr Tyr Cys
                85                  90                  95

Ala Ala Gly Pro Leu Thr Lys Arg Arg Gln Cys Val Pro Gly Asp Phe
            100                 105                 110

Ser Met Asp Phe Trp Gly Glu Gly Thr Leu Val Thr Val Ser Ser
        115                 120                 125
```

<210> SEQ ID NO 20
<211> LENGTH: 26
<212> TYPE: PRT
<213> ORGANISM: Artificial Sequence
<220> FEATURE:
<223> OTHER INFORMATION: nanobody sequence

```
<400> SEQUENCE: 20

Glu Val Gln Leu Val Glu Ser Gly Gly Lys Leu Val Gln Ala Gly Gly
1               5                   10                  15

Ser Leu Arg Leu Ser Cys Ser Ala Ser Gly
            20                  25

<210> SEQ ID NO 21
<211> LENGTH: 26
<212> TYPE: PRT
<213> ORGANISM: Artificial Sequence
<220> FEATURE:
<223> OTHER INFORMATION: nanobody sequence

<400> SEQUENCE: 21

Glu Val Gln Leu Val Glu Ser Gly Gly Gly Leu Val Gln Pro Gly Gly
1               5                   10                  15

Ser Leu Thr Leu Ser Cys Ala Ala Ser Gly
            20                  25

<210> SEQ ID NO 22
<211> LENGTH: 26
<212> TYPE: PRT
<213> ORGANISM: Artificial Sequence
<220> FEATURE:
<223> OTHER INFORMATION: nanobody sequence

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly
            20                  25

<210> SEQ ID NO 23
<211> LENGTH: 26
<212> TYPE: PRT
<213> ORGANISM: Artificial Sequence
<220> FEATURE:
<223> OTHER INFORMATION: nanobody sequence

<400> SEQUENCE: 23

Arg Gly Ala Ala Gly Gly Val Trp Gly Arg Leu Gly Ala Gly Trp Gly
1               5                   10                  15

Ser Leu Ser Leu Ser Cys Ala Ala Ser Gly
            20                  25

<210> SEQ ID NO 24
<211> LENGTH: 26
<212> TYPE: PRT
<213> ORGANISM: Artificial Sequence
<220> FEATURE:
<223> OTHER INFORMATION: nanobody sequence

<400> SEQUENCE: 24

Glu Val Gln Leu Val Glu Ser Gly Gly Lys Leu Val Gln Ala Gly Gly
1               5                   10                  15

Ser Leu Arg Leu Ser Cys Ser Ala Ser Gly
            20                  25

<210> SEQ ID NO 25
<211> LENGTH: 26
<212> TYPE: PRT
<213> ORGANISM: Artificial Sequence
<220> FEATURE:
<223> OTHER INFORMATION: nanobody sequence
```

<400> SEQUENCE: 25

Glu Val Gln Leu Val Glu Ser Gly Gly Lys Leu Val Gln Ala Gly Gly
1               5                   10                  15

Ser Leu Arg Leu Ser Cys Ser Ala Ser Gly
            20                  25

<210> SEQ ID NO 26
<211> LENGTH: 26
<212> TYPE: PRT
<213> ORGANISM: Artificial Sequence
<220> FEATURE:
<223> OTHER INFORMATION: nanobody sequence

<400> SEQUENCE: 26

Glu Val Gln Leu Val Glu Ser Gly Gly Gly Leu Val Gln Ala Gly Gly
1               5                   10                  15

Ser Leu Arg Leu Ser Cys Ala Ala Ser Gly
            20                  25

<210> SEQ ID NO 27
<211> LENGTH: 26
<212> TYPE: PRT
<213> ORGANISM: Artificial Sequence
<220> FEATURE:
<223> OTHER INFORMATION: nanobody sequence

<400> SEQUENCE: 27

Glu Met Gln Leu Val Glu Ser Gly Gly Gly Leu Val Gln Ala Gly Gly
1               5                   10                  15

Ser Leu Arg Leu Ser Cys Ala Ala Ser Gly
            20                  25

<210> SEQ ID NO 28
<211> LENGTH: 26
<212> TYPE: PRT
<213> ORGANISM: Artificial Sequence
<220> FEATURE:
<223> OTHER INFORMATION: nanobody sequence

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Val Val Ser Gly
            20                  25

<210> SEQ ID NO 29
<211> LENGTH: 26
<212> TYPE: PRT
<213> ORGANISM: Artificial Sequence
<220> FEATURE:
<223> OTHER INFORMATION: nanobody sequence

<400> SEQUENCE: 29

Glu Val Gln Leu Val Glu Ser Gly Gly Gly Leu Val Gln Pro Gly Gly
1               5                   10                  15

Ser Leu Glu Leu Ser Cys Thr Val Ser Gly
            20                  25

<210> SEQ ID NO 30
<211> LENGTH: 26
<212> TYPE: PRT
<213> ORGANISM: Artificial Sequence
<220> FEATURE:

```
<223> OTHER INFORMATION: nanobody sequence

<400> SEQUENCE: 30

Glu Val Gln Leu Val Glu Ser Gly Gly Gly Leu Val Gln Ala Gly Gly
1               5                   10                  15

Ser Leu Arg Leu Ser Cys Ala Ala Ser Gly
            20                  25

<210> SEQ ID NO 31
<211> LENGTH: 30
<212> TYPE: PRT
<213> ORGANISM: Artificial Sequence
<220> FEATURE:
<223> OTHER INFORMATION: nanobody sequence

<400> SEQUENCE: 31

Ala Val Gln Leu Val Glu Ser Gly Gly Gly Leu Val Gln Ala Gly Gly
1               5                   10                  15

Ser Leu Arg Leu Ser Cys Ala Ala Ser Gly Asn Phe Phe Arg
            20                  25                  30

<210> SEQ ID NO 32
<211> LENGTH: 30
<212> TYPE: PRT
<213> ORGANISM: Artificial Sequence
<220> FEATURE:
<223> OTHER INFORMATION: nanobody sequence

<400> SEQUENCE: 32

Lys Val Gln Leu Val Glu Ser Gly Gly Gly Leu Val Gln Ala Gly Gly
1               5                   10                  15

Ser Leu Arg Leu Ser Cys Ala Ala Ser Gly Ser Pro Ile Ser
            20                  25                  30

<210> SEQ ID NO 33
<211> LENGTH: 30
<212> TYPE: PRT
<213> ORGANISM: Artificial Sequence
<220> FEATURE:
<223> OTHER INFORMATION: nanobody sequence

<400> SEQUENCE: 33

Glu Val Gln Leu Val Glu Ser Gly Gly Gly Leu Val Gln Pro Gly Glu
1               5                   10                  15

Ser Leu Arg Leu Ser Cys Thr Ala Ser Arg Phe Met Leu Asp
            20                  25                  30

<210> SEQ ID NO 34
<211> LENGTH: 11
<212> TYPE: PRT
<213> ORGANISM: Artificial Sequence
<220> FEATURE:
<223> OTHER INFORMATION: nanobody sequence

<400> SEQUENCE: 34

Arg Thr Phe Ser Phe Ser Thr Ser Thr Met Gly
1               5                   10

<210> SEQ ID NO 35
<211> LENGTH: 9
<212> TYPE: PRT
<213> ORGANISM: Artificial Sequence
<220> FEATURE:
<223> OTHER INFORMATION: nanobody sequence
```

```
<400> SEQUENCE: 35

Ile Ala Phe Asn Tyr Tyr Ser Met Ser
1               5

<210> SEQ ID NO 36
<211> LENGTH: 9
<212> TYPE: PRT
<213> ORGANISM: Artificial Sequence
<220> FEATURE:
<223> OTHER INFORMATION: nanobody sequence

<400> SEQUENCE: 36

Phe Thr Phe Arg Asn Tyr Asp Met Ser
1               5

<210> SEQ ID NO 37
<211> LENGTH: 9
<212> TYPE: PRT
<213> ORGANISM: Artificial Sequence
<220> FEATURE:
<223> OTHER INFORMATION: nanobody sequence

<400> SEQUENCE: 37

Ser Thr Phe Asn Asn Ser Val Met Gly
1               5

<210> SEQ ID NO 38
<211> LENGTH: 11
<212> TYPE: PRT
<213> ORGANISM: Artificial Sequence
<220> FEATURE:
<223> OTHER INFORMATION: nanobody sequence

<400> SEQUENCE: 38

Arg Thr Phe Ser Phe Ser Thr Ser Thr Met Gly
1               5                   10

<210> SEQ ID NO 39
<211> LENGTH: 11
<212> TYPE: PRT
<213> ORGANISM: Artificial Sequence
<220> FEATURE:
<223> OTHER INFORMATION: nanobody sequence

<400> SEQUENCE: 39

Arg Thr Phe Ser Phe Ser Thr Ser Thr Met Gly
1               5                   10

<210> SEQ ID NO 40
<211> LENGTH: 9
<212> TYPE: PRT
<213> ORGANISM: Artificial Sequence
<220> FEATURE:
<223> OTHER INFORMATION: nanobody sequence

<400> SEQUENCE: 40

Arg Thr Phe Arg His Tyr Ala Met Gly
1               5

<210> SEQ ID NO 41
<211> LENGTH: 9
<212> TYPE: PRT
<213> ORGANISM: Artificial Sequence
<220> FEATURE:
<223> OTHER INFORMATION: nanobody sequence

<400> SEQUENCE: 41
```

```
Arg Thr Phe Arg His Tyr Ala Met Gly
1               5

<210> SEQ ID NO 42
<211> LENGTH: 9
<212> TYPE: PRT
<213> ORGANISM: Artificial Sequence
<220> FEATURE:
<223> OTHER INFORMATION: nanobody sequence

<400> SEQUENCE: 42

Phe Thr Val Asp Asp Tyr Ala Ile Gly
1               5

<210> SEQ ID NO 43
<211> LENGTH: 9
<212> TYPE: PRT
<213> ORGANISM: Artificial Sequence
<220> FEATURE:
<223> OTHER INFORMATION: nanobody sequence

<400> SEQUENCE: 43

Ser Ile Phe Ser Thr Ser Ala Met Ala
1               5

<210> SEQ ID NO 44
<211> LENGTH: 9
<212> TYPE: PRT
<213> ORGANISM: Artificial Sequence
<220> FEATURE:
<223> OTHER INFORMATION: nanobody sequence

<400> SEQUENCE: 44

Ile Thr Phe Ser Ser Tyr Ala Met Gly
1               5

<210> SEQ ID NO 45
<211> LENGTH: 5
<212> TYPE: PRT
<213> ORGANISM: Artificial Sequence
<220> FEATURE:
<223> OTHER INFORMATION: nanobody sequence

<400> SEQUENCE: 45

Val Asn Thr Met Ala
1               5

<210> SEQ ID NO 46
<211> LENGTH: 5
<212> TYPE: PRT
<213> ORGANISM: Artificial Sequence
<220> FEATURE:
<223> OTHER INFORMATION: nanobody sequence

<400> SEQUENCE: 46

Ser Tyr Ala Met Gly
1               5

<210> SEQ ID NO 47
<211> LENGTH: 5
<212> TYPE: PRT
<213> ORGANISM: Artificial Sequence
<220> FEATURE:
<223> OTHER INFORMATION: nanobody sequence

<400> SEQUENCE: 47
```

Tyr Tyr Asp Ile Gly
1               5

<210> SEQ ID NO 48
<211> LENGTH: 14
<212> TYPE: PRT
<213> ORGANISM: Artificial Sequence
<220> FEATURE:
<223> OTHER INFORMATION: nanobody sequence

<400> SEQUENCE: 48

Trp Phe Arg Gln Ala Pro Gly Lys Glu Leu Glu Phe Val Ala
1               5                   10

<210> SEQ ID NO 49
<211> LENGTH: 14
<212> TYPE: PRT
<213> ORGANISM: Artificial Sequence
<220> FEATURE:
<223> OTHER INFORMATION: nanobody sequence

<400> SEQUENCE: 49

Trp His Arg Gln Ala Pro Gly Lys Gln Arg Thr Leu Val Ala
1               5                   10

<210> SEQ ID NO 50
<211> LENGTH: 14
<212> TYPE: PRT
<213> ORGANISM: Artificial Sequence
<220> FEATURE:
<223> OTHER INFORMATION: nanobody sequence

<400> SEQUENCE: 50

Trp Val Arg Gln Ala Pro Gly Lys Gly Pro Glu Trp Val Ser
1               5                   10

<210> SEQ ID NO 51
<211> LENGTH: 14
<212> TYPE: PRT
<213> ORGANISM: Artificial Sequence
<220> FEATURE:
<223> OTHER INFORMATION: nanobody sequence

<400> SEQUENCE: 51

Trp Tyr Arg Gln Ala Pro Gly Lys Gln Arg Glu Leu Val Ala
1               5                   10

<210> SEQ ID NO 52
<211> LENGTH: 14
<212> TYPE: PRT
<213> ORGANISM: Artificial Sequence
<220> FEATURE:
<223> OTHER INFORMATION: nanobody sequence

<400> SEQUENCE: 52

Trp Phe Arg Gln Ala Pro Gly Lys Glu Leu Glu Phe Val Ala
1               5                   10

<210> SEQ ID NO 53
<211> LENGTH: 14
<212> TYPE: PRT
<213> ORGANISM: Artificial Sequence
<220> FEATURE:
<223> OTHER INFORMATION: nanobody sequence

<400> SEQUENCE: 53

Trp Phe Arg Gln Ala Pro Gly Lys Glu Leu Glu Phe Val Ala

```
1               5                   10
```

<210> SEQ ID NO 54
<211> LENGTH: 14
<212> TYPE: PRT
<213> ORGANISM: Artificial Sequence
<220> FEATURE:
<223> OTHER INFORMATION: nanobody sequence

<400> SEQUENCE: 54

```
Trp Phe Arg Gln Ala Pro Gly Lys Glu Arg Glu Phe Val Ala
1               5                   10
```

<210> SEQ ID NO 55
<211> LENGTH: 14
<212> TYPE: PRT
<213> ORGANISM: Artificial Sequence
<220> FEATURE:
<223> OTHER INFORMATION: nanobody sequence

<400> SEQUENCE: 55

```
Trp Phe Arg Gln Ala Pro Gly Lys Glu Arg Glu Phe Val Ala
1               5                   10
```

<210> SEQ ID NO 56
<211> LENGTH: 14
<212> TYPE: PRT
<213> ORGANISM: Artificial Sequence
<220> FEATURE:
<223> OTHER INFORMATION: nanobody sequence

<400> SEQUENCE: 56

```
Trp Phe Arg Gln Ala Pro Gly Lys Glu Arg Glu Gly Ile Ser
1               5                   10
```

<210> SEQ ID NO 57
<211> LENGTH: 14
<212> TYPE: PRT
<213> ORGANISM: Artificial Sequence
<220> FEATURE:
<223> OTHER INFORMATION: nanobody sequence

<400> SEQUENCE: 57

```
Trp Tyr Arg Gln Val Pro Gly Lys Pro Arg Trp Leu Val Ala
1               5                   10
```

<210> SEQ ID NO 58
<211> LENGTH: 14
<212> TYPE: PRT
<213> ORGANISM: Artificial Sequence
<220> FEATURE:
<223> OTHER INFORMATION: nanobody sequence

<400> SEQUENCE: 58

```
Trp Tyr Arg Gln Ala Pro Gly Lys Gln Arg Glu Leu Val Ala
1               5                   10
```

<210> SEQ ID NO 59
<211> LENGTH: 14
<212> TYPE: PRT
<213> ORGANISM: Artificial Sequence
<220> FEATURE:
<223> OTHER INFORMATION: nanobody sequence

<400> SEQUENCE: 59

```
Trp Tyr Arg Gln Ala Pro Gly Lys Gln Arg Glu Leu Val Ala
1               5                   10
```

```
<210> SEQ ID NO 60
<211> LENGTH: 14
<212> TYPE: PRT
<213> ORGANISM: Artificial Sequence
<220> FEATURE:
<223> OTHER INFORMATION: nanobody sequence

<400> SEQUENCE: 60

Trp Tyr Arg Gln Ala Pro Gly Lys Pro Arg Glu Leu Val Ala
1               5                   10

<210> SEQ ID NO 61
<211> LENGTH: 14
<212> TYPE: PRT
<213> ORGANISM: Artificial Sequence
<220> FEATURE:
<223> OTHER INFORMATION: nanobody sequence

<400> SEQUENCE: 61

Trp Phe Arg Gln Ala Pro Gly Lys Glu Arg Glu Gly Val Ser
1               5                   10

<210> SEQ ID NO 62
<211> LENGTH: 8
<212> TYPE: PRT
<213> ORGANISM: Artificial Sequence
<220> FEATURE:
<223> OTHER INFORMATION: nanobody sequence

<400> SEQUENCE: 62

Ala Ile Asp Trp Ser Asp Phe Asn
1               5

<210> SEQ ID NO 63
<211> LENGTH: 8
<212> TYPE: PRT
<213> ORGANISM: Artificial Sequence
<220> FEATURE:
<223> OTHER INFORMATION: nanobody sequence

<400> SEQUENCE: 63

Asp Ile Ser Pro Gly Gly His Thr
1               5

<210> SEQ ID NO 64
<211> LENGTH: 8
<212> TYPE: PRT
<213> ORGANISM: Artificial Sequence
<220> FEATURE:
<223> OTHER INFORMATION: nanobody sequence

<400> SEQUENCE: 64

Tyr Met Asn Ser Gly Gly Gly Gly
1               5

<210> SEQ ID NO 65
<211> LENGTH: 8
<212> TYPE: PRT
<213> ORGANISM: Artificial Sequence
<220> FEATURE:
<223> OTHER INFORMATION: nanobody sequence

<400> SEQUENCE: 65

Asp Ile Ser Gly Gly Gly Val Thr
1               5
```

<210> SEQ ID NO 66
<211> LENGTH: 8
<212> TYPE: PRT
<213> ORGANISM: Artificial Sequence
<220> FEATURE:
<223> OTHER INFORMATION: nanobody sequence

<400> SEQUENCE: 66

Ala Ile Asp Trp Ser Asp Phe Asn
1               5

<210> SEQ ID NO 67
<211> LENGTH: 8
<212> TYPE: PRT
<213> ORGANISM: Artificial Sequence
<220> FEATURE:
<223> OTHER INFORMATION: nanobody sequence

<400> SEQUENCE: 67

Ala Ile Asp Trp Ser Asp Phe Asn
1               5

<210> SEQ ID NO 68
<211> LENGTH: 8
<212> TYPE: PRT
<213> ORGANISM: Artificial Sequence
<220> FEATURE:
<223> OTHER INFORMATION: nanobody sequence

<400> SEQUENCE: 68

Ala Ile Ser Ser Tyr Gly Ser Thr
1               5

<210> SEQ ID NO 69
<211> LENGTH: 8
<212> TYPE: PRT
<213> ORGANISM: Artificial Sequence
<220> FEATURE:
<223> OTHER INFORMATION: nanobody sequence

<400> SEQUENCE: 69

Ala Ile Ser Ser Tyr Gly Ser Thr
1               5

<210> SEQ ID NO 70
<211> LENGTH: 8
<212> TYPE: PRT
<213> ORGANISM: Artificial Sequence
<220> FEATURE:
<223> OTHER INFORMATION: nanobody sequence

<400> SEQUENCE: 70

Cys Ile Thr Ser Ser Asp Gly Asn
1               5

<210> SEQ ID NO 71
<211> LENGTH: 8
<212> TYPE: PRT
<213> ORGANISM: Artificial Sequence
<220> FEATURE:
<223> OTHER INFORMATION: nanobody sequence

<400> SEQUENCE: 71

Thr Ile Thr Arg Asp Gly Thr Thr
1               5

```
<210> SEQ ID NO 72
<211> LENGTH: 8
<212> TYPE: PRT
<213> ORGANISM: Artificial Sequence
<220> FEATURE:
<223> OTHER INFORMATION: nanobody sequence

<400> SEQUENCE: 72

Glu Ile Ser Asp Gly Gly Gly Thr
1               5

<210> SEQ ID NO 73
<211> LENGTH: 16
<212> TYPE: PRT
<213> ORGANISM: Artificial Sequence
<220> FEATURE:
<223> OTHER INFORMATION: nanobody sequence

<400> SEQUENCE: 73

Asp Ile Thr Arg Gly Asp Arg Thr Asn Tyr Ala Asp Thr Val Asn Gly
1               5                   10                  15

<210> SEQ ID NO 74
<211> LENGTH: 16
<212> TYPE: PRT
<213> ORGANISM: Artificial Sequence
<220> FEATURE:
<223> OTHER INFORMATION: nanobody sequence

<400> SEQUENCE: 74

Arg Ile Tyr Thr Gly Gly Thr Ala Trp Tyr Glu Asp Ser Val Lys Gly
1               5                   10                  15

<210> SEQ ID NO 75
<211> LENGTH: 17
<212> TYPE: PRT
<213> ORGANISM: Artificial Sequence
<220> FEATURE:
<223> OTHER INFORMATION: nanobody sequence

<400> SEQUENCE: 75

Cys Arg Phe Thr Asn Asp Gly Ser Thr Ala Tyr Ala Asp Ser Val Lys
1               5                   10                  15

Gly

<210> SEQ ID NO 76
<211> LENGTH: 41
<212> TYPE: PRT
<213> ORGANISM: Artificial Sequence
<220> FEATURE:
<223> OTHER INFORMATION: nanobody sequence

<400> SEQUENCE: 76

Thr Tyr Tyr Ala Asp Ser Val Lys Gly Arg Phe Thr Ile Ser Arg His
1               5                   10                  15

Asn Pro Arg Asn Ser Val Tyr Leu Gln Leu Asn Ser Leu Lys Pro Glu
                20                  25                  30

Asp Thr Ala Val Tyr Tyr Cys Ala Ala
            35                  40

<210> SEQ ID NO 77
<211> LENGTH: 40
<212> TYPE: PRT
<213> ORGANISM: Artificial Sequence
<220> FEATURE:
<223> OTHER INFORMATION: nanobody sequence
```

<400> SEQUENCE: 77

Glu Tyr Glu Asp Ser Val Lys Gly Arg Phe Thr Ile Ser Arg Asp Asn
1               5                   10                  15

Phe Lys Asn Thr Met Thr Leu His Met Asn Ser Leu Lys Pro Glu Asp
            20                  25                  30

Thr Ala Val Tyr Phe Cys Ala Ala
        35                  40

<210> SEQ ID NO 78
<211> LENGTH: 41
<212> TYPE: PRT
<213> ORGANISM: Artificial Sequence
<220> FEATURE:
<223> OTHER INFORMATION: nanobody sequence

<400> SEQUENCE: 78

Thr Ala Tyr Ala Asp Ser Val Lys Gly Arg Phe Thr Ile Ser Arg Asp
1               5                   10                  15

Asn Ala Lys Asn Thr Leu Cys Leu Gln Met Asn Ser Leu Lys Pro Glu
            20                  25                  30

Asp Thr Ala Val Tyr Tyr Cys Ala Thr
        35                  40

<210> SEQ ID NO 79
<211> LENGTH: 40
<212> TYPE: PRT
<213> ORGANISM: Artificial Sequence
<220> FEATURE:
<223> OTHER INFORMATION: nanobody sequence

<400> SEQUENCE: 79

Asn Tyr Ala Asp Ser Val Lys Gly Arg Phe Thr Ile Ser Arg Asp Asn
1               5                   10                  15

Ala Lys Asn Met Val Tyr Leu Gln Met His Ile Leu Lys Pro Glu Asp
            20                  25                  30

Thr Ala Val Tyr Tyr Cys Asn Val
        35                  40

<210> SEQ ID NO 80
<211> LENGTH: 41
<212> TYPE: PRT
<213> ORGANISM: Artificial Sequence
<220> FEATURE:
<223> OTHER INFORMATION: nanobody sequence

<400> SEQUENCE: 80

Thr Tyr Tyr Ala Asp Ser Val Lys Gly Arg Phe Thr Ile Ser Arg His
1               5                   10                  15

Asn Pro Arg Asn Ser Val Tyr Leu Gln Leu Asn Ser Leu Lys Pro Glu
            20                  25                  30

Asp Thr Ala Val Tyr Tyr Cys Ala Ala
        35                  40

<210> SEQ ID NO 81
<211> LENGTH: 41
<212> TYPE: PRT
<213> ORGANISM: Artificial Sequence
<220> FEATURE:
<223> OTHER INFORMATION: nanobody sequence

<400> SEQUENCE: 81

Thr Tyr Tyr Ala Asp Ser Val Lys Gly Arg Phe Ile Ile Ser Arg His
1               5                   10                  15

Asn Pro Arg Asn Ser Val Tyr Leu Gln Leu Asn Ser Leu Lys Pro Glu
            20                  25                  30

Asp Thr Ala Val Tyr Tyr Cys Ala Ala
        35                  40

<210> SEQ ID NO 82
<211> LENGTH: 41
<212> TYPE: PRT
<213> ORGANISM: Artificial Sequence
<220> FEATURE:
<223> OTHER INFORMATION: nanobody sequence

<400> SEQUENCE: 82

Asp Tyr Gly Asp Ser Val Lys Gly Arg Phe Thr Ile Ser Arg Asp Asp
1               5                   10                  15

Ala Lys Asn Thr Val Pro Leu Gln Met Asn Ser Leu Lys Pro Glu Asp
            20                  25                  30

Thr Ala Val Tyr Tyr Cys Ala Ala Ala
        35                  40

<210> SEQ ID NO 83
<211> LENGTH: 41
<212> TYPE: PRT
<213> ORGANISM: Artificial Sequence
<220> FEATURE:
<223> OTHER INFORMATION: nanobody sequence

<400> SEQUENCE: 83

Asp Tyr Gly Asp Ser Val Lys Gly Arg Phe Thr Ile Ser Arg Asp Asp
1               5                   10                  15

Ala Lys Asn Thr Val Pro Leu Gln Met Asn Ser Leu Lys Pro Glu Asp
            20                  25                  30

Thr Ala Val Tyr Tyr Cys Ala Ala Ala
        35                  40

<210> SEQ ID NO 84
<211> LENGTH: 41
<212> TYPE: PRT
<213> ORGANISM: Artificial Sequence
<220> FEATURE:
<223> OTHER INFORMATION: nanobody sequence

<400> SEQUENCE: 84

Thr Tyr Tyr Ala Leu Ser Val Lys Gly Arg Phe Thr Ala Ser Ser Asp
1               5                   10                  15

Asn Ala Lys Asn Thr Val Tyr Leu Gln Met Asn Ser Leu Asn Pro Glu
            20                  25                  30

Asp Thr Ala Val Tyr Tyr Cys Ala Ala
        35                  40

<210> SEQ ID NO 85
<211> LENGTH: 40
<212> TYPE: PRT
<213> ORGANISM: Artificial Sequence
<220> FEATURE:
<223> OTHER INFORMATION: nanobody sequence

<400> SEQUENCE: 85

Asn Tyr Ile Asp Ser Val Gln Gly Arg Phe Thr Ile Ser Arg Asp Asn
1               5                   10                  15

```
Ala Lys Asn Met Ile Tyr Leu Arg Met Asn Ser Leu Lys Pro Glu Asp
            20                  25                  30

Thr Ala Val Tyr Tyr Cys Val Thr
        35                  40

<210> SEQ ID NO 86
<211> LENGTH: 40
<212> TYPE: PRT
<213> ORGANISM: Artificial Sequence
<220> FEATURE:
<223> OTHER INFORMATION: nanobody sequence

<400> SEQUENCE: 86

Tyr Ser Ala Asp Ser Val Lys Gly Arg Phe Thr Ile Ser Arg Asp Asn
1               5                   10                  15

Ala Lys Asn Thr Val Tyr Leu Gln Met Thr Ser Leu Arg Pro Glu Asp
            20                  25                  30

Thr Ala Val Tyr Tyr Cys Asn Ala
        35                  40

<210> SEQ ID NO 87
<211> LENGTH: 32
<212> TYPE: PRT
<213> ORGANISM: Artificial Sequence
<220> FEATURE:
<223> OTHER INFORMATION: nanobody sequence

<400> SEQUENCE: 87

Arg Phe Thr Ile Ser Arg Asp Asn Val Arg Asn Thr Val Tyr Leu Gln
1               5                   10                  15

Met Asn Gly Leu Arg Pro Glu Asp Thr Ala Ala Tyr Tyr Cys Tyr Ala
            20                  25                  30

<210> SEQ ID NO 88
<211> LENGTH: 32
<212> TYPE: PRT
<213> ORGANISM: Artificial Sequence
<220> FEATURE:
<223> OTHER INFORMATION: nanobody sequence

<400> SEQUENCE: 88

Arg Phe Thr Ile Ser Arg Asp Asn Ala Gln Asn Thr Val Tyr Leu Gln
1               5                   10                  15

Met Asn Ser Leu Lys Ser Glu Asp Thr Ala Val Tyr Tyr Cys His Gly
            20                  25                  30

<210> SEQ ID NO 89
<211> LENGTH: 32
<212> TYPE: PRT
<213> ORGANISM: Artificial Sequence
<220> FEATURE:
<223> OTHER INFORMATION: nanobody sequence

<400> SEQUENCE: 89

Arg Phe Thr Ile Ser Arg Asp Ile Val Lys His Thr Val Tyr Leu Gln
1               5                   10                  15

Met Asn Ser Leu Gln Pro Glu Asp Thr Ala Val Tyr Tyr Cys Ala Ala
            20                  25                  30

<210> SEQ ID NO 90
<211> LENGTH: 19
<212> TYPE: PRT
<213> ORGANISM: Artificial Sequence
<220> FEATURE:
```

-continued

<223> OTHER INFORMATION: nanobody sequence

<400> SEQUENCE: 90

His Ser Glu Thr Arg Gly Gly Thr Arg Tyr Phe Asp Arg Pro Ser Leu
1               5                   10                  15

Tyr Asn Tyr

<210> SEQ ID NO 91
<211> LENGTH: 10
<212> TYPE: PRT
<213> ORGANISM: Artificial Sequence
<220> FEATURE:
<223> OTHER INFORMATION: nanobody sequence

<400> SEQUENCE: 91

Arg Leu Arg Phe Glu Val Ser Ser Asn Tyr
1               5                   10

<210> SEQ ID NO 92
<211> LENGTH: 7
<212> TYPE: PRT
<213> ORGANISM: Artificial Sequence
<220> FEATURE:
<223> OTHER INFORMATION: nanobody sequence

<400> SEQUENCE: 92

Glu Lys Pro Leu Gly Gly Ala
1               5

<210> SEQ ID NO 93
<211> LENGTH: 10
<212> TYPE: PRT
<213> ORGANISM: Artificial Sequence
<220> FEATURE:
<223> OTHER INFORMATION: nanobody sequence

<400> SEQUENCE: 93

Lys Arg Arg Phe Pro Ile Trp Arg Asp Tyr
1               5                   10

<210> SEQ ID NO 94
<211> LENGTH: 19
<212> TYPE: PRT
<213> ORGANISM: Artificial Sequence
<220> FEATURE:
<223> OTHER INFORMATION: nanobody sequence

<400> SEQUENCE: 94

His Ser Glu Thr Arg Asp Gly Thr Arg Thr Phe Asp Arg Pro Ser Leu
1               5                   10                  15

Tyr Asn Tyr

<210> SEQ ID NO 95
<211> LENGTH: 19
<212> TYPE: PRT
<213> ORGANISM: Artificial Sequence
<220> FEATURE:
<223> OTHER INFORMATION: nanobody sequence

<400> SEQUENCE: 95

His Ser Glu Thr Arg Gly Gly Thr Arg Tyr Phe Asp Arg Pro Ser Leu
1               5                   10                  15

Tyr Asn Tyr

```
<210> SEQ ID NO 96
<211> LENGTH: 20
<212> TYPE: PRT
<213> ORGANISM: Artificial Sequence
<220> FEATURE:
<223> OTHER INFORMATION: nanobody sequence

<400> SEQUENCE: 96

Asp Glu Thr Leu Gly Ala Val Pro Asn Phe Arg Leu His Glu Lys Tyr
1               5                   10                  15

Glu Tyr Glu Tyr
            20

<210> SEQ ID NO 97
<211> LENGTH: 20
<212> TYPE: PRT
<213> ORGANISM: Artificial Sequence
<220> FEATURE:
<223> OTHER INFORMATION: nanobody sequence

<400> SEQUENCE: 97

Asp Glu Thr Leu Gly Ala Val Pro Asn Phe Arg Leu His Glu Lys Tyr
1               5                   10                  15

Glu Tyr Glu Tyr
            20

<210> SEQ ID NO 98
<211> LENGTH: 15
<212> TYPE: PRT
<213> ORGANISM: Artificial Sequence
<220> FEATURE:
<223> OTHER INFORMATION: nanobody sequence

<400> SEQUENCE: 98

Asp Pro Val Arg Arg Gly Trp Gly Cys Arg Asp His Tyr Lys Tyr
1               5                   10                  15

<210> SEQ ID NO 99
<211> LENGTH: 7
<212> TYPE: PRT
<213> ORGANISM: Artificial Sequence
<220> FEATURE:
<223> OTHER INFORMATION: nanobody sequence

<400> SEQUENCE: 99

Ile Leu Ser Gly Lys Lys Thr
1               5

<210> SEQ ID NO 100
<211> LENGTH: 8
<212> TYPE: PRT
<213> ORGANISM: Artificial Sequence
<220> FEATURE:
<223> OTHER INFORMATION: nanobody sequence

<400> SEQUENCE: 100

Leu Phe Thr Ser Asp Trp Phe Gly
1               5

<210> SEQ ID NO 101
<211> LENGTH: 12
<212> TYPE: PRT
<213> ORGANISM: Artificial Sequence
<220> FEATURE:
<223> OTHER INFORMATION: nanobody sequence

<400> SEQUENCE: 101
```

Val Ile Glu Leu Gly Val Leu Glu Pro Arg Asp Tyr
1               5                   10

<210> SEQ ID NO 102
<211> LENGTH: 6
<212> TYPE: PRT
<213> ORGANISM: Artificial Sequence
<220> FEATURE:
<223> OTHER INFORMATION: nanobody sequence

<400> SEQUENCE: 102

Arg Val Arg Tyr Asp Tyr
1               5

<210> SEQ ID NO 103
<211> LENGTH: 18
<212> TYPE: PRT
<213> ORGANISM: Artificial Sequence
<220> FEATURE:
<223> OTHER INFORMATION: nanobody sequence

<400> SEQUENCE: 103

Gly Pro Leu Thr Lys Arg Arg Gln Cys Val Pro Gly Asp Phe Ser Met
1               5                   10                  15

Asp Phe

<210> SEQ ID NO 104
<211> LENGTH: 12
<212> TYPE: PRT
<213> ORGANISM: Artificial Sequence
<220> FEATURE:
<223> OTHER INFORMATION: nanobody sequence

<400> SEQUENCE: 104

Trp Gly Gln Gly Thr Gln Val Thr Val Ser Ser Ala
1               5                   10

<210> SEQ ID NO 105
<211> LENGTH: 12
<212> TYPE: PRT
<213> ORGANISM: Artificial Sequence
<220> FEATURE:
<223> OTHER INFORMATION: nanobody sequence

<400> SEQUENCE: 105

Trp Gly Gln Gly Thr Gln Val Thr Val Ser Ser Ala
1               5                   10

<210> SEQ ID NO 106
<211> LENGTH: 12
<212> TYPE: PRT
<213> ORGANISM: Artificial Sequence
<220> FEATURE:
<223> OTHER INFORMATION: nanobody sequence

<400> SEQUENCE: 106

Trp Gly Gln Gly Thr Gln Val Thr Val Ser Ser Ala
1               5                   10

<210> SEQ ID NO 107
<211> LENGTH: 12
<212> TYPE: PRT
<213> ORGANISM: Artificial Sequence
<220> FEATURE:
<223> OTHER INFORMATION: nanobody sequence

```
<400> SEQUENCE: 107

Trp Gly Lys Gly Thr Leu Val Thr Val Ser Ser Ala
1               5                   10

<210> SEQ ID NO 108
<211> LENGTH: 12
<212> TYPE: PRT
<213> ORGANISM: Artificial Sequence
<220> FEATURE:
<223> OTHER INFORMATION: nanobody sequence

<400> SEQUENCE: 108

Trp Gly Gln Gly Thr Gln Val Thr Val Ser Ser Ala
1               5                   10

<210> SEQ ID NO 109
<211> LENGTH: 12
<212> TYPE: PRT
<213> ORGANISM: Artificial Sequence
<220> FEATURE:
<223> OTHER INFORMATION: nanobody sequence

<400> SEQUENCE: 109

Trp Gly Gln Gly Thr Gln Val Thr Val Ser Ser Ala
1               5                   10

<210> SEQ ID NO 110
<211> LENGTH: 12
<212> TYPE: PRT
<213> ORGANISM: Artificial Sequence
<220> FEATURE:
<223> OTHER INFORMATION: nanobody sequence

<400> SEQUENCE: 110

Trp Gly Gln Gly Thr Gln Val Thr Val Ser Ser Ala
1               5                   10

<210> SEQ ID NO 111
<211> LENGTH: 12
<212> TYPE: PRT
<213> ORGANISM: Artificial Sequence
<220> FEATURE:
<223> OTHER INFORMATION: nanobody sequence

<400> SEQUENCE: 111

Trp Gly Gln Gly Thr Gln Val Thr Val Ser Ser Ala
1               5                   10

<210> SEQ ID NO 112
<211> LENGTH: 12
<212> TYPE: PRT
<213> ORGANISM: Artificial Sequence
<220> FEATURE:
<223> OTHER INFORMATION: nanobody sequence

<400> SEQUENCE: 112

Trp Gly Gln Gly Thr Gln Val Thr Val Ser Ser Ala
1               5                   10

<210> SEQ ID NO 113
<211> LENGTH: 12
<212> TYPE: PRT
<213> ORGANISM: Artificial Sequence
<220> FEATURE:
<223> OTHER INFORMATION: nanobody sequence

<400> SEQUENCE: 113
```

-continued

Trp Gly Gln Gly Thr Gln Val Thr Val Ser Ser Ala
1               5                   10

<210> SEQ ID NO 114
<211> LENGTH: 12
<212> TYPE: PRT
<213> ORGANISM: Artificial Sequence
<220> FEATURE:
<223> OTHER INFORMATION: nanobody sequence

<400> SEQUENCE: 114

Trp Gly Gln Gly Thr Gln Val Thr Val Ser Ser Ala
1               5                   10

<210> SEQ ID NO 115
<211> LENGTH: 11
<212> TYPE: PRT
<213> ORGANISM: Artificial Sequence
<220> FEATURE:
<223> OTHER INFORMATION: nanobody sequence

<400> SEQUENCE: 115

Trp Gly Gln Gly Thr Gln Val Thr Val Ser Ser
1               5                   10

<210> SEQ ID NO 116
<211> LENGTH: 11
<212> TYPE: PRT
<213> ORGANISM: Artificial Sequence
<220> FEATURE:
<223> OTHER INFORMATION: nanobody sequence

<400> SEQUENCE: 116

Trp Gly Gln Gly Thr Gln Val Thr Val Ser Ser
1               5                   10

<210> SEQ ID NO 117
<211> LENGTH: 11
<212> TYPE: PRT
<213> ORGANISM: Artificial Sequence
<220> FEATURE:
<223> OTHER INFORMATION: nanobody sequence

<400> SEQUENCE: 117

Trp Gly Glu Gly Thr Leu Val Thr Val Ser Ser
1               5                   10

<210> SEQ ID NO 118
<211> LENGTH: 385
<212> TYPE: PRT
<213> ORGANISM: Artificial Sequence
<220> FEATURE:
<223> OTHER INFORMATION: nanobody sequence

<400> SEQUENCE: 118

Met Ala Leu Pro Val Thr Ala Leu Leu Leu Pro Leu Ala Leu Leu
1               5                   10                  15

His Ala Ala Arg Pro Asp Tyr Lys Asp Asp Asp Lys Arg Ser Met
                20                  25                  30

Ala Glu Val Gln Leu Val Glu Ser Gly Gly Leu Val Gln Pro Gly
            35                  40                  45

Gly Ser Leu Thr Leu Ser Cys Ala Ala Ser Gly Ile Ala Phe Asn Tyr
        50                  55                  60

Tyr Ser Met Ser Trp His Arg Gln Ala Pro Gly Lys Gln Arg Thr Leu

```
            65                  70                  75                  80
Val Ala Asp Ile Ser Pro Gly Gly His Thr Glu Tyr Glu Asp Ser Val
                    85                  90                  95

Lys Gly Arg Phe Thr Ile Ser Arg Asp Asn Phe Lys Asn Thr Met Thr
                100                 105                 110

Leu His Met Asn Ser Leu Lys Pro Glu Asp Thr Ala Val Tyr Phe Cys
                115                 120                 125

Ala Ala Arg Leu Arg Phe Glu Val Ser Ser Asn Tyr Trp Gly Gln Gly
                130                 135                 140

Thr Gln Val Thr Val Ser Ser Leu Glu Pro Arg Asp Cys Gly Cys Lys
145                 150                 155                 160

Pro Cys Ile Cys Thr Val Pro Glu Val Ser Ser Val Ser Val Ser Val
                165                 170                 175

Phe Ile Phe Pro Pro Lys Pro Lys Asp Val Leu Leu Ile Ser Leu Phe
                180                 185                 190

Pro Lys Val Thr Cys Val Val Val Asp Ile Ser Lys Asp Asp Pro Glu
                195                 200                 205

Val Gln Phe Ser Trp Phe Val Asp Asp Val Glu Val His Thr Ala Gln
                210                 215                 220

Thr Gln Pro Arg Glu Glu Gln Phe Asn Ser Thr Phe Arg Ser Val Ser
225                 230                 235                 240

Glu Leu Pro Ile Met His Gln Asp Trp Leu Asn Gly Lys Glu Phe Lys
                245                 250                 255

Cys Arg Val Asn Ser Ala Ala Phe Pro Ala Pro Ile Glu Lys Thr Ile
                260                 265                 270

Ser Lys Thr Lys Gly Arg Pro Lys Ala Pro Gln Val Tyr Thr Ile Pro
                275                 280                 285

Pro Pro Lys Glu Gln Met Ala Lys Asp Lys Val Ser Leu Thr Cys Met
                290                 295                 300

Ile Thr Asp Phe Phe Pro Glu Asp Ile Thr Val Glu Trp Gln Trp Asn
305                 310                 315                 320

Gly Gln Pro Ala Glu Asn Tyr Lys Asn Thr Gln Pro Ile Met Asp Thr
                325                 330                 335

Asp Gly Ser Tyr Phe Val Tyr Ser Lys Leu Asn Val Gln Lys Ser Asn
                340                 345                 350

Trp Glu Ala Gly Asn Thr Phe Thr Cys Ser Val Leu His Glu Gly Leu
                355                 360                 365

His Asn His His Thr Glu Lys Ser Leu Ser His Ser Pro Gly Lys Gly
                370                 375                 380

Lys
385

<210> SEQ ID NO 119
<211> LENGTH: 263
<212> TYPE: PRT
<213> ORGANISM: Artificial Sequence
<220> FEATURE:
<223> OTHER INFORMATION: nanobody sequence

<400> SEQUENCE: 119

Glu Val Gln Leu Val Glu Ser Gly Gly Gly Leu Val Gln Ala Gly Gly
1               5                   10                  15

Ser Leu Arg Leu Ser Cys Ala Ala Ser Gly Ser Pro Ile Ser Ser Tyr
                20                  25                  30

Ala Met Gly Trp Tyr Arg Gln Ala Pro Gly Lys Pro Arg Glu Leu Val
```

```
            35                  40                  45
Ala Arg Ile Tyr Thr Gly Gly Thr Ala Trp Tyr Glu Asp Ser Val Lys
 50                  55                  60

Gly Arg Phe Thr Ile Ser Arg Asp Asn Ala Gln Asn Thr Val Tyr Leu
 65                  70                  75                  80

Gln Met Asn Ser Leu Lys Ser Glu Asp Thr Ala Val Tyr Tyr Cys His
                 85                  90                  95

Gly Arg Val Arg Tyr Asp Tyr Trp Gly Gln Gly Thr Gln Val Thr Val
                100                 105                 110

Ser Ser Gly Gly Gly Gly Ser Gly Gly Gly Ser Gly Gly Gly Gly
            115                 120                 125

Ser Gly Gly Gly Gly Ser Gly Gly Gly Ser Gly Gly Gly Ser
        130                 135                 140

Gly Gly Gly Gly Ser Glu Val Gln Leu Val Glu Ser Gly Gly Gly Leu
145                 150                 155                 160

Val Gln Ala Gly Gly Ser Leu Arg Leu Ser Cys Ala Ala Ser Gly Ser
                165                 170                 175

Pro Ile Ser Ser Tyr Ala Met Gly Trp Tyr Arg Gln Ala Pro Gly Lys
                180                 185                 190

Pro Arg Glu Leu Val Ala Arg Ile Tyr Thr Gly Gly Thr Ala Trp Tyr
                195                 200                 205

Glu Asp Ser Val Lys Gly Arg Phe Thr Ile Ser Arg Asp Asn Ala Gln
210                 215                 220

Asn Thr Val Tyr Leu Gln Met Asn Ser Leu Lys Ser Glu Asp Thr Ala
225                 230                 235                 240

Val Tyr Tyr Cys His Gly Arg Val Arg Tyr Asp Tyr Trp Gly Gln Gly
                245                 250                 255

Thr Gln Val Thr Val Ser Ser
            260

<210> SEQ ID NO 120
<211> LENGTH: 410
<212> TYPE: PRT
<213> ORGANISM: Artificial Sequence
<220> FEATURE:
<223> OTHER INFORMATION: nanobody sequence

<400> SEQUENCE: 120

Glu Val Gln Leu Val Glu Ser Gly Gly Gly Leu Val Gln Ala Gly Gly
 1                   5                  10                  15

Ser Leu Arg Leu Ser Cys Ala Ala Ser Gly Ser Pro Ile Ser Ser Tyr
                 20                  25                  30

Ala Met Gly Trp Tyr Arg Gln Ala Pro Gly Lys Pro Arg Glu Leu Val
             35                  40                  45

Ala Arg Ile Tyr Thr Gly Gly Thr Ala Trp Tyr Glu Asp Ser Val Lys
 50                  55                  60

Gly Arg Phe Thr Ile Ser Arg Asp Asn Ala Gln Asn Thr Val Tyr Leu
 65                  70                  75                  80

Gln Met Asn Ser Leu Lys Ser Glu Asp Thr Ala Val Tyr Tyr Cys His
                 85                  90                  95

Gly Arg Val Arg Tyr Asp Tyr Trp Gly Gln Gly Thr Gln Val Thr Val
                100                 105                 110

Ser Ser Gly Gly Gly Gly Ser Gly Gly Gly Ser Gly Gly Gly Gly
            115                 120                 125

Ser Gly Gly Gly Gly Ser Gly Gly Gly Gly Ser Gly Gly Gly Gly Ser
```

```
            130                 135                 140
Gly Gly Gly Gly Ser Glu Val Gln Leu Val Glu Ser Gly Gly Leu
145                 150                 155                 160

Val Gln Ala Gly Gly Ser Leu Arg Leu Ser Cys Ala Ala Ser Gly
                165                 170                 175

Pro Ile Ser Ser Tyr Ala Met Gly Trp Tyr Arg Gln Ala Pro Gly Lys
            180                 185                 190

Pro Arg Glu Leu Val Ala Arg Ile Tyr Thr Gly Gly Thr Ala Trp Tyr
                195                 200                 205

Glu Asp Ser Val Lys Gly Arg Phe Thr Ile Ser Arg Asp Asn Ala Gln
            210                 215                 220

Asn Thr Val Tyr Leu Gln Met Asn Ser Leu Lys Ser Glu Asp Thr Ala
225                 230                 235                 240

Val Tyr Tyr Cys His Gly Arg Val Arg Tyr Asp Tyr Trp Gly Gln Gly
                245                 250                 255

Thr Gln Val Thr Val Ser Ser Gly Gly Gly Gly Ser Gly Gly Gly Ser
            260                 265                 270

Glu Val Gln Leu Val Glu Ser Gly Gly Gly Leu Val Gln Pro Gly Asn
            275                 280                 285

Ser Leu Arg Leu Ser Cys Ala Ala Ser Gly Phe Thr Phe Ser Ser Phe
            290                 295                 300

Gly Met Ser Trp Val Arg Gln Ala Pro Gly Lys Gly Leu Glu Trp Val
305                 310                 315                 320

Ser Ser Ile Ser Gly Ser Gly Ser Asp Thr Leu Tyr Ala Asp Ser Val
                325                 330                 335

Lys Gly Arg Phe Thr Ile Ser Arg Asp Asn Ala Lys Thr Thr Leu Tyr
                340                 345                 350

Leu Gln Met Asn Ser Leu Arg Pro Glu Asp Thr Ala Val Tyr Tyr Cys
            355                 360                 365

Thr Ile Gly Gly Ser Leu Ser Arg Ser Ser Gln Gly Thr Leu Val Thr
            370                 375                 380

Val Ser Ser Ala Ala Ala Glu Gln Lys Leu Ile Ser Glu Glu Asp Leu
385                 390                 395                 400

Asn Gly Ala Ala His His His His His His
                405                 410

<210> SEQ ID NO 121
<211> LENGTH: 289
<212> TYPE: PRT
<213> ORGANISM: Artificial Sequence
<220> FEATURE:
<223> OTHER INFORMATION: nanobody sequence

<400> SEQUENCE: 121

Glu Val Gln Leu Val Glu Ser Gly Gly Gly Leu Val Gln Pro Gly Glu
1               5                   10                  15

Ser Leu Arg Leu Ser Cys Thr Ala Ser Arg Phe Met Leu Asp Tyr Tyr
                20                  25                  30

Asp Ile Gly Trp Phe Arg Gln Ala Pro Gly Lys Glu Arg Glu Gly Val
            35                  40                  45

Ser Cys Arg Phe Thr Asn Asp Gly Ser Thr Ala Tyr Ala Asp Ser Val
            50                  55                  60

Lys Gly Arg Phe Thr Ile Ser Arg Asp Ile Val Lys His Thr Val Tyr
65                  70                  75                  80

Leu Gln Met Asn Ser Leu Gln Pro Glu Asp Thr Ala Val Tyr Tyr Cys
```

```
                85                  90                  95
Ala Ala Gly Pro Leu Thr Lys Arg Arg Gln Cys Val Pro Gly Asp Phe
            100                 105                 110
Ser Met Asp Phe Trp Gly Glu Gly Thr Leu Val Thr Val Ser Ser Gly
            115                 120                 125
Gly Gly Gly Ser Gly Gly Gly Ser Gly Gly Gly Ser Gly Gly
            130                 135                 140
Gly Gly Ser Gly Gly Gly Ser Gly Gly Gly Ser Gly Gly
145                 150                 155                 160
Gly Ser Glu Val Gln Leu Val Glu Ser Gly Gly Gly Leu Val Gln Pro
                165                 170                 175
Gly Glu Ser Leu Arg Leu Ser Cys Thr Ala Ser Arg Phe Met Leu Asp
                180                 185                 190
Tyr Tyr Asp Ile Gly Trp Phe Arg Gln Ala Pro Gly Lys Glu Arg Glu
                195                 200                 205
Gly Val Ser Cys Arg Phe Thr Asn Asp Gly Ser Thr Ala Tyr Ala Asp
            210                 215                 220
Ser Val Lys Gly Arg Phe Thr Ile Ser Arg Asp Ile Val Lys His Thr
225                 230                 235                 240
Val Tyr Leu Gln Met Asn Ser Leu Gln Pro Glu Asp Thr Ala Val Tyr
                245                 250                 255
Tyr Cys Ala Ala Gly Pro Leu Thr Lys Arg Arg Gln Cys Val Pro Gly
            260                 265                 270
Asp Phe Ser Met Asp Phe Trp Gly Glu Gly Thr Leu Val Thr Val Ser
            275                 280                 285
Ser

<210> SEQ ID NO 122
<211> LENGTH: 436
<212> TYPE: PRT
<213> ORGANISM: Artificial Sequence
<220> FEATURE:
<223> OTHER INFORMATION: nanobody sequence

<400> SEQUENCE: 122

Glu Val Gln Leu Val Glu Ser Gly Gly Gly Leu Val Gln Pro Gly Glu
1               5                   10                  15
Ser Leu Arg Leu Ser Cys Thr Ala Ser Arg Phe Met Leu Asp Tyr Tyr
                20                  25                  30
Asp Ile Gly Trp Phe Arg Gln Ala Pro Gly Lys Glu Arg Glu Gly Val
            35                  40                  45
Ser Cys Arg Phe Thr Asn Asp Gly Ser Thr Ala Tyr Ala Asp Ser Val
50                  55                  60
Lys Gly Arg Phe Thr Ile Ser Arg Asp Ile Val Lys His Thr Val Tyr
65                  70                  75                  80
Leu Gln Met Asn Ser Leu Gln Pro Glu Asp Thr Ala Val Tyr Tyr Cys
                85                  90                  95
Ala Ala Gly Pro Leu Thr Lys Arg Arg Gln Cys Val Pro Gly Asp Phe
            100                 105                 110
Ser Met Asp Phe Trp Gly Glu Gly Thr Leu Val Thr Val Ser Ser Gly
            115                 120                 125
Gly Gly Ser Gly Gly Gly Gly Ser Gly Gly Gly Ser Gly Gly
            130                 135                 140
Gly Gly Ser Gly Gly Gly Gly Ser Gly Gly Gly Ser Gly Gly
145                 150                 155                 160
```

```
Gly Ser Glu Val Gln Leu Val Glu Ser Gly Gly Leu Val Gln Pro
            165                 170                 175

Gly Glu Ser Leu Arg Leu Ser Cys Thr Ala Ser Arg Phe Met Leu Asp
            180                 185                 190

Tyr Tyr Asp Ile Gly Trp Phe Arg Gln Ala Pro Gly Lys Glu Arg Glu
            195                 200                 205

Gly Val Ser Cys Arg Phe Thr Asn Asp Gly Ser Thr Ala Tyr Ala Asp
            210                 215                 220

Ser Val Lys Gly Arg Phe Thr Ile Ser Arg Asp Ile Val Lys His Thr
225                 230                 235                 240

Val Tyr Leu Gln Met Asn Ser Leu Gln Pro Glu Asp Thr Ala Val Tyr
            245                 250                 255

Tyr Cys Ala Ala Gly Pro Leu Thr Lys Arg Arg Gln Cys Val Pro Gly
            260                 265                 270

Asp Phe Ser Met Asp Phe Trp Gly Glu Gly Thr Leu Val Thr Val Ser
            275                 280                 285

Ser Gly Gly Gly Gly Ser Gly Gly Gly Ser Glu Val Gln Leu Val Glu
            290                 295                 300

Ser Gly Gly Gly Leu Val Gln Pro Gly Asn Ser Leu Arg Leu Ser Cys
305                 310                 315                 320

Ala Ala Ser Gly Phe Thr Phe Ser Ser Phe Gly Met Ser Trp Val Arg
            325                 330                 335

Gln Ala Pro Gly Lys Gly Leu Glu Trp Val Ser Ser Ile Ser Gly Ser
            340                 345                 350

Gly Ser Asp Thr Leu Tyr Ala Asp Ser Val Lys Gly Arg Phe Thr Ile
            355                 360                 365

Ser Arg Asp Asn Ala Lys Thr Thr Leu Tyr Leu Gln Met Asn Ser Leu
            370                 375                 380

Arg Pro Glu Asp Thr Ala Val Tyr Tyr Cys Thr Ile Gly Gly Ser Leu
385                 390                 395                 400

Ser Arg Ser Ser Gln Gly Thr Leu Val Thr Val Ser Ser Ala Ala Ala
            405                 410                 415

Glu Gln Lys Leu Ile Ser Glu Asp Leu Asn Gly Ala Ala His His
            420                 425                 430

His His His His
        435

<210> SEQ ID NO 123
<211> LENGTH: 275
<212> TYPE: PRT
<213> ORGANISM: Artificial Sequence
<220> FEATURE:
<223> OTHER INFORMATION: nanobody sequence

<400> SEQUENCE: 123

Glu Val Gln Leu Val Glu Ser Gly Gly Leu Val Gln Ala Gly Gly
1               5                   10                  15

Ser Leu Arg Leu Ser Cys Ala Ala Ser Gly Asn Phe Arg Val Asn
            20                  25                  30

Thr Met Ala Trp Tyr Arg Gln Ala Pro Gly Lys Gln Arg Glu Leu Val
            35                  40                  45

Ala Asp Ile Thr Arg Gly Asp Arg Thr Asn Tyr Ala Asp Thr Val Asn
        50                  55                  60

Gly Arg Phe Thr Ile Ser Arg Asp Asn Val Arg Asn Thr Val Tyr Leu
65                  70                  75                  80
```

```
Gln Met Asn Gly Leu Arg Pro Glu Asp Thr Ala Ala Tyr Tyr Cys Tyr
                85                  90                  95

Ala Val Ile Glu Leu Gly Val Leu Glu Pro Arg Asp Tyr Trp Gly Gln
            100                 105                 110

Gly Thr Gln Val Thr Val Ser Ser Gly Gly Gly Ser Gly Gly Gly
        115                 120                 125

Gly Ser Gly Gly Gly Ser Gly Gly Gly Ser Gly Gly Gly
    130                 135                 140

Ser Gly Gly Gly Ser Gly Gly Gly Ser Glu Val Gln Leu Val
145                 150                 155                 160

Glu Ser Gly Gly Leu Val Gln Ala Gly Gly Ser Leu Arg Leu Ser
                165                 170                 175

Cys Ala Ala Ser Gly Asn Phe Phe Arg Val Asn Thr Met Ala Trp Tyr
            180                 185                 190

Arg Gln Ala Pro Gly Lys Gln Arg Glu Leu Val Ala Asp Ile Thr Arg
            195                 200                 205

Gly Asp Arg Thr Asn Tyr Ala Asp Thr Val Asn Gly Arg Phe Thr Ile
        210                 215                 220

Ser Arg Asp Asn Val Arg Asn Thr Val Tyr Leu Gln Met Asn Gly Leu
225                 230                 235                 240

Arg Pro Glu Asp Thr Ala Ala Tyr Tyr Cys Tyr Ala Val Ile Glu Leu
                245                 250                 255

Gly Val Leu Glu Pro Arg Asp Tyr Trp Gly Gln Gly Thr Gln Val Thr
            260                 265                 270

Val Ser Ser
    275

<210> SEQ ID NO 124
<211> LENGTH: 422
<212> TYPE: PRT
<213> ORGANISM: Artificial Sequence
<220> FEATURE:
<223> OTHER INFORMATION: nanobody sequence

<400> SEQUENCE: 124

Glu Val Gln Leu Val Glu Ser Gly Gly Gly Leu Val Gln Ala Gly Gly
1               5                   10                  15

Ser Leu Arg Leu Ser Cys Ala Ala Ser Gly Asn Phe Phe Arg Val Asn
            20                  25                  30

Thr Met Ala Trp Tyr Arg Gln Ala Pro Gly Lys Gln Arg Glu Leu Val
        35                  40                  45

Ala Asp Ile Thr Arg Gly Asp Arg Thr Asn Tyr Ala Asp Thr Val Asn
50                  55                  60

Gly Arg Phe Thr Ile Ser Arg Asp Asn Val Arg Asn Thr Val Tyr Leu
65                  70                  75                  80

Gln Met Asn Gly Leu Arg Pro Glu Asp Thr Ala Ala Tyr Tyr Cys Tyr
                85                  90                  95

Ala Val Ile Glu Leu Gly Val Leu Glu Pro Arg Asp Tyr Trp Gly Gln
            100                 105                 110

Gly Thr Gln Val Thr Val Ser Ser Gly Gly Gly Ser Gly Gly Gly
        115                 120                 125

Gly Ser Gly Gly Gly Gly Ser Gly Gly Gly Ser Gly Gly Gly
    130                 135                 140

Ser Gly Gly Gly Gly Ser Gly Gly Gly Ser Glu Val Gln Leu Val
145                 150                 155                 160
```

-continued

Glu Ser Gly Gly Gly Leu Val Gln Ala Gly Gly Ser Leu Arg Leu Ser
            165                 170                 175

Cys Ala Ala Ser Gly Asn Phe Phe Arg Val Asn Thr Met Ala Trp Tyr
        180                 185                 190

Arg Gln Ala Pro Gly Lys Gln Arg Glu Leu Val Ala Asp Ile Thr Arg
            195                 200                 205

Gly Asp Arg Thr Asn Tyr Ala Asp Thr Val Asn Gly Arg Phe Thr Ile
        210                 215                 220

Ser Arg Asp Asn Val Arg Asn Thr Val Tyr Leu Gln Met Asn Gly Leu
225                 230                 235                 240

Arg Pro Glu Asp Thr Ala Ala Tyr Tyr Cys Tyr Ala Val Ile Glu Leu
            245                 250                 255

Gly Val Leu Glu Pro Arg Asp Tyr Trp Gly Gln Gly Thr Gln Val Thr
            260                 265                 270

Val Ser Ser Gly Gly Gly Gly Ser Gly Gly Gly Ser Glu Val Gln Leu
        275                 280                 285

Val Glu Ser Gly Gly Gly Leu Val Gln Pro Gly Asn Ser Leu Arg Leu
    290                 295                 300

Ser Cys Ala Ala Ser Gly Phe Thr Phe Ser Ser Phe Gly Met Ser Trp
305                 310                 315                 320

Val Arg Gln Ala Pro Gly Lys Gly Leu Glu Trp Val Ser Ser Ile Ser
            325                 330                 335

Gly Ser Gly Ser Asp Thr Leu Tyr Ala Asp Ser Val Lys Gly Arg Phe
            340                 345                 350

Thr Ile Ser Arg Asp Asn Ala Lys Thr Thr Leu Tyr Leu Gln Met Asn
        355                 360                 365

Ser Leu Arg Pro Glu Asp Thr Ala Val Tyr Tyr Cys Thr Ile Gly Gly
    370                 375                 380

Ser Leu Ser Arg Ser Ser Gln Gly Thr Leu Val Thr Val Ser Ser Ala
385                 390                 395                 400

Ala Ala Glu Gln Lys Leu Ile Ser Glu Glu Asp Leu Asn Gly Ala Ala
            405                 410                 415

His His His His His His
            420

<210> SEQ ID NO 125
<211> LENGTH: 115
<212> TYPE: PRT
<213> ORGANISM: Artificial Sequence
<220> FEATURE:
<223> OTHER INFORMATION: nanobody sequence

<400> SEQUENCE: 125

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

```
Thr Ile Gly Gly Ser Leu Ser Arg Ser Ser Gln Gly Thr Leu Val Thr
            100                 105                 110
Val Ser Ser
        115

<210> SEQ ID NO 126
<211> LENGTH: 138
<212> TYPE: PRT
<213> ORGANISM: Artificial Sequence
<220> FEATURE:
<223> OTHER INFORMATION: nanobody sequence

<400> SEQUENCE: 126

Glu Val Gln Leu Val Glu Ser Gly Gly Gly Leu Val Gln Pro Gly Asn
1               5                   10                  15
Ser Leu Arg Leu Ser Cys Ala Ala Ser Gly Phe Thr Phe Ser Ser Phe
            20                  25                  30
Gly Met Ser Trp Val Arg Gln Ala Pro Gly Lys Gly Leu Glu Trp Val
        35                  40                  45
Ser Ser Ile Ser Gly Ser Gly Ser Asp Thr Leu Tyr Ala Asp Ser Val
    50                  55                  60
Lys Gly Arg Phe Thr Ile Ser Arg Asp Asn Ala Lys Thr Thr Leu Tyr
65                  70                  75                  80
Leu Gln Met Asn Ser Leu Arg Pro Glu Asp Thr Ala Val Tyr Tyr Cys
                85                  90                  95
Thr Ile Gly Gly Ser Leu Ser Arg Ser Ser Gln Gly Thr Leu Val Thr
            100                 105                 110
Val Ser Ser Ala Ala Ala Glu Gln Lys Leu Ile Ser Glu Glu Asp Leu
        115                 120                 125
Asn Gly Ala Ala His His His His His His
        130                 135

<210> SEQ ID NO 127
<211> LENGTH: 34
<212> TYPE: PRT
<213> ORGANISM: Artificial Sequence
<220> FEATURE:
<223> OTHER INFORMATION: tag sequence

<400> SEQUENCE: 127

Gly Ala Ala Asp Tyr Lys Asp His Asp Gly Asp Tyr Lys Asp His Asp
1               5                   10                  15
Ile Asp Tyr Lys Asp Asp Asp Asp Lys Gly Ala Ala His His His His
            20                  25                  30
His His

<210> SEQ ID NO 128
<211> LENGTH: 5
<212> TYPE: PRT
<213> ORGANISM: Artificial Sequence
<220> FEATURE:
<223> OTHER INFORMATION: linker sequence

<400> SEQUENCE: 128

Gly Gly Gly Gly Ser
1               5

<210> SEQ ID NO 129
<211> LENGTH: 7
<212> TYPE: PRT
```

```
<213> ORGANISM: Artificial Sequence
<220> FEATURE:
<223> OTHER INFORMATION: linker sequence

<400> SEQUENCE: 129

Ser Gly Gly Ser Gly Gly Ser
1               5

<210> SEQ ID NO 130
<211> LENGTH: 9
<212> TYPE: PRT
<213> ORGANISM: Artificial Sequence
<220> FEATURE:
<223> OTHER INFORMATION: linker sequence

<400> SEQUENCE: 130

Gly Gly Gly Gly Ser Gly Gly Gly Ser
1               5

<210> SEQ ID NO 131
<211> LENGTH: 10
<212> TYPE: PRT
<213> ORGANISM: Artificial Sequence
<220> FEATURE:
<223> OTHER INFORMATION: linker sequence

<400> SEQUENCE: 131

Gly Gly Gly Gly Ser Gly Gly Gly Gly Ser
1               5                   10

<210> SEQ ID NO 132
<211> LENGTH: 15
<212> TYPE: PRT
<213> ORGANISM: Artificial Sequence
<220> FEATURE:
<223> OTHER INFORMATION: linker sequence

<400> SEQUENCE: 132

Gly Gly Gly Gly Ser Gly Gly Gly Gly Ser Gly Gly Gly Gly Ser
1               5                   10                  15

<210> SEQ ID NO 133
<211> LENGTH: 18
<212> TYPE: PRT
<213> ORGANISM: Artificial Sequence
<220> FEATURE:
<223> OTHER INFORMATION: linker sequence

<400> SEQUENCE: 133

Gly Gly Gly Gly Ser Gly Gly Gly Ser Gly Gly Gly Gly Gly
1               5                   10                  15

Gly Ser

<210> SEQ ID NO 134
<211> LENGTH: 20
<212> TYPE: PRT
<213> ORGANISM: Artificial Sequence
<220> FEATURE:
<223> OTHER INFORMATION: linker sequence

<400> SEQUENCE: 134

Gly Gly Gly Gly Ser Gly Gly Gly Gly Ser Gly Gly Gly Gly Ser Gly
1               5                   10                  15

Gly Gly Gly Ser
            20
```

<210> SEQ ID NO 135
<211> LENGTH: 25
<212> TYPE: PRT
<213> ORGANISM: Artificial Sequence
<220> FEATURE:
<223> OTHER INFORMATION: linker sequence

<400> SEQUENCE: 135

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 136
<211> LENGTH: 30
<212> TYPE: PRT
<213> ORGANISM: Artificial Sequence
<220> FEATURE:
<223> OTHER INFORMATION: linker sequence

<400> SEQUENCE: 136

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 137
<211> LENGTH: 35
<212> TYPE: PRT
<213> ORGANISM: Artificial Sequence
<220> FEATURE:
<223> OTHER INFORMATION: linker sequence

<400> SEQUENCE: 137

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35

<210> SEQ ID NO 138
<211> LENGTH: 98
<212> TYPE: PRT
<213> ORGANISM: Artificial Sequence
<220> FEATURE:
<223> OTHER INFORMATION: nanobody sequence

<400> SEQUENCE: 138

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Tyr
            20                  25                  30

Ala Ile Gly Trp Phe Arg Gln Ala Pro Gly Lys Glu Arg Glu Gly Val
                35                  40                  45

Ser Cys Ile Ser Ser Ser Asp Gly Ser Thr Tyr Tyr Ala Asp Ser Val
        50                  55                  60

Lys Gly Arg Phe Thr Ile Ser Arg Asp Asn Ala Lys Asn Thr Val Tyr
65                  70                  75                  80

```
Leu Gln Met Asn Ser Leu Lys Pro Glu Asp Thr Ala Val Tyr Tyr Cys
                85                  90                  95
Ala Ala
```

P2X7 RECEPTOR ANTAGONISTS AND AGONISTS

RELATED APPLICATIONS

This application is a national stage filing under 35 U.S.C. § 371 of international application PCT/EP2013/061257, filed May 31, 2013, which was published under PCT Article 21(2) in English, and claims the benefit under 35 U.S.C. § 119(e) of U.S. provisional application Ser. No. 61/654,417, filed Jun. 1, 2012, the disclosures of which are incorporated by reference herein in their entireties.

FIELD OF THE INVENTION

The present invention relates to biological materials related to the P2X7 receptor and more in particular to polypeptides, nucleic acids encoding such polypeptides; to methods for preparing such polypeptides; to host cells expressing or capable of expressing such polypeptides; to compositions and in particular to pharmaceutical compositions that comprise such polypeptides, for prophylactic, therapeutic or diagnostic purposes.

BACKGROUND

Purine nucleotides are well established as extracellular signaling molecules. P2X receptors are ATP-gated cation channels that mediate fast excitatory transmission, e.g., in diverse regions of the brain and spinal cord. The P2X7 subtype has the unusual property of changing its ion selectivity during prolonged exposure to ATP, which results in progressive dilation of the channel pore and the development of permeability to molecules as large as 900 Da. The P2X7 receptor was originally described in cells of hematopoietic origin, including macrophages, microglia, and certain lymphocytes, and mediates the influx of Ca2+ and Na+ ions, as well as the release of proinflammatory cytokines. P2X7 receptors may affect neuronal cell death through their ability to regulate the processing and release of interleukin-1β, a key mediator in neurodegeneration, chronic inflammation, and chronic pain. Activation of P2X7 receptors provides an inflammatory stimulus, and P2X7 receptor-deficient mice have substantially attenuated inflammatory responses, including models of neuropathic and chronic inflammatory pain. Moreover, P2X7 receptor activity, by regulating the release of proinflammatory cytokines, may be involved in the pathophysiology of depression. The P2X7 receptor may thus represent a critical communication link between the nervous and immune systems (Skaper et al. 2010 FASEB J. 24:337-345). The localisation of the P2X7 receptor to key cells of the immune system, coupled with its ability to release important inflammatory mediators from these cells suggests a potential role of P2X7 receptor antagonists in the treatment of a wide range of diseases including pain and neurodegenerative disorders, while providing a target for therapeutic exploitation.

In cancer where apoptotic cell death is an important mechanism of disease, P2X7 with its direct effect in apoptosis plays a significant role as it was shown in skin cancers and uterine epithelial cancers compared to normal tissues. Perhaps P2X7 will be of future use as biomarker to distinct normal from cancer uterine epithelial tissues.

Early apoptotic cell death to the retina in diabetes in rodent models has been linked to P2X7 activation in that part of the eye, suggesting a possible connection to diabetic microvascular injury.

It has been reported that P2X7 receptor polymorphisms may be linked to hypertension in a family based quantitative genetic association study, with a strong association of single nucleotide polymorphism rs591874 in the first intron of P2X7 and nocturnal diastolic blood pressure. P2X7 receptors are expressed in cells of the cardiovascular system and drugs affecting this signaling system may provide new therapies in hypertension and prevention of thrombotic events.

Expression of P2X7 receptors in healthy kidney is very little if any. In contrast, expression of P2X7 is increased in diseased renal tissue and immunohistochemistry of the glomeruli of two rodent models of kidney disease has shown that the predominant expression is in podocytes, endothelial and mesangial cells. A potential role for P2X7 receptors has been described for polycystic kidney disease and renal fibrosis.

Since ATP plays key roles in neurotransmission and neuromodulation, purine receptor subfamilies, including P2X7, have been involved in various pathological conditions. This pathophysiology of central nervous system (CNS) disorders includes brain trauma, ischemia, neurodegenerative and neuropsychiatric diseases. When injury happens, large amounts of ATP are released in the extracellular environment which are important for triggering cellular responses to trauma. In this situation, expression levels of P2X4 and P2X7 changes which might stimulate the migration and chemotaxis of resting microglia to the site of damage. P2X7 plays an important role in controlling microglia proliferation and death.

Cerebral ischemia can produce and exacerbate problems to the CNS which include stroke and it is possible that the P2X7 receptor which is expressed on microglia, is involved in cortical damage as a consequence of glucose/oxygen deprivation.

Neuroinflammation plays a major role in the pathogenesis of a number of neurodegenerative diseases such as Alzheimer's disease and Parkinson's disease. Although the precise mechanism is obscure, dysregulation of the signaling transduction pathway in microglia may enhance inflammation, leading to synaptic dysfunction and ultimately to neuronal cell death. The expression and function of the P2X7 receptor is significantly up-regulated in the post-mortem brain of Alzheimer's disease patients and various neurodegenerative disease animal models. This supports the role of the P2X7R pathway in the progression of neurodegeneration. Blocking P2X7R using brilliant blue G, a P2X7R antagonist that can cross the blood-brain barrier, has been shown to result in the amelioration of neuropathology in various animal models. Synaptic alterations and increased susceptibility to neuronal death are known contributors to Huntington's disease (HD) symptomatology. Decreased metabolism has long been associated with HD. Recent findings have demonstrated reduced neuronal apoptosis in *Caenorhabditis elegons* and *Drosophila* models of HD by drugs that diminish ATP production. Extracellular ATP has been reported to elicit neuronal death through stimulation of P2X7 receptors and hence, alteration in P2X7-mediated calcium permeability may contribute to HD synaptic dysfunction and increased neuronal apoptosis. Using mouse and cellular models of HD, increased P2X7-receptor level and altered P2X7-mediated calcium permeability in somata and terminals of HD neurons has been demonstrated and in vivo administration of the P2X7-antagonist Brilliant Blue-G (BBG) to HD mice prevented neuronal apoptosis and attenuated body weight loss and motor-coordination deficits.

Taken together, these results raise the possibility for the P2X7R signaling pathway as therapeutic target for treating various neurodegenerative diseases including AD and HD.

Multiple sclerosis (MS) is an immunogenic, relapsing, chronic inflammatory disease. There is a huge potential for biologics as therapeutics for MS. The first generation of cytokines (IFN-γ-1a, IFN-γ-1b) and antibodies (against CD52, CD49d, CD25, CD20) yielded both promising and disappointing results in the clinic, but it is clear that there still is high medical need for therapeutics that relieve inflammation by targeting lymphocytes via novel mechanisms of action or that target chronically activated microglia and macrophages.

Although well validated, ion channels represent an underexploited target class for the treatment of MS. Development of drugs against ion channels has been hampered because small molecule inhibitors in general lack specificity and affect relatives of the target and even unrelated proteins.

P2X7 receptor is expressed on myeloid cells as well as on CNS glial cells, and P2X7 activation has been shown to increase both glial and T-cell activation. These properties suggest a role in the development of autoimmune diseases including MS. P2X7 deficiency in an animal model of MS, experimental autoimmune encephalomyelitis (EAE), was shown to result in compensatory changes leading to increased T-cell cytokine production, and activated T-cells were detected in the brains of P2X7 null mice with no clinical signs. The greatly reduced incidence of disease suggested that an initiating event is absent in these mice and points to a role for astroglial P2X7 in development of EAE disease.

Matute et al (J. Neuroscience 2007: 27(35):9525-9533) have shown that Enhanced ATP signaling in vitro and in vivo leads to oligodendrocyte death via P2X7 receptor-mediated $Ca^{2+}$ toxicity and that P2X7 receptors mediate tissue damage underlying the neurological deficits associated with well-established models of MS. In turn, the increased expression of P2X7 receptors in axon tracts before lesions are formed in MS suggests that this feature constitutes a risk factor associated with newly forming lesions in this disease. Blockade of ATP P2X7 receptors therefore has potent neuroprotective properties, suggesting that this mechanism could be exploited to halt the progression of tissue damage MS.

P2X7 specific polyclonal and monoclonal antibodies have been described (Adriouch et al., 2005 "Probing the expression and function of the P2X7 purinoceptor with antibodies raised by genetic immunization" Cell Immunol 236:72-77; Seman et al. 2003. NAD-induced T cell death: ADP-ribosylation of cell surface proteins by ART2 activates the cytolytic P2X7 purinoceptor. Immunity 19:571-582). It was indicated that these antibodies are useful tools for further characterization of the structure and function of P2X7. US patent application No 20100173799 describes Nanobodies that bind P2X7.

SUMMARY OF THE INVENTION

The present invention provides polypeptides with improved prophylactic, therapeutic and/or pharmacological properties, in addition to other advantageous properties (such as, for example, improved ease of preparation, good stability, and/or reduced costs of goods), compared to the prior art amino acid sequences and antibodies.

Based on extensive screening, characterization and combinatory strategies, the present inventors surprisingly observed that polypeptides comprising immunoglobulin single variable domains recognizing similar epitopes had different cross-reactivities and modulating activities. In addition, the present invention provides multivalent polypeptides comprising two or more immunoglobulin single variable domains that show improved properties for modulating P2X7 activity compared to the P2X7 neutralizing molecules described in the prior art. The inventors surprisingly observed that bivalent polypeptides comprising two P2X7-binding immunoglobulin single variable domains showed a significant increase in P2X7-modulating efficacy as compared to the P2X7 modulating capacity of their monovalent P2X7-binding building blocks alone or the prior art monoclonal antibody (mAb) L4. Moreover, bivalent, bispecific P2X7-binding building blocks showed improved detection sensitivity. For this purpose, the present invention in addition also makes available a number of highly advantageous immunoglobulin single variable domains that specifically bind P2X7 and/or that are capable of significantly modulating, inhibiting or neutralizing P2X7. Wholly unexpected, the present inventors identified agonists of the P2X7 receptor activity. These P2X7-binding immunoglobulin single variable domains and polypeptides comprising the same form further aspects of the invention.

Furthermore, the polypeptides of the invention demonstrated a significant reduction of inflammation in in vivo models. In a rodent model of experimental nephritis we clearly demonstrated the successful treatment of antibody-mediated glomerulonephritis with P2X7 antagonists (cf. Example 3).

As further described herein, preferably, the amino acid sequences of the invention are immunoglobulin single variable domains ("ISV's"). An immunoglobulin single variable domain is an amino acid sequence that:

comprises an immunoglobulin fold or that, under suitable conditions (such as physiological conditions) is capable of forming an immunoglobulin fold (i.e., by folding), i.e., so as to form an immunoglobulin variable domain (such as, for example, a VH, VL or VHH domain); and that forms (or under such suitable conditions is capable of forming) an immunoglobulin variable domain that comprises a functional antigen binding activity (in the sense that it does not require an interaction with another immunoglobulin variable domain (such as a VH-VL interaction) to form a functional antigen binding site).

Amino acid sequences of the invention that are ISV's are also referred to herein as "ISV's of the invention". Some preferred examples of immunoglobulin single variable domains suitable for use in the invention will become clear from the further description herein, and for example comprise VHH's and/or (other) Nanobodies (preferred), such as humanized VHH's or camelized VH's, such as camelized human VH, dAb's and (single) domain antibodies.

As such, the ISV, polypeptides and compositions of the present invention can be used for the diagnosis, prevention and treatment of diseases and disorders of the present invention (herein also "diseases and disorders of the present invention") and include, but are not limited to diseases such as inflammatory bowel disease (IBD), rheumatoid arthritis, osteoarthritis, cancer, diabetes, nephritis, neuropathic pain, epilepsy, neurodegenerative diseases such as AD and HD, MS and cardiovascular diseases, including stroke and hypertension, ischemia, as well as other disorders and diseases described herein. In particular, the polypeptides and compositions of the present invention can be used for the diagnosis, prevention and treatment of diseases involving P2X7 mediated disorders, including apoptosis.

Generally, said "diseases and disorders of the present invention" can be defined as diseases and disorders that can be diagnosed, prevented and/or treated, respectively, by suitably administering to a subject in need thereof (i.e., having the disease or disorder or at least one symptom thereof and/or at risk of attracting or developing the disease or disorder) of either a polypeptide or composition of the invention (and in particular, of a pharmaceutically active amount thereof) and/or of a known active principle active against P2X7 and in particular human P2X7 (SEQ ID NO: 1-3) and its isoforms or a biological pathway or mechanism in which P2X7 and in particular human P2X7 (SEQ NO: 1-3) or its isoforms is involved (and in particular, of a pharmaceutically active amount thereof).

In particular, the ISVs and polypeptides of the present invention can be used for the diagnosis, prevention and treatment of diseases and disorders of the present invention which are characterized by excessive and/or unwanted P2X7 and in particular human P2X7 (SEQ ID NO: 1-3) or its isoforms gating mediated by ATP. Examples of such diseases and disorders of the present invention will again be clear to the skilled person based on the disclosure herein.

Thus, without being limited thereto, the immunoglobulin single variable domains and polypeptides of the invention can for example be used to diagnose, prevent and/or to treat all diseases and disorders that are currently being diagnosed, prevented or treated with active principles that can modulate P2X7 and in particular human P2X7 (SEQ ID NO: 1-3) or its isoforms-mediated gating, such as those mentioned in the diseases and prior art cited above. It is also envisaged that the polypeptides of the invention can be used to diagnose, prevent and/or to treat all diseases and disorders for which treatment with such active principles is currently being developed, has been proposed, or will be proposed or developed in the future. In addition, it is envisaged that, because of their favourable properties as further described herein, the polypeptides of the present invention may be used for the diagnosis, prevention and treatment of other diseases and disorders than those for which these known active principles are being used or will be proposed or developed; and/or that the polypeptides of the present invention may provide new methods and regimens for treating the diseases and disorders described herein.

Other applications and uses of the immunoglobulin single variable domains and polypeptides of the invention will become clear to the skilled person from the further disclosure herein.

Generally, it is an object of the invention to provide pharmacologically active agents, as well as compositions comprising the same, that can be used in the diagnosis, prevention and/or treatment of diseases and/or disorders of the invention; and to provide methods for the diagnosis, prevention and/or treatment of such diseases and disorders that involve the administration and/or use of such agents and compositions.

In particular, it is an object of the invention to provide such pharmacologically active agents, compositions and/or methods that have certain advantages compared to the agents, compositions and/or methods that are currently used and/or known in the art. These advantages will become clear from the further description below.

More in particular, it is an object of the invention to provide therapeutic proteins that can be used as pharmacologically active agents, as well as compositions comprising the same, for the diagnosis, prevention and/or treatment of diseases and/or disorders of the invention and of the further diseases and disorders mentioned herein; and to provide methods for the diagnosis, prevention and/or treatment of such diseases and disorders that involve the administration and/or the use of such therapeutic proteins and compositions.

Accordingly, it is a specific object of the present invention to provide immunoglobulin single variable domains that are directed against P2X7, in particular against P2X7 from a warm-blooded animal, more in particular against P2X7 from a mammal such as e.g., mouse, and especially against human P2X7 (SEQ ID NO: 1-3) or its isoforms; and to provide proteins and polypeptides comprising or essentially consisting of at least one such immunoglobulin single variable domain.

In particular, it is a specific object of the present invention to provide such immunoglobulin single variable domains and such proteins and/or polypeptides that are suitable for prophylactic, therapeutic and/or diagnostic use in a warm-blooded animal, and in particular in a mammal, and more in particular in a human being.

More in particular, it is a specific object of the present invention to provide such immunoglobulin single variable domains and such proteins and/or polypeptides that can be used for the prevention, treatment, alleviation and/or diagnosis of one or more diseases, disorders or conditions associated with P2X7 and/or mediated by P2X7 (such as the diseases, disorders and conditions mentioned herein) in a warm-blooded animal, in particular in a mammal, and more in particular in a human being.

It is also a specific object of the invention to provide such immunoglobulin single variable domains and such proteins and/or polypeptides that can be used in the preparation of pharmaceutical or veterinary compositions for the prevention and/or treatment of one or more diseases, disorders or conditions associated with and/or mediated by P2X7 (such as the diseases, disorders and conditions mentioned herein) in a warm-blooded animal, in particular in a mammal, and more in particular in a human being.

In the invention, generally, these objects are achieved by the use of the immunoglobulin single variable domains, proteins, polypeptides and compositions that are described herein.

In general, the invention provides immunoglobulin single variable domains that are directed against (as defined herein) and/or can specifically bind (as defined herein) to P2X7 and in particular human P2X7 (SEQ ID NO: 1-3) or its isoforms; as well as compounds and constructs, and in particular proteins and polypeptides, that comprise at least one such amino acid sequence or immunoglobulin single variable domain.

More in particular, the invention provides immunoglobulin single variable domains and polypeptides that can bind to P2X7 and in particular human P2X7 (SEQ ID NO: 1-3) or its isoforms with an affinity (suitably measured and/or expressed as a $K_D$-value (actual or apparent), a $K_A$-value (actual or apparent), a $k_{on}$-rate and/or a $k_{off}$-rate, as well as compounds and constructs, and in particular proteins and polypeptides, that comprise at least one such amino acid sequence or immunoglobulin single variable domain.

Also, the immunoglobulin single variable domains and polypeptides that can bind to P2X7 and in particular human P2X7 (SEQ ID NO: 1-3) or its isoforms may be characterized by biological potency, suitably measured and/or expressed as an $IC_{50}$ value, as further described and defined herein, for instance, such as by Alphascreen®; as well as compounds and constructs, and in particular proteins and polypeptides, that comprise at least one such amino acid sequence or immunoglobulin single variable domain.

In particular aspect, the immunoglobulin single variable domains and/or polypeptides of the invention are such that they bind to human P2X7 (SEQ ID NO: 1-3) or its isoforms with an IC50 of 100 nM or lower, such as 50 nM or lower, more preferably of 30 nM or lower, even more preferably of 20 nM or lower, most preferably of 10 nM or lower, such as 5 nM, in an Alphascreen assay.

It will be appreciated that binding of the immunoglobulin single variable domains and/or polypeptides of the invention to (human) P2X7 may result in inhibiting the activity of extracellular ATP on P2X7 or displacing ATP from (human) P2X7 as described herein. It will further be appreciated that binding of the immunoglobulin single variable domains and/or polypeptides of the invention to (human) P2X7 may result in inhibiting gating, such as described herein.

The efficacy of the immunoglobulin single variable domains and polypeptides of the invention, and of compositions comprising the same, can be tested using any suitable in vitro assay, cell-based assay, in vivo assay and/or animal model known per se, or any combination thereof, depending on the specific disease or disorder involved. Suitable assays and animal models will be clear to the skilled person, and for example include the assays and animal models used in the experimental part below and in the prior art cited herein.

Some preferred technical values for binding, displacing or other in vivo and/or in vitro potency of the immunoglobulin single variable domains or polypeptides of the invention to P2X7 and in particular human P2X7 (SEQ ID NO: 1-3) or its isoforms will become clear from the further description and examples herein.

For binding to P2X7 and in particular human P2X7 (SEQ ID NO: 1-3) or its isoforms, an amino acid sequence of the invention will usually contain within its amino acid sequence one or more amino acid residues or one or more stretches of amino acid residues (i.e., with each "stretch" comprising two or amino acid residues that are adjacent to each other or in close proximity to each other, i.e., in the primary or tertiary structure of the amino acid sequence) via which the amino acid sequence of the invention can bind to P2X7 and in particular human P2X7 (SEQ ID NO: 1-3) or its isoforms, which amino acid residues or stretches of amino acid residues thus form the "site" for binding to P2X7 and in particular human P2X7 (SEQ ID NO: 1-3) or its isoforms (also referred to herein as the "antigen binding site").

Generally, when an amino acid sequence of the invention (or a compound, construct or polypeptide comprising the same) is intended for administration to a subject (for example for therapeutic and/or diagnostic purposes as described herein), it is preferably either an amino acid sequence that does not occur naturally in said subject; or, when it does occur naturally in said subject, is in essentially isolated form (as defined herein).

It will also be clear to the skilled person that for pharmaceutical use, the immunoglobulin single variable domains of the invention (as well as compounds, constructs and polypeptides comprising the same) are preferably directed against P2X7 and in particular human P2X7 (SEQ ID NO: 1-3) or its isoforms; whereas for veterinary purposes, the immunoglobulin single variable domains and polypeptides of the invention are preferably directed against P2X7 from the species to be treated, or at least cross-reactive with P2X7 from the species to be treated.

Also, according to the invention, immunoglobulin single variable domains and polypeptides that are directed against P2X7 from a first species of warm-blooded animal may or may not show cross-reactivity with P2X7 from one or more other species of warm-blooded animal. For example, immunoglobulin single variable domains and polypeptides directed against human P2X7 and in particular human P2X7 (SEQ ID NO: 1-3) or its isoforms may or may not show cross reactivity with P2X7 from one or more other species of primates (such as, without limitation, monkeys from the genus *Macaca* (such as, and in particular, cynomolgus monkeys (*Macaca fascicularis*) and/or rhesus monkeys (*Macaca mulatta*)) and baboon (*Papio ursinus*)) and/or with P2X7 from one or more species of animals that are often used in animal models for diseases (for example mouse, rat, rabbit, pig or dog), and in particular in animal models for diseases and disorders associated with P2X7 and in particular human P2X7 (SEQ ID NO: 1-3) or its isoforms (such as the species and animal models mentioned herein). In this respect, it will be clear to the skilled person that such cross-reactivity, when present, may have advantages from a drug development point of view, since it allows the immunoglobulin single variable domains and polypeptides against P2X7 and in particular human P2X7 (SEQ ID NO: 1-3) or its isoforms to be tested in such disease models.

More generally, immunoglobulin single variable domains and polypeptides of the invention that are cross-reactive with P2X7 from multiple species of mammal will usually be advantageous for use in veterinary applications, since it will allow the same amino acid sequence or polypeptide to be used across multiple species. Thus, it is also encompassed within the scope of the invention that immunoglobulin single variable domains and polypeptides directed against P2X7 from one species of animal (such as immunoglobulin single variable domains and polypeptides against human P2X7 (SEQ ID NO: 1-3) or its isoforms) can be used in the treatment of another species of animal, as long as the use of the immunoglobulin single variable domains and/or polypeptides provide the desired effects in the species to be treated.

The present invention is in its broadest sense also not particularly limited to or defined by a specific antigenic determinant, epitope, part, domain, subunit or confirmation (where applicable) of P2X7 and in particular human P2X7 (SEQ ID NO: 1-3) or its isoforms against which the immunoglobulin single variable domains and polypeptides of the invention are directed. For example, the immunoglobulin single variable domains and polypeptides may or may not be directed against the ATP/P2X7 interaction site, and are as further defined herein.

As further described herein, a polypeptide of the invention may contain two or more immunoglobulin single variable domains of the invention that are directed against P2X7 and in particular human P2X7 (SEQ ID NO: 1-3) or its isoforms. Generally, such polypeptides will bind to P2X7 and in particular human P2X7 (SEQ ID NO: 1-3) or its isoforms with increased avidity compared to a single amino acid sequence of the invention. Such a polypeptide may for example comprise two immunoglobulin single variable domains of the invention that are directed against the same antigenic determinant, epitope, part, domain, subunit or confirmation (where applicable) of P2X7 and in particular human P2X7 (SEQ ID NO: 1-3) or its isoforms (which may or may not be an interaction site); or comprise at least one "first" amino acid sequence of the invention that is directed against a first antigenic determinant, epitope, part, domain, subunit or conformation (where applicable) of P2X7 and in particular human P2X7 (SEQ ID NO: 1-3) or its isoforms (which may or may not be an interaction site); and at least one "second" amino acid sequence of the invention that is directed against a second antigenic determinant, epitope, part, domain, subunit or conformation (where applicable) different from the first (and which again may or may not be an interaction site). Preferably, in such "biparatopic" polypeptides of the invention, at least one amino acid sequence of the invention is directed against an interaction site (as defined herein), although the invention in its broadest sense is not limited thereto. For instance, polypeptides of the invention may be formatted e.g. in a biparatopic way such as to combine monovalent building blocks directed against different epitopes as characterized in the experimental part.

Also, when the target is part of a binding pair (for example, a receptor-ligand binding pair), the immunoglobulin single variable domains and polypeptides may be such that they compete with the cognate binding partners, e.g., ATP for binding to P2X7, and/or such that they (fully or partially) neutralize binding of the binding partner to the target.

It is also expected that the immunoglobulin single variable domains and polypeptides of the invention will generally bind to all naturally occurring or synthetic analogs, variants, mutants, alleles, parts and fragments of P2X7 and in particular human P2X7 (SEQ ID NO: 1-3) or its isoforms; or at least to those analogs, variants, mutants, alleles, parts and fragments of P2X7 and in particular human P2X7 (SEQ ID NO: 1-3) or its isoforms that contain one or more antigenic determinants or epitopes that are essentially the same as the antigenic determinant(s) or epitope(s) to which the immunoglobulin single variable domains and polypeptides of the invention bind to P2X7 and in particular human P2X7 (SEQ ID NO: 1-3) or its isoforms. Again, in such a case, the immunoglobulin single variable domains and polypeptides of the invention may bind to such analogs, variants, mutants, alleles, parts and fragments with an affinity and/or specificity that are the same as, or that are different from (i.e. higher than or lower than), the affinity and specificity with which the immunoglobulin single variable domains of the invention bind to (wild-type) P2X7.

Since the P2X7 receptor probably functions as a multimeric form, e.g., a trimeric, and particularly a homotrimeric form, it is within the scope of the invention that the immunoglobulin single variable domains and polypeptides of the invention i) only bind to P2X7 and in particular human P2X7 (SEQ ID NO: 1-3) or its isoforms in monomeric form, ii) only bind to P2X7 and in particular human P2X7 (SEQ ID NO: 1-3) or its isoforms in multimeric/trimeric form, or iii) bind to both the monomeric and the multimeric form. In a preferred aspect of the invention, the polypeptides of the invention prevent formation of (homo) trimeric human P2X7 complexes.

Also, as will be clear to the skilled person, proteins or polypeptides that contain two or more immunoglobulin single variable domains directed against P2X7 and in particular human P2X7 (SEQ ID NO: 1-3) or its isoforms, e.g., "biparatopic" polypeptides of the invention, may bind with higher avidity to P2X7 and in particular human P2X7 (SEQ ID NO: 1-3) or its isoforms than the corresponding monomeric amino acid sequence(s). For example, and without limitation, proteins or polypeptides that contain two or more immunoglobulin single variable domains directed against different epitopes of P2X7 and in particular human P2X7 (SEQ ID NO: 1-3) or its isoforms may (and usually will) bind with higher avidity than each of the different monomers, and proteins or polypeptides that contain two or more immunoglobulin single variable domains directed against P2X7 and in particular human P2X7 (SEQ ID NO: 1-3) or its isoforms may (and usually will) bind also with higher avidity to a multimer (e.g., (homo)trimer) of P2X7 and in particular to a multimer (e.g., (homo)trimer) of human P2X7 (SEQ ID NO: 1-3) or its isoforms.

Generally, immunoglobulin single variable domains and polypeptides of the invention will at least bind to those forms of P2X7 and in particular human P2X7 (SEQ ID NO: 1-3) or its isoforms (including monomeric, multimeric, associated and different conformational forms) that are the most relevant from a biological and/or therapeutic point of view, as will be clear to the skilled person.

It is also within the scope of the invention to use parts, fragments, analogs, mutants, variants, alleles and/or derivatives of the immunoglobulin single variable domains and polypeptides of the invention, and/or to use proteins or polypeptides comprising or essentially consisting of one or more of such parts, fragments, analogs, mutants, variants, alleles and/or derivatives, as long as these are suitable for the uses envisaged herein. Such parts, fragments, analogs, mutants, variants, alleles and/or derivatives will usually contain (at least part of) a functional antigen-binding site for binding against P2X7 and in particular human P2X7 (SEQ ID NO: 1-3) or its isoforms; and more preferably will be capable of specific binding to P2X7 and in particular human P2X7 (SEQ ID NO: 1-3) or its isoforms, and even more preferably capable of binding to P2X7 and in particular human P2X7 (SEQ ID NO: 1-3) or its isoforms with an EC50 value, average $K_i$, $IC_{50}$ value concerning binding, gating, shedding and/or other measures as further described herein, (e.g., in the experimental part) that is as defined herein and such parts, fragments, analogues, mutants, variants, alleles and/or derivatives may be more potent, more stable, more soluble and may have the same epitope. Some non-limiting examples of such parts, fragments, analogues, mutants, variants, alleles, derivatives, proteins and/or polypeptides will become clear from the further description herein. Additional fragments or polypeptides of the invention may also be provided by suitably combining (i.e., by linking or genetic fusion) one or more (smaller) parts or fragments as described herein.

Preferred multiparatopic such as biparatopic) polypeptides of the invention comprise or essentially consist of two or more immunoglobulin single variable domains wherein, in at least one of the immunoglobulin single variable domains, the CDR sequences have at least 70% amino acid identity, preferably at least 80% amino acid identity, more preferably at least 90% amino acid identity, such as 95% amino acid identity or more, or even essentially 100% amino acid identity with the CDR sequences of at least one of the immunoglobulin single variable domains with SEQ ID NO's: 6-19 (Table B-3).

In a preferred aspect, the multiparatopic (such as biparatopic) polypeptides of the invention comprise or essentially consist of two or more immunoglobulin single variable domains, wherein at least one of the immunoglobulin single variable domains cross-blocks the binding to P2X7 of at least one of the immunoglobulin single variable domains with SEQ ID NO's: 6-19 and/or is cross-blocked from binding to P2X7 by at least one of the immunoglobulin single variable domains with SEQ ID NO's: 6-19.

In a preferred aspect of the invention, the multiparatopic (such as biparatopic) polypeptides of the invention comprise or essentially consist of two or more immunoglobulin single variable domains, wherein a first immunoglobulin single variable domain is chosen from SEQ ID NO's: 6-19 and a second immunoglobulin single variable domain is chosen from SEQ ID NO's: 6-19, wherein the first immunoglobulin single variable domain and the second immunoglobulin single variable domain may be the same or different.

In a preferred aspect, each of the two or more immunoglobulin single variable domains of the multiparatopic (such as biparatopic) polypeptide of the invention, that is directed against P2X7 belongs to a different epitope bin or family. Accordingly, the present invention relates to a polypeptide comprising or essentially consisting of two or more immunoglobulin single variable domains directed against P2X7, wherein each of the two or more immunoglobulin single variable domains that are directed against P2X7 belongs to a different epitope bin. Immunoglobulin single variable domains that belong to a different epitope bin do preferably not cross-compete with each other for binding the target, P2X7. Accordingly, the present invention relates to a polypeptide comprising or essentially consisting of two or more immunoglobulin single variable domains against P2X7, wherein the first immunoglobulin single variable domain does not cross-block the binding to P2X7 of the second immunoglobulin single variable domain and/or wherein the first immunoglobulin single variable is not cross-blocked from binding to P2X7 by the second immunoglobulin single variable domain.

Preferably, the polypeptide of the invention is selected from any of SEQ ID NOs: 118-124.

The multivalent, such as multiparatopic, polypeptides of the invention can generally be provided (and in particular, purposefully designed for a specific biological action) by suitably linking (optionally via suitable linkers) or combining two or more (monovalent) immunoglobulin single variable domains (or by suitably linking or combining nucleotide sequences encoding such (monovalent) immunoglobulin single variable domains to provide a nucleic acid that encodes the desired multivalent construct, and then suitably expressing said multivalent construct). Thus, it is clear that the invention not only makes available the multivalent, preferably multiparatopic, polypeptides described herein, but also provides—by making available the monovalent polypeptides described herein—the skilled person with a range of different "binding domains" or "binding units" that can be used as "building blocks" to provide a range of different multivalent, preferably multiparatopic (and in particular biparatopic) polypeptides (which may have different binding affinities, avidities, specificities, potencies and/or efficacies) through the use of suitable "building blocks" as described herein The immunoglobulin single variable domains of the present invention may be coupled via Fc-tails, as known in the art, e.g., as detailed in Example 1.3. For instance, a coding sequence of an ISV may be fused in frame with the coding sequence of an IgG1-Fc ("Nb-Fc"), cloned into an expression vector and expressed (see e.g., Scheuplein et al. 2010 "A recombinant heavy chain antibody approach blocks ART2 mediated deletion of an iNKT cell population that upon activation inhibits autoimmune diabetes" J. Autoimmun 34: 145-54). Individual Nb-Fc's may be mixed, forming homodimers and/or heterodimers. Alternatively, two individual Nb-Fc's—preferably two different Nb-Fc's—may be cloned in one expression vector and expressed.

The various immunoglobulin single variable domains and/or monovalent polypeptides of the invention (and/or nucleotide sequences and/or nucleic acids encoding the same) and their use of as "building blocks" in or for preparation of multivalent and/or multiparatopic polypeptides (or nucleotide sequences/nucleic acids encoding the same) form an aspect of the invention.

The monovalent polypeptides of the invention may essentially consist of an immunoglobulin single variable domain selected from a light chain variable domain sequence (e.g., a $V_L$-sequence) and from a heavy chain variable domain sequence (e.g., a $V_H$-sequence). The monovalent polypeptides of the invention may essentially consist of an immunoglobulin single variable domain selected from a heavy chain variable domain sequence that is derived from a conventional four-chain antibody and from a heavy chain variable domain sequence that is derived from heavy chain antibody. The monovalent polypeptides of the invention may essentially consist of an immunoglobulin single variable domain selected from a domain antibody (or an amino acid that is suitable for use as a domain antibody), a single domain antibody (or an amino acid that is suitable for use as a single domain antibody), a "dAb" (or an amino acid that is suitable for use as a dAb) or a Nanobody (including but not limited to a $V_{HH}$). In a preferred aspect, the monovalent polypeptide of the invention essentially consists of a partially or fully humanized Nanobody, such as a partially or fully humanized VHH.

As described above, the invention also relates to the use of a monovalent polypeptide as described herein in preparing a multivalent, preferably multiparatopic polypeptide of the invention. Accordingly, the present invention relates to the use of a monovalent polypeptide of the invention as a binding domain or binding unit in preparing a multivalent polypeptide of the invention.

The invention further relates to a polypeptides (also referred to herein as a "polypeptide(s) of the invention") that comprises or essentially consists of one or more monovalent polypeptide or one or more multivalent, preferably multiparatopic, polypeptide of the invention, and optionally further comprises one or more other groups, residues, moieties or binding units, optionally linked via one or more peptidic linkers. As will become clear to the skilled person from the further disclosure herein, such further groups, residues, moieties, binding units or amino acid sequences may or may not provide further functionality to the monovalent or multivalent, preferably multiparatopic, polypeptide of the invention and may or may not modify the properties of the monovalent or multivalent polypeptide of the invention.

The invention also relates to nucleic acids or nucleotide sequences that encode a polypeptide of the invention. Such a nucleic acid will also be referred to herein as "nucleic acid(s) of the invention" and may for example be in the form of a genetic construct, as further described herein. Accordingly, the present invention also relates to a nucleic acid or nucleotide sequence that is in the form of a genetic construct.

Nucleic acids encoding a monovalent polypeptide of the invention can be linked to obtain a nucleic acid encoding a multivalent, preferably multiparatopic, polypeptide of the invention. Accordingly, the present invention also relates to the use of a nucleic acid or nucleotide sequence that encodes a monovalent polypeptide of the invention for the preparation of a genetic construct that encodes a multivalent, preferably multiparatopic, polypeptide of the invention.

The invention further relates to a host or host cell that expresses (or that under suitable circumstances is capable of expressing) a polypeptide of the invention; and/or that contains a nucleic acid of the invention. Some preferred but non-limiting examples of such hosts or host cells will become clear from the further description herein.

The invention further relates to a composition containing or comprising at least one polypeptide of the invention and/or at least one nucleic acid of the invention, and optionally one or more further components of such compositions known per se, i.e., depending on the intended use of the composition. Such a composition may for example be a pharmaceutical composition (as described herein) or a veterinary composition. Some preferred but non-limiting examples of such compositions will become clear from the further description herein.

The invention further relates to methods for preparing polypeptides, nucleic acids, host cells, and compositions described herein.

In particular, the present invention relates to:
(I) an immunoglobulin single variable domain that can bind P2X7, preferably human P2X7 (SEQ ID NO: 1-3) with a Kd of less than 50 nM,
(II) The immunoglobulin single variable domain according to (I), wherein the immunoglobulin single variable domain comprises an amino acid sequence of formula 1:
FR1-CDR1-FR2-CDR2-FR3-CDR3-FR4 (1); wherein FR1 to FR4 refer to framework regions 1 to 4 and are framework regions (FRs) of an immunoglobulin single variable domain; and
wherein CDR1 is chosen from the group consisting of:
SEQ ID NOs: 34-47,
polypeptides that have at least 80% amino acid identity with SEQ ID NOs: 34-47, and
polypeptides that have 3, 2, or 1 amino acid difference with SEQ ID NOs: 34-47; and
wherein CDR2 is chosen from the group consisting of:
SEQ ID NOs: 62-75;
polypeptides that have at least 80% amino acid identity with SEQ ID NOs: 62-75; and
polypeptides that have 3, 2, or 1 amino acid difference with SEQ ID NOs: 62-75; and
wherein CDR3 is chosen from the group consisting of:
SEQ ID NOs: 90-103;
polypeptides that have at least 80% amino acid identity with at least one of the immunoglobulin single variable domains of SEQ ID NOs: 90-103; and
polypeptides that have 3, 2, or 1 amino acid difference with SEQ ID NOs: 90-103.
(III) The immunoglobulin single variable domain according to (II), wherein the framework regions (FRs) have a sequence identity of more than 80% with the FRs of SEQ ID NOs: 6-19.
(IV) The immunoglobulin single variable domain according to (I), wherein the immunoglobulin single variable domain comprises an amino acid sequence with the formula 1:

FR1-CDR1-FR2-CDR2-FR3-CDR3-FR4 (1);

wherein FR1 to FR4 refer to framework regions 1 to 4 and are framework regions of an immunoglobulin single variable domain; wherein CDR1 is SEQ ID NO: 34, wherein CDR2 is SEQ ID NO: 62; and wherein CDR3 is SEQ ID NO: 90.
(V) The immunoglobulin single variable domain according to claim (I), wherein the immunoglobulin single variable domain comprises an amino acid sequence with the formula 1:

FR1-CDR1-FR2-CDR2-FR3-CDR3-FR4 (1);

wherein FR1 to FR4 refer to framework regions 1 to 4 and are framework regions of an immunoglobulin single variable domain; wherein CDR1 is SEQ ID NO: 35, wherein CDR2 is SEQ ID NO: 63; and wherein CDR3 is SEQ ID NO: 91.
(VI) The immunoglobulin single variable domain according to (I), wherein the immunoglobulin single variable domain comprises an amino acid sequence with the formula 1:

FR1-CDR1-FR2-CDR2-FR3-CDR3-FR4 (1);

wherein FR1 to FR4 refer to framework regions 1 to 4 and are framework regions of an immunoglobulin single variable domain; wherein CDR1 is SEQ ID NO: 40, wherein CDR2 is SEQ ID NO: 68; and wherein CDR3 is SEQ ID NO: 96.
(VII) A polypeptide comprising an immunoglobulin single variable domain according to any of (I)-(VI),
(VIII) The polypeptide according to (VII), wherein the polypeptide is selected from the group consisting of polypeptides that have an amino acid sequence with a sequence identity of more than 80% with SEQ ID NOs: 6-19.
(IX) The polypeptide according to (VII) or (VIII), wherein the polypeptide is selected from the group consisting of polypeptides that have an amino acid sequence with a sequence identity of more than 80% with SEQ ID NOs: 6-19.
(X) The polypeptide according to any of (VII)-(IX), additionally comprising an immunoglobulin single variable domain binding human serum albumin such as e.g., Alb8 (SEQ ID NO: 126) or Alb11 (SEQ ID NO: 125).
(XI) The immunoglobulin single variable domain according to any of (I)-(VI) or the polypeptide according to any of (VII)-(X), wherein the IC50 in an Alphascreen assay is 30 nM or lower.
(XII) The immunoglobulin single variable domain according to any of (I)-(VI) or the polypeptide according to any of (VII)-(X), wherein the IC50 in an Alphascreen assay is 3 nM or lower.
(XIII) A nucleic acid sequence encoding i) an immunoglobulin single variable domain according to any of (I)-(VI), (XI), or (XII), or ii) a polypeptide according to any of (VII)-(X).
(XIV). A pharmaceutical composition comprising i) an immunoglobulin single variable domain according to any of (I)-(VI), (XI), or (XII), or ii) a polypeptide according to any of (VII)-(X); and optionally a pharmaceutically acceptable excipient.
(XV) An immunoglobulin single variable domain according to any of (I)-(VI), (XI), or (XII), or a polypeptide according to any of (VII)-(X), for use in treating P2X7 associated diseases, including but not limiting to MS, IBD, neuropathic pain, epilepsy, stroke, diabetes, hypertension and cancer.
(XVI) A method for producing an immunoglobulin single variable domain according to any of (I)-(VI), (XI), or (XII), or a polypeptide according to any of (VII)-(X), said method at least comprising the steps of:
 a) expressing, in a suitable host cell or host organism or in another suitable expression system, a nucleic acid or nucleotide sequence according to (XIII); optionally followed by:
 b) isolating and/or purifying said immunoglobulin single variable domain or said polypeptide.
(XVII) Method for screening immunoglobulin single variable domains directed against P2X7 and in particular human P2X7 (SEQ ID NOs: 1-3) that comprises at least the steps of:
 a) providing a set, collection or library of immunoglobulin single variable domains; and
 b) screening said set, collection or library of immunoglobulin single variable domains for immunoglobulin single variable domains that can bind to and/or have affinity for P2X7 and in particular human P2X7 (SEQ ID NOs: 1-3); and
 c) isolating the amino acid sequence(s) that can bind to and/or have affinity for P2X7 and in particular human P2X7 (SEQ ID NO: 1-3).

(XVIII) An immunoglobulin single variable domain that can bind P2X7 with a Kd of less than 50 nM, wherein the binding of said immunoglobulin single variable domain to said P2X7 inhibits the activity of P2X7.

Other aspects, embodiments, advantages and applications of the invention will become clear from the further description herein. Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

BRIEF DESCRIPTION OF THE DRAWINGS

(FIG. 1A, FIG. 1B) Schematic diagram of immunization scheme and P2X7 cDNA expression vectors. Llamas were immunized with a DNA-prime> protein boost strategy (Koch-Nolte et al., 2007 FASEB J. 21, 3490-3498). After 4 ballistic DNA immunizations, animals were boosted with HEK cells stably transfected with mP2X7 and hP2X7 and recombinant mP2X7 adsorbed on beads. Cocktails of cDNA constructs for mP2X7 and hP2X7 were adsorbed on 1 μm gold particles. Llamas received 12 shots each with 1 μg DNA/mg gold per immunization, a boost with HEK cells stably expressing mP2X7 ($2 \times 10^7$, pretreated for 15 min with 1 mM ATP) or hP2X7 ($3 \times 10^7$), and a final boost with mouse P2X7 immuno-precipitated with HANO43 and HANO44 immobilized on AminoLink agarose beads (Pierce) (5 μg/50 μl beads). Phage libraries were generated from blood samples collected at the end of each phase of immunization (PBL 1-6).

(FIG. 1C) FACS analyses of P2X7 expression levels on stably transfected HEK cells used for immunization with Alexa647-conjugated mAbs HANO44 (anti-mP2X7) (Möller et al. 2007 Purinergic Signalling DOI 10.1007/s11302-007-9084-9) and L4 (anti-hP2X7) (Buell et al, 1998 Blood, 92 pp 3521-3528). Un-transfected cells stained with the same antibodies were used as controls (grey histograms).

(FIG. 1D) SDS-PAGE analysis of bead-bound recombinant mP2X7 used for immunization (IP, lane 4). mP2X7 (80 kd, red arrow) was immunoprecipitated from lysates of HEK cells stably transfected with mP2X7 (lysate, lane 1) using mAb HANO44 immobilized on agarose beads (amino-link, Pierce) (matrix, lane 5, control IP with beads only).

FIGS. 2A-2B. FACS analyses of selected Nbs for P2X7 binding.

Crude periplasma lysates with Nbs from the first (A) and second (B) selections were pre-incubated with FITC-conjugated anti-myc antibody and added to mixture of untransfected HEK cells and HEK_hP2X7 cells. Cells were washed and data collected by flow cytometry (FACS Calibur). Positive clones show a bimodal staining (delineation of P2X7 positive cells from wt cells) whereas negative clones show a single peak. Grey histograms show unstained control cells.

Figure 1A:
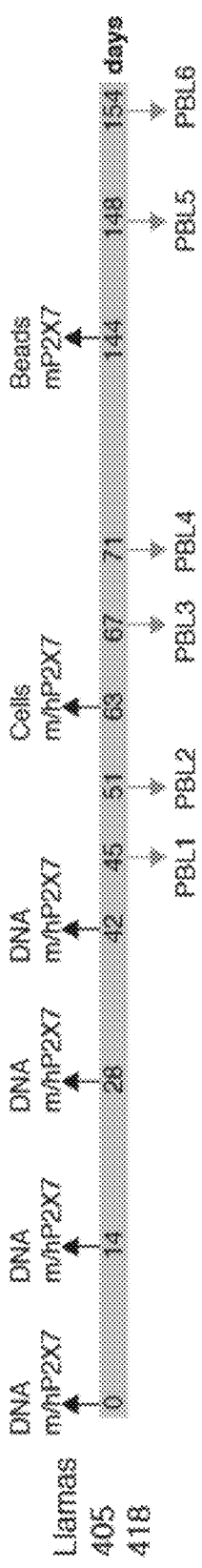
FIGS. 1A-1D. Immunization scheme and sample preparation and for llamas 405 and 418.
Figure 1B:
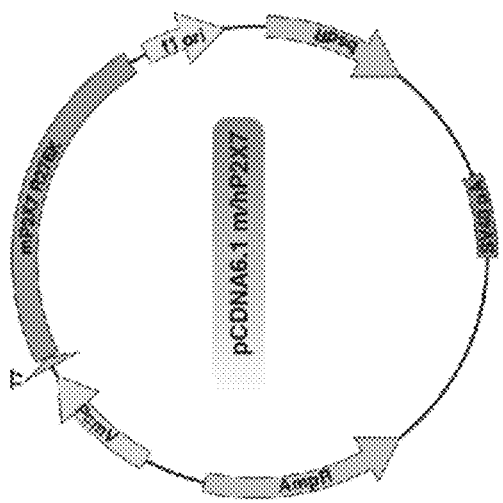
Figure 1C:
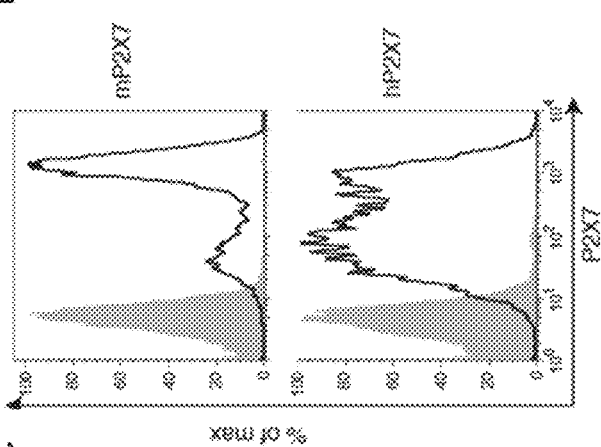
Figure 1D:
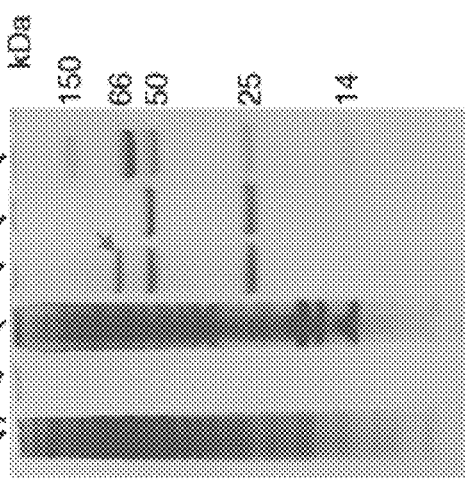
Figure 3:
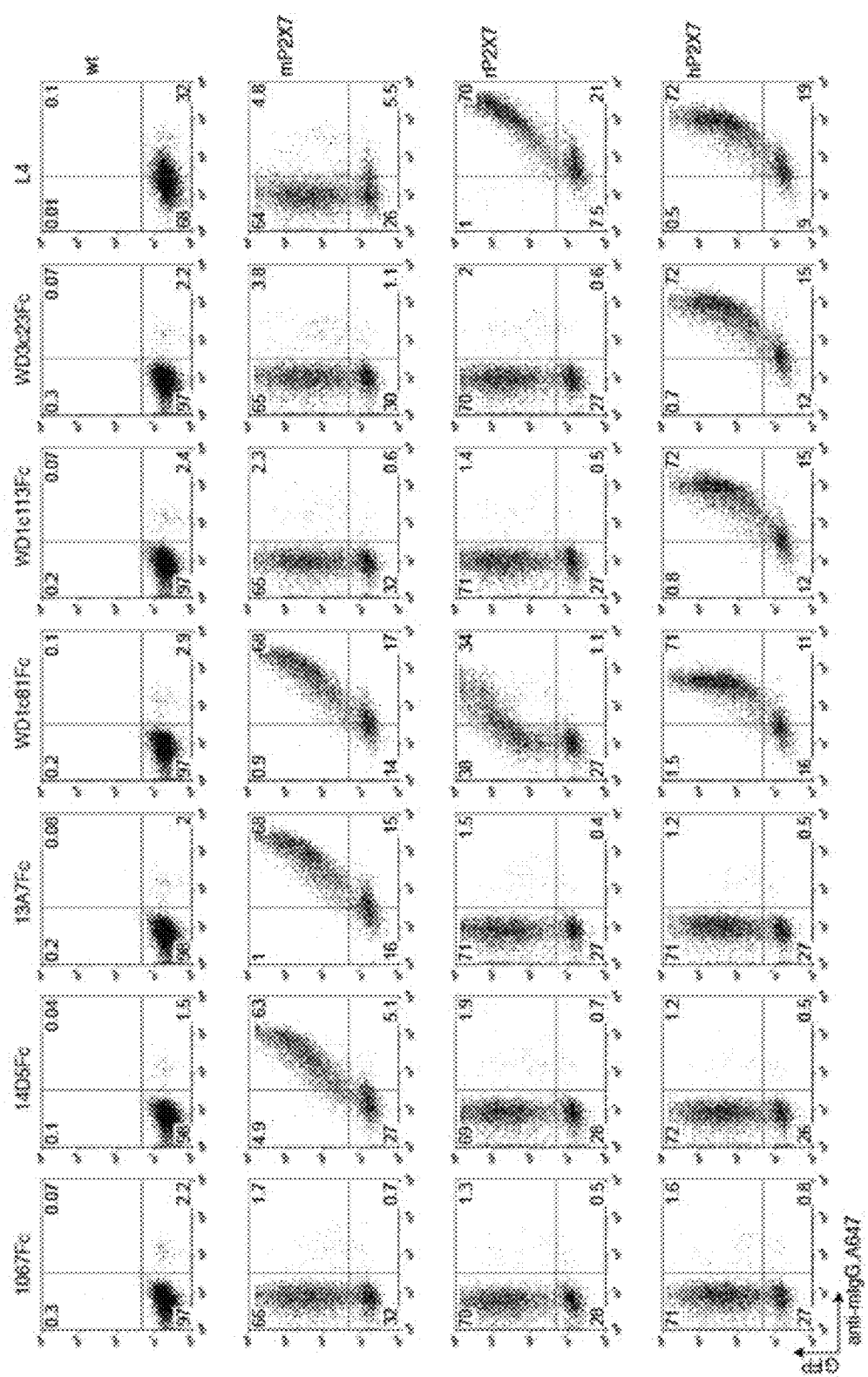

FIG. 3. FACS analyses of specificities of anti-hP2X7 Nbs.

HEK cells were co-transfected with expression constructs for GFP and either mP2X7, rP2X7, or hP2X7. 24 h post transfection cells were harvested by gentle trypsinization and incubated with Nb-Fc fusion proteins or mAb L4 as indicated on top. Bound antibodies were detected with Alexa647-conjugated anti-mouse IgG. For control, untransfected HEK cells (wt) were subjected to the same staining procedures.

Figure 4:
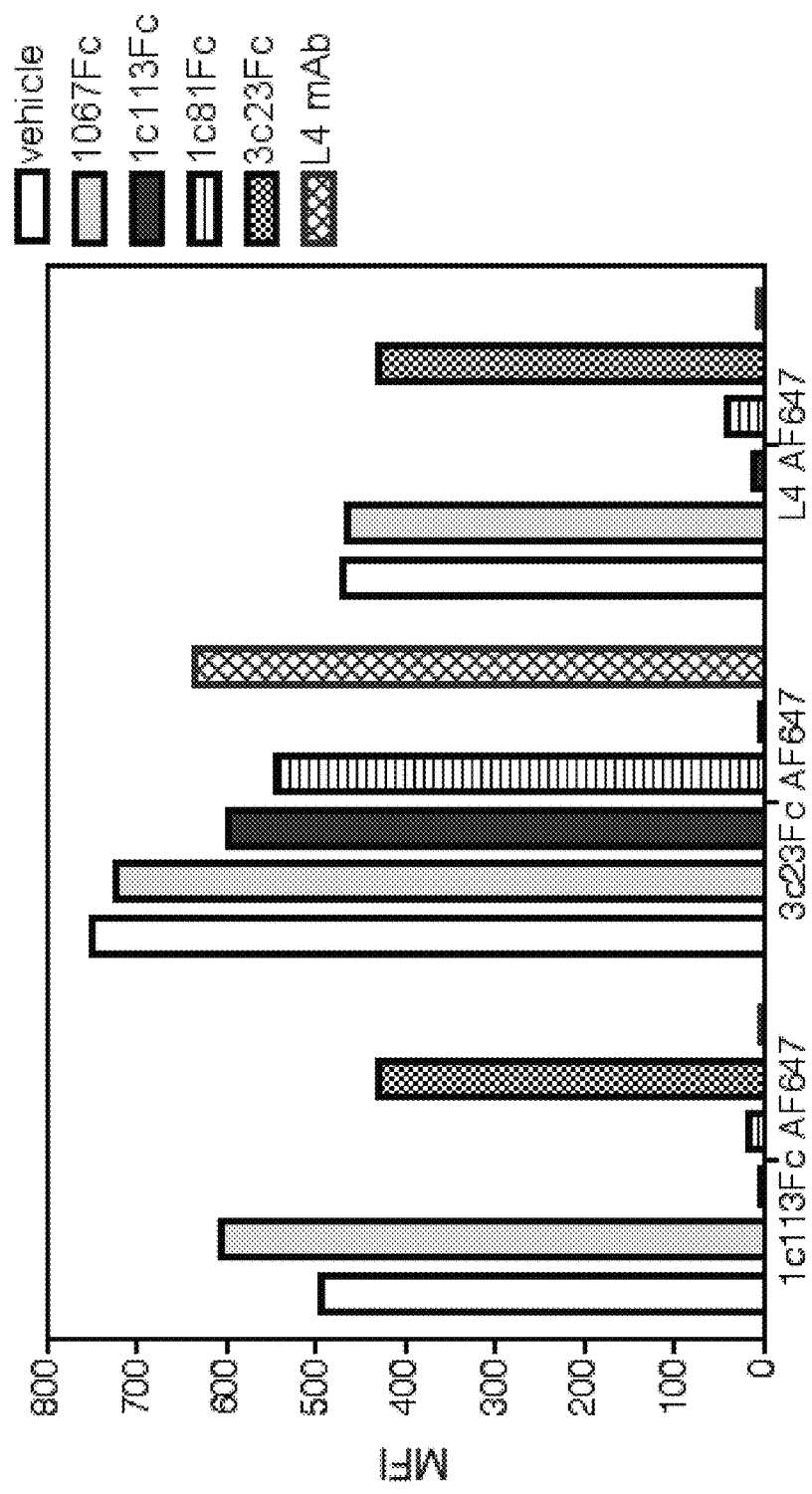

FIG. 4. Cross-blockade analysis of anti-hP2X7 Nbs.

$5 \times 10^5$ HEK cells stably transfected with hP2X7 were incubated with 3 μg of respective unconjugated antibodies in 95 μl of complete DMEM for 15 min at room temperature. Without washing, 1 μl (~250 ng) of Alexa Fluor 647-conjugated 1c113-Fc, 3c23-Fc or mAb L4 was added and incubation was continued at 4° C. for 20 min. Cells were washed and analyzed by flow cytometry (FACS Calibur, BD). MFI, mean fluorescence intensity. Alexa 647-conjugates of Nb-Fc or mAb used for staining are indicated below the panel, Nb-Fc and mAb used for blocking are indicated on the top right. (Vehicle=medium without blocking Abs).

Figure 5A:
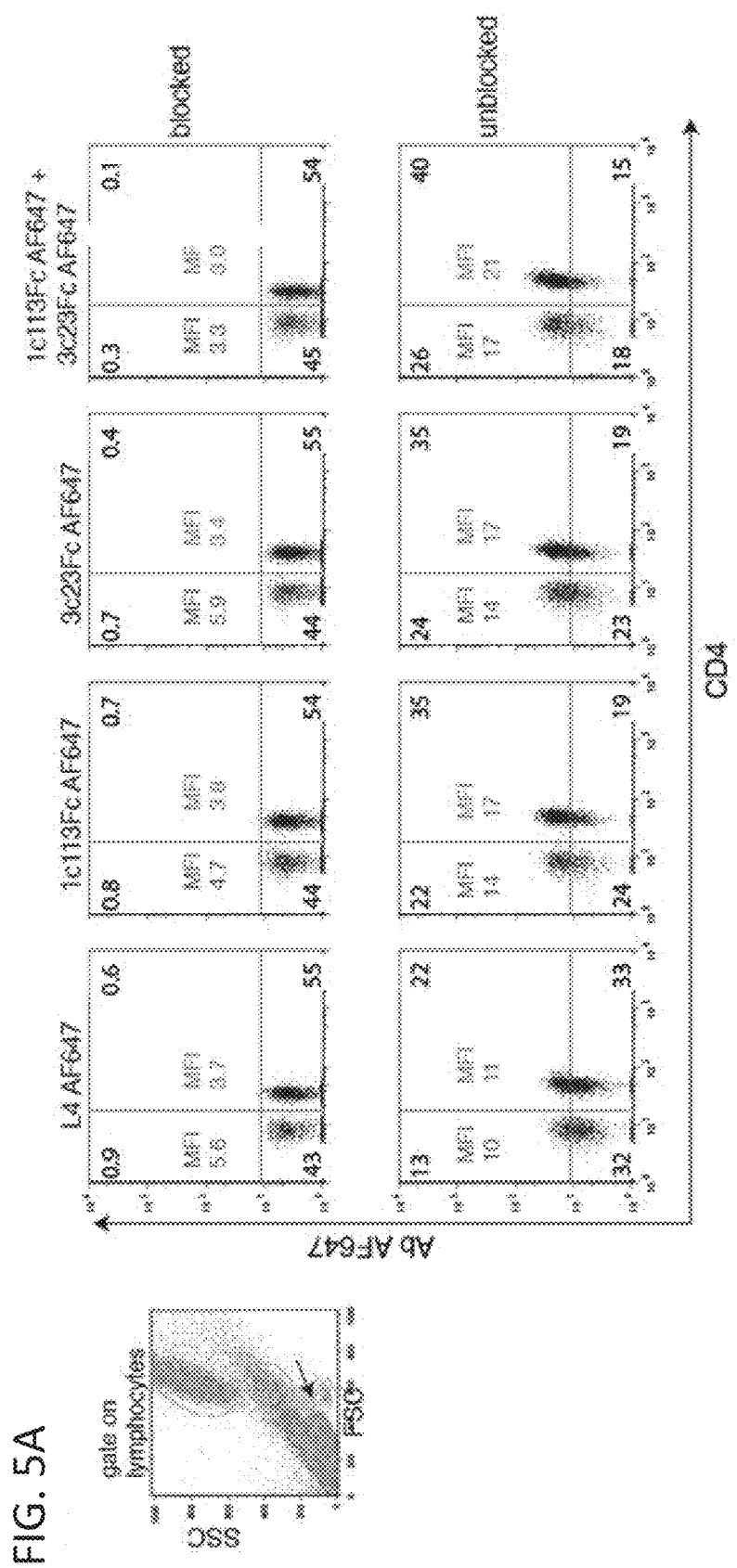
Figure 5B:
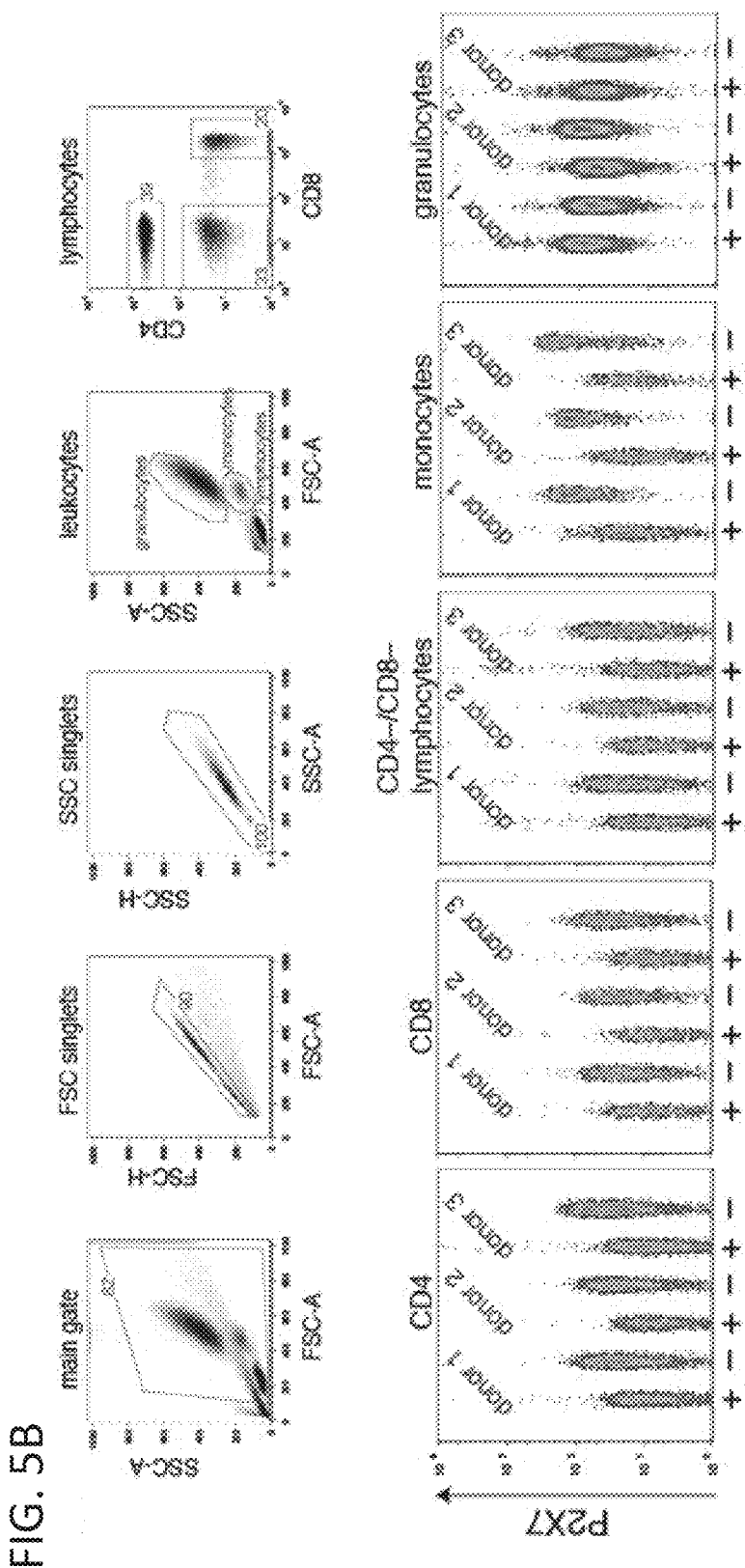

FIGS. 5A-5B. Improved staining of P2X7 on primary leukocytes with a combination of hP2X7-specific Nbs 1c113-Fc and 3c23-Fc.

(FIG. 5A) 100 μl blood aliquots from a single donor were pre-incubated with a combination of 3 μg each of 1c113-Fc and 3c23-Fc ("blocked"). Parallel aliquots were incubated with 3 μg of 1067-Fc only ("unblocked"). After 30-min incubation at room temperature, a mastermix of conjugated antibodies was added: 1c113-Fc Alexa647 (~250 ng); 3c23-Fc Alexa647 (~250 ng); and anti-CD4 Pacific Blue. Cells were incubated on ice for 30 min for antibody staining. Erythrocytes were lysed by 10 min room temperature incubation with 2 ml 1×BD Lysis solution. Cells were washed once with 3 ml complete RPMI 5% FCS and analysed by flow cytometry (FACS Cantoll, B D). Lymphocytes were gated based on low forward scatter (FSC) vs. sideward scatter (SSC) (arrowhead). Black numbers indicate the percentage of cells in the respective quadrant. Left and right MFI values indicate the mean fluorescent intensity of CD4⁻ and CD4⁺ lymphocytes, respectively.

(FIG. 5B) FACS analyses of PBL from three different donors were performed as in (A), with an additional anti-CD8 Alexa488 staining mAb. Gating of granulocytes, monocytes, and lymphocytes was based on FSC and SSC as indicated. Gating of CD4⁺ T cells, CD8⁺ T cells and CD4⁻/CD8⁻ lymphocytes was based on cell surface staining of CD4 and CD8. Expression of P2X7 is shown in a concatenate representation. Preincubation with unstained blocking and nonblocking Nb-Fc is indicated by (+) and (−), respectively, below the panels.

Figure 6A:
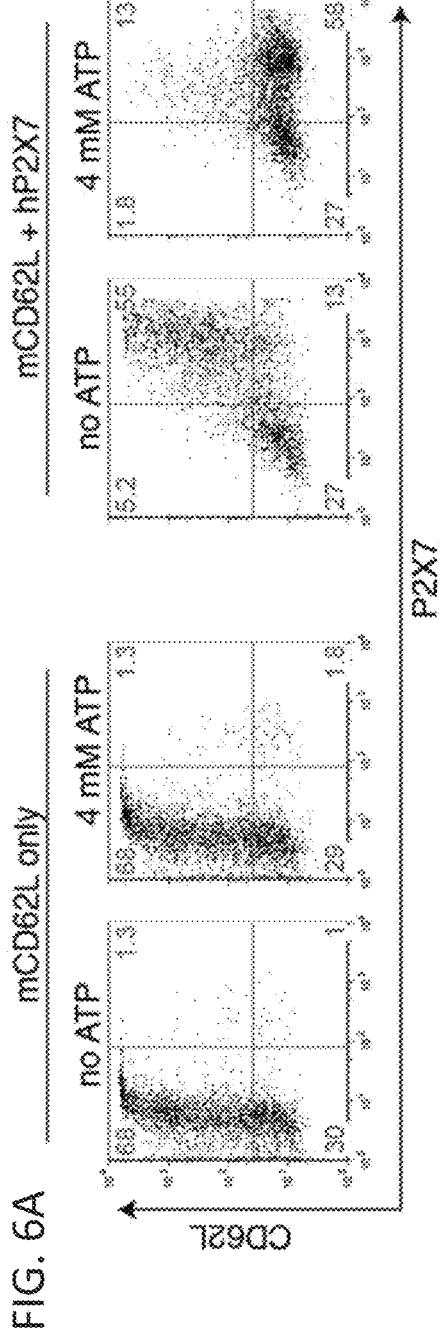
Figure 6B:
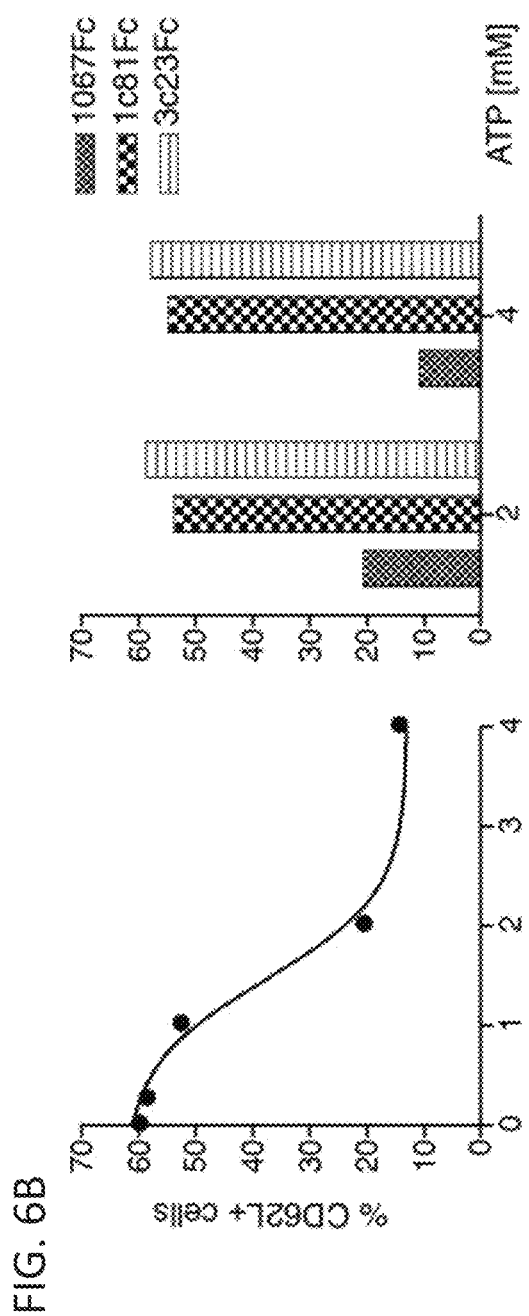

FIGS. 6A-6B. Nbs 1c81 and 3c23 block ATP-induced shedding of CD62L in transfected HEK cells.

(FIG. 6A) HEK cells were transfected with cDNA constructs for CD62L only, or co-transfected with constructs for CD62L and hP2X7. 24 h post transfection, cells were harvested and shedding of CD62L was induced by incubating cells for 60 min with 4 mM ATP in complete DMEM medium at 37° C.

(FIG. 6B) In an ATP dose response assay, P2X7 and CD62L co-transfected cells were incubated with 0.25, 1, 2 or 4 mM ATP for 60 min at 37° C. Aliquots of cells were pre-incubated with 2 μg of Nb-Fc fusion proteins 1c81-Fc or 3c23-Fc or with a control Nb-Fc (anti-hCD38 1067-Fc) for 15 min at room temperature prior to a 60-min incubation with 2 mM or 4 mM ATP. Cells were washed once with 150 μl of complete medium and stained for 30 min at 4° C. to detect CD62L (MEL-14 PE) and P2X7 (L4 AF647) expression. After a further wash, cells were analyzed by flow cytometry (FACS Calibur, BD).

Figure 7:
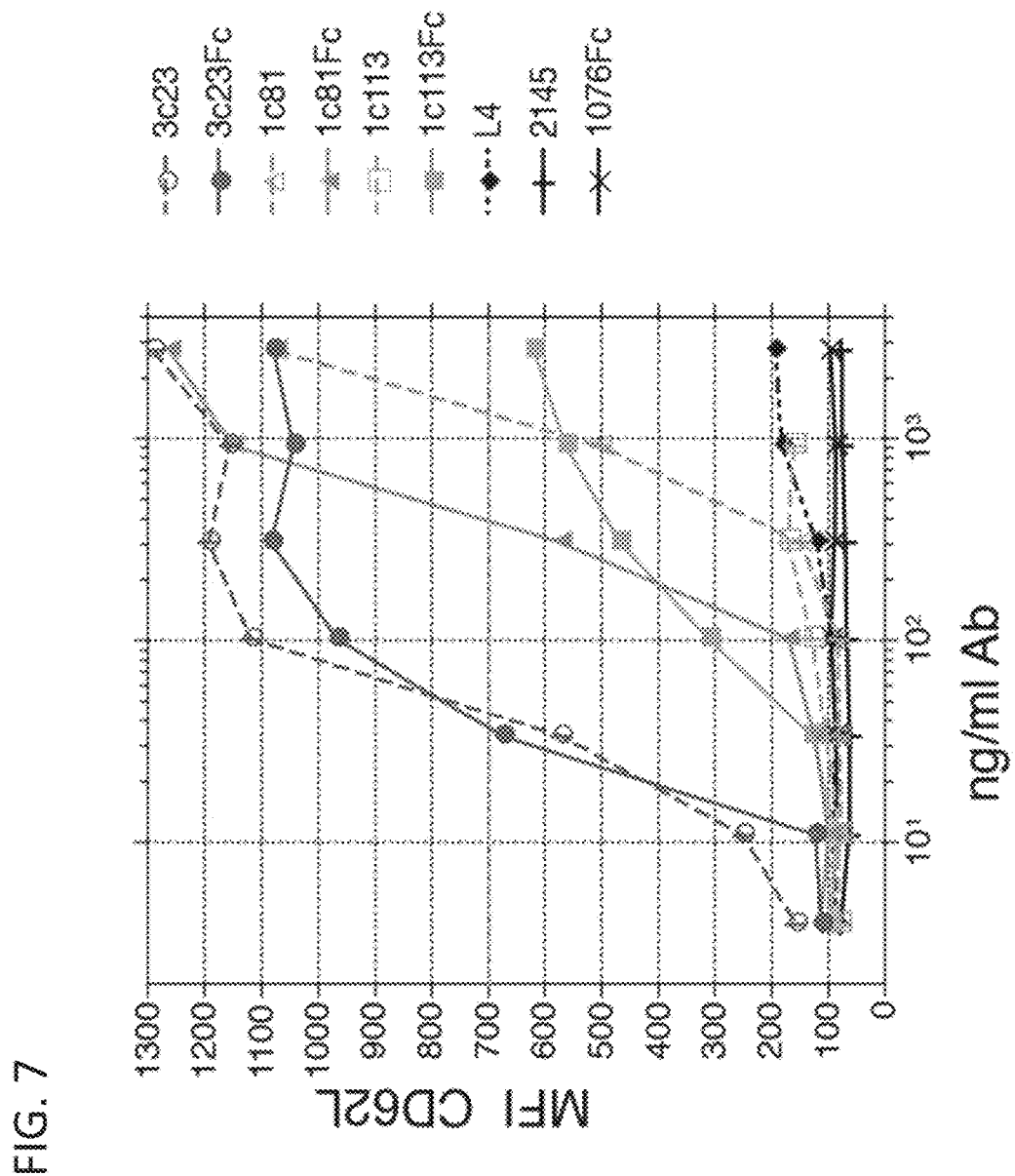

FIG. 7. Nbs 3c23 and 1c81 block ATP-induced shedding of CD62L in transfected HEK cells.

HEK cells were co-transfected with cDNA constructs for GFP, CD62L and hP2X7. 24 h post transfection, cells were harvested and pre-incubated for 15 min at RT in 80 µl of DMEM medium with the indicated Nbs, titrated in 1:3 dilution steps. Highest and lowest Nb concentrations were 2.8 µg/ml and 4 ng/ml. ATP was added to final concentration of 4 n/M. Cells were incubated for 60 min at 37° C. and then stained for CD62L before flow cytometry. Mean fluorescence intensity (MFI) for CD62L cell surface staining was calculated after gating on GFP+ cells. $IC_{50}$ values were calculated at half-maximal CD62L MFI (marked with dotted red line (see Table 3).

Figures 8A, 8B, 8C:
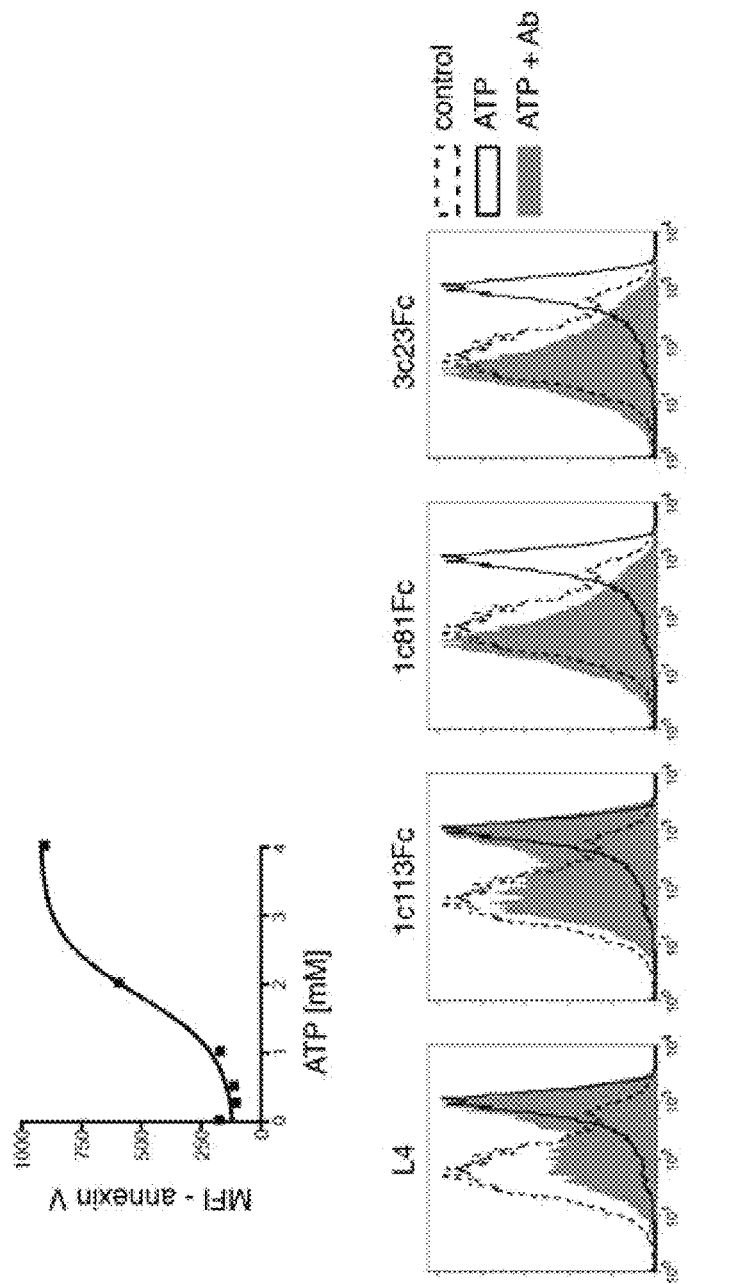

FIG. 8A-8C. Nanobodies 1c81 and 3c23 prevent ATP-induced externalization of phosphatidylserine by RPMI 8226 cells.

(FIG. 8A) P2X7 expression on RPMI 8226 cells was detected by staining $2 \times 10^5$ cells with a cocktail of Alexa647-conjugated 1c113-Fc and 3c23-Fc as in FIG. 5. Grey histograms=cells pre-incubated with excess unconjugated 1c113-Fc and 3c23-Fc, open histograms=cells preincubated with excess control 1067-Fc.

(FIG. 8B) Cells were incubated for 60 min at 37° C. with the indicated concentrations of ATP before staining for PS with APC-conjugated Annexin V.

(FIG. 8C). RPMI 8226 cells were pre-incubated with 0.5 µg of 1067-Fc, 1c113-Fc, 1c81-Fc, 3c23-Fc or mAb L4 for 15 min at room temperature, before addition of ATP to a final concentration of 0 (control) or 4 mM. Cells were further incubated at 37° C. for 60 min and washed once with Annexin V staining buffer prior to staining with APC-conjugated Annexin V. Cells were analysed by flow cytometry (FACS Canto II, BD).

Figure 9:
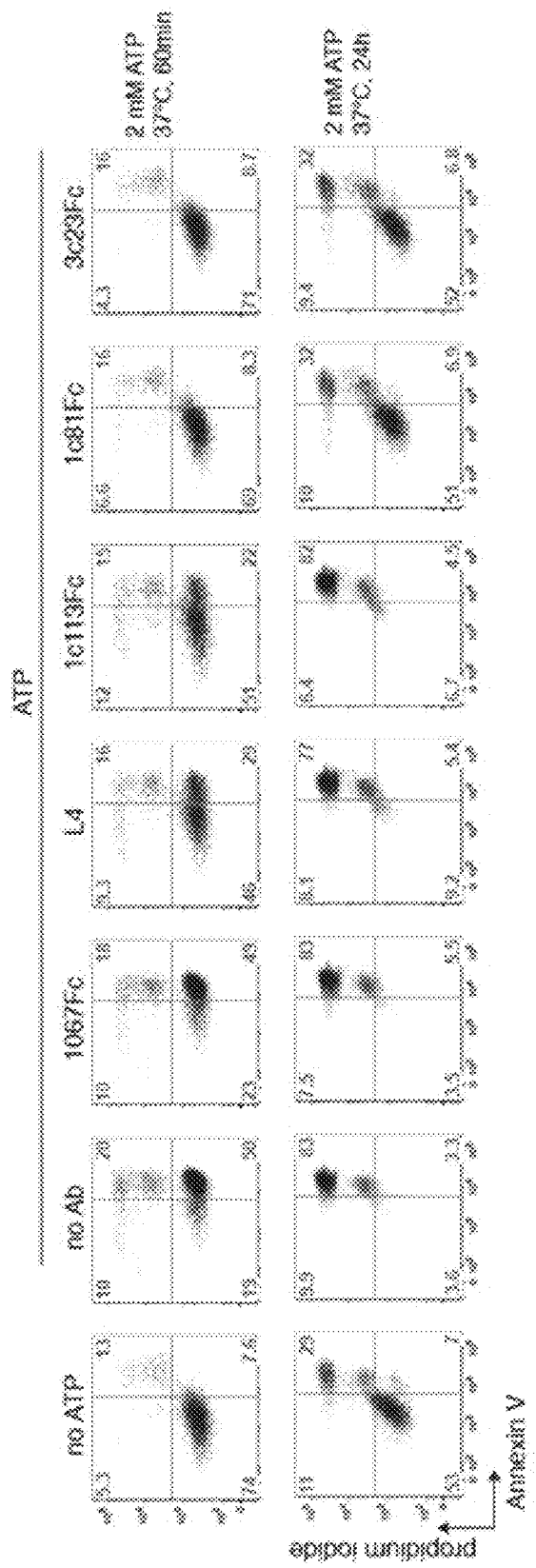

FIG. 9. Nbs 1c81 and 3c23 prevent P2X7-mediated cell death of RPMI 8226 cells.

RPMI 8226 cells ($5 \times 10^5$ cells in 150 µl medium) were pre-incubated with 900 ng of respective Fc fusion proteins or mAb L4 for 10 min at room temperature. 150 µl ATP of a 4 mM stock was added also to final ATP concentration of 2 mM (1:2 dilution) and final antibody concentration of 3 µg/ml. Cells were incubated at 37° C. for 60 min or 24 h, washed once in Annexin V staining buffer and stained for exposition of phosphatidylserine with APC-conjugated Annexin V and cell death with propidium iodide. Data collection was carried out by flow cytometry (FACS Canto II, BD).

Figure 10:
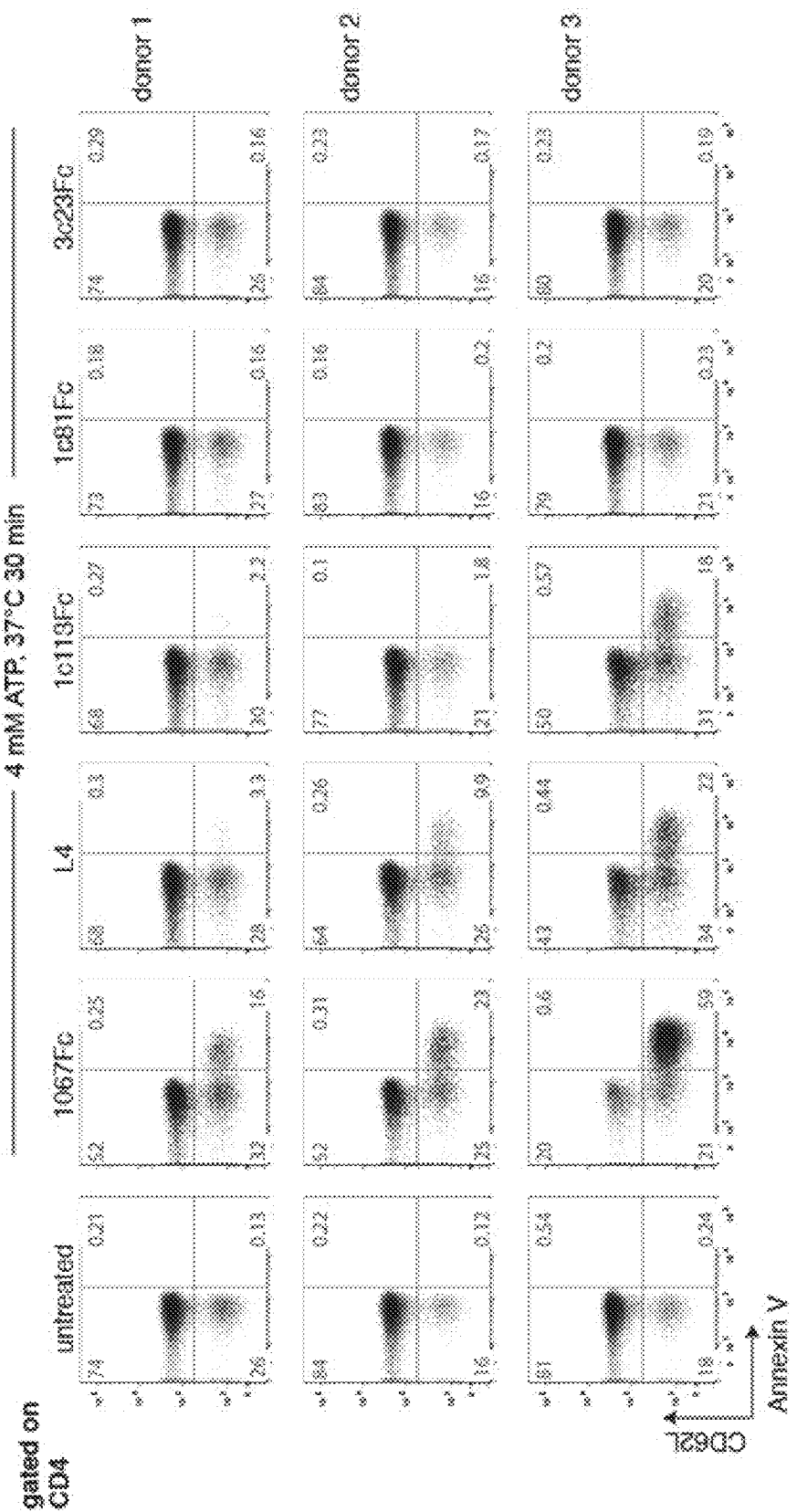

FIG. 10. Nbs 1c81 and 3c23 block ATP-induced externalization of PS and shedding of CD62L by human T cells.

100 µl aliquots of full blood from 3 donors were pre-incubated with 0.5 µg of 1067-Fc, 1c113-Fc, 1c81-Fc, 3c23-Fc or 1 µg of mAb L4 for 30-min at RT, before addition of 100 µl medium (untreated control) or an 8 mM ATP stock solution in complete medium. Cells were incubated at 37° C. for 30 min, washed once with Annexin V staining buffer, and stained with a mastermix of anti-CD62L FITC, Annexin V-APC, anti-CD4 APC/Cγ7, and anti-CD8 Pacific Blue for 60 min at RT. Erythrocytes were lysed by a 10 min incubation in 2 ml 1×BD Lysis solution. Cells were washed once with 1.5 ml Annexin V staining buffer and analysed by flow cytometry (FACS Canto II, BD). $CD4^+$ and $CD8^+$ T cells were gated sequentially as in FIG. 5 on the basis of low FSC and SSC, and staining for CD4 and CD8. Blood samples were from the same donors as those analyzed in FIG. 5.

Figure 11A:
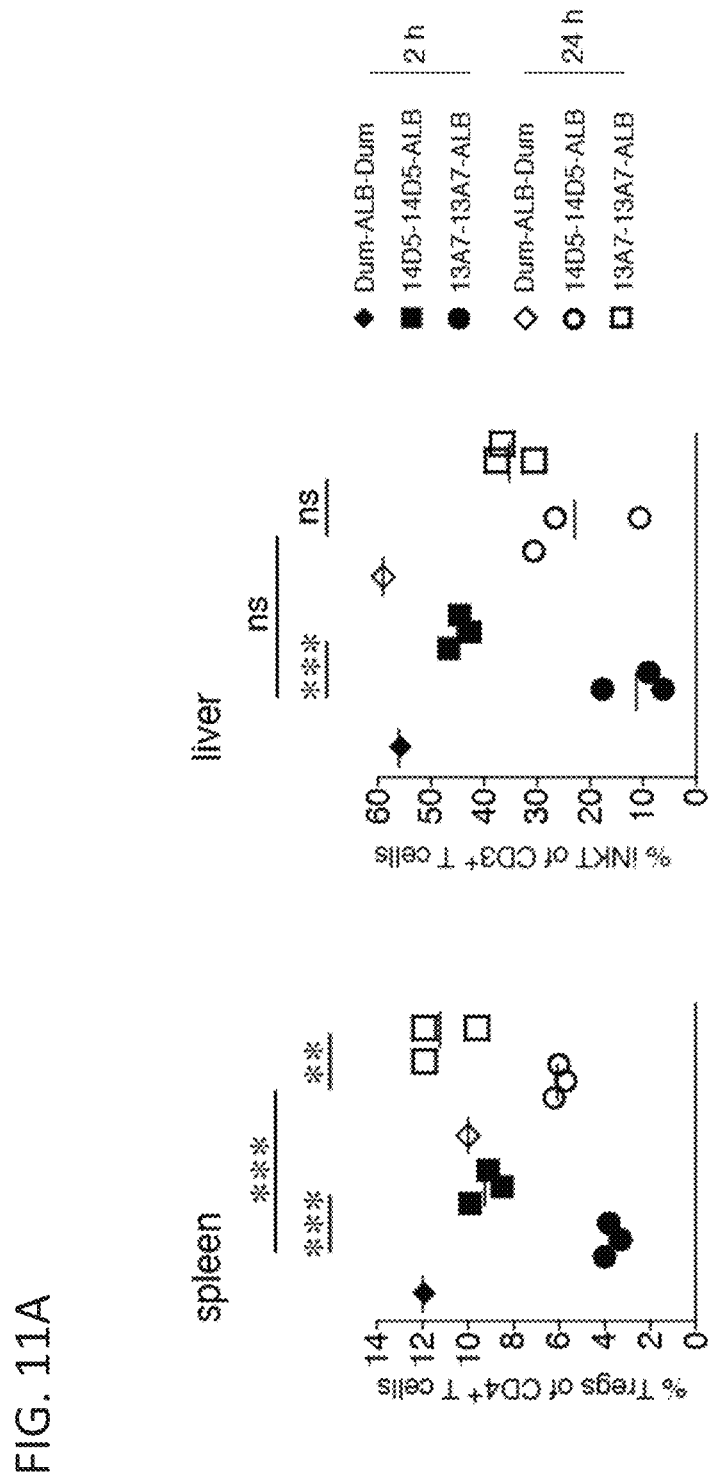
Figure 11B:
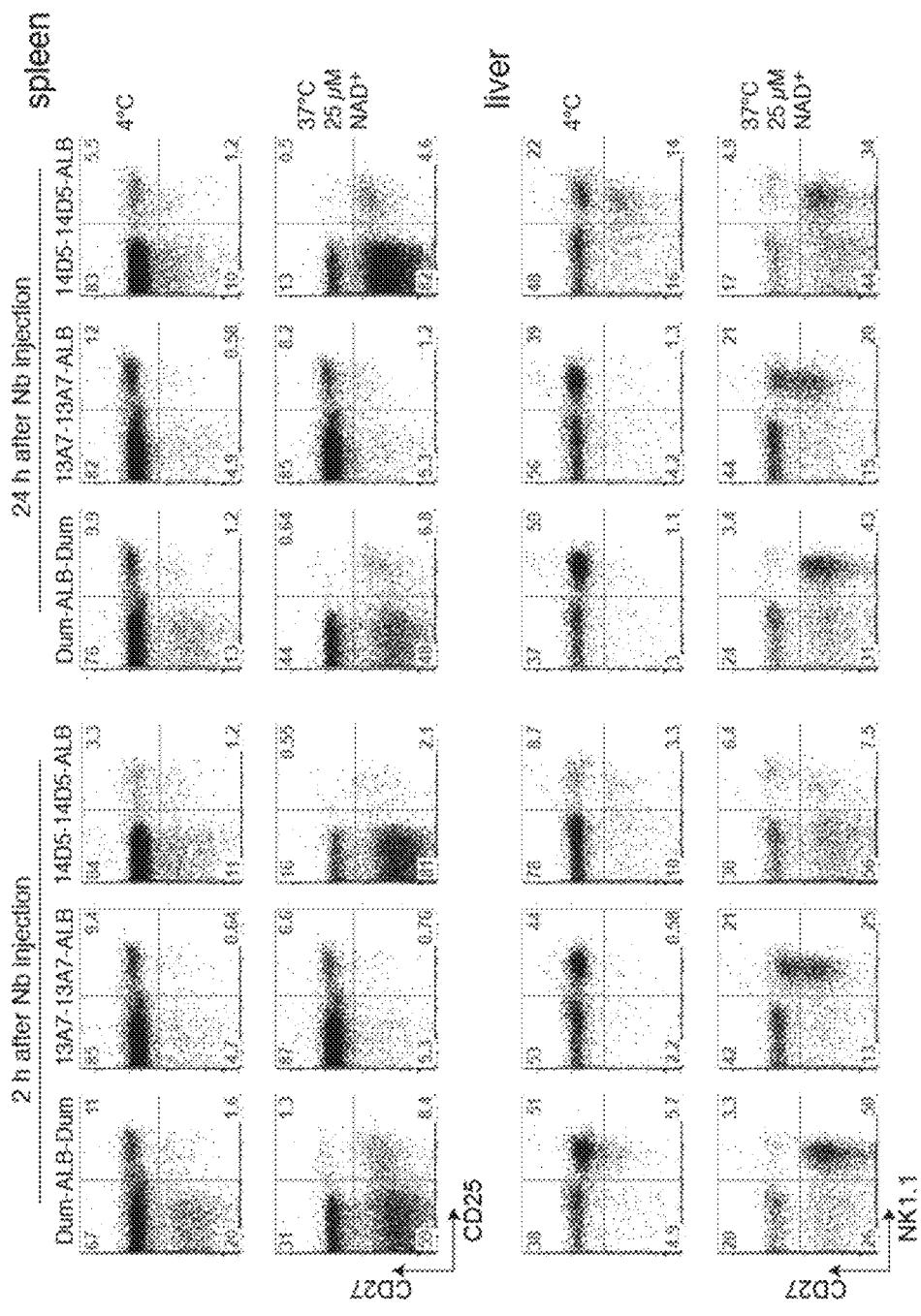
Figure 11C:
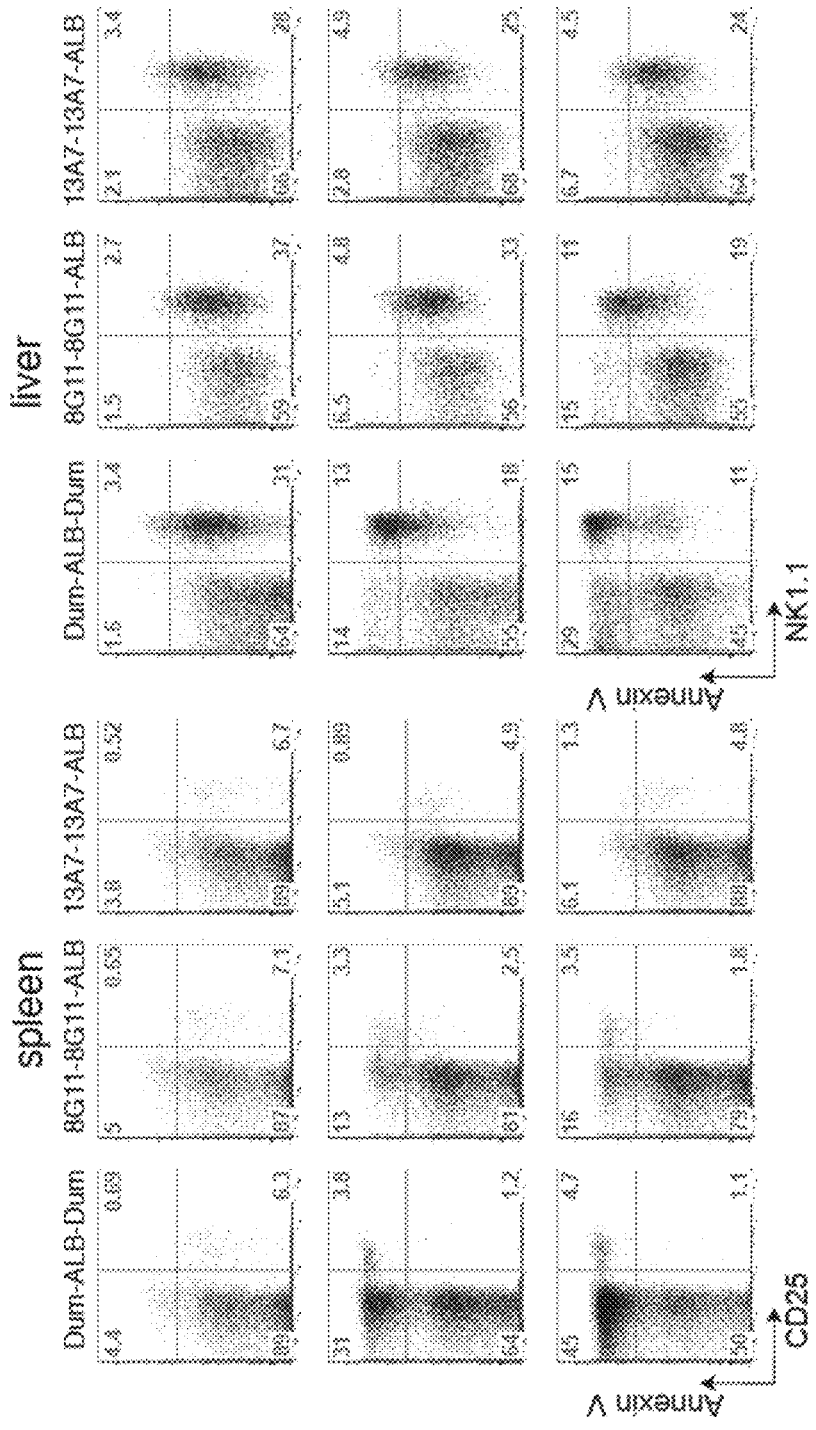

FIGS. 11A-11C. Kinetic analyses of in vivo blockade/enhancement of P2X7 by systemically injected HLE-Nbs (FIG. 11A) Splenocytes and liver cells were prepared 2 h and 24 h after i.v. injection of half-life extended Nbs (bi-specific for P2X7 and albumin) 13A7-13A7-Alb8 (20 µg), 14D5-14D5-Alb8 (100 µg), or a control Nb (100 µg). Cells were co-stained with antibodies against CD3, CD4, CD25, and NK1.1 and analyzed by flow cytometry. Frequencies of Tregs (percentage of CD4+ cells) and of iNKT cells (percentage of CD3+ cells) were calculated with the FlowJo software. P<0.01, *P<0.001 (two-tailed Student's t-test).

(FIG. 11B) Shedding of CD27 was monitored by co-staining with anti-CD27 following treatment of cells ex vivo with 25 µM NAD+, or solvent (sol) (spleen: gated on CD4+ cells; liver: gated on CD3+ cells).

(FIG. 11C) Cells were prepared 2 h after injection of half-life extended Nbs 13A7-13A7-Alb8, 8G11-8G11-Alb8, or a control Nb (200 µg i.v.) and were stained as in (a, b). Externalization of phosphatidylserine was monitored by co-staining with Annexin V following treatment of cells ex vivo with 250 µM ATP, 25 µM NAD+, or solvent (sol) (spleen: gated on CD4+ cells; liver: gated on CD3+ cells).

FIG. 12A-12F. Systemic administration of Nb 13A7 alleviates, of Nb 14D5 potentiates disease parameters in antibody-induced glomerulonephritis.

Time course of treatments in the model of antibody-induced nephritis. Groups of 6 week old C57BL6 mice (n=6) were injected i.v. with half-life extended Nbs 13A7-13A7-Alb8, 14D5-14D5-Alb8, or a control Nb (50 µg) 2 h before injection of anti-podocyte (AP) or pre-immune (P1) serum. Mice received additional injections of Nbs (25 µg) every 3 days. Three days after the last Nb injection, mice were sacrificed and kidneys and serum were subjected to further analyses.

(FIG. 12A) Albumin in urine was quantified by ELISA, creatinine levels were determined by automated measurement.

(FIG. 12B) On the day of sacrifice, blood urea nitrogen, serum triglycerides and serum cholesterol levels were determined by automated measurement; IL-6 in serum and MCP-1 in urine were quantified by ELISA. Significance was assessed with the Mann Whitney U test.

(FIG. 12C) Splenocytes were incubated in the absence (PBS) or presence of NAD+ for 30 min and then stained for CD4, CD25, and CD27 before FACS analyses. Gating was performed on CD4+CD25+ Tregs. Tregs from mice treated with the P2X7 agonistic Nb 14D5 contained a lower proportion of CD27+ T cells, all of which were sensitive to NAD+-induced loss of CD27; Tregs from mice treated with the P2X7 antagonistic Nb 13A7 were resistant to NAD+-induced shedding of CD27.

(FIG. 12D) Kidney sections were stained with PAS (top). Tubular protein casts are marked by asterisks.

(FIG. 12E) Kidney sections were stained with the DNA-staining dye draq5, a fluorochrome-conjugated mAb against the T cell marker CD3, and a fluorochrome-conjugated mAb against nephrin, a podocyte membrane protein at the renal filtration barrier (bottom). Podocyte nuclei are marked by asterisks. Kidney sections from mice treated with Nb 14D5 show stronger periglomerular infiltration of CD3+ T cells and disrupted staining for nephrin than mice treated with Nb 13A7 or the control Nb.

(FIG. 12F) Kidney sections were stained with draq5 and fluorochrome conjugated mAbs against nephrin, the complement factor 3 (C3), and IgG before immunofluorescence microscopy. Sections from mice treated with AP serum (but not from mice treated with PI serum) show glomerular deposits of IgG and 3. The pattern of IgG deposits is regular in mice treated with Nb 13A7, but is partially disrupted in mice treated with the control Nb and strongly disrupted in mice treated with Nb 14D5.

Figure 13A:
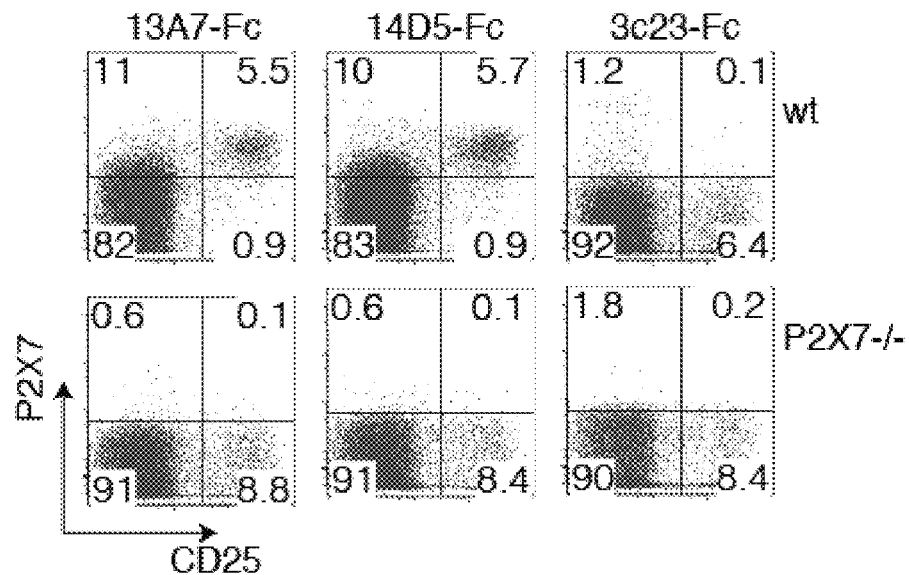
Figure 13B:
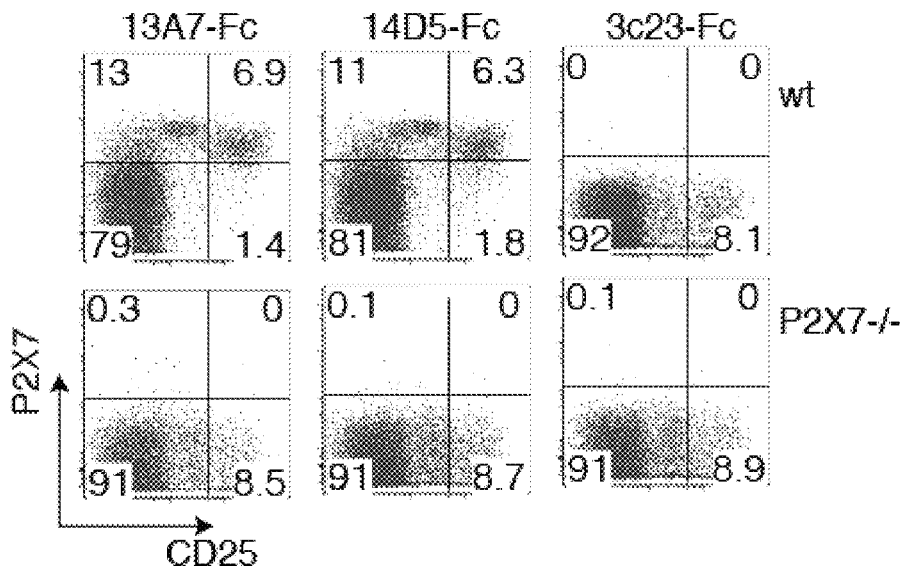
Figure 13C:
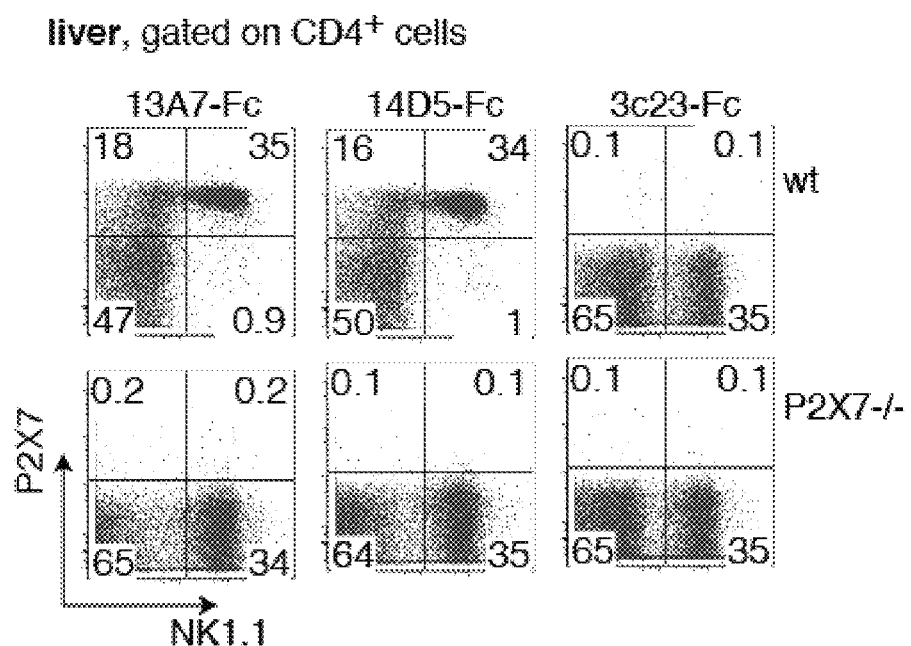

FIG. 13. Nb-Fc fusion proteins of Nbs 13A7 and 14D5 detect P2X7 on lymphocytes from lymph nodes, spleen and liver Lymphocytes from lymph nodes, spleen or liver of wild type and P2X7−/− mice were co-stained with fluorochrome-conjugated mouse P2X7-specific 13A7-Fc, 14D5-Fc or human P2X7-specific 3c23-Fc (negative control) and with antibodies against CD4, CD25, and NK1.1 before flow cytometry.

Figure 14:
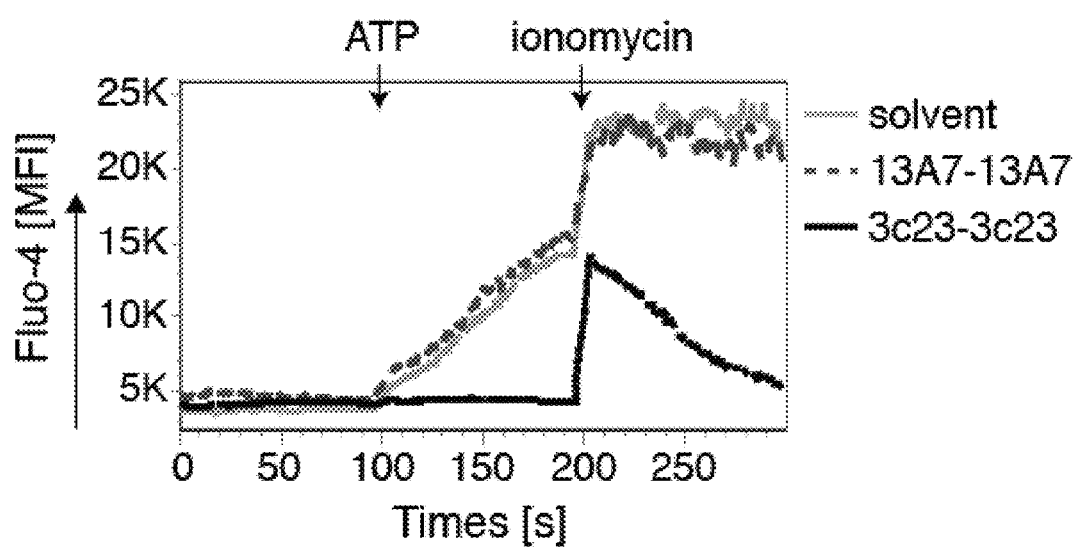

FIG. 14. Nb 3c23 blocks ATP-induced Calcium influx in human RPMI 8226 lymphoma cells RPMI 8226 cells were loaded with the $Ca^{2+}$ indicator Fluo-4. Real time flow cytometry analyses were performed (BD FACS Canto). Cells were washed and resuspended in PBS supplemented with $Ca^{2+}$ and $Mg^{2+}$ (Invitrogen) in the absence (solvent) or presence of the human P2X7-specific Nb 3c23-3c23 or mouse P2X7-specific Nb 13A7-13A7 (negative control) and analyzed by flow cytometry (BD FACS-Canto). An infrared lamp was used to maintain a constant sample temperature of 37° C. After equilibration for 100 sec, ATP was added to a final concentration of 2 mM and incubation was continued for 100 sec before addition of ionomycin to a final concentration of 5 µM.

Figure 15:
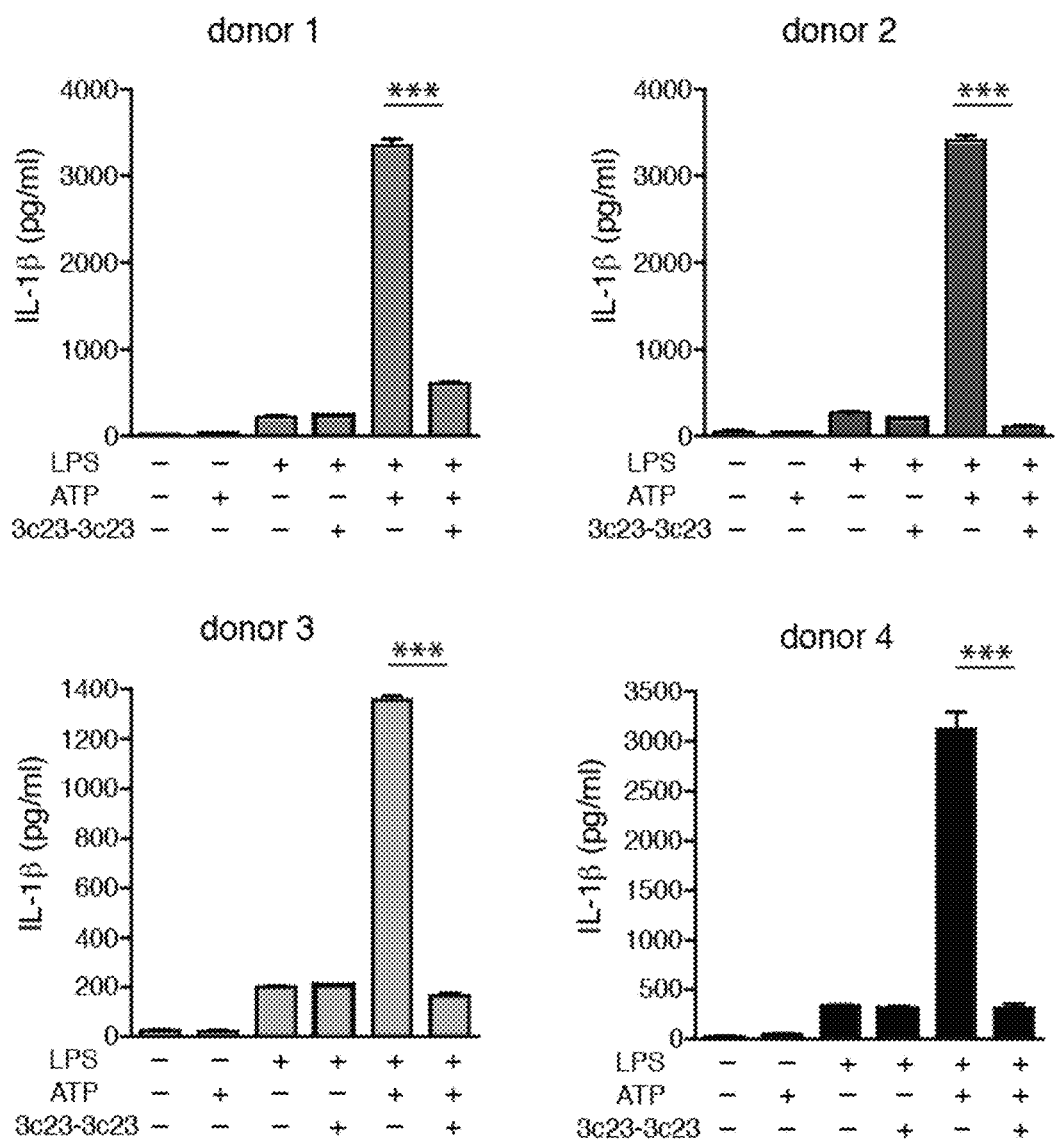

FIG. 15. Nb 3c23 blocks ATP-induced release of IL-1β from human blood cells.

Aliquots of heparinized whole blood from four donors were incubated in the absence or presence of Nb 3c23-3c23 for 2 h with LPS (1 µg/ml) before addition of ATP to a final concentration of 5 mM and further incubation for 1 h at 37° C. Plasma was prepared by centrifugation of samples and IL-1β levels in plasma were determined by ELISA (R&D Systems). ***P<0.001 (One-way ANOVA).

Figure 16:
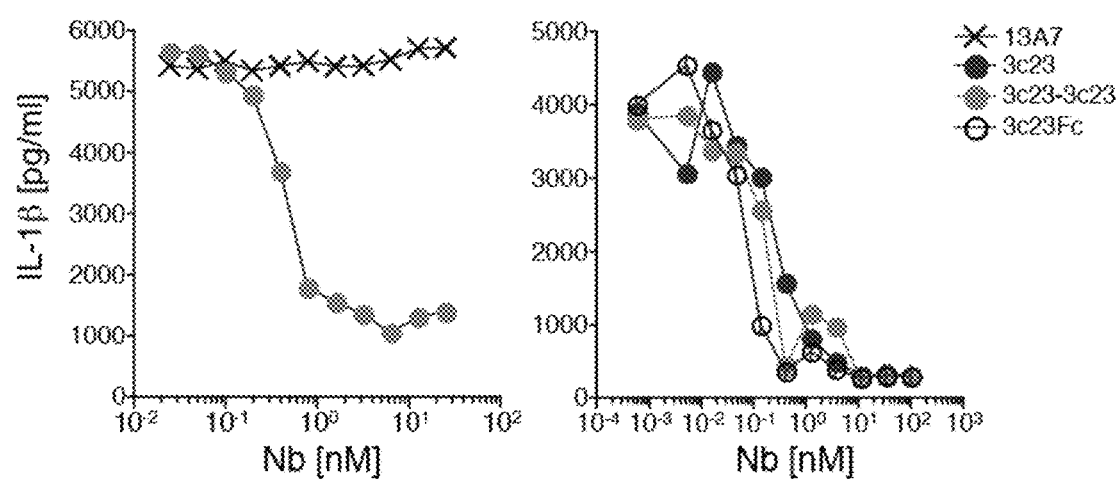

FIG. 16. Dose response analysis of Nb 3c23 blocking ATP-induced release of IL-1β from human blood cells.

Aliquots of heparinized whole blood were incubated in the absence or presence of the indicated concentrations of Nb 3c23, 3c23-3c23, and 3c23Fc for 2 h with LPS (1 µg/ml) before addition of ATP to a final concentration of 2 mM and further incubation for 1 h at 37° C. Plasma was prepared by centrifugation of cells and IL-1β levels in plasma were determined by ELISA (R&D Systems). Mouse P2X7-specific Nb 13A7 was used as a negative control.

Figure 17:
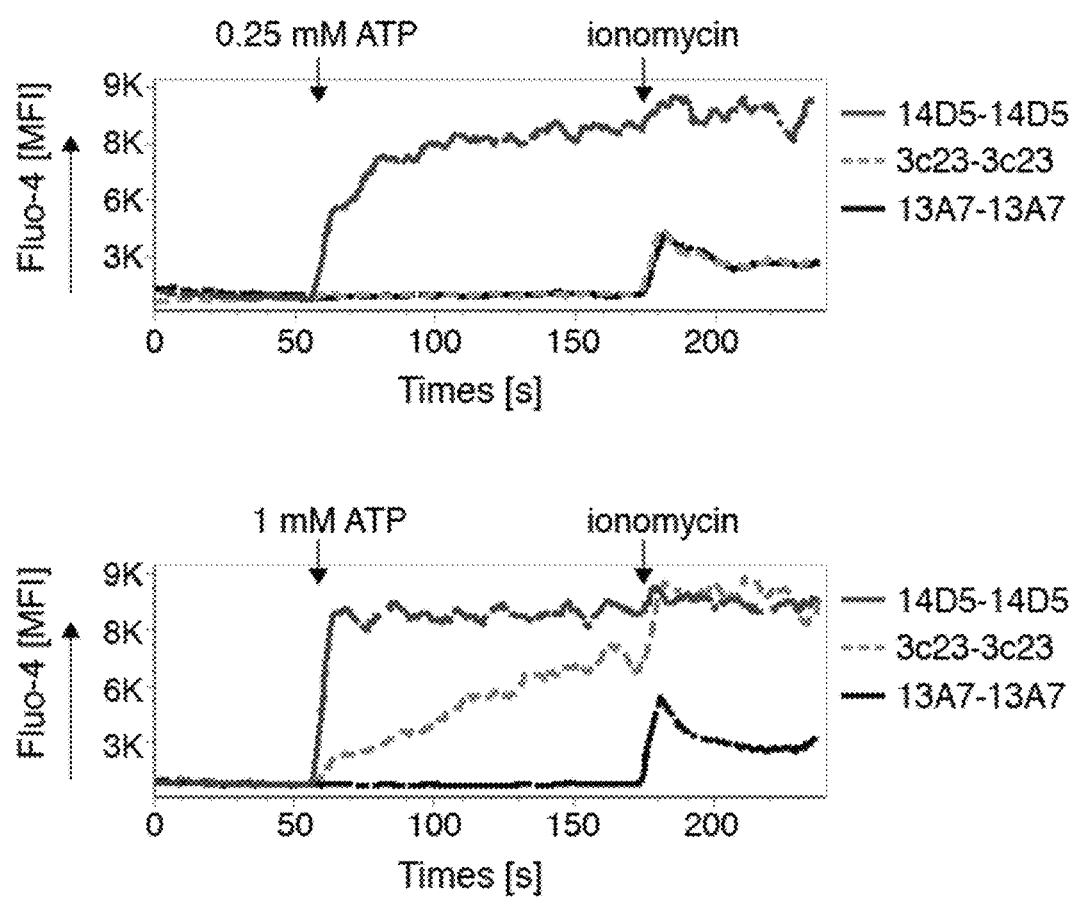

FIG. 17. Nb 13A7 blocks, Nb 14D5 potentiates ATP-induced calcium influx in HEK cells stably transfected with mouse P2X7

Real time flow cytometry analyses of mouse-P2X7 transfected HEK cells loaded with the $Ca^{2+}$ indicator Fluo-4 in the presence of the mouse P2X7-specific Nb 14D5-14D5, Nb 13A7-13A7 or human P2X7-specific Nb 3c23-3c23 (negative control) at a concentration of 1 µg/ml Nb. After equilibration for 60 sec, cells were exposed to extracellular ATP to a final concentration of 250 µM or 1 mM and, two minutes later, to the $Ca^{2+}$ ionophore ionomycin at a concentration of 5 µM. An infrared lamp was used to maintain a constant sample temperature of 37° C.

Figure 18:
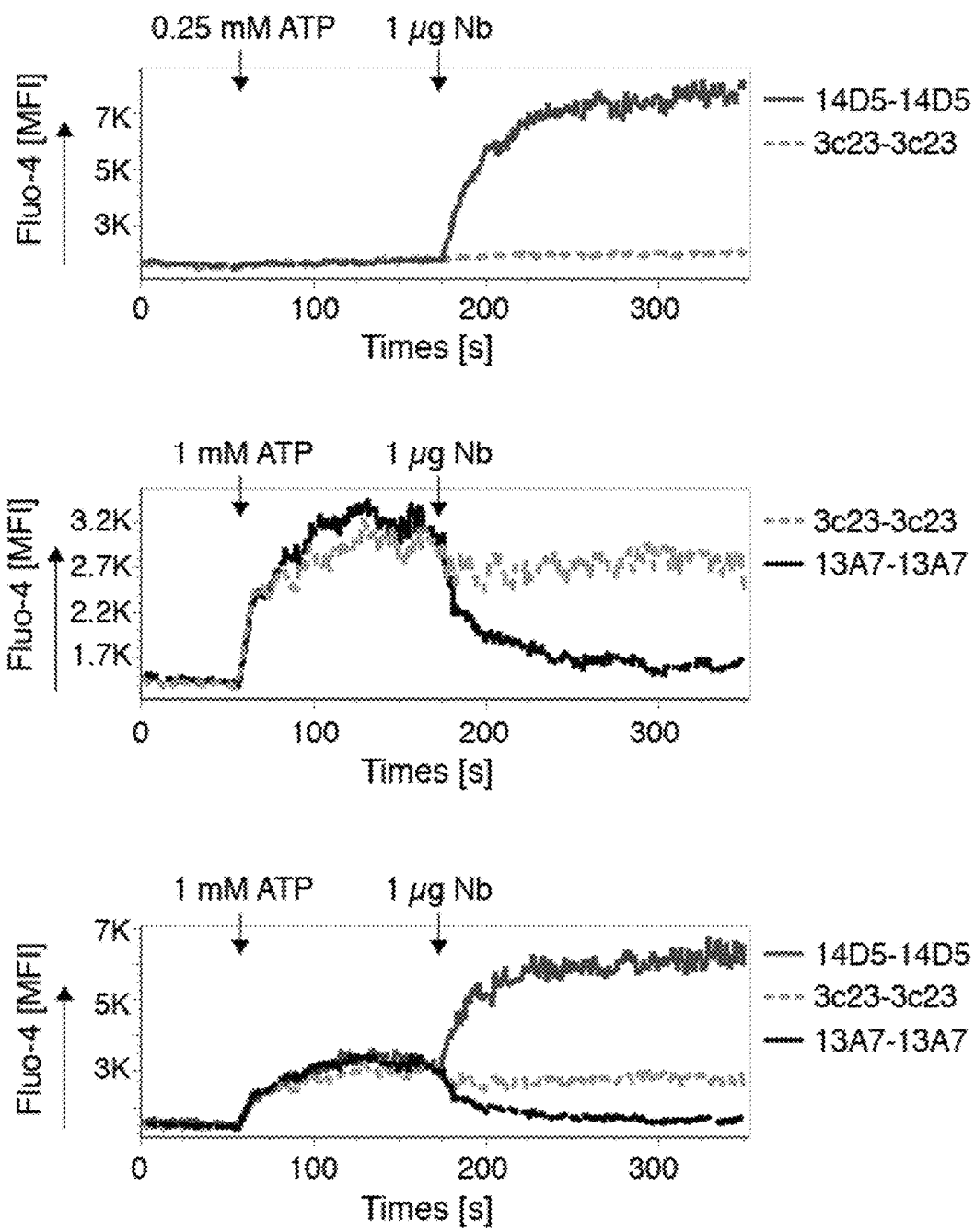

FIG. 18. Nb 13A7 reverses, Nb 14D5 induces and potentiates ATP-mediated calcium influx in HEK cells stably transfected with mouse P2X7

Real time flow cytometry analyses of mouse-P2X7 transfected HEK cells loaded with the $Ca^{2+}$ indicator Fluo-4. After equilibration for 60 sec, cells were incubated with indicated concentrations of ATP for two minutes before treatment with mouse P2X7-specific Nb 14D5-14D5, Nb 13A7-13A7 or the human P2X7-specific Nb 3c23-3c23 to a final concentration of 2 µg/ml Nb. An infrared lamp was used to maintain a constant sample temperature of 37° C.

Figure 19:
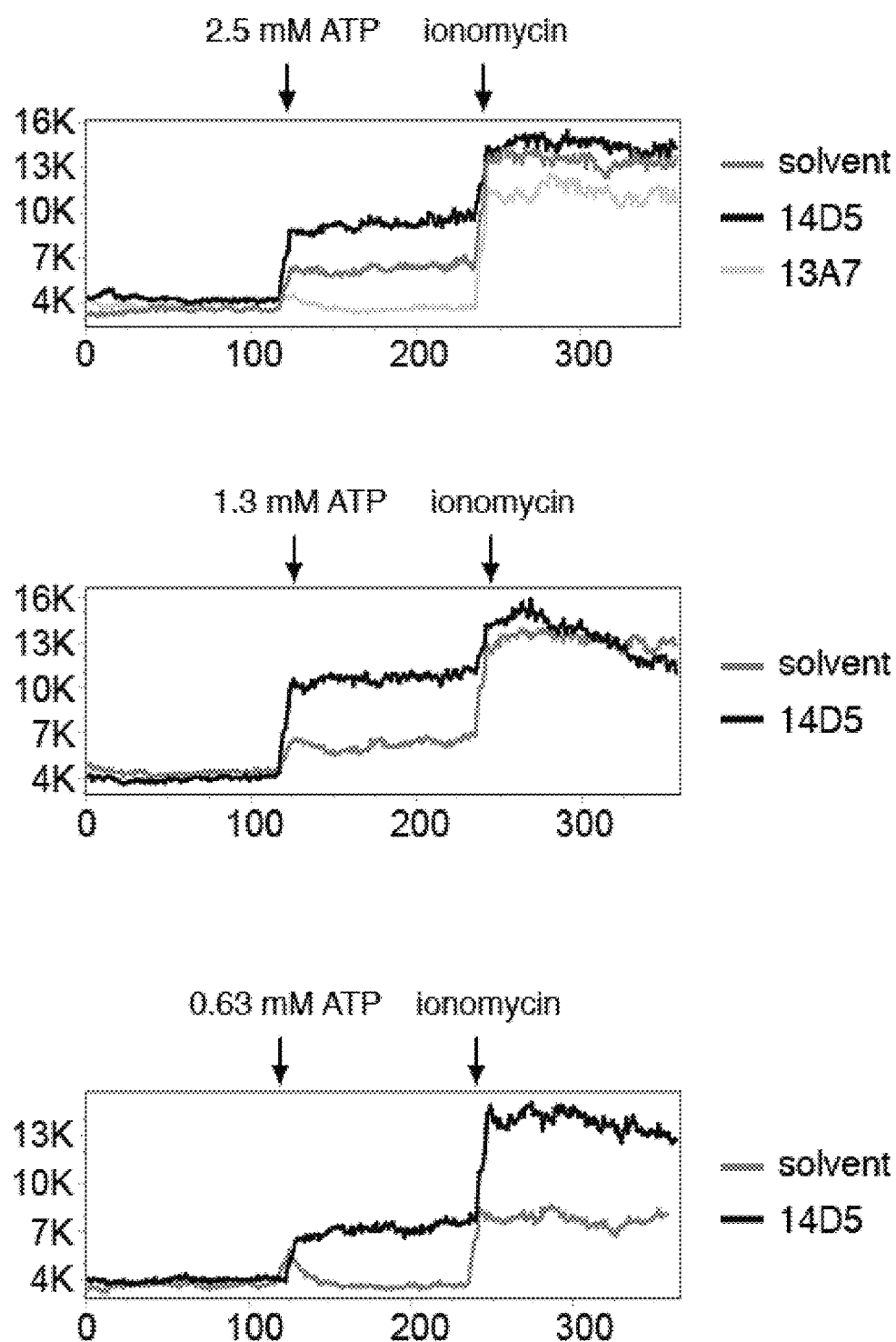

FIG. 19. Nb 13A7 blocks, Nb 14D5 potentiates ATP-induced Calcium influx in mouse peritoneal macrophages Mouse peritoneal macrophages were loaded with the $Ca^{2+}$ indicator Fluo-4. Real time flow cytometry analyses were performed (BD FACS Canto). Cells were washed and resuspended in PBS supplemented with $Ca^{2+}$ and $Mg^{2+}$ (Invitrogen) in the absence (solvent) or presence of the P2X7-potentiating Nb 14D5 or the P2X7-antagonizing Nb 13A7 (1 µg/500 µl). An infrared lamp was used to maintain a constant sample temperature of 37° C. After equilibration for 120 sec, cells were exposed to the indicated concentrations of extracellular ATP and two minutes later to the $Ca^{2+}$ ionophore ionomycin to a final concentration of 1 µM.

FIG. 20A-20B. Nb 13A7 blocks, Nb 14D5 potentiates the processing and secretion of IL-1β by peritoneal macrophages Heparinized blood from wildtype or P2X7−/− mice as incubated in the presence of monovalent Nbs (1 µg/200 µl) 14D5, 13A7, or solvent for 2 h with LPS (1 µg/ml) before addition of ATP to the indicated final concentrations and further incubation for 30 min at 37° C.

(FIG. 20A) Samples were centrifuged and IL-1β levels in plasma were analyzed by ELISA (Biolegend).

(FIG. 20b) Erythrocytes were lysed and blood leukocytes were stained in two steps, first with fluorochrome-conjugated mAbs specific for CD11b, Ly-6C, and Ly-6G. Cells were then fixed (2% PFA) and permeabilized (PBS containing 0.3% saponin and 0.1% BSA) before further staining for pro-IL-1β (e-Bioscience). Flow cytometry analyses were performed (BD FACS Canto) and gating was performed on CD11b+Ly-6C$^{hi}$ monocytes.

Figure 21A:
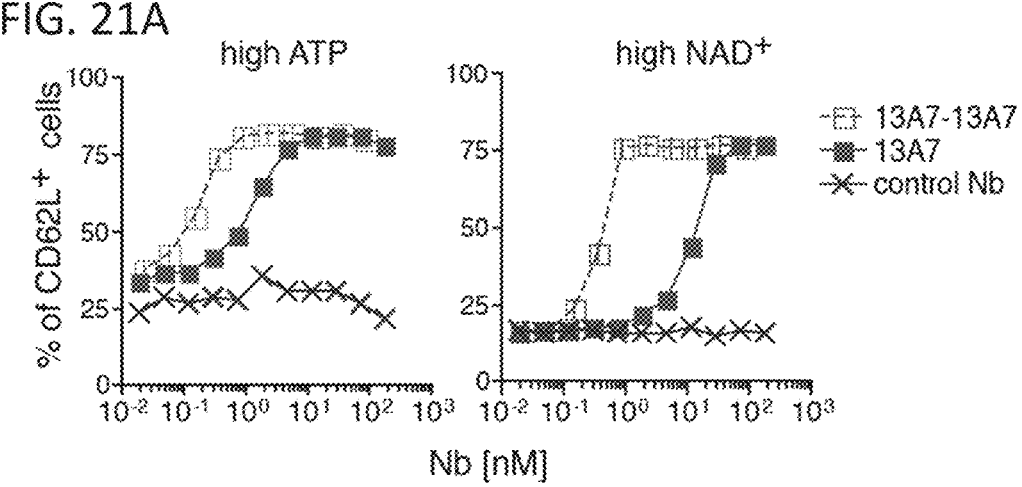
Figure 21B:
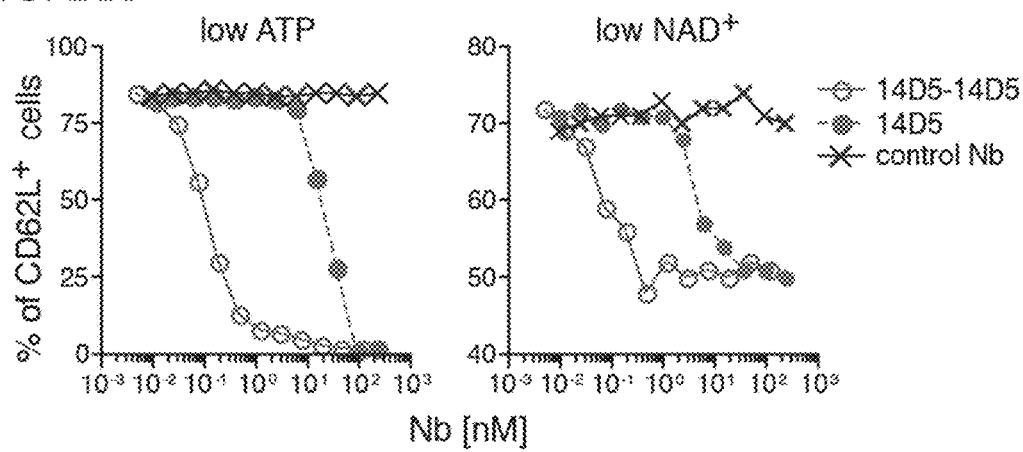

FIGS. 21A-21B. Nb 13A7 blocks, Nb14D5 potentiates shedding of CD62L by Yac-1 murine lymphoma cells in response to extracellular ATP or NAD$^+$ Cell surface expression of CD62L on mouse Yac-1 lymphoma cells was monitored by flow cytometry following treatment of cells for 20 min at 37° C. with ATP or NAD$^+$ in the presence of 13A7 (a), 14D5 (b), or a control Nip. The concentrations of ATP and NAD$^+$ used were above (a) and below (b) the threshold for activation of P2X7 in these cells (100 µM and 20 µM in (a) and 30 µM and 1.5 µM in (b), respectively).

Figure 22:
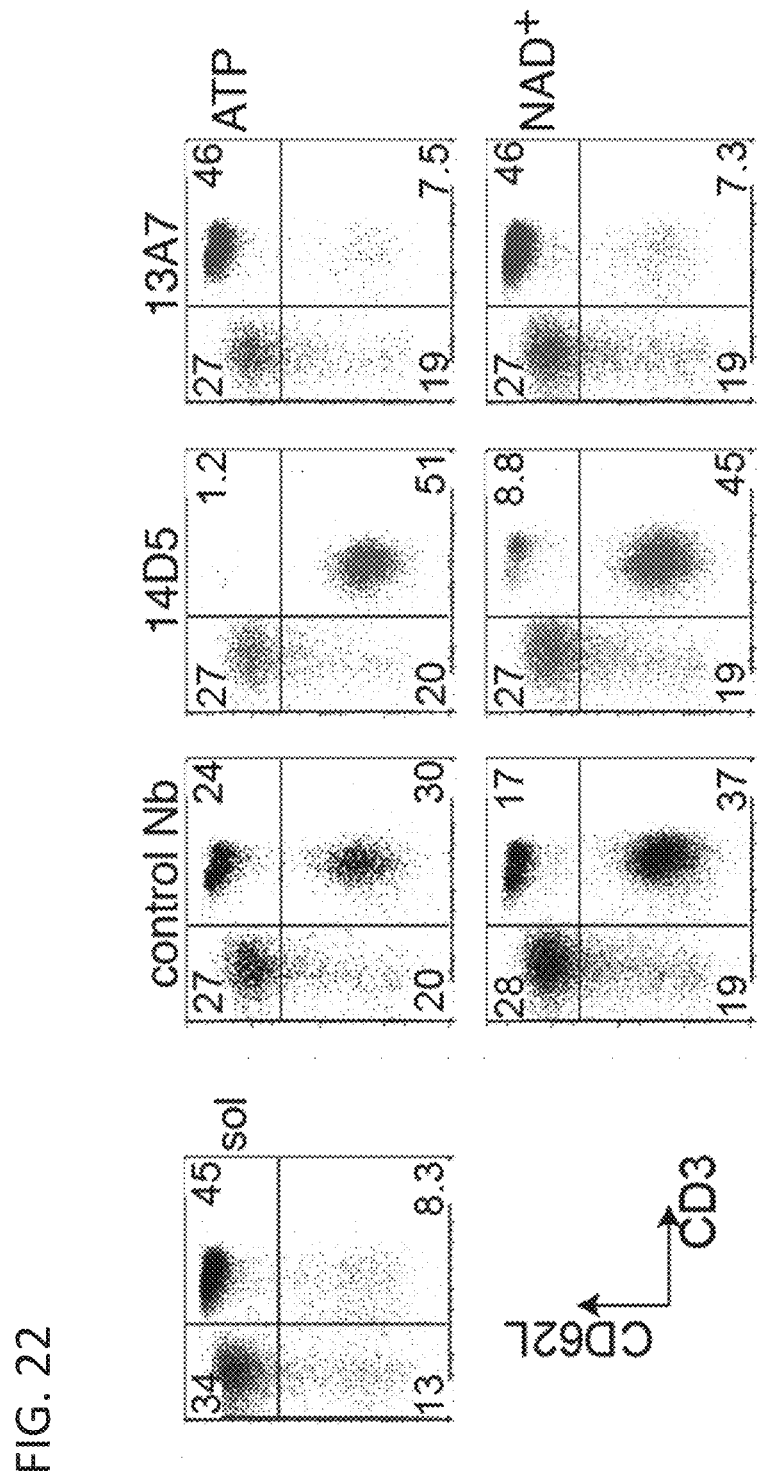

FIG. 22, Nb 13A7 blocks, Nb14D5 potentiates shedding of CD62L by primary mouse T cells in response to extracellular ATP or NAD$^+$ Flow cytometry analyses of splenocytes treated for 20 min at 37° C. with 200 µM ATP or 50 µM NAD$^+$ in the presence of 14D5, 13A7, or a control Nb before staining for CD3 and CD62L. Control cells were incubated in solvent (sol) at 4° C. in the absence of ATP or NAD.

DETAILED DESCRIPTION

Immunoglobulin sequences, such as antibodies and antigen binding fragments derived there from (e.g. immunoglobulin single variable domains) are used to specifically target their respective antigens in research and therapeutic applications. The generation of immunoglobulin single variable domains such as e.g., VHHs may involve the immunization of an experimental animal such as a Llama, construction of phage libraries from immune tissue, selection of phage displaying antigen binding immunoglobulin single variable domains and screening of said domains and engineered constructs thereof for the desired specificities (WO 9404678). Alternatively, similar immunoglobulin single variable domains such as e.g. dAbs can be generated by selecting phage displaying antigen binding immunoglobulin single variable domains directly from naive or synthetic libraries and subsequent screening of said domains and engineered constructs thereof for the desired specificities (Ward et al., Nature, 1989, 341: 544-6; Holt et al., Trends Biotechnol., 2003, 21(11):484-490; as well as for example WO 06/030220, WO 06/003388 and other published patent applications of Domantis Ltd.). Unfortunately, the use of monoclonal and/or heavily engineered antibodies also carries a high manufacturing cost and may result in suboptimal tumor penetration compared to other strategies.

The present invention relates to particular polypeptides, also referred to as "polypeptides of the invention" or "immunoglobulin single variable domain of the invention" or "ISV of the invention" that comprise or, more preferably, essentially consist of (i) a first building block consisting essentially of one immunoglobulin single variable domain, wherein said immunoglobulin single variable domain is directed against P2X7 and in particular against human P2X7; (ii) optionally a second building block consisting essentially of or comprising an immunoglobulin single variable domain, wherein said immunoglobulin single variable domain is directed against P2X7 and in particular against human P2X7; and (iii) optionally a third building block, comprising or consisting essentially of an immunoglobulin single variable domain, wherein said immunoglobulin single variable domain is directed against serum albumin and in particular against human serum albumin (and even more preferably wherein said immunoglobulin single variable domain is Alb8 or Alb11 (as herein defined)). Furthermore, the invention also relates to nucleic acids encoding such polypeptides; to methods for preparing such polypeptides; to host cells expressing or capable of expressing such polypeptides; to compositions and in particular to pharmaceutical compositions that comprise such polypeptides, nucleic acids and/or host cells; and to uses of such polypeptides, nucleic acids, host cells and/or compositions for prophylactic, therapeutic or diagnostic purposes. Other aspects, embodiments, advantages and applications of the invention will become clear from the further description herein.

In this study, various anti-P2X7 Nanobodies were developed and characterized for their potential in diagnosis and therapy of inflammatory diseases, including nephritis.

Definitions

Unless indicated or defined otherwise, all terms used have their usual meaning in the art, which will be clear to the skilled person. Reference is for example made to the standard handbooks, such as Sambrook et al. (Molecular Cloning; A Laboratory Manual (2nd Ed.) Vols. 1-3, Cold Spring Harbor Laboratory Press, 1989), F. Ausubel et al, (Current protocols in molecular biology, Green Publishing and Wiley Interscience, New York, 1987), Lewin (Genes II, John Wiley & Sons, New York, N.Y., 1985), Old et al. (Principles of Gene Manipulation: An Introduction to Genetic Engineering (2nd edition) University of California Press, Berkeley, Calif., 1981); Roitt et al, (Immunology (6th. Ed.) Mosby/Elsevier, Edinburgh, 2001), Roitt et al. (Roitt's Essential Immunology (10$^{th}$ Ed.) Blackwell Publishing, UK, 2001), and Janeway et al, (Immunobiology (6th Ed.) Garland Science Publishing/Churchill Livingstone, N.Y., 2005), as well as to the general background art cited herein.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta (Adv. Drug Deilv. Rev, 58 (5-6): 640-56, 2006), Levin and Weiss (Mol. Biosyst, 2(1): 49-57, 2006), Irving et al. (J. Immunol. Methods 248(1-2): 31-45, 2001), Schmitz et al, (Placenta 21 Suppl. A: 5106-12, 2000), Gonzales et al. (Tumour Biol. 26(1): 31-43, 2005), which describe techniques for protein engineering, such as affinity maturation and other techniques for improving the specificity and other desired properties of proteins such as immunoglobulins.

The term "sequence" as used herein (for example in terms like "immunoglobulin sequence", "antibody sequence", "variable domain sequence", "$V_{HH}$ sequence" or "protein sequence"), should generally be understood to include both the relevant amino acid sequence as well as nucleic acids or nucleotide sequences encoding the same, unless the context requires a more limited interpretation.

Amino acid residues will be indicated according to the standard three-letter or one-letter amino acid code. Reference is made to Table A-2 on page 48 of WO 08/020079.

A nucleic acid or amino acid is considered to be "(in) (essentially) isolated (form)"—for example, compared to the reaction medium or cultivation medium from which it has been obtained—when it has been separated from at least one other component with which it is usually associated in said source or medium, such as another nucleic acid, another protein/polypeptide, another biological component or macromolecule or at least one contaminant, impurity or minor component. In particular, a nucleic acid or amino acid is considered "(essentially) isolated" when it has been purified at least 2-fold, in particular at least 10-fold, more in particular at least 100-fold, and up to 1000-fold or more. A nucleic acid or amino acid that is "in (essentially) isolated form" is preferably essentially homogeneous, as determined using a suitable technique, such as a suitable chromatographical technique, such as polyacrylamide-gel electrophoresis.

When a nucleotide sequence or amino acid sequence is said to "comprise" another nucleotide sequence or amino acid sequence, respectively, or to "essentially consist of" another nucleotide sequence or amino acid sequence, this may mean that the latter nucleotide sequence or amino acid sequence has been incorporated into the first mentioned nucleotide sequence or amino acid sequence, respectively, but more usually this generally means that the first mentioned nucleotide sequence or amino acid sequence comprises within its sequence a stretch of nucleotides or amino acid residues, respectively, that has the same nucleotide sequence or amino acid sequence, respectively, as the latter sequence, irrespective of how the first mentioned sequence has actually been generated or obtained (which may for example be by any suitable method described herein). By means of a non-limiting example, when a polypeptide of the invention is said to comprise an immunoglobulin single variable domain, this may mean that said immunoglobulin single variable domain sequence has been incorporated into the sequence of the polypeptide of the invention, but more usually this generally means that the polypeptide of the invention contains within its sequence the sequence of the immunoglobulin single variable domains irrespective of how said polypeptide of the invention has been generated or obtained. Also, when a nucleic acid or nucleotide sequence is said to comprise another nucleotide sequence, the first mentioned nucleic acid or nucleotide sequence is preferably such that, when it is expressed into an expression product (e.g., a polypeptide), the amino acid sequence encoded by the latter nucleotide sequence forms part of said expression product (in other words, that the latter nucleotide sequence is in the same reading frame as the first mentioned, larger nucleic acid or nucleotide sequence).

By "essentially consist of" is meant that the immunoglobulin single variable domain used in the method of the invention either is exactly the same as the polypeptide of the invention or corresponds to the polypeptide of the invention which has a limited number of amino acid residues, such as 1-20 amino acid residues, for example 1-10 amino acid residues and preferably 1-6 amino acid residues, such as 1, 2, 3, 4, 5 or 6 amino acid residues, added at the amino terminal end, at the carboxy terminal end, or at both the amino terminal end and the carboxy terminal end of the immunoglobulin single variable domain.

For the purposes of comparing two or more nucleotide sequences, the percentage of "sequence identity" between a first nucleotide sequence and a second nucleotide sequence may be calculated by dividing [the number of nucleotides in the first nucleotide sequence that are identical to the nucleotides at the corresponding positions in the second nucleotide sequence] by [the total number of nucleotides in the first nucleotide sequence] and multiplying by [100%], in which each deletion, insertion, substitution or addition of a nucleotide in the second nucleotide sequence—compared to the first nucleotide sequence—is considered as a difference at a single nucleotide (position). Alternatively, the degree of sequence identity between two or more nucleotide sequences may be calculated using a known computer algorithm for sequence alignment such as NCBI Blast v2.0, using standard settings. Some other techniques, computer algorithms and settings for determining the degree of sequence identity are for example described in WO 04/037999, EP 0967284, EP 1085089, WO 00/55318, WO 00/78972, WO 98/49185 and GB 2357768. Usually, for the purpose of determining the percentage of "sequence identity" between two nucleotide sequences in accordance with the calculation method outlined hereinabove, the nucleotide sequence with the greatest number of nucleotides will be taken as the "first" nucleotide sequence, and the other nucleotide sequence will be taken as the "second" nucleotide sequence.

For the purposes of comparing two or more amino acid sequences, the percentage of "sequence identity" between a first amino acid sequence and a second amino acid sequence (also referred to herein as "amino acid identity") may be calculated by dividing [the number of amino acid residues in the first amino acid sequence that are identical to the amino acid residues at the corresponding positions in the second amino acid sequence] by [the total number of amino acid residues in the first amino acid sequence] and multiplying by [100%], in which each deletion, insertion, substitution or addition of an amino acid residue in the second amino acid sequence—compared to the first amino acid sequence—is considered as a difference at a single amino acid residue (position), i.e. as an "amino acid difference" as defined herein. Alternatively, the degree of sequence identity between two amino acid sequences may be calculated using a known computer algorithm, such as those mentioned above for determining the degree of sequence identity for nucleotide sequences, again using standard settings. Usually, for the purpose of determining the percentage of "sequence identity" between two amino acid sequences in accordance with the calculation method outlined hereinabove, the amino acid sequence with the greatest number of amino acid residues will be taken as the "first" amino acid sequence, and the other amino acid sequence will be taken as the "second" amino acid sequence.

Also, in determining the degree of sequence identity between two amino acid sequences, the skilled person may take into account so-called "conservative" amino acid substitutions, which can generally be described as amino acid substitutions in which an amino acid residue is replaced with another amino acid residue of similar chemical structure and which has little or essentially no influence on the function, activity or other biological properties of the polypeptide. Such conservative amino acid substitutions are well known in the art, for example from WO 04/037999, GB 335768, WO 98/49185, WO 00/46383 and WO 01/09300; and (preferred) types and/or combinations of such substitutions may be selected on the basis of the pertinent teachings from WO 04/037999 as well as WO 98/49185 and from the further references cited therein.

Such conservative substitutions preferably are substitutions in which one amino acid within the following groups (a)-(e) is substituted by another amino acid residue within the same group: (a) small aliphatic, nonpolar or slightly polar residues: Ala, Ser, Thr, Pro and Gly; (b) polar, negatively charged residues and their (uncharged) amides: Asp, Asn, Glu and Gln; (c) polar, positively charged residues: His, Arg and Lys; (d) large aliphatic, nonpolar residues: Met, Leu, Ile, Val and Cys; and (e) aromatic residues: Phe, Tyr and Trp. Particularly preferred conservative substitutions are as follows: Ala into Gly or into Ser; Arg into Lys; Asn into Gin or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

Any amino acid substitutions applied to the polypeptides described herein may also be based on the analysis of the frequencies of amino acid variations between homologous proteins of different species developed by Schulz et al. ("Principles of Protein Structure", Springer-Verlag, 1978), on the analyses of structure forming potentials developed by Chou and Fasman (Biochemistry 13: 211, 1974; Adv. Enzymol., 47: 45-149, 1978), and on the analysis of hydrophobicity patterns in proteins developed by Eisenberg et al. (Proc. Natl. Acad Sci. USA 81: 140-144, 1984), Kyte and Doolittle (J. Molec. Biol. 157: 105-132, 1981), and Goldman et al. (Ann. Rev. Biophys. Chem. 15: 321-353, 1986), all incorporated herein in their entirety by reference. Information on the primary, secondary and tertiary structure of Nanobodies is given in the description herein and in the general background art cited above. Also, for this purpose, the crystal structure of a $V_{HH}$ domain from a llama is for example given by Desmyter et al, (Nature Structural Biology, 3: 803, 1996), Spinelli et al. (Natural Structural Biology, 3: 752-757, 1996) and Decanniere et al. (Structure, 7 (4): 361, 1999). Further information about some of the amino acid residues that in conventional $V_H$ domains form the $V_H/V_L$ interface and potential camelizing substitutions on these positions can be found in the prior art cited above.

Amino acid sequences and nucleic acid sequences are said to be "exactly the same" if they have 100% sequence identity (as defined herein) over their entire length;

When comparing two amino acid sequences, the term "amino acid difference" refers to an insertion, deletion or substitution of a single amino acid residue on a position of the first sequence, compared to the second sequence; it being understood that two amino acid sequences can contain one, two or more such amino acid differences. More particularly, in the amino acid sequences and/or polypeptides of the present invention, the term "amino acid difference" refers to an insertion, deletion or substitution of a single amino acid residue on a position of the CDR sequence specified in c), f) or i), compared to the CDR sequence of respectively a), d) or g); it being understood that the CDR sequence of c), f) and i) can contain one, two or maximal three such amino acid differences compared to the CDR sequence of respectively a), d) or g) (supra).

The "amino acid difference" can be any one, two or maximal three substitutions, deletions or insertions, or any combination thereof, that either improves the properties of the polypeptide of the invention or that at least do not detract too much from the desired properties or from the balance or combination of desired properties of the polypeptide of the invention. In this respect, the resulting polypeptide of the invention should at least bind P2X7 with the same, about the same, or a higher affinity compared to the polypeptide comprising the one or more CDR sequences without the one, two or maximal three substitutions, deletions or insertions, said affinity as measured by surface plasmon resonance.

In this respect, the amino acid sequence according to c), f) and/or i) may be an amino acid sequence that is derived from an amino acid sequence according to a), d) and/or g) respectively by means of affinity maturation using one or more techniques of affinity maturation known per se (supra).

For example, and depending on the host organism used to express the polypeptide of the invention, such deletions and/or substitutions may be designed in such a way that one or more sites for post-translational modification (such as one or more glycosylation sites) are removed, as will be within the ability of the person skilled in the art.

The terms "epitope" and "antigenic determinant", which can be used interchangeably, refer to the part of a macromolecule, such as a polypeptide or protein, that is recognized by antigen-binding molecules, such as immunoglobulins, conventional antibodies, immunoglobulin single variable domains and/or polypeptides of the invention, and more particularly by the antigen-binding site of said molecules. Epitopes define the minimum binding site for an immunoglobulin, and thus represent the target of specificity of an immunoglobulin.

The part of an antigen-binding molecule (such as an immunoglobulin, a conventional antibody, an immunoglobulin single variable domain and/or a polypeptide of the invention) that recognizes the epitope is called a "paratope".

A polypeptide (such as an immunoglobulin, an antibody, an immunoglobulin single variable domain, a polypeptide of the invention, or generally an antigen binding molecule or a fragment thereof) that can "bind to" or "specifically bind to", that "has affinity for" and/or that has specificity for a certain epitope, antigen or protein (or for at least one part, fragment or epitope thereof) is said to be "against" or "directed against" said epitope, antigen or protein or is a "binding" molecule with respect to such epitope, antigen or protein, or is said to be "anti"-epitope, "anti"-antigen or "anti"-protein (e.g. "anti"-P2X7).

The term "specificity" has the meaning given to it in paragraph n) on pages 53-56 of WO 08/020079; and as mentioned therein refers to the number of different types of antigens or antigenic determinants to which a particular antigen-binding molecule or antigen-binding protein (such as an immunoglobulin single variable domain and/or a polypeptide of the invention) molecule can bind. The specificity of an antigen-binding protein can be determined based on affinity and/or avidity, as described on pages 53-56 of WO 08/020079 (incorporated herein by reference), which also describes some preferred techniques for measuring binding between an antigen-binding molecule (such as an immunoglobulin single variable domain and/or polypeptide of the invention) and the pertinent antigen. Typically, antigen-binding proteins (such as the immunoglobulin single variable domains and/or polypeptides of the invention) will bind to their antigen with a dissociation constant ($K_D$) of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e., with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^4$ mol/liter (or any $K_A$ value lower than $10^4$ M$^{-1}$) liters/mol is generally considered to indicate non-specific binding. Preferably, a monovalent polypeptide of the invention will bind to the desired antigen with an affinity less than 500 nM, preferably less than 200 nM, more preferably less than 10 nM, such as e.g. between 10 and 5 nM or less. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as the other techniques mentioned herein. As will be clear to the skilled person, and as described on pages 53-56 of WO 08/020079, the dissociation constant may be the actual or apparent dissociation constant. Methods for determining the dissociation constant will be clear to the skilled person, and for example include the techniques mentioned on pages 53-56 of WO 08/020079.

An immunoglobulin single variable domain and/or polypeptide is said to be "specific for" a first target or antigen compared to a second target or antigen when it binds to the first antigen with an affinity (as described above, and suitably expressed as a $K_D$ value, $K_A$ value, $K_{off}$ rate and/or $K_{on}$ rate) that is at least 10 times, such as at least 100 times, and preferably at least 1000 times, and up to 10000 times or more better than the affinity with which immunoglobulin single variable domain and/or polypeptide binds to the second target or antigen. For example, the immunoglobulin single variable domain and/or polypeptide may bind to the first target or antigen with a $K_D$ value that is at least 10 times less, such as at least 100 times less, and preferably at least 1000 times less, such as 10,000 times less or even less than that, than the $K_D$ with which said immunoglobulin single variable domain and/or polypeptide binds to the second target or antigen. Preferably, when an immunoglobulin single variable domain and/or polypeptide is "specific for" a first target or antigen compared to a second target or antigen, it is directed against (as defined herein) said first target or antigen, but not directed against said second target or antigen.

The terms "(cross)-block", "(cross)-blocked", "(cross)-blocking", "competitive binding", "(cross)-compete", "(cross)-competing" and "(cross)-competition" are used interchangeably herein to mean the ability of an immunoglobulin, antibody, immunoglobulin single variable domain, polypeptide or other binding agent to interfere with the binding of other immunoglobulins, antibodies, immunoglobulin single variable domains, polypeptides or binding agents to a given target. The extent to which an immunoglobulin, antibody, immunoglobulin single variable domain, polypeptide or other binding agent is able to interfere with the binding of another to the target, and therefore whether it can be said to cross-block according to the invention, can be determined using competition binding assays. One particularly suitable quantitative cross-blocking assay uses a Biacore instrument which can measure the extent of interactions using surface plasmon resonance technology. Another suitable quantitative cross-blocking assay uses an ELISA-based approach to measure competition between immunoglobulins, antibodies, immunoglobulin single variable domains, polypeptides or other binding agents in terms of their binding to the target.

The following generally describes a suitable Biacore assay for determining whether an immunoglobulin, antibody, immunoglobulin single variable domain, polypeptide or other binding agent cross-blocks or is capable of cross-blocking according to the invention. It will be appreciated that the assay can be used with any of the immunoglobulins, antibodies, immunoglobulin single variable domains, polypeptides or other binding agents described herein. The Biacore instrument (for example the Biacore 3000) is operated in line with the manufacturer's recommendations. Thus in one cross-blocking assay, the target protein (e.g., P2X7) is coupled to a CM5 Biacore chip using standard amine coupling chemistry to generate a surface that is coated with the target. Typically 200-800 resonance units of the target would be coupled to the chip (an amount that gives easily measurable levels of binding but that is readily saturable by the concentrations of test reagent being used). Two test binding agents (termed A* and B*) to be assessed for their ability to cross-block each other are mixed at a one to one molar ratio of binding sites in a suitable buffer to create the test mixture. When calculating the concentrations on a binding site basis the molecular weight of a binding agent is assumed to be the total molecular weight of the binding agent divided by the number of target binding sites on that binding agent. The concentration of each binding agent in the test mix should be high enough to readily saturate the binding sites for that binding agent on the target molecules captured on the Biacore chip. The binding agents in the mixture are at the same molar concentration (on a binding basis) and that concentration would typically be between 1.00 and 1.5 micromolar (on a binding site basis). Separate solutions containing A* alone and B* alone are also prepared. A* and B* in these solutions should be in the same buffer and at the same concentration as in the test mix. The test mixture is passed over the target-coated Biacore chip and the total amount of binding recorded. The chip is then treated in such a way as to remove the bound binding agents without damaging the chip-bound target. Typically this is done by treating the chip with 30 mM HCl for 60 seconds. The solution of A* alone is then passed over the target-coated surface and the amount of binding recorded. The chip is again treated to remove all of the bound binding agents without damaging the chip-bound target. The solution of B* alone is then passed over the target-coated surface and the amount of binding recorded. The maximum theoretical binding of the mixture of A* and B* is next calculated, and is the sum of the binding of each binding agent when passed over the target surface alone. If the actual recorded binding of the mixture is less than this theoretical maximum then the two binding agents are said to cross-block each other. Thus, in general, a cross-blocking immunoglobulin, antibody immunoglobulin single variable domain, polypeptide or other binding agent according to the invention is one which will bind to the target in the above Biacore cross-blocking assay such that during the assay and in the presence of a second immunoglobulin, antibody, immunoglobulin single variable domain, polypeptide or other binding agent the recorded binding is between 80% and 0.1% (e.g., 80% to 4%) of the maximum theoretical binding, specifically between 75% and 0.1% (e.g., 75% to 4%) of the maximum theoretical binding, and more specifically between 70% and 0.1% (e.g., 70% to 4%) of maximum theoretical binding (as just defined above) of the two immunoglobulins, antibodies, immunoglobulin single variable domains, polypeptides or binding agents in combination. The Biacore assay described above is a primary assay used to determine if immunoglobulins, antibodies, immunoglobulin single variable domains, polypeptide or other binding agents cross-block each other according to the invention. On rare occasions particular immunoglobulins, antibodies, immunoglobulin single variable domains, polypeptides or other binding agents may not bind to a target coupled via amine chemistry to a CM5 Biacore chip (this usually occurs when the relevant binding site on the target is masked or destroyed by the coupling to the chip). In such cases cross-blocking can be determined using a tagged version of the target, for example an N-terminal His-tagged version. In this particular format, an anti-His antibody would be coupled to the Biacore chip and then the His-tagged target would be passed over the surface of the chip and captured by the anti-His antibody. The cross blocking analysis would be carried out essentially as described above, except that after each chip regeneration cycle, new His-tagged target would be loaded back onto the anti-His antibody coated surface. In addition to the example given using N-terminal His-tagged target, C-terminal His-tagged target could alternatively be used. Furthermore, various other tags and tag binding protein combinations that are known in the art could be used for such a cross-blocking analysis (e.g. HA tag with anti-HA antibodies; FLAG tag with anti-FLAG antibodies; biotin tag with streptavidin).

The following generally describes an ELISA assay for determining whether an immunoglobulin, antibody, immunoglobulin single variable domain, polypeptide or other binding agent directed against a target (e.g., P2X7) cross-blocks or is capable of cross-blocking as defined herein. It will be appreciated that the assay can be used with any of the immunoglobulins, antibodies, immunoglobulin single variable domains, polypeptides or other binding agents described herein. The general principal of the assay is to have an immunoglobulin, antibody, immunoglobulin single variable domain, polypeptide or binding agent that is directed against the target coated onto the wells of an ELISA plate. An excess amount of a second, potentially cross-blocking, anti-target immunoglobulin, antibody, immunoglobulin single variable domain or polypeptide is added in solution (i.e., not bound to the ELISA plate). A limited amount of the target is then added to the wells. The coated immunoglobulin, antibody, immunoglobulin single variable domain or polypeptide and the immunoglobulin, antibody, immunoglobulin single variable domain or polypeptide in solution compete for binding of the limited number of target molecules. The plate is washed to remove excess target that has not been bound by the coated immunoglobulin, antibody, immunoglobulin single variable domain or polypeptide and to also remove the second, solution phase immunoglobulin, antibody, immunoglobulin single variable domain or polypeptide as well as any complexes formed between the second, solution phase immunoglobulin, antibody, immunoglobulin single variable domain or polypeptide and target. The amount of bound target is then measured using a reagent that is appropriate to detect the target. An immunoglobulin, antibody, immunoglobulin single variable domain or polypeptide in solution that is able to cross-block the coated immunoglobulin, antibody, immunoglobulin single variable domain or polypeptide will be able to cause a decrease in the number of target molecules that the coated immunoglobulin, antibody, immunoglobulin single variable domain or polypeptide can bind relative to the number of target molecules that the coated immunoglobulin, antibody, immunoglobulin single variable domain or polypeptide can bind in the absence of the second, solution phase, immunoglobulin, antibody, immunoglobulin single variable domain or polypeptide. In the instance where the first immunoglobulin, antibody, immunoglobulin single variable domain or polypeptide, e.g. an Ab-X, is chosen to be the immobilized immunoglobulin, antibody, immunoglobulin single variable domain or polypeptide, it is coated onto the wells of the ELISA plate, after which the plates are blocked with a suitable blocking solution to minimize non-specific binding of reagents that are subsequently added. An excess amount of the second immunoglobulin, antibody, immunoglobulin single variable domain or polypeptide, i.e., Ab-Y, is then added to the ELISA plate such that the moles of Ab-Y target binding sites per well are at least 10 fold higher than the moles of Ab-X target binding sites that were used, per well, during the coating of the ELISA plate. Target is then added such that the moles of target added per well are at least 25-fold lower than the moles of Ab-X target binding sites that were used for coating each well. Following a suitable incubation period the ELISA plate is washed and a reagent for detecting the target is added to measure the amount of target specifically bound by the coated anti-target immunoglobulin, antibody, immunoglobulin single variable domain or polypeptide (in this case Ab-X). The background signal for the assay is defined as the signal obtained in wells with the coated immunoglobulin, antibody, immunoglobulin single variable domain or polypeptide (in this case Ab-X), second solution phase immunoglobulin single variable domain or polypeptide (in this case Ab-Y), target buffer only (i.e., without target) and target detection reagents. The positive control signal for the assay is defined as the signal obtained in wells with the coated immunoglobulin, antibody, immunoglobulin single variable domain or polypeptide (in this case Ab-X), second solution phase immunoglobulin, antibody, immunoglobulin single variable domain or polypeptide buffer only (i.e. without second solution phase immunoglobulin, antibody, immunoglobulin single variable domain or polypeptide), target and target detection reagents. The ELISA assay may be run in such a manner so as to have the positive control signal be at least 6 times the background signal. To avoid any artefacts (e.g. significantly different affinities between Ab-X and Ab-Y for the target) resulting from the choice of which immunoglobulin, antibody, immunoglobulin single variable domain or polypeptide to use as the coating immunoglobulin, antibody, immunoglobulin single variable domain or polypeptide and which to use as the second (competitor) immunoglobulin, antibody, immunoglobulin single variable domain or polypeptide, the cross-blocking assay may to be run in two formats: 1) format 1 is where Ab-X is the immunoglobulin, antibody, immunoglobulin single variable domain or polypeptide that is coated onto the ELISA plate and Ab-Y is the competitor immunoglobulin, antibody, immunoglobulin single variable domain or polypeptide that is in solution and 2) format 2 is where Ab-Y is the immunoglobulin, antibody, immunoglobulin single variable domain or polypeptide that is coated onto the ELISA plate and Ab-X is the competitor immunoglobulin, antibody, immunoglobulin single variable domain or polypeptide that is in solution. Ab-X and Ab-Y are defined as cross-blocking if, either in format 1 or in format 2, the solution phase anti-target immunoglobulin, antibody, immunoglobulin single variable domain or polypeptide is able to cause a reduction of between 60% and 100%, specifically between 70% and 100%, and more specifically between 80% and 100%, of the target detection signal {i.e. the amount of target bound by the coated immunoglobulin, antibody, immunoglobulin single variable domain or polypeptide) as compared to the target detection signal obtained in the absence of the solution phase anti-target immunoglobulin, antibody, immunoglobulin single variable domain or polypeptide (i.e., the positive control wells).

"Epitope binning" refers to the use of competitive binding assays or cross-blocking assays to identify pairs of immunoglobulins, antibodies, immunoglobulin single variable domains, polypeptides, or other binding agents that are, or are not, capable of binding the target (e.g., P2X7) simultaneously thereby identifying immunoglobulins, antibodies, immunoglobulin single variable domains, polypeptides or other binding agents that bind to the same, or overlapping epitopes on the target.

An "epitope bin" as used in the present specification therefore is a family of immunoglobulins, antibodies, immunoglobulin single variable domains, polypeptides, or other binding agents having the same or overlapping binding specificity. As described above, the sorting of the immunoglobulins, antibodies, immunoglobulin single variable domains, polypeptides, or other binding agents into epitope bins is based on cross-competition (cross-blocking) of the immunoglobulins, antibodies, immunoglobulin single variable domains, polypeptides, or other binding agents for antigen binding. The cross-competition (cross-blocking) assay analyzes the simultaneous binding (pairing) of the immunoglobulins, antibodies, immunoglobulin single variable domains, polypeptides or other binding agents to the antigen and groups together immunoglobulins, antibodies, immunoglobulin single variable domains, polypeptides, or other binding agents with similar pairing profiles. Immunoglobulins, antibodies, immunoglobulin single variable domains, polypeptides or other binding agents with similar profiles (i.e., belonging to the same epitope bin) may bind to the same, closely related and/or overlapping epitopes.

An amino acid sequence is said to be "cross-reactive" for two different antigens or antigenic determinants (such as e.g. serum albumin from two different species of mammal, such as e.g. human serum albumin and cyno serum albumin, such as e.g. P2X7 from different mammals) if it is specific for (as defined herein) both these different antigens or antigenic determinants.

It is noted that as used herein 'can specifically bind to' and 'specifically binds to' are used synonymously and refer to the ability to specifically bind to the respectively indicated entity.

The term "P2X7" as used herein refers to proteins that form the (homo-)trimeric extracellular ATP-gated cation channel "P2X7 receptor", especially the proteins represented by SEQ ID NOs: 1-5, as well as all of its isoforms, especially SEQ ID NOs: 1-3 and its isoforms. The (human) isoforms include all splice variants, e.g., P2X7(b)-P2X7(k), as well as all single nucleotide polymorphisms identified in the human P2X7 receptor, and including forms with alternative N termini and Trans Membrane Domain 1 (all as known in the art, see e.g. Cheewatrakoolpong et al. (2005) *Biochem. Biophys. Res. Commun.* 332, 17-27 and Feng et al. (2006) *J. Biol. Chem* 281, 17228-17237). Gating of the P2X7 receptor induces activation of the inflammasome and of the cell surface metalloprotease.

The term "potency" of a polypeptide of the invention, as used herein, is a function of the amount of polypeptide of the invention required for its specific effect to occur. It is measured simply as the inverse of the $IC_{50}$ for that polypeptide. It refers to the capacity of said polypeptide of the invention to neutralize P2X7 activity; such as to modulate, inhibit and/or prevent P2X7 activity, to modulate, inhibit and/or prevent triggering of tissue-damaging inflammation induced by P2X7 activity.

The potency may be measured by any suitable assay known in the art or described herein, such as e.g. as described in the Example section.

In contrast, the "efficacy" of the polypeptide of the invention measures the maximum strength of the effect itself, at saturating polypeptide concentrations. Efficacy indicates the maximum response achievable from the polypeptide of the invention. It refers to the ability of a polypeptide to produce the desired (therapeutic) effect.

In the context of the present invention, "modulating" or "to modulate" generally means reducing or inhibiting as well as increasing, potentiating or enhancing the activity of P2X7 and in particular human P2X7 (SEQ ID NO: 1-3) and its isoforms, as measured using a suitable in vitro, cellular or in vivo assay (such as those mentioned herein). In particular, reducing or inhibiting as well as increasing or enhancing the activity of P2X7 and in particular human P2X7 (SEQ ID NO: 1-3) and its isoforms, as measured using a suitable in vitro, cellular or in vivo assay (such as those mentioned herein), by at least 1%, preferably at least 5%, such as at least 10% or at least 25%, for example by at least 50%, at least 60%, at least 70%, at least 80%, or 90% or more, compared to the activity of P2X7 and in particular human P2X7 (SEQ ID NO: 1-3) and its isoforms in the same assay under the same conditions but without the presence of the polypeptide of the invention.

Modulating may for example involve reducing or inhibiting the binding of extracellular ATP to P2X7 receptor or reducing or inhibiting NAD-dependent ADP-ribosylation at Arg 125 of P2X7 receptor. Modulating may for example involve reducing or inhibiting gating by P2X7 receptor. Gating of the P2X7 receptor induces activation of the inflammasome, activation of cell surface metalloprotease, ecto-domain shedding by TACE, externalization of phosphatidylserine (PS) and/or apoptosis.

Alternatively, modulating may involve increasing, potentiating or enhancing gating by P2X7 receptor.

The "half-life" of a polypeptide of the invention can generally be defined as described in paragraph o) on page 57 of WO 08/020079 and as mentioned therein refers to the time taken for the serum concentration of the polypeptide to be reduced by 50%, in vivo, for example due to degradation of the polypeptide and/or clearance or sequestration of the polypeptide by natural mechanisms. The in vivo half-life of a polypeptide of the invention can be determined in any manner known per se, such as by pharmacokinetic analysis. Suitable techniques will be clear to the person skilled in the art, and may for example generally be as described in paragraph o) on page 57 of WO 08/020079. As also mentioned in paragraph o) on page 57 of WO 08/020079, the half-life can be expressed using parameters such as the t1/2-alpha, t1/2-beta and the area under the curve (AUC). Reference is for example made to the standard handbooks, such as Kenneth et al (Chemical Stability of Pharmaceuticals: A Handbook for Pharmacists, John Wiley & Sons Inc, 1986) and M Gibaldi and D Perron ("Pharmacokinetics", Marcel Dekker, 2nd Rev. Edition, 1982). The terms "increase in half-life" or "increased half-life" are also as defined in paragraph o) on page 57 of WO 08/020079 and in particular refer to an increase in the t1/2-beta, either with or without an increase in the t1/2-alpha and/or the AUC or both.

Unless indicated otherwise, the term "immunoglobulin"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively).

The term "domain" (of a polypeptide or protein) as used herein refers to a folded protein structure which has the ability to retain its tertiary structure independently of the rest of the protein. Generally, domains are responsible for discrete functional properties of proteins, and in many cases may be added, removed or transferred to other proteins without loss of function of the remainder of the protein and/or of the domain.

The term "immunoglobulin domain" as used herein refers to a globular region of an antibody chain (such as e.g., a chain of a conventional 4-chain antibody or of a heavy chain antibody), or to a polypeptide that essentially consists of such a globular region. Immunoglobulin domains are characterized in that they retain the immunoglobulin fold characteristic of antibody molecules, which consists of a two-layer sandwich of about seven antiparallel beta-strands arranged in two beta-sheets, optionally stabilized by a conserved disulphide bond.

The term "immunoglobulin variable domain" as used herein means an immunoglobulin domain essentially consisting of four "framework regions" which are referred to in the art and herein below as "framework region 1" or "FR1"; as "framework region 2" or "FR2"; as "framework region 3" or "FR3"; and as "framework region 4" or "FR4", respectively; which framework regions are interrupted by three "complementarity determining regions" or "CDRs", which are referred to in the art and herein below as "complementarity determining region 1" or "CDR1"; as "complementarity determining region 2" or "CDR2"; and as "complementarity determining region 3" or "CDR3", respectively. Thus, the general structure or sequence of an immunoglobulin variable domain can be indicated as follows: FR1-CDR1-FR2-CDR2-FR3-CDR3-FR4. It is the immunoglobulin variable domain(s) that confer specificity to an antibody for the antigen by carrying the antigen-binding site.

The term "immunoglobulin single variable domain", interchangeably used with "single variable domain", defines molecules wherein the antigen binding site is present on, and formed by, a single immunoglobulin domain. This sets immunoglobulin single variable domains apart from "conventional" immunoglobulins or their fragments, wherein two immunoglobulin domains, in particular two variable domains, interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e., a total of 6 CDRs will be involved in antigen binding site formation.

In view of the above definition, the antigen-binding domain of a conventional 4-chain antibody (such as an IgG, IgM, IgA, IgD or IgE molecule; known in the art) or of a Fab fragment, a F(ab')2 fragment, an Fv fragment such as a disulphide linked Fv or a scFv fragment, or a diabody (all known in the art) derived from such conventional 4-chain antibody, would normally not be regarded as an immunoglobulin single variable domain, as, in these cases, binding to the respective epitope of an antigen would normally not occur by one (single) immunoglobulin domain but by a pair of (associating) immunoglobulin domains such as light and heavy chain variable domains, i.e., by a VH-VL pair of immunoglobulin domains, which jointly bind to an epitope of the respective antigen.

In contrast, immunoglobulin single variable domains are capable of specifically binding to an epitope of the antigen without pairing with an additional immunoglobulin variable domain. The binding site of an immunoglobulin single variable domain is formed by a single VH/VHH or VL domain. Hence, the antigen binding site of an immunoglobulin single variable domain is formed by no more than three CDRs.

As such, the single variable domain may be a light chain variable domain sequence (e.g., a VL-sequence) or a suitable fragment thereof; or a heavy chain variable domain sequence (e.g., a VH-sequence or VHH sequence) or a suitable fragment thereof; as long as it is capable of forming a single antigen binding unit (i.e., a functional antigen binding unit that essentially consists of the single variable domain, such that the single antigen binding domain does not need to interact with another variable domain to form a functional antigen binding unit).

In one embodiment of the invention, the immunoglobulin single variable domains are heavy chain variable domain sequences (e.g., a VH-sequence); more specifically, the immunoglobulin single variable domains can be heavy chain variable domain sequences that are derived from a conventional four-chain antibody or heavy chain variable domain sequences that are derived from a heavy chain antibody.

For example, the immunoglobulin single variable domain may be a (single) domain antibody (or an amino acid that is suitable for use as a (single) domain antibody), a "dAb" or dAb (or an amino acid that is suitable for use as a dAb) or a Nanobody (as defined herein, and including but not limited to a VHH); other single variable domains, or any suitable fragment of any one thereof.

In particular, the immunoglobulin single variable domain may be a Nanobody® (as defined herein) or a suitable fragment thereof. [Note: Nanabody®, Nanobodies® and Nanoclone® are registered trademarks of Ablynx N. V.] For a general description of Nanobodies, reference is made to the further description below, as well as to the prior art cited herein, such as e.g. described in WO 08/020079 (page 16).

"VHH domains", also known as VHHs, $V_HH$ domains, VHH antibody fragments, and VHH antibodies, have originally been described as the antigen binding immunoglobulin (variable) domain of "heavy chain antibodies" (i.e. of "antibodies devoid of light chains"; Hamers-Casterman et al. Nature 363: 446-448, 1993). The term "VHH domain" has been chosen in order to distinguish these variable domains from the heavy chain variable domains that are present in conventional 4-chain antibodies (which are referred to herein as "$V_H$ domains" or "VH domains") and from the light chain variable domains that are present in conventional 4-chain antibodies (which are referred to herein as "$V_L$ domains" or "VL domains"). For a further description of VHH's and Nanobodies, reference is made to the review article by Muyldermans (Reviews in Molecular Biotechnology 74: 277-302, 2001), as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1134231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N. V. and Ablynx N. V.; WO 01/90190 by the National Research Council of Canada; WO 03/025020 (=EP 1 433 793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N. V. and the further published patent applications by Ablynx N. V. Reference is also made to the further prior art mentioned in these applications, and in particular to the list of references mentioned on pages 41-43 of the International application WO 06/040153, which list and references are incorporated herein by reference. As described in these references, Nanobodies (in particular VHH sequences and partially humanized Nanobodies) can in particular be characterized by the presence of one or more "Hallmark residues" in one or more of the framework sequences. A further description of the Nanobodies, including humanization and/or camelization of Nanobodies, as well as other modifications, parts or fragments, derivatives or "Nanobody fusions", multivalent constructs (including some non-limiting examples of linker sequences) and different modifications to increase the half-life of the Nanobodies and their preparations can be found e.g. in WO 08/101985 and WO 08/142164. For a further general description of Nanobodies, reference is made to the prior art cited herein, such as e.g. described in WO 08/020079 (page 16).

"Domain antibodies", also known as "Dab"s, "Domain Antibodies", and "dAbs" (the terms "Domain Antibodies" and "dAbs" being used as trademarks by the GlaxoSmithKline group of companies) have been described in e.g. EP 0368684, Ward et al. (Nature 341: 544-546, 1989), Holt et al. (Tends in Biotechnology 21: 484-490, 2003) and WO 03/002609 as well as for example WO 04/068820, WO 06/030220, WO 06/003388 and other published patent applications of Domantis Ltd. Domain antibodies essentially correspond to the VH or VL domains of non-camelid mammalians, in particular human 4-chain antibodies. In order to bind an epitope as a single antigen binding domain, i.e. without being paired with a VL or VH domain, respectively, specific selection for such antigen binding properties is required, e.g. by using libraries of human single VH or VL domain sequences. Domain antibodies have, like VHHs, a molecular weight of approximately 13 to approximately 16 kDa and, if derived from fully human sequences, do not require humanization for e.g. therapeutic use in humans.

It should also be noted that, although less preferred in the context of the present invention because they are not of mammalian origin, single variable domains can be derived from certain species of shark (for example, the so-called "IgNAR domains", see for example WO 05/18629).

Thus, in the meaning of the present invention, the term "immunoglobulin single variable domain" or "single variable domain" comprises polypeptides which are derived from a non-human source, preferably a camelid, preferably a camelid heavy chain antibody. They may be humanized, as previously described. Moreover, the term comprises polypeptides derived from non-camelid sources, e.g. mouse or human, which have been "camelized", as e.g. described in Davies and Riechman (FEBS 339: 285-290, 1994; Biotechonol, 13: 475-479, 1995; Prot. Eng. 9: 531-537, 1996) and Riechman and Muyldermans (J. Immunol. Methods 231: 25-38, 1999).

The amino acid residues of a VHH domain are numbered according to the general numbering for $V_E$, domains given by Kabat et al. ("Sequence of proteins of immunological interest", US Public Health Services, NIH Bethesda, Md., Publication No. 91), as applied to VHH domains from Camelids, as shown e.g. in FIG. 2 of Riechmann and Muyldermans (J. Immunol. Methods 231: 25-38, 1999). Alternative methods for numbering the amino acid residues of $V_H$ domains, which methods can also be applied in an analogous manner to VHH domains, are known in the art. However, in the present description, claims and figures, the numbering according to Kabat applied to VHH domains as described above will be followed, unless indicated otherwise.

It should be noted that—as is well known in the art for $V_H$ domains and for VHH domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. The total number of amino acid residues in a VH domain and a VHH domain will usually be in the range of from 110 to 120, often between 112 and 115. It should however be noted that smaller and longer sequences may also be suitable for the purposes described herein.

Determination of CDR regions may also be done according to different methods. In the CDR determination according to Kabat, FR1 of a VHH comprises the amino acid residues at positions 1-30, CDR1 of a VHH comprises the amino acid residues at positions 31-35, FR2 of a VHH comprises the amino acids at positions 36-49, CDR2 of a VHH comprises the amino acid residues at positions 50-65, FR3 of a VHH comprises the amino acid residues at positions 66-94, CDR3 of a VHH comprises the amino acid residues at positions 95-102, and FR4 of a VHH comprises the amino acid residues at positions 103-113.

CDR sequences may be determined according to Kontermann and Dübel (Eds., Antibody Engineering, vol 2, Springer Verlag Heidelberg Berlin, Martin, Chapter 3, pp. 33-51, 2010). According to this method, FR1 comprises the amino acid residues at positions 1-25, CDR1 comprises the amino acid residues at positions 26-35, FR2 comprises the amino acids at positions 36-49, CDR2 comprises the amino acid residues at positions 50-58, FR3 comprises the amino acid residues at positions 59-94, CDR3 comprises the amino acid residues at positions 95-102, and FR4 comprises the amino acid residues at positions 103-113.

Immunoglobulin single variable domains such as Domain antibodies and Nanobodies (including VHH domains) can be subjected to humanization. In particular, humanized immunoglobulin single variable domains, such as Nanobodies (including VHH domains) may be immunoglobulin single variable domains that are as generally defined for in the previous paragraphs, but in which at least one amino acid residue is present (and in particular, in at least one of the framework residues) that is and/or that corresponds to a humanizing substitution (as defined herein). Potentially useful humanizing substitutions can be ascertained by comparing the sequence of the framework regions of a naturally occurring $V_{HH}$ sequence with the corresponding framework sequence of one or more closely related human $V_H$ sequences, after which one or more of the potentially useful humanizing substitutions (or combinations thereof) thus determined can be introduced into said $V_{HH}$ sequence (in any manner known per se, as further described herein) and the resulting humanized $V_{HH}$ sequences can be tested for affinity for the target, for stability, for ease and level of expression, and/or for other desired properties. In this way, by means of a limited degree of trial and error, other suitable humanizing substitutions (or suitable combinations thereof) can be determined by the skilled person based on the disclosure herein. Also, based on the foregoing, (the framework regions of) an immunoglobulin single variable domain, such as a Nanobody (including VHH domains) may be partially humanized or fully humanized.

Immunoglobulin single variable domains such as Domain antibodies and Nanobodies (including VHH domains and humanized VHH domains), can also be subjected to affinity maturation by introducing one or more alterations in the amino acid sequence of one or more CDRs, which alterations result in an improved affinity of the resulting immunoglobulin single variable domain for its respective antigen, as compared to the respective parent molecule. Affinity-matured immunoglobulin single variable domain molecules of the invention may be prepared by methods known in the art, for example, as described by Marks et al. (Biotechnology 10:779-783, 1992), Barbas, et al. (Proc. Nat. Acad. Sci, USA 91: 3809-3813, 1994), Shier et al. (Gene 169: 147-155, 1995), Yelton et al. (Immunol. 155: 1994-2004, 1995), Jackson et al. (J. Immunol. 154: 3310-9, 1995), Hawkins et al. (J. Mot. Biol. 226: 889 896, 1992), Johnson and Hawkins (Affinity maturation of antibodies using phage display, Oxford University Press, 1996).

The process of designing/selecting and/or preparing a polypeptide, starting from an immunoglobulin single variable domain such as a Domain antibody or a Nanobody, is also referred to herein as "formatting" said immunoglobulin single variable domain; and an immunoglobulin single variable domain that is made part of a polypeptide is said to be "formatted" or to be "in the format of" said polypeptide. Examples of ways in which an immunoglobulin single variable domain can be formatted and examples of such formats will be clear to the skilled person based on the disclosure herein; and such formatted immunoglobulin single variable domain form a further aspect of the invention.

For example, and without limitation, one or more immunoglobulin single variable domains may be used as a "binding unit", "binding domain" or "building block" (these terms are used interchangeable) for the preparation of a polypeptide, which may optionally contain one or more further immunoglobulin single variable domains that can serve as a binding unit (i.e. against the same or another epitope on P2X7 and/or against one or more other antigens, proteins or targets than P2X7).

Monovalent polypeptides comprise or essentially consist of only one binding unit (such as e.g. immunoglobulin single variable domains). Polypeptides that comprise two or more binding units (such as e.g. immunoglobulin single variable domains) will also be referred to herein as "multivalent" polypeptides, and the binding units/immunoglobulin single variable domains present in such polypeptides will also be referred to herein as being in a "multivalent format". For example a "bivalent" polypeptide may comprise two immunoglobulin single variable domains, optionally linked via a linker sequence, whereas a "trivalent" polypeptide may comprises three immunoglobulin single variable domains, optionally linked via two linker sequences; etc.

In a multivalent polypeptide, the two or more immunoglobulin single variable domains may be the same or different, and may be directed against the same antigen or antigenic determinant (for example against the same part(s)

or epitope(s) or against different parts or epitopes) or may alternatively be directed against different antigens or antigenic determinants; or any suitable combination thereof. Polypeptides that contain at least two binding units (such as e.g. immunoglobulin single variable domains) in which at least one binding unit is directed against a first antigen (i.e. P2X7) and at least binding unit is directed against a second antigen (i.e. different from P2X7) will also be referred to as "multispecific" polypeptides, and the binding units (such as e.g. immunoglobulin single variable domains) present in such polypeptides will also be referred to herein as being in a "multispecific format". Thus, for example, a "bispecific" polypeptide of the invention is a polypeptide that comprises at least one immunoglobulin single variable domain directed against a first antigen (i.e. P2X7) and at least one further immunoglobulin single variable domain directed against a second antigen (i.e. different from P2X7), whereas a "trispecific" polypeptide of the invention is a polypeptide that comprises at least one immunoglobulin single variable domain directed against a first antigen (i.e. P2X7), at least one further immunoglobulin single variable domain directed against a second antigen (i.e. different from P2X7) and at least one further immunoglobulin single variable domain directed against a third antigen (i.e. different from both P2X7 and the second antigen); etc.

"Multiparatopic polypeptides", such as e.g. "biparatopic polypeptides" or "triparatopic polypeptides", comprise or essentially consist of two or more binding units that each have a different paratope (as will be further described herein; see chapter on multivalent polypeptides of the invention).
P2X7

The ISVs and polypeptides of the present invention can generally be used to modulate, and in particular inhibit and/or prevent, binding of ATP to P2X7 or extracellular ATP mediated activation of P2X7, and in particular human P2X7 (see Table B-2), and thus to modulate, and in particular inhibit or prevent, gating by P2X7 and in particular human P2X7 (SEQ ID NO: 1-3) and/or to modulate the biological mechanisms, responses and effects associated with such gating (P2X7 building blocks). Preferably, the ISVs of the invention are chosen from the group consisting of 1c81-like sequences, 3c23-like sequences, 1c113-like sequences, 13a7-like sequences and 14d5-like sequences.

The amino acid sequences provided by the invention are preferably in essentially isolated form (as defined herein), or form part of a protein or polypeptide of the invention (as defined herein), which may comprise or essentially consist of one or more amino acid sequences of the invention and which may optionally further comprise one or more further amino acid sequences (all optionally linked via one or more suitable linkers). For example, and without limitation, the one or more amino acid sequences of the invention may be used as a binding unit in such a protein or polypeptide, which may optionally contain one or more further amino acid sequences that can serve as a binding unit (i.e. against one or more other targets than P2X7), so as to provide a monovalent, multivalent or multispecific polypeptide of the invention, respectively, all as described herein. Such a protein or polypeptide may also be in essentially isolated form (as defined herein).

The amino acid sequences and polypeptides of the invention as such preferably essentially consist of a single amino acid chain that is not linked via disulphide bridges to any other amino acid sequence or chain (but that may or may not contain one or more intramolecular disulphide bridges. For example, it is known that Nanobodies—as described herein—may sometimes contain a disulphide bridge between CDR3 and CDR1 or FR2). However, it should be noted that one or more amino acid sequences of the invention may be linked to each other and/or to other amino acid sequences (e.g., via disulphide bridges) to provide peptide constructs that may also be useful in the invention (for example Fab' fragments, F(ab')$_2$ fragments, ScFv constructs, "diabodies" and other multispecific constructs. Reference is for example made to the review by Holliger and Hudson, Nat Biotechnol. 2005 September; 23(9):1126-36).

Generally, when an amino acid sequence of the invention (or a compound, construct or polypeptide comprising the same) is intended for administration to a subject (for example for therapeutic and/or diagnostic purposes as described herein), it is preferably either an amino acid sequence that does not occur naturally in said subject; or, when it does occur naturally in said subject, in essentially isolated form (as defined herein).

Furthermore, an amino acid sequence of the invention may optionally, and in addition to the at least one binding site for binding against P2X7, contain one or more further binding sites for binding against other antigens, proteins or targets.

In the present description and claims, the following terms are defined as follows:

A) 1CB1-like sequences: a 1C81-like sequences: a "1C81-like sequence", "1C81-like ISV" or "1C81-like building block" is defined as an ISV (as described herein) that comprises:
  a) a CDR1 which comprises or essentially consists of either (i) the amino acid sequence RTFSFSTSTMG (SEQ ID NO:34) or (ii) an amino acid sequence that has only 3, 2 or 1 amino acid difference(s) (as defined herein) with the amino acid sequence RTFSFSTSTMG (SEQ ID NO:34); and/or
  b) a CDR2 which comprises or essentially consists of either (i) the amino acid sequence AIDWSDFN (SEQ ID NO:62) or (ii) an amino acid sequence that has at least 80%, such as at least 85%, for example at least 90% or more than 95% sequence identity with the amino acid sequence AIDWSDFN (SEQ ID NO:62); or (iii) an amino acid sequence that has only 7, 6, 5, 4, 3, 2 or 1 amino acid difference(s) (as defined herein) with the amino acid sequence AIDWSDFN (SEQ ID NO:62); and/or
  c) a CDR3 which comprises or essentially consists of either (i) the amino acid sequence HSETRGG-TRYFDRPSLYNY (SEQ ID NO:90) or (ii) an amino acid sequence that has at least 80%, such as at least 85%, for example at least 90% or more than 95% sequence identity with the amino acid sequence HSE-TRGGTRYFDRPSLYNY (SEQ ID NO:90); or (iii) an amino acid sequence that has only 7, 6, 5, 4, 3, 2 or 1 amino acid difference(s) (as defined herein with the amino acid sequence HSETRGGTRYFDRPSLYNY (SEQ ID NO:90);
  in which the framework sequences present in such an ISV are as further described herein, and in which CDR1, CDR2 and CDR3 are preferably such that the 1C81-like ISV has a modulating activity, which can be determined by any suitable assay known to the person skilled in the art, such as, for instance, by means of Alphascreen assays (as known in the art) or by cell based assays (e.g. such as described herein).
  Preferably, the modulating activity is determined by an ATP-induced shedding of CD62L in transfected NEK cells based assay, for instance, such as described in Examples 1.7 or 1.8. Preferably, the 1C81-like ISV has a modulating activity with an IC50 of less than 250 nM, more preferably, less than 200 nM, 175 nM or even less, such as less than 150 nM or 125 nM or even more preferably of less than 110 nM; or is determined by an ATP-induced externalization of phosphatidylserine (PS) by human T cells, for instance, such as described in Example 1.11; or is determined by an ATP-induced shedding of CD62L (PS) by human T cells, for instance, such as described in Example 1.11; or is determined by prevention of P2X7-mediated cell death of RPMI 8226 cells, for instance, such as described in Example 1.10.

Preferably, in such a 1C81-like sequence, CDR1 and CDR2 are as defined under a) and b), respectively; or CDR1 and CDR3 are as defined under a) and c), respectively; or CDR2 and CDR3 are as defined under b) and c), respectively. More preferably, in such a 1C81-like sequence, CDR1, CDR2 and CDR3 are all as defined under a), b) and c), respectively. Again, in such an 1C81-like sequence, CDR1, CDR2 and CDR3 are preferably such that the 1C81-like ISV has a modulating activity, which can be determined by any suitable assay known to the person skilled in the art, such as, for instance, by means of Alphascreen assays) or by cell based assays (e.g., such as described herein).

Preferably, the modulating activity is determined by an ATP-induced shedding of CD62L in transfected HEK cells based assay, for instance, such as described in Examples 1.7 or 1.8. Preferably, the 1C81-like ISV has a modulating activity with an IC50 of less than 250 nM, more preferably, less than 200 nM, 175 nM or even less, such as less than 150 nM or 125 nM or even more preferably of less than 110 nM; or is determined by an ATP-induced externalization of phosphatidylserine (PS) by human T cells, for instance, such as described in Example 1.11; or is determined by an ATP-induced shedding of CD62L (PS) by human T cells, for instance, such as described in Example 1.11; or is determined by prevention of P2X7-mediated cell death of RPMI 8226 cells, for instance, such as described in Example 1.10.

For example, in such an 1C81-like sequence: CDR1 may comprise or essentially consist of the amino acid sequence RTFSFSTSTMG (SEQ ID NO:34) (with CDR2 and CDR3 being as defined under b) and c), respectively); and/or CDR2 may comprise or essentially consist of the amino acid sequence AIDWSDFN (SEQ ID NO:62) (with CDR1 and CDR3 being as defined under a) and c), respectively); and/or CDR3 may comprise or essentially consist of the amino acid sequence HSETRGGTRYFDRPSLYNY (SEQ ID NO:90) (with CDR1 and CDR2 being as defined under a) and b), respectively). Particularly, when an 1C81-like sequence is according to this aspect: CDR1 may comprise or essentially consist of the amino acid sequence RTFSFSTSTMG (SEQ ID NO:34) and CDR2 may comprise or essentially consist of the amino acid sequence AIDWSDFN (SEQ ID NO:62)(with CDR3 being as defined under c) above); and/or CDR1 may comprise or essentially consist of the amino acid sequence RTFSFSTSTMG (SEQ ID NO:34) and CDR3 may comprise or essentially consist of the amino acid sequence HSETRGGTRYFDRPSLYNY (SEQ ID NO:90)(with CDR2 being as defined under b) above); and/or CDR2 may comprise or essentially consist of the amino acid sequence AIDWSDFN (SEQ ID NO:62) and CDR3 may comprise or essentially consist of the amino acid sequence HSETRGGTRYFDRPSLYNY (SEQ ID NO:90) (with CDR1 being as defined under a) above). Again, in such 1C81-like sequences, CDR1, CDR2 and CDR3 are preferably such that the 1C81-like ISV has a modulating activity, which can be determined by any suitable assay known to the person skilled in the art, such as, for instance, by means of Alphascreen assays (e.g. such as described herein) or by cell based assays (e.g., such as described herein), Preferably, the modulating activity is determined by an ATP-induced shedding of CD62L in transfected HEK cells based assay, for instance, such as described in Examples 1.7 or 1.8. Preferably, the 1C81-like ISV has a modulating activity with an IC50 of less than 250 nM, more preferably, less than 200 nM, 175 nM or even less, such as less than 150 nM or 125 nM or even more preferably of less than 110 nM; or is determined by an ATP-induced externalization of phosphatidylserine (PS) by human T cells, for instance, such as described in Example 1.11; or is determined by an ATP-induced shedding of CD62L (PS) by human T cells, for instance, such as described in Example 1.11; or is determined by prevention of P2X7-mediated cell death of RPMI 8226 cells, for instance, such as described in Example 1.10.

In a specifically preferred aspect, a "1C81-like sequence", "1C81-like ISV" or "1C81-like building block" is an ISV that comprises:

d) a CDR1 which is either (i) the amino acid sequence RTFSFSTSTMG (SEQ ID NO:34) or (ii) an amino acid sequence that has only 3, 2 or 1 amino acid difference(s) (as defined herein) with the amino acid sequence RTFSFSTSTMG (SEQ ID NO:34); and/or e) a CDR2 which is either (i) the amino acid sequence AIDWSDFN (SEQ ID NO:62) or (ii) an amino acid sequence that has at least 80%, such as at least 85%, for example at least 90% or more than 95% sequence identity with the amino acid sequence AIDWSDFN (SEQ ID NO:62); or (iii) an amino acid sequence that has only 7, 6, 5, 4, 3, 2 or 1 amino acid difference(s) (as defined herein) with the amino acid sequence AIDWSDFN (SEQ ID NO:62); and/or f) a CDR3 which is either (i) the amino acid sequence HSETRGGTRYFDRPSLYNY (SEQ ID NO:90) or (ii) an amino acid sequence that has at least 80%, such as at least 85%, for example at least 90% or more than 95% sequence identity with the amino acid sequence HSETRGGTRYFDRPSLYNY (SEQ ID NO:90); or (iii) an amino acid sequence that has only 7, 6, 5, 4, 3, 2 or 1 amino acid difference(s) (as defined herein) with the amino acid sequence HSETRGG-TRYFDRPSLYNY (SEQ ID NO:90);

in which the framework sequences present in such an ISV are as further described herein, and in which CDR1, CDR2 and CDR3 are preferably such that the 1C81-like ISV has a modulating activity, which can be determined by any suitable assay known to the person skilled in the art, such as, for instance, by means of Alphascreen assays (e.g., such as described herein) or by cell based assays (e.g. such as described herein).

Preferably, the modulating activity is determined by an ATP-induced shedding of CD62L in transfected HEK cells based assay, for instance, such as described in Examples 1.7 or 1.8. Preferably, the 1C81-like ISV has a modulating activity with an IC50 of less than 250 nM, more preferably, less than 200 nM, 175 nM or even less, such as less than 150 nM or 125 nM or even more preferably of less than 110 nM; or is determined by an ATP-induced externalization of phosphatidylserine (PS) by human T cells, for instance, such as described in Example 1.11; or is determined by an ATP-induced shedding of CD62), (PS) by human T cells, for instance, such as described in Example 1.11; or is determined by prevention of P2X7-mediated cell death of RPMI 8226 cells, for instance, such as described in Example 1.10.

Preferably, in a 1C81-like sequence according to this specifically preferred aspect, CDR1 and CDR2 are as defined under d) and e), respectively; or CDR1 and CDR3 are as defined under d) and f), respectively; or CDR2 and CDR3 are as defined under e) and f), respectively. More preferably, in such a 1C81-like sequence, CDR1, CDR2 and CDR3 are all as defined under d), e) and f), respectively. Again, in such an 1C81-like sequence, CDR1, CDR2 and CDR3 are preferably such that the 1C81-like ISV has a modulating activity, which can be determined by any suitable assay known to the person skilled in the art, such as, for instance, by means of Alphascreen assays (e.g. such as described herein) or by cell based assays (e.g., such as described herein).

Preferably, the modulating activity is determined by an ATP-induced shedding of CD62L in transfected HEK cells based assay, for instance, such as described in Examples 1.7 or 1.8. Preferably, the 1C81-like ISV has a modulating activity with an IC50 of less than 250 nM, more preferably, less than 200 nM, 175 nM or even less, such as less than 150 nM or 125 nM or even more preferably of less than 110 nM; or is determined by an ATP-induced externalization of phosphatidylserine (PS) by human T cells, for instance, such as described in Example 1.11; or is determined by an ATP-induced shedding of CD62L (PS) by human T cells, for instance, such as described in Example 1.11; or is determined by prevention of P2X7-mediated cell death of RPMI 8226 cells, for instance, such as described in Example 1.10.

For example, in a 1C81-like sequence according to this specifically preferred aspect: CDR1 is the amino acid sequence RTFSFSTSTMG (SEQ ID NO:34) (with CDR2 and CDR3 being as defined under e) and f), respectively); and/or CDR2 is the amino acid sequence AIDWSDFN (SEQ ID NO:62) (with CDR1 and CDR3 being as defined under d) and f), respectively); and/or CDR3 is the amino acid sequence HSETRGG-TRYFDRPSLYNY (SEQ ID NO:90)(with CDR1 and CDR2 being as defined under d) and e), respectively). Particularly, when an 1C81-like sequence is according to this aspect: CDR1 is the amino acid sequence RTFSFSTSTMG (SEQ ID NO:34) and CDR2 is the amino acid sequence AIDWSDEN (SEQ ID NO:62) (with CDR3 being as defined under f) above); and/or CDR1 is the amino acid sequence RTFSFSTSTMG (SEQ ID NO:34) and CDR3 is the amino acid sequence HSETRGGTRYFDRPSLYNY (SEQ ID NO:90) (with CDR2 being as defined under e) above); and/or CDR2 is the amino acid sequence AIDWSDEN (SEQ ID NO:62) and CDR3 is HSETRGGTRYFDRPSLYNY (HQ ID NO:90) (with CDR1 being as defined under d) above). Again, in such 1C81-like sequences, CDR1, CDR2 and CDR3 are preferably such that the 1C81-like ISV has a modulating activity, which can be determined by any suitable assay known to the person skilled in the art, such as, for instance, by means of Alphascreen assays (e.g., such as described herein) or by cell based assays (e.g., such as described herein).

Preferably, the modulating activity is determined by an ATP-induced shedding of CD62L in transfected HEK cells based assay, for instance, such as described in Examples 1.7 or 1.8. Preferably, the 1C81-like ISV has a modulating activity with an IC50 of less than 250 nM, more preferably, less than 200 nM, 175 nM or even less, such as less than 150 nM or 125 nM or even more preferably of less than 110 nM; or is determined by an ATP-induced externalization of phosphatidylserine (PS) by human T cells, for instance, such as described in Example 1.11; or is determined by an ATP-induced shedding of CD62L (PS) by human T cells, for instance, such as described in Example 1.11; or is determined by prevention of P2X7-mediated cell death of RPMI 8226 cells, for instance, such as described in Example 1.10.

In a particularly preferred 1C81-like sequence: CDR1 is the amino acid sequence RTFSFSTSTMG (SEQ ID NO:34), CDR2 is the amino acid sequence AIDWSDFN (SEQ ID NO:62); and CDR3 is the amino acid sequence HSETRGGTRYFDRPSLYNY (SEQ ID NO:90).

In all the 1C81-like sequence described in this section A), the framework sequences may be as further described herein. Preferably, the framework sequences are such that the framework sequences have at least 80%, such as at least 85%, for example at least 90%, such as at least 95% sequence identity with the framework sequences of 1C81 (which, for example, can be determined by determining the overall degree of sequence identity of a given sequence with the sequence of 1C81 while disregarding the CDR's in the calculation). Again, the combination of CDR's and frameworks present in a given sequence are preferably such that the resulting 1C81-like ISV has a modulating activity, which can be determined by any suitable assay known to the person skilled in the art, such as, for instance, by means of Alphascreen assays (e.g. such as described herein) or by cell based assays (e.g. such as described herein).

Preferably, the modulating activity is determined by an ATP-induced shedding of CD62L, in transfected HEK cells based assay, for instance, such as described in Examples 1.7 or 1.8. Preferably, the 1C81-like ISV has a modulating activity with an IC50 of less than 250 nM, more preferably, less than 200 nM, 175 nM or even less, such as less than 150 nM or 125 nM or even more preferably of less than 110 nM; or is determined by an ATP-induced externalization of phosphatidylserine (PS) by human T cells, for instance, such as described in Example 1.11; or is determined by an ATP-induced shedding of CD62L (PS) by human T cells, for instance, such as described in Example 1.11; or is determined by prevention of P2X7-mediated cell death of RPMI 8226 cells, for instance, such as described in Example 1.10, In one specific aspect, a 1C81-like sequence is an ISV that has at least 70%, such at least 80%, for example at least 85%, such as at least 90% or more than 95% sequence identity with SEQ NO: 6. For example, in an 1C81-like sequence according to this aspect, the CDR's may be according to the specifically preferred aspect described above, and may in particularly (but without limitation) be RTFSFSTSTMG (SEQ ID NO:34)(CDR1); AID-WSDFN (SEQ ID NO:62)(CDR2); and HSETRGG- TRYFDRPSLYNY (SEQ ID NO:90) (CDR3). Again, preferably, the combination of CDR's and frameworks present in such a 1C81-like ISV are preferably such that the resulting 1C81-like ISV has a modulating activity, which can be determined by any suitable assay known to the person skilled in the art, such as, for instance, by means of Alphascreen assays (e.g. such as described herein) or by cell based assays (e.g. such as described herein).

Preferably, the modulating activity is determined by an ATP-induced shedding of CD62L in transfected HEK cells based assay, for instance, such as described in Examples 1.7 or 1.8. Preferably, the 1C81-like ISV has a modulating activity with an IC50 of less than 250 nM, more preferably, less than 200 nM, 175 nM or even less, such as less than 150 nM or 125 nM or even more preferably of less than 110 nM; or is determined by an ATP-induced externalization of phosphatidylserine (PS) by human T cells, for instance, such as described in Example 1.11; or is determined by an ATP-induced shedding of CD62L (PS) by human T cells, for instance, such as described in Example 1.11; or is determined by prevention of P2X7-mediated cell death of RPMI 8226 cells, for instance, such as described in Example 1.10.

In one particular aspect, any 1C81-like sequence may be a humanized and/or sequence optimized sequence, as further described herein.

B) 3C23-like sequences: a "3C23-like sequence", "3C23-like ISV" or "3C23-like building block" is defined as an ISV (as described herein) that comprises:
  a) a CDR1 which comprises or essentially consists of either (i) the amino acid sequence RTFRHYAMG (SEQ ID NO:40) or (ii) an amino acid sequence that has only 3, 2 or 1 amino acid difference(s) (as defined herein) with the amino acid sequence RTFRHYAMG (SEQ ID NO:40); and/or
  b) a CDR2 which comprises or essentially consists of either (i) the amino acid sequence AISSYGST (SEQ ID NO:68) or (ii) an amino acid sequence that has at least 80%, such as at least 85%, for example at least 90% or more than 95% sequence identity with the amino acid sequence AISSYGST (SEQ ID NO:68); or (iii) an amino acid sequence that has only 7, 6, 5, 4, 3, 2 or 1 amino acid difference(s) (as defined herein) with the amino acid sequence AISSYGST (SEQ ID NO:68); and/or
  c) a CDR3 which comprises or essentially consists of either (i) the amino acid sequence DETLGAVPNFRLHEKYEYEY (SEQ ID NO:96) or (ii) an amino acid sequence that has at least 80%, such as at least 85%, for example at least 90% or more than 95% sequence identity with the amino acid sequence DETLGAVPNFRLHEKYEYEY (SEQ ID NO:96); or (iii) an amino acid sequence that has only 7, 6, 5, 4, 3, 2 or 1 amino acid difference(s) (as defined herein) with the amino acid sequence DETLGAVPNFRLHEKYEYEY (SEQ ID NO:96);

in which the framework sequences present in such an ISV are as further described herein, and in which CDR1, CDR2 and CDR3 are preferably such that the 3C23-like ISV has a modulating activity, which can be determined by any suitable assay known to the person skilled in the art, such as, for instance, by means of Alphascreen assays (as known in the art) or by cell based assays (e.g. such as described herein).

Preferably, the modulating activity is determined by an ATP-induced shedding of CD62L in transfected HEK cells based assay, for instance, such as described in Examples 1.7 or 1.8. Preferably, the 3C23-like ISV has a modulating activity with an IC50 of less than 100 nM, more preferably, less than 50 nM, 25 nM or even less, such as less than 20 nM or 15 nM, 10 nM, 8 nM or even more preferably of less than 5 nM; or is determined by an ATP-induced externalization of phosphatidylserine (PS) by human T cells, for instance, such as described in Example 1.11; or is determined by an ATP-induced shedding of CD62L (PS) by human T cells, for instance, such as described in Example 1.11; or is determined by prevention of P2X7-mediated cell death of RPMI 8226 cells, for instance, such as described in Example 1.10.

Preferably, in such a 3C23-like sequence, CDR1 and CDR2 are as defined under a) and b), respectively; or CDR1 and CDR3 are as defined under a) and c), respectively; or CDR2 and CDR3 are as defined under b) and c), respectively. More preferably, in such a 3C23-like sequence, CDR1, CDR2 and CDR3 are all as defined under a), b) and c), respectively. Again, in such an 3C23-like sequence, CDR1, CDR2 and CDR3 are preferably such that the 3C23-like ISV has a modulating activity, which can be determined by any suitable assay known to the person skilled in the art, such as, for instance, by means of Alphascreen assays) or by cell based assays (e.g. such as described herein).

Preferably, the modulating activity is determined by an ATP-induced shedding of CD62L in transfected HEK cells based assay, for instance, such as described in Examples 1.7 or 1.8. Preferably, the 3C23-like ISV has a modulating activity with an IC50 of less than 100 nM, more preferably, less than 50 nM, 25 nM or even less, such as less than 20 nM or 15 nM, 10 nM, 8 nM or even more preferably of less than 5 nM; or is determined by an ATP-induced externalization of phosphatidylserine (PS) by human T cells, for instance, such as described in Example 1.11; or is determined by an ATP-induced shedding of CD62L (PS) by human T cells, for instance, such as described in Example 1.11; or is determined by prevention of P2X7-mediated cell death of RPMI 8226 cells, for instance, such as described in Example 1.10.

For example, in such an 3C23-like sequence; CDR1 may comprise or essentially consist of the amino acid sequence RTFRHYAMG (SEQ ID NO:40) (with CDR2 and CDR3 being as defined under b) and c), respectively); and/or CDR2 may comprise or essentially consist of the amino acid sequence AISSYGST (SEQ ID NO:68) (with CDR1 and CDR3 being as defined under a) and c), respectively); and/or CDR3 may comprise or essentially consist of the amino acid sequence DETLGAVPNFRLHEKYEYEY (SEQ ID NO:96) (with CDR1 and CDR2 being as defined under a) and b), respectively). Particularly, when an 3C23-like sequence is according to this aspect: CDR1 may comprise or essentially consist of the amino acid sequence RTFRHYAMG (SEQ ID NO:40) and CDR2 may comprise or essentially consist of the amino acid sequence AISSYGST (SEQ ID NO:68) (with CDR3 being as defined under c) above); and/or CDR1 may comprise or essentially consist of the amino acid sequence RTFRHYAMG (SEQ ID NO:40) and CDR3 may comprise or essentially consist of the amino acid sequence DETLGAVPNFRLHEKYEYEY (SEQ ID NO:96)

(with CDR2 being as defined under b) above); and/or CDR2 may comprise or essentially consist of the amino acid sequence AISSYGST (SEQ ID NO:68) and CDR3 may comprise or essentially consist of the amino acid sequence DETLGAVPNFRLHEKYEYEY (SEQ ID NO:96) (with CDR1 being as defined under a) above). Again, in such 3C23-like sequences, CDR1, CDR2 and CDR3 are preferably such that the 3C23-like ISV has a modulating activity, which can be determined by any suitable assay known to the person skilled in the art, such as, for instance, by means of Alphascreen assays (e.g. such as described herein) or by cell based assays (e.g. such as described herein).

Preferably, the modulating activity is determined by an ATP-induced shedding of CD62L in transfected HEK cells based assay, for instance, such as described in Examples 1.7 or 1.8. Preferably, the 3C23-like ISV has a modulating activity with an IC50 of less than 100 nM, more preferably, less than 50 nM, 25 nM or even less, such as less than 20 nM or 15 nM, 10 nM, 8 nM or even more preferably of less than 5 nM; or is determined by an ATP-induced externalization of phosphatidylserine (PS) by human T cells, for instance, such as described in Example 1.11; or is determined by an ATP-induced shedding of CD62L (PS) by human T cells, for instance, such as described in Example 1.11; or is determined by prevention of P2X7-mediated cell death of RPMI 8226 cells, for instance, such as described in Example 1.10.

In a specifically preferred aspect, a "3C23-like sequence", "3C23-like ISV" or "3C23-like building block" is an ISV that comprises:
d) a CDR1 which is either (i) the amino acid sequence RTFRHYAMG (SEQ NO:40) or (ii) an amino acid sequence that has only 3, 2 or 1 amino acid difference(s) (as defined herein) with the amino acid sequence RTFRHYAMG (SEQ ID NO:40); and/or
e) a CDR2 which is either (i) the amino acid sequence AISSYGST (SEQ ID NO:68) or (ii) an amino acid sequence that has at least 80%, such as at least 85%, for example at least 90% or more than 95% sequence identity with the amino acid sequence AISSYGST (SEQ ID NO:68); or (iii) an amino acid sequence that has only 7, 6, 5, 4, 3, 2 or 1 amino acid difference(s) (as defined herein with the amino acid sequence AISSYGST (SEQ ID NO:68); and/or
f) a CDR3 which is either (i) the amino acid sequence DETLGAVPNFRLHEKYEYEY (SEQ ID NO:96) or (ii) an amino acid sequence that has at least 80%, such as at least 85%, for example at least 90% or more than 95% sequence identity with the amino acid sequence DETLGAVPNFRLHEKYEYEY (SEQ ID NO:96); or (iii) an amino acid sequence that has only 7, 6, 5, 4, 3, 2 or 1 amino acid difference(s) (as defined herein) with the amino acid sequence DETLGAVPNFRLHEKYEYEY (SEQ ID NO:96);
in which the framework sequences present in such an ISV are as further described herein, and in which CDR1, CDR2 and CDR3 are preferably such that the 3C23-like ISV has a modulating activity, which can be determined by any suitable assay known to the person skilled in the art, such as, for instance, by means of Alphascreen assays (e.g. such as described herein) or by cell based assays (e.g. such as described herein).

Preferably, the modulating activity is determined by an ATP-induced shedding of CD62L in transfected HEK cells based assay, for instance, such as described in Examples 1.7 or 1.8. Preferably, the 3C23-like ISV has a modulating activity with an IC50 of less than 100 nM, more preferably, less than 50 nM, 25 nM or even less, such as less than 20 nM or 15 nM, 10 nM, 8 nM or even more preferably of less than 5 nM; or is determined by an ATP-induced externalization of phosphatidylserine (PS) by human T cells, for instance, such as described in Example 1.11; or is determined by an ATP-induced shedding of CD62L (PS) by human T cells, for instance, such as described in Example 1.11; or is determined by prevention of P2X7-mediated cell death of RPMI 8226 cells, for instance, such as described in Example 1.10, Preferably, in a 3C23-like sequence according to this specifically preferred aspect, CDR1 and CDR2 are as defined under d) and e), respectively; or CDR1 and CDR3 are as defined under d) and f), respectively; or CDR2 and CDR3 are as defined under e) and f), respectively. More preferably, in such a 3C23-like sequence, CDR1, CDR2 and CDR3 are all as defined under d), e) and f), respectively. Again, in such an 3C23-like sequence, CDR1, CDR2 and CDR3 are preferably such that the 3C23-like ISV has a modulating activity, which can be determined by any suitable assay known to the person skilled in the art, such as, for instance, by means of Alphascreen assays (e.g. such as described herein) or by cell based assays (e.g. such as described herein).

Preferably, the modulating activity is determined by an ATP-induced shedding of CD62L in transfected HEK cells based assay, for instance, such as described in Examples 1.7 or 1.8. Preferably, the 3C23-like ISV has a modulating activity with an IC50 of less than 100 nM, more preferably, less than 50 nM, 25 nM or even less, such as less than 20 nM or 15 nM, 10 nM, 8 nM or even more preferably of less than 5 nM; or is determined by an ATP-induced externalization of phosphatidylserine (PS) by human T cells, for instance, such as described in Example 1.11; or is determined by an ATP-induced shedding of CD62L (PS) by human T cells, for instance, such as described in Example 1.11; or is determined by prevention of P2X7-mediated cell death of RPMI 8226 cells, for instance, such as described in Example 1.10.

For example, in a 3C23-like sequence according to this specifically preferred aspect: CDR1 is the amino acid sequence RTFRHYAMG (SEQ ID NO:40) (with CDR2 and CDR3 being as defined under e) and f), respectively); and/or CDR2 is the amino acid sequence AISSYGST (SEQ ID NO:68) (with CDR1 and CDR3 being as defined under d) and f), respectively); and/or CDR3 is the amino acid sequence DETLGAVPNFRLHEKYEYEY (SEQ ID NO:96) (with CDR1 and CDR2 being as defined under d) and e), respectively). Particularly, when an 3C23-like sequence is according to this aspect: CDR1 is the amino acid sequence RTFRHYAMG (SEQ ID NO:40) and CDR2 is the amino acid sequence AISSYGST (SEQ ID NO:68) (with CDR3 being as defined under f) above); and/or CDR1 is the amino acid sequence RTFRHYAMG (SEQ ID NO:40) and CDR3 is the amino acid sequence DETLGAVPNFRLHEKYEYEY (SEQ ID NO:96) (with CDR2 being as defined under e) above); and/or CDR2 is the amino acid sequence AISSYGST and CDR3 is DETLGAVPNFRLHEKYEYEY (SEQ ID NO:96) (with CDR1 being as defined under d) above). Again, in such 3C23-like sequences, CDR1, CDR2 and CDR3 are preferably such that the 3C23-like ISV has a modulating activity, which can be determined by any suitable assay known to the person skilled in the art, such as, for instance, by means of Alphascreen assays (e.g. such as described herein) or by cell based assays (e.g. such as described herein).

Preferably, the modulating activity is determined by an ATP-induced shedding of CD62L in transfected HEK cells based assay, for instance, such as described in Examples 1.7 or 1.8. Preferably, the 3C23-like ISV has a modulating activity with an IC50 of less than 100 nM, more preferably, less than 50 nM, 25 nM or even less, such as less than 20 nM or 15 nM, 10 nM, 8 nM or even more preferably of less than 5 nM; or is determined by an ATP-induced externalization of phosphatidylserine (PS) by human T cells, for instance, such as described in Example 1.11; or is determined by an ATP-induced shedding of CD62L (PS) by human T cells, for instance, such as described in Example 1.11; or is determined by prevention of P2X7-mediated cell death of RPMI 8226 cells, for instance, such as described in Example 1.10, In a particularly preferred 3C23-like sequence: CDR1 is the amino acid sequence RTFRHYAMG (SEQ ID NO:40), CDR2 is the amino acid sequence AISSYGST (SEQ ID NO:68); and CDR3 is the amino acid sequence DETLGAVPNFRLHEKYEYEY (SEQ ID NO:96).

In all the 3C23-like sequence described in this section B), the framework sequences may be as further described herein. Preferably, the framework sequences are such that the framework sequences have at least 80%, such as at least 85%, for example at least 90%, such as at least 95% sequence identity with the framework sequences of 3C23 (which, for example, can be determined by determining the overall degree of sequence identity of a given sequence with the sequence of 3C23 while disregarding the CDR's in the calculation). Again, the combination of CDR's and frameworks present in a given sequence are preferably such that the resulting 3C23-like ISV has a modulating activity, which can be determined by any suitable assay known to the person skilled in the art, such as, for instance, by means of Alphascreen assays (e.g. such as described herein) or by cell based assays (e.g. such as described herein).

Preferably, the modulating activity is determined by an ATP-induced shedding of CD62L in transfected HEK cells based assay, for instance, such as described in Examples 1.7 or 1.8. Preferably, the 3C23-like ISV has a modulating activity with an IC50 of less than 100 nM, more preferably, less than 50 nM, 25 nM or even less, such as less than 20 nM or 15 nM, 10 nM, 8 nM or even more preferably of less than 5 nM; or is determined by an ATP-induced externalization of phosphatidylserine (PS) by human T cells, for instance, such as described in Example 1.11; or is determined by an ATP-induced shedding of CD62L (PS) by human T cells, for instance, such as described in Example 1.11; or is determined by prevention of P2X7-mediated cell death of RPMI 8226 cells, for instance, such as described in Example 1.10, In one specific aspect, a 3C23-like sequence is an ISV that has at least 70%, such at least 80%, for example at least 85%, such as at least 90% or more than 95% sequence identity with SEQ ID NO: 6. For example, in an 3C23-like sequence according to this aspect, the CDR's may be according to the specifically preferred aspect described above, and may in particularly (but without limitation) be RTFRHYAMG (SEQ ID NO:40) (CDR1); AISSYGST (SEQ ID NO:68) (CDR2); and DETLGAVPNFRLHEKYEYEY (SEQ ID NO:96) (CDR3). Again, preferably, the combination of CDR's and frameworks present in such a 3C23-like ISV are preferably such that the resulting 3C23-like ISV has a modulating activity, which can be determined by any suitable assay known to the person skilled in the art, such as, for instance, by means of Alphascreen assays (e.g. such as described herein) or by cell based assays (e.g. such as described herein).

Preferably, the modulating activity is determined by an ATP-induced shedding of CD62L in transfected HEK cells based assay, for instance, such as described in Examples 1.7 or 1.8. Preferably, the 3C23-like ISV has a modulating activity with an IC50 of less than 100 nM, more preferably, less than 50 nM, 25 nM or even less, such as less than 20 nM or 15 nM, 10 nM, 8 nM or even more preferably of less than 5 nM; or is determined by an ATP-induced externalization of phosphatidylserine (PS) by human T cells, for instance, such as described in Example 1.11; or is determined by an ATP-induced shedding of CD62L (PS) by human T cells, for instance, such as described in Example 1.11; or is determined by prevention of P2X7-mediated cell death of RPMI 8226 cells, for instance, such as described in Example 1.10.

In one particular aspect, any 3C23-like sequence may be a humanized and/or sequence optimized sequence, as further described herein, C) 1C113-like sequences: a "1C113-like sequence", "1C113-like ISV" or "1C113-like building block" is defined as an ISV (as described herein) that comprises:
  a) a CDR1 which comprises or essentially consists of either (i) the amino acid sequence IAFNYYSMS (SEQ ID NO:35) or (ii) an amino acid sequence that has only 3, 2 or 1 amino acid difference(s) (as defined herein) with the amino acid sequence IAFNYYSMS (SEQ ID NO:35); and/or
  b) a CDR2 which comprises or essentially consists of either (i) the amino acid sequence DISPGGHT (SEQ ID NO:63) or (ii) an amino acid sequence that has at least 80%, such as at least 85%, for example at least 90% or more than 95% sequence identity with the amino acid sequence DISPGGHT (SEQ ID NO:63); or (iii) an amino acid sequence that has only 7, 6, 5, 4, 3, 2 or 1 amino acid difference(s) (as defined herein) with the amino acid sequence DISPGGHT (SEQ ID NO:63); and/or
  c) a CDR3 which comprises or essentially consists of either (i) the amino acid sequence RLRFEVSSNY (SEQ ID NO:91) or (ii) an amino acid sequence that has at least 80%, such as at least 85%, for example at least 90% or more than 95% sequence identity with the amino acid sequence RLRFEVSSNY (SEQ ID NO:91); or (iii) an amino acid sequence that has only 7, 6, 5, 4, 3, 2 or 1 amino acid difference(s) (as defined herein) with the amino acid sequence RLRFEVSSNY (SEQ ID NO:91);
  in which the framework sequences present in such an ISV are as further described herein, and in which CDR1, CDR2 and CDR3 are preferably such that the 1C113-like ISV has a modulating activity, which can be determined by any suitable assay known to the person skilled in the art, such as, for instance, by means of Alphascreen assays (as known in the art) or by cell based assays (e.g. such as described herein).

Preferably, the modulating activity is determined by an ATP-induced shedding of CD62L in transfected HEK cells based assay; or is determined by an ATP-induced externalization of phosphatidylserine (PS) by human T cells; or is determined by an ATP-induced shedding of CD62L (PS) by human T cells; or is determined by prevention of P2X7-mediated cell death of RPMI 8226 cells, Preferably, in such a 1C113-like sequence, CDR1 and CDR2 are as defined under a) and b), respectively; or CDR1 and CDR3 are as defined under a) and c), respectively; or CDR2 and CDR3 are as defined under b) and c) respectively. More preferably, in such a 1C113-like sequence, CDR1, CDR2 and CDR3 are all as defined under a), b) and c), respectively. Again, in such an 1C113-like sequence, CDR1, CDR2 and CDR3 are preferably such that the 1C113-like ISV has a modulating activity, which can be determined by any suitable assay known to the person skilled in the art, such as, for instance, by means of Alphascreen assays) or by cell based assays (e.g. such as described herein).

Preferably, the modulating activity is determined by an ATP-induced shedding of CD62L in transfected HEK cells based assay; or is determined by an ATP-induced externalization of phosphatidylserine (PS) by human T cells; or is determined by an ATP-induced shedding of CD62L (PS) by human T cells; or is determined by prevention of P2X7-mediated cell death of RPMI 8226 cells.

For example, in such an 1C113-like sequence: CDR1 may comprise or essentially consist of the amino acid sequence IAFNYYSMS (SEQ ID NO:35) (with CDR2 and CDR3 being as defined under b) and c), respectively); and/or CDR2 may comprise or essentially consist of the amino acid sequence DISPGGHT (SEQ ID NO:63) (with CDR1 and CDR3 being as defined under a) and c), respectively); and/or CDR3 may comprise or essentially consist of the amino acid sequence RLRFEVSSNY (SEQ ID NO:91) (with CDR1 and CDR2 being as defined under a) and b), respectively). Particularly, when an 1C113-like sequence is according to this aspect: CDR1 may comprise or essentially consist of the amino acid sequence IAFNYYSMS (SEQ ID NO:35) and CDR2 may comprise or essentially consist of the amino acid sequence DISPGGHT (SEQ ID NO:63) (with CDR3 being as defined under c) above); and/or CDR1 may comprise or essentially consist of the amino acid sequence IAFNYYSMS (SEQ ID NO:35) and CDR3 may comprise or essentially consist of the amino acid sequence RLRFEVSSNY (SEQ ID NO:91) (with CDR2 being as defined under b) above); and/or CDR2 may comprise or essentially consist of the amino acid sequence DISPGGHT (SEQ ID NO:63) and CDR3 may comprise or essentially consist of the amino acid sequence RLRFEVSSNY (SEQ ID NO:91) (with CDR1 being as defined under a) above). Again, in such 1C113-like sequences, CDR1, CDR2 and CDR3 are preferably such that the 1C113-like ISV has a modulating activity, which can be determined by any suitable assay known to the person skilled in the art, such as, for instance, by means of Alphascreen assays (e.g. such as described herein) or by cell based assays (e.g. such as described herein).

Preferably, the modulating activity is determined by an ATP-induced shedding of CD62L in transfected HEK cells based assay; or is determined by an ATP-induced externalization of phosphatidylserine (PS) by human T cells; or is determined by an ATP-induced shedding of CD62L (PS) by human T cells; or is determined by prevention of P2X7-mediated cell death of RPMI 8226 cells, In a specifically preferred aspect, a "1C113-like sequence", "1C113-like ISV" or "1C113-like building block" is an ISV that comprises:

d) a CDR1 which is either (i) the amino acid sequence IAFNYYSMS (SEQ ID NO:35) or (ii) an amino acid sequence that has only 3, 2 or 1 amino acid difference(s) (as defined herein) with the amino acid sequence IAFNYYSMS (SEQ ID NO:35); and/or e) a CDR2 which is either (1) the amino acid sequence DISPGGHT (SEQ ID NO:63) or (ii) an amino acid sequence that has at least 80%, such as at least 85%, for example at least 90% or more than 95% sequence identity with the amino acid sequence DISPGGHT (SEQ ID NO:63); or (iii) an amino acid sequence that has only 7, 6, 5, 4, 3, 2 or 1 amino acid difference(s) (as defined herein) with the amino acid sequence DISPGGHT; and/or f) a CDR3 which is either (i) the amino acid sequence RLRFEVSSNY (SEQ ID NO:91) or (i an amino acid sequence that has at least 80%, such as at least 85%, for example at least 90% or more than 95% sequence identity with the amino acid sequence RLRFEVSSNY (SEQ ID NO:91); or (iii) an amino acid sequence that has only 7, 6, 5, 4, 3, 2 or 1 amino acid difference(s) (as defined herein) with the amino acid sequence RLRFEVSSNY (SEQ ID NO:91);

in which the framework sequences present in such an ISV are as further described herein, and in which CDR1, CDR2 and CDR3 are preferably such that the 1C113-like ISV has a modulating activity, which can be determined by any suitable assay known to the person skilled in the art, such as, for instance, by means of Alphascreen assays (e.g. such as described herein) or by cell based assays (e.g. such as described herein), Preferably, the modulating activity is determined by an ATP-induced shedding of CD62L in transfected HEK cells based assay; or is determined by an ATP-induced externalization of phosphatidylserine (PS) by human T cells; or is determined by an ATP-induced shedding of CD62L (PS) by human T cells; or is determined by prevention of P2X7-mediated cell death of RPMI 8226 cells, Preferably, in a 1C113-like sequence according to this specifically preferred aspect, CDR1 and CDR2 are as defined under d) and e), respectively; or CDR1 and CDR3 are as defined under d) and f), respectively; or CDR2 and CDR3 are as defined under e) and f), respectively. More preferably, in such a 1C113-like sequence, CDR1, CDR2 and CDR3 are all as defined under d), e) and f), respectively. Again, in such an 1C113-like sequence, CDR1, CDR2 and CDR3 are preferably such that the 1C113-like ISV has a modulating activity, which can be determined by any suitable assay known to the person skilled in the art, such as, for instance, by means of Alphascreen assays (e.g. such as described herein) or by cell based assays (e.g. such as described herein).

Preferably, the modulating activity is determined by an ATP-induced shedding of CD62L in transfected HEK cells based assay; or is determined by an ATP-induced externalization of phosphatidylserine (PS) by human T cells; or is determined by an ATP-induced shedding of CD62L (PS) by human T cells; or is determined by prevention of P2X7-mediated cell death of RPMI 8226 cells.

For example, in a 1C113-like sequence according to this specifically preferred aspect: CDR1 is the amino acid sequence IAFNYYSMS (SEQ ID NO:35) (with CDR2 and CDR3 being as defined under e) and f), respectively); and/or CDR2 is the amino acid sequence DISPGGHT (SEQ ID NO:63) (with CDR1 and CDR3 being as defined under d) and f), respectively); and/or CDR3 is the amino acid sequence RLRFEVSSNY (SEQ ID NO:91) (with CDR1 and CDR2 being as defined under d) and e), respectively). Particularly, when an 1C113-like sequence is according to this aspect: CDR1 is the amino acid sequence IAFNYYSMS (SEQ ID NO:35) and CDR2 is the amino acid sequence DISPGGHT (SEQ ID NO:63) (with CDR3 being as defined under f) above); and/or CDR1 is the amino acid sequence IAFNYYSMS (SEQ ID NO:35) and CDR3 is the amino acid sequence RLRFEVSSNY (SEQ ID NO:91) (with CDR2 being as defined under e) above); and/or CDR2 is the amino acid sequence DISPGGHT (SEQ ID NO:63) and CDR3 is RLRFEVSSNY (SEQ ID NO:91) (with CDR1 being as defined under d) above). Again, in such 1C113-like sequences, CDR1, CDR2 and CDR3 are preferably such that the 1C113-like ISV has a modulating activity, which can be determined by any suitable assay known to the person skilled in the art, such as, for instance, by means of Alphascreen assays (e.g. such as described herein) or by cell based assays (e.g. such as described herein).

Preferably, the modulating activity is determined by an ATP-induced shedding of CD62L in transfected HEK cells based assay; or is determined by an ATP-induced externalization of phosphatidylserine (PS) by human T cells; or is determined by an ATP-induced shedding of CD62L (PS) by human T cells; or is determined by prevention of P2X7-mediated cell death of RPMI 8226 cells.

In a particularly preferred 1C113-like sequence: CDR1 is the amino acid sequence IAFNYYSMS, CDR2 is the amino acid sequence DISPGGHT (SEQ ID NO:63); and CDR3 is the amino acid sequence RLRFEVSSNY (SEQ ID NO:91).

In all the 1C113-like sequence described in this section C), the framework sequences may be as further described herein. Preferably, the framework sequences are such that the framework sequences have at least 80%, such as at least 85%, for example at least 90%, such as at least 95% sequence identity with the framework sequences of 1C113 (which, for example, can be determined by determining the overall degree of sequence identity of a given sequence with the sequence of 1C113 while disregarding the CDR's in the calculation). Again, the combination of CDR's and frameworks present in a given sequence are preferably such that the resulting 1C113-like ISV has a modulating activity, which can be determined by any suitable assay known to the person skilled in the art, such as, for instance, by means of Alphascreen assays (e.g. such as described herein) or by cell based assays (e.g. such as described herein).

Preferably, the modulating activity is determined by an ATP-induced shedding of CD62L in transfected HEK cells based assay; or is determined by an ATP-induced externalization of phosphatidylserine (PS) by human T cells; or is determined by an ATP-induced shedding of CD62L (PS) by human T cells; or is determined by prevention of P2X7-mediated cell death of RPMI 8226 cells.

In one specific aspect, a 1C113-like sequence is an ISV that has at least 70%, such at least 80%, for example at least 85%, such as at least 90% or more than 95% sequence identity with SEQ ID NO: 6. For example, in an 1C113-like sequence according to this aspect, the CDR's may be according to the specifically preferred aspect described above, and may in particularly (but without limitation) be IAFNYYSMS (SEQ ID NO:35) (CDR1); DISPGGHT (SEQ ID NO:63) (CDR2); and RLRFEVSSNY (SEQ ID NO:91) (CDR3). Again, preferably, the combination of CDR's and frameworks present in such a 1C113-like ISV are preferably such that the resulting 1C113-like ISV has a modulating activity, which can be determined by any suitable assay known to the person skilled in the art, such as, for instance, by means of Alphascreen assays (e.g. such as described herein) or by cell based assays (e.g. such as described herein).

Preferably, the modulating activity is determined by an ATP-induced shedding of CD62L in transfected HEK cells based assay; or is determined by an ATP-induced externalization of phosphatidylserine (PS) by human T cells; or is determined by an ATP-induced shedding of CD62L (PS) by human T cells; or is determined by prevention of P2X7-mediated cell death of RPMI 8226 cells.

In one particular aspect, any 1C113-like sequence may be a humanized and/or sequence optimized sequence, as further described herein.

D) 13A7-like sequences: a "13A7-like sequence", "13A7-like ISV" or "13A7-like building block" is defined as an ISV (as described herein) that comprises:
  a) a CDR1 which comprises or essentially consists of either (i) the amino acid sequence YYDIG (SEQ ID NO:47) or (ii) an amino acid sequence that has only 3, 2 or 1 amino acid difference(s) (as defined herein) with the amino acid sequence YYDIG (SEQ ID NO:47); and/or
  b) a CDR2 which comprises or essentially consists of either (i) the amino acid sequence CRFTNDGSTAYADSVKG (SEQ ID NO:75) or (ii) an amino acid sequence that has at least 80%, such as at least 85%, for example at least 90% or more than 95% sequence identity with the amino acid sequence CRFTNDGSTAYADSVKG (SEQ NO:75); or (iii) an amino acid sequence that has only 7, 6, 5, 4, 3, 2 or 1 amino acid difference(s) (as defined herein) with the amino acid sequence CRFTNDGSTAYADSVKG (SEQ ID NO:75); and/or
  c) a CDR3 which comprises or essentially consists of either (i) the amino acid sequence GPLTKRRQCVPGDFSMDF (SEQ ID NO:103) or (ii) an amino acid sequence that has at least 80%, such as at least 85%, for example at least 90% or more than 95% sequence identity with the amino acid sequence GPLTKRRQCVPGDFSMDF (SEQ ID NO:103); or (Hi) an amino acid sequence that has only 7, 6, 5, 4, 3, 2 or 1 amino acid difference(s) (as defined herein) with the amino acid sequence GPLTKRRQCVPGDFSMDF (SEQ ID NO:103);
  in which the framework sequences present in such an ISV are as further described herein, and in which CDR1, CDR2 and CDR3 are preferably such that the 13A7-like ISV has a modulating activity, which can be determined by any suitable assay known to the person skilled in the art, such as, for instance, by means of Alphascreen assays (as known in the art), by cell based assays (as known in the art), by in vivo assays.

Preferably, the modulating activity is determined by an ATP-induced shedding of CD27 or modulating of PS externalization of in spleen and liver cells from mice injected with 13A7-like ISVs, for instance, such as described in Example 2.3. Preferably, the 13A7-like ISV has a modulating activity which is determined in an anti-podocyte induced nephritis model as described in Example 3, Preferably, in such a 13A7-like sequence, CDR1 and CDR2 are as defined under a) and b), respectively; or CDR1 and CDR3 are as defined under a) and c), respectively; or CDR2 and CDR3 are as defined under b) and c), respectively. More preferably, in such a 13A7-like sequence, CDR1, CDR2 and CDR3 are all as defined under a), b) and c), respectively. Again, in such an 13A7-like sequence, CDR1, CDR2 and CDR3 are preferably such that the 13A7-like ISV has a modulating activity, which can be determined by any suitable assay known to the person skilled in the art, such as, for instance, by means of Alphascreen assays) or by cell based assays (e.g. such as described herein).

Preferably, the modulating activity is determined by an ATP-induced shedding of CD27 or modulating of PS externalization of in spleen and liver cells from mice injected with 13A7-like ISVs, for instance, in such as described in Example 2.3. Preferably, the 13A7-like ISV has a modulating activity which is determined in an anti-podocyte induced nephritis model as described in Example 3.

For example, in such an 13A7-like sequence: CDR1 may comprise or essentially consist of the amino acid sequence YYDIG (SEQ ID NO:47) (with CDR2 and CDR3 being as defined under b) and c), respectively); and/or CDR2 may comprise or essentially consist of the amino acid sequence CRFTNDGSTAYADSVKG (SEQ ID NO:75) (with CDR1 and CDR3 being as defined under a) and c), respectively); and/or CDR3 may comprise or essentially consist of the amino acid sequence GPLTKRRQCVPGDFSMDF (SEQ ID NO:103) (with CDR1 and CDR2 being as defined under a) and b), respectively). Particularly, when an 13A7-like sequence is according to this aspect: CDR1 may comprise or essentially consist of the amino acid sequence YYDIG (SEQ ID NO:47) and CDR2 may comprise or essentially consist of the amino acid sequence CRFTNDGSTAYADSVKG (SEQ ID NO:75) (with CDR3 being as defined under c) above); and/or CDR1 may comprise or essentially consist of the amino acid sequence YYDIG (SEQ ID NO:47) and CDR3 may comprise or essentially consist of the amino acid sequence GPLTKRRQCVPGDFSMDF (SEQ ID NO:103) (with CDR2 being as defined under b) above); and/or CDR2 may comprise or essentially consist of the amino acid sequence CRFTNDGSTAYADSVKG (SEQ ID NO:75) and CDR3 may comprise or essentially consist of the amino acid sequence GPLTKRRQCVPGDFSMDF (SEQ ID NO:103) (with CDR1 being as defined under a) above). Again, in such 13A7-like sequences, CDR1, CDR2 and CDR3 are preferably such that the 13A7-like ISV has a modulating activity, which can be determined by any suitable assay known to the person skilled in the art, such as, for instance, by means of Alphascreen assays (e.g. such as described herein) or by cell based assays (e.g. such as described herein).

Preferably, the modulating activity is determined by an ATP-induced shedding of CD27 or modulating of PS externalization of in spleen and liver cells from mice injected with 13A7-like ISVs, for instance, such as described in Example 2.3. Preferably, the 13A7-like ISV has a modulating activity which is determined in an anti-podocyte induced nephritis model as described in Example 3.

In a specifically preferred aspect, a "13A7-like sequence", "13A7-like ISV" or "13A7-like building block" is an ISV that comprises:

d) a CDR1 which is either (i) the amino acid sequence YYDIG (SEQ ID NO:47) or (ii) an amino acid sequence that has only 3, 2 or 1 amino acid difference(s) (as defined herein) with the amino acid sequence YYDIG (SEQ ID NO:47); and/or e) a CDR2 which is either (i) the amino acid sequence CRFTNDGSTAYADSVKG (SEQ ID NO:75) or (ii) an amino acid sequence that has at least 80%, such as at least 85%, for example at least 90% or more than 95% sequence identity with the amino acid sequence CRFTNDGSTAYADSVKG (SEQ ID NO:75); or (iii) an amino acid sequence that has only 7, 6, 5, 4, 3, 2 or 1 amino acid difference(s) (as defined herein) with the amino acid sequence CRFTNDGSTAYADSVKG (SEQ ID NO:75); and/or f) a CDR3 which is either (i) the amino acid sequence GPLTKRRQCVPGDFSMDF (SEQ ID NO:103) or (ii) an amino acid sequence that has at least 80%, such as at least 85%, for example at least 90% or more than 95% sequence identity with the amino acid sequence GPLTKRRQCVPGDFSMDF (SEQ ID NO:103); or (iii) an amino acid sequence that has only 7, 6, 5, 4, 3, 2 or 1 amino acid difference(s) (as defined herein) with the amino acid sequence GPLTKRRQCVPGDFSMDF (SEQ ID NO:103);

in which the framework sequences present in such an ISV are as further described herein, and in which CDR1, CDR2 and CDR3 are preferably such that the 13A7-like ISV has a modulating activity, which can be determined by any suitable assay known to the person skilled in the art, such as, for instance, by means of Alphascreen assays (e.g. such as described herein) or by cell based assays (e.g. such as described herein), Preferably, the modulating activity is determined by an ATP-induced shedding of CD27 or modulating of PS externalization of in spleen and liver cells from mice injected with 13A7-like ISVs, for instance, such as described in Example 2.3. Preferably, the 13A7-like ISV has a modulating activity which is determined in an anti-podocyte induced nephritis model as described in Example 3.

Preferably, in a 13A7-like sequence according to this specifically preferred aspect, CDR1 and CDR2 are as defined under d) and e), respectively; or CDR1 and CDR3 are as defined under d) and 1), respectively; or CDR2 and CDR3 are as defined under e) and f), respectively. More preferably, in such a 13A7-like sequence, CDR1, CDR2 and CDR3 are all as defined under d), e) and f), respectively. Again, in such an 13A7-like sequence, CDR1, CDR2 and CDR3 are preferably such that the 13A7-like ISV has a modulating activity, which can be determined by any suitable assay known to the person skilled in the art, such as, for instance, by means of Alphascreen assays (e.g. such as described herein) or by cell based assays (e.g. such as described herein).

Preferably, the modulating activity is determined by an ATP-induced shedding of CD27 or modulating of PS externalization of in spleen and liver cells from mice injected with 13A7-like ISVs, for instance, such as described in Example 2.3. Preferably, the 13A7-like ISV has a modulating activity which is determined in an anti-podocyte induced nephritis model as described in Example 3.

For example, in a 13A7-like sequence according to this specifically preferred aspect: CDR1 is the amino acid sequence YYDIG (SEQ ID NO:47) (with CDR2 and CDR3 being as defined under e) and f), respectively); and/or CDR2 is the amino acid sequence CRFTNDG-STAYADSVKG (SEQ ID NO:75) (with CDR1 and CDR3 being as defined under d) and f), respectively); and/or CDR3 is the amino acid sequence GPLT-KRRQCVPGDFSMDF (SEQ ID NO:103) (with CDR1 and CDR2 being as defined under d) and e), respectively). Particularly, when an 13A7-like sequence is according to this aspect: CDR1 is the amino acid sequence YYDIG (SEQ ID NO:47) and CDR2 is the amino acid sequence CRFTNDGSTAYADSVKG (with CDR3 being as defined under f) above); and/or CDR1 is the amino acid sequence YYDIG (SEQ ID NO:47) and CDR3 is the amino acid sequence GPLT-KRRQCVPGDFSMDF (SEQ ID NO:103) (with CDR2 being as defined under e) above); and/or CDR2 is the amino acid sequence CRFTNDGSTAYADSVKG (SEQ ID NO:75) and CDR3 is GPLTKRRQCVPGD-FSMDF (SEQ ID NO:103) (with CDR1 being as defined under d) above). Again, in such 13A7-like sequences, CDR1, CDR2 and CDR3 are preferably such that the 13A7-like ISV has a modulating activity, which can be determined by any suitable assay known to the person skilled in the art, such as, for instance, by means of Alphascreen assays (e.g. such as described herein) or by cell based assays (e.g. such as described herein).

Preferably, the modulating activity is determined by an ATP-induced shedding of CD27 or modulating of PS externalization of in spleen and liver cells from mice injected with 13A7-like ISVs, for instance, such as described in Example 2.3. Preferably, the 13A7-like ISV has a modulating activity which is determined in an anti-podocyte induced nephritis model as described in Example 3, In a particularly preferred 13A7-like sequence: CDR1 is the amino acid sequence YYDIG (SEQ ID NO:47), CDR2 is the amino acid sequence CRFTNDGSTAY-ADSVKG (SEQ ID NO:75); and CDR3 is the amino acid sequence GPLTKRRQCVPGDFSMDF (SEQ ID NO:103).

In all the 13A7-like sequence described in this section D), the framework sequences may be as further described herein. Preferably, the framework sequences are such that the framework sequences have at least 80%, such as at least 85%, for example at least 90%, such as at least 95% sequence identity with the framework sequences of 13A7 (which, for example, can be determined by determining the overall degree of sequence identity of a given sequence with the sequence of 13A7 while disregarding the CDR's in the calculation). Again, the combination of CDR's and frameworks present in a given sequence are preferably such that the resulting 13A7-like ISV has a modulating activity, which can be determined by any suitable assay known to the person skilled in the art, such as, for instance, by means of Alphascreen assays (e.g. such as described herein) or by cell based assays (e.g. such as described herein).

Preferably, the modulating activity is determined by an ATP-induced shedding of CD27 or modulating of PS externalization of in spleen and liver cells from mice injected with 13A7-like ISVs, for instance, such as described in Example 2.3. Preferably, the 13A7-like ISV has a modulating activity which is determined in an anti-podocyte induced nephritis model as described in Example 3.

In one specific aspect, a 13A7-like sequence is an ISV that has at least 70%, such at least 80%, for example at least 85%, such as at least 90% or more than 95% sequence identity with SEQ ID NO: 6. For example, in an 13A7-like sequence according to this aspect, the CDR's may be according to the specifically preferred aspect described above, and may in particularly (but without limitation) be YYDIG (SEQ ID NO:47) (CDR1); CRFTNDGSTAYADSVKG (SEQ ID NO:75) (CDR2); and GPLTKRRQCVPGDFSIVIDF (SEQ ID NO:103) (CDR3). Again, preferably, the combination of CDR's and frameworks present in such a 13A7-like ISV are preferably such that the resulting 13A7-like ISV has a modulating activity, which can be determined by any suitable assay known to the person skilled in the art, such as, for instance, by means of Alphascreen assays (e.g. such as described herein) or by cell based assays (e.g. such as described herein).

Preferably, the modulating activity is determined by an ATP-induced shedding of CD27 or modulating of PS externalization of in spleen and liver cells from mice injected with 13A7-like ISVs, for instance, such as described in Example 2.3. Preferably, the 13A7-like ISV has a modulating activity which is determined in an anti-podocyte induced nephritis model as described in Example 3.

In one particular aspect, any 13A7-like sequence may be a humanized and/or sequence optimized sequence, as further described herein.

E) 14D5-like sequences: a "14D5-like sequence", "14D5-like ISV" or "14D5-like building block" is defined as an ISV (as described herein) that comprises:
a) a CDR1 which comprises or essentially consists of either (i) the amino acid sequence SYAMG (SEQ ID NO:46) or (ii) an amino acid sequence that has only 3, 2 or 1 amino acid difference(s) (as defined herein) with the amino acid sequence SYAMG (SEQ ID NO:46); and/or
b) a CDR2 which comprises or essentially consists of either (i) the amino acid sequence RIYTGGTAW-YEDSVKG (SEQ ID NO:74) or (ii) an amino acid sequence that has at least 80%, such as at least 85%, for example at least 90% or more than 95% sequence identity with the amino acid sequence RIYTGGTAW-YEDSVKG (SEQ ID NO:74); or (iii) an amino acid sequence that has only 7, 6, 5, 4, 3, 2 or 1 amino acid difference(s) (as defined herein) with the amino acid sequence RIYTGGTAWYEDSVKG (SEQ ID NO:74); and/or
c) a CDR3 which comprises or essentially consists of either (i) the amino acid sequence RVRYDY (SEQ ID NO:102) or (ii) an amino acid sequence that has at least 80%, such as at least 85%, for example at least 90% or more than 95% sequence identity with the amino acid sequence RVRYDY (SEQ NO:102); or (iii) an amino acid sequence that has only 7, 6, 5, 4, 3, 2 or 1 amino acid difference(s) (as defined herein) with the amino acid sequence RVRYDY;

in which the framework sequences present in such an ISV are as further described herein, and in which CDR1, CDR2 and CDR3 are preferably such that the 14D5-like ISV has a modulating activity, which can be determined by any suitable assay known to the person skilled in the art, such as, for instance, by means of Alphascreen assays (as known in the art), by cell based assays (as known in the art), by in vivo assays, Preferably, the modulating activity is determined by an ATP-induced shedding of CD27 or modulating of PS externalization of in spleen and liver cells from mice injected with 14D5-like ISVs, for instance, such as described in Example 2.2. Preferably, the 14D5-like ISV has a modulating activity which is determined in an anti-podocyte induced nephritis model as described in Example 3.

Preferably, in such a 14D5-like sequence, CDR1 and CDR2 are as defined under a) and b), respectively; or CDR1 and CDR3 are as defined under a) and c), respectively; or CDR2 and CDR3 are as defined under b) and c), respectively. More preferably, in such a 14D5-like sequence, CDR1, CDR2 and CDR3 are all as defined under a), b) and c), respectively. Again, in such an 14D5-like sequence, CDR1, CDR2 and CDR3 are preferably such that the 14D5-like ISV has a modulating activity, which can be determined by any suitable assay known to the person skilled in the art, such as, for instance, by means of Alphascreen assays) or by cell based assays (e.g. such as described herein).

Preferably, the modulating activity is determined by an ATP-induced shedding of CD27 or modulating of PS externalization of in spleen and liver cells from mice injected with 14D5-like ISVs, for instance, such as described in Example 2.2. Preferably, the 14D5-like ISV has a modulating activity which is determined in an anti-podocyte induced nephritis model as described in Example 3.

For example, in such an 14D5-like sequence: CDR1 may comprise or essentially consist of the amino acid sequence SYAMG (SEQ ID NO:46) (with CDR2 and CDR3 being as defined under b) and c), respectively); and/or CDR2 may comprise or essentially consist of the amino acid sequence RIYTGGTAWYEDSVKG (SEQ ID NO:74) (with CDR1 and CDR3 being as defined under a) and c), respectively); and/or CDR3 may comprise or essentially consist of the amino acid sequence RVRYDY (with CDR1 and CDR2 being as defined under a) and b), respectively). Particularly, when an 14D5-like sequence is according to this aspect: CDR1 may comprise or essentially consist of the amino acid sequence SYAMG (SEQ ID NO:46) and CDR2 may comprise or essentially consist of the amino acid sequence RIYTGGTAWYEDSVKG (SEQ ID NO:74) (with CDR3 being as defined under c) above); and/or CDR1 may comprise or essentially consist of the amino acid sequence SYAMG (SEQ ID NO:46) and CDR3 may comprise or essentially consist of the amino acid sequence RVRYDY (SEQ ID NO:102) (with CDR2 being as defined under b) above); and/or CDR2 may comprise or essentially consist of the amino acid sequence RIYTGGTAWYEDSVKG (SEQ ID NO:74) and CDR3 may comprise or essentially consist of the amino acid sequence RVRYDY (SEQ ID NO:102) (with CDR1 being as defined under a) above). Again, in such 14D5-like sequences, CDR1, CDR2 and CDR3 are preferably such that the 14D5-like ISV has a modulating activity, which can be determined by any suitable assay known to the person skilled in the art, such as, for instance, by means of Alphascreen assays (e.g. such as described herein) or by cell based assays (e.g. such as described herein).

Preferably, the modulating activity is determined by an ATP-induced shedding of CD27 or modulating of PS externalization of in spleen and liver cells from mice injected with 14D5-like ISVs, for instance, such as described in Example 2.2. Preferably, the 14D5-like ISV has a modulating activity which is determined in an anti-podocyte induced nephritis model as described in Example 3.

In a specifically preferred aspect, a "14D5-like sequence", "14D5-like ISV" or "14D5-like building block" is an ISV that comprises:

d) a CDR1 which is either (i) the amino acid sequence SYAMG (SEQ ID NO:46) or (ii) an amino acid sequence that has only 3, 2 or 1 amino acid difference(s) (as defined herein) with the amino acid sequence SYAMG (SEQ ID NO:46); and/or e) a CDR2 which is either (i) the amino acid sequence RIYTGGTAWYEDSVKG (SEQ ID NO:74) or (ii) an amino acid sequence that has at least 80%, such as at least 85%, for example at least 90% or more than 95% sequence identity with the amino acid sequence RIYTGGTAWYEDSVKG (SEQ ID NO:74); or (iii) an amino acid sequence that has only 7, 6, 5, 4, 3, 2 or 1 amino acid difference(s) (as defined herein) with the amino acid sequence RIYTGGTAWYEDSVKG (SEQ ID NO:74); and/or f) a CDR3 which is either (i) the amino acid sequence RVRYDY (SEQ ID NO:102) or (ii) an amino acid sequence that has at least 80%, such as at least 85%, for example at least 90% or more than 95% sequence identity with the amino acid sequence RVRYDY (SEQ ID NO:102); or (iii) an amino acid sequence that has only 7, 6, 5, 4, 3, 2 or 1 amino acid difference(s) (as defined herein) with the amino acid sequence RVRYDY (SEQ ID NO:102);

in which the framework sequences present in such an ISV are as further described herein, and in which CDR1, CDR2 and CDR3 are preferably such that the 14D5-like ISV has a modulating activity, which can be determined by any suitable assay known to the person skilled in the art, such as, for instance, by means of Alphascreen assays (e.g. such as described herein) or by cell based assays (e.g. such as described herein).

Preferably, the modulating activity is determined by an ATP-induced shedding of CD27 or modulating of PS externalization of in spleen and liver cells from mice injected with 14D5-like ISVs, for instance, such as described in Example 2.2. Preferably, the 14D5-like ISV has a modulating activity which is determined in an anti-podocyte induced nephritis model as described in Example 3.

Preferably, in a 14D5-like sequence according to this specifically preferred aspect, CDR1 and CDR2 are as defined under d) and e), respectively; or CDR1 and CDR3 are as defined under d) and f), respectively; or CDR2 and CDR3 are as defined under e) and f), respectively. More preferably, in such a 14D5-like co sequence, CDR1, CDR2 and CDR3 are all as defined under d), e) and f), respectively.

Again, in such an 14D5-like sequence, CDR1, CDR2 and CDR3 are preferably such that the 14D5-like ISV has a modulating activity, which can be determined by any suitable assay known to the person skilled in the art, such as, for instance, by means of Alphascreen assays (e.g. such as described herein) or by cell based assays (e.g. such as described herein).

Preferably, the modulating activity is determined by an ATP-induced shedding of CD27 or modulating of PS externalization of in spleen and liver cells from mice injected with 14D5-like ISVs, for instance, such as described in Example 2.2. Preferably, the 14D5-like ISV has a modulating activity which is determined in an anti-podocyte induced nephritis model as described in Example 3, For example, in a 14D5-like sequence according to this specifically preferred aspect: CDR1 is the amino acid sequence SYAMG (SEQ ID NO:46) (with CDR2 and CDR3 being as defined under e) and f), respectively); and/or CDR2 is the amino acid sequence RIYTGGTAWYEDSVKG (SEQ ID NO:74) (with CDR1 and CDR3 being as defined under d) and f), respectively); and/or CDR3 is the amino acid sequence RVRYDY (SEQ ID NO:102) (with CDR1 and CDR2 being as defined under d) and e), respectively). Particularly, when an 14D5-like sequence is according to this aspect: CDR1 is the amino acid sequence SYAMG (SEQ ID NO:46) and CDR2 is the amino acid sequence RIYTGGTAWYEDSVKG (SEQ ID NO:74) (with CDR3 being as defined under f) above); and/or CDR1 is the amino acid sequence SYAMG (SEQ ID NO:46) and CDR3 is the amino acid sequence RVRYDY (SEQ ID NO:102) (with CDR2 being as defined under e) above); and/or CDR2 is the amino acid sequence RIYTGGTAWYEDSVKG (SEQ ID NO:74) and CDR3 is RVRYDY (with CDR1 being as defined under d) above). Again, in such 14D5-like sequences, CDR1, CDR2 and CDR3 are preferably such that the 14D5-like ISV has a modulating activity, which can be determined by any suitable assay known to the person skilled in the art, such as, for instance, by means of Alphascreen assays (e.g. such as described herein) or by cell based assays (e.g. such as described herein).

Preferably, the modulating activity is determined by an ATP-induced shedding of CD27 or modulating of PS externalization of in spleen and liver cells from mice injected with 14D5-like ISVs, for instance, such as described in Example 2.2. Preferably, the 14D5-like ISV has a modulating activity which is determined in an anti-podocyte induced nephritis model as described in Example 3.

In a particularly preferred 14D5-like sequence: CDR1 is the amino acid sequence SYAMG (SEQ ID NO:46), CDR2 is the amino acid sequence RIYTGGTAWYEDSVKG (SEQ ID NO:74); and CDR3 is the amino acid sequence RVRYDY (SEQ ID NO:102).

In all the 14D5-like sequence described in this section E), the framework sequences may be as further described herein. Preferably, the framework sequences are such that the framework sequences have at least 80%, such as at least 85%, for example at least 90%, such as at least 95% sequence identity with the framework sequences of 14D5 (which, for example, can be determined by determining the overall degree of sequence identity of a given sequence with the sequence of 14D5 while disregarding the CDR's in the calculation). Again, the combination of CDR's and frameworks present in a given sequence are preferably such that the resulting 14D5-like ISV has a modulating activity, which can be determined by any suitable assay known to the person skilled in the art, such as, for instance, by means of Alphascreen assays (e.g. such as described herein) or by cell based assays (e.g. such as described herein).

Preferably, the modulating activity is determined by an ATP-induced shedding of CD27 or modulating of PS externalization of in spleen and liver cells from mice injected with 14D5-like ISVs, for instance, such as described in Example 2.2. Preferably, the 14D5-like ISV has a modulating activity which is determined in an anti-podocyte induced nephritis model as described in Example 3.

In one specific aspect, a 14D5-like sequence is an ISV that has at least 70%, such at least 80%, for example at least 85%, such as at least 90% or more than 95% sequence identity with SEQ ID NO: 6. For example, in an 14D5-like sequence according to this aspect, the CDR's may be according to the specifically preferred aspect described above, and may in particularly (but without limitation) be SYAMG (SEQ ID NO:46) (CDR1); RIYTGGTAWYEDSVKG (SEQ ID NO:74) (CDR2); and RVRYDY (SEQ ID NO:102) (CDR3). Again, preferably, the combination of CDR's and frameworks present in such a 14D5-like ISV are preferably such that the resulting 14D5-like ISV has a modulating activity, which can be determined by any suitable assay known to the person skilled in the art, such as, for instance, by means of Alphascreen assays (e.g. such as described herein) or by cell based assays (e.g. such as described herein).

Preferably, the modulating activity is determined by an ATP-induced shedding of CD27 or modulating of PS externalization of in spleen and liver cells from mice injected with 14D5-like ISVs, for instance, such as described in Example 2.2. Preferably, the 14D5-like ISV has a modulating activity which is determined in anti-podocyte induced nephritis model as described in Example 3, In one particular aspect, any 14D5-like sequence may be a humanized and/or sequence optimized sequence, as further described herein.

As described in Example 1.5, the ISVs of the invention can be grouped into different epitope bins or families, by means of cross-blocking analyses as detailed herein. Group A ISVs are represented by 1c81-like ISVs and 1c113-like ISVs, while Group B ISVs are represented by 3c23-like ISVs.

As described in Example 1.4, the ISVs of the invention can be grouped based on the presence or absence of cross-reactivity. "human-specific" ISVs are represented by 3c23-like ISVs and 1c113-like ISVs; "human/rat/mouse-specific" ISVs are represented by 1c81-like ISVs; "mouse-specific" ISVs are represented by 13A7-like ISVs and 14D5-like ISVs.

Generally, immunoglobulin single variable domains (in particular $V_{HH}$ sequences and sequence optimized immunoglobulin single variable domains) can in particular be characterized by the presence of one or more "Hallmark residues" (as described herein) in one or more of the framework sequences (again as further described herein).

Thus, generally, an immunoglobulin single variable domain can be defined as an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively.

In a preferred aspect, the invention provides polypeptides comprising at least an immunoglobulin single variable domain that is an amino acid sequence with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and in which:

i) at least one of the amino acid residues at positions 11, 37, 44, 45, 47, 83, 84, 103, 104 and 108 according to the Kabat numbering are chosen from the Hallmark residues mentioned in Table A-1 below; and in which:

ii) said amino acid sequence has at least 80%, more preferably 90%, even more preferably 95% amino acid identity with at least one of the immunoglobulin single variable domains as shown in WO 2009/138519 (see SEQ ID NOs: 1 to 125 in WO 2009/138519), in which for the purposes of determining the degree of amino acid identity, the amino acid residues that form the CDR sequences (indicated with X in the sequences) are disregarded; and in which:

iii) the CDR sequences are generally as further defined herein (e.g. the CDR1, CDR2 and CDR3 in a combination as provided in Table (B-2), note that the CDR definitions are calculated according to the Kabat numbering system).

fragments derived from different immunoglobulin sequences, PCR assembly using overlapping primers, and similar techniques for engineering immunoglobulin sequences well known to the skilled person; or any suitable combination of any of the foregoing as further described herein.

The present invention provides stretches of amino acid residues (SEQ ID NOs: 34-47, SEQ ID NOs: 62-75 and SEQ ID NOs: 90-103; Table B-1) that are particularly suited for binding to P2X7. These stretches of amino acid residues may be present in, and/or may be incorporated into, a polypeptide of the invention, in particular in such a way that they form (part of) the antigen binding site of the polypeptide of the invention. These stretches of amino acid residues have been generated as CDR sequences of heavy chain antibodies or $V_{HH}$ sequences that were raised against the P2X7. These stretches of amino acid residues are also referred to herein as "CDR sequences of the invention" (i.e. as "CDR1 sequences of the invention", "CDR2 sequences of the invention" and "CDR3 sequences of the invention", respectively).

It should however be noted that the invention in its broadest sense is not limited to a specific structural role or

TABLE A-1

Hallmark Residues in VHHs

| Position | Human $V_H3$ | Hallmark Residues |
|---|---|---|
| 11 | L, V; predominantly L | L, S, V, M, W, F, T, Q, E, A, R, G, K, Y, N, P, I; preferably L |
| 37 | V, I, F; usually V | $F^{(1)}$, Y, V, L, A, H, S, I, W, C, N, G, D, T, P, preferably $F^{(1)}$ or Y |
| 44[8] | G | $E^{(3)}$, $Q^{(3)}$, $G^{(2)}$, D, A, K, R, L, P, S, V, H, T, N, W, M, I; preferably $G^{(2)}$, $E^{(3)}$ or $Q^{(3)}$; most preferably $G^{(2)}$ or $Q^{(3)}$ |
| 45[8] | L | $L^{(2)}$, $R^{(3)}$, P, H, F, G, Q, S, E, T, Y, C, I, D, V; preferably $L^{(2)}$ or $R^{(3)}$ |
| 47[8] | W, Y | $F^{(1)}$, $L^{(1)}$ or $W^{(2)}$ G, I, S, A, V, M, R, Y, E, P, T, C, H, K, Q, N, D; preferably $W^{(2)}$, $L^{(1)}$ or $F^{(1)}$ |
| 83 | R or K; usually R | R, $K^{(5)}$, T, $E^{(5)}$, Q, N, S, I, V, G, M, L, A, D, Y, H; preferably K or R; most preferably K |
| 84 | A, T, D; predominantly A | $P^{(5)}$, S, H, L, A, V, I, T, F, D, R, Y, N, Q, G, E; preferably P |
| 103 | W | $W^{(4)}$, $R^{(6)}$, G, S, K, A, M, Y, L, F, T, N, V, Q, $P^{(6)}$, E, C; preferably W |
| 104 | G | G, A, S, T, D, P, N, E, C, L; preferably G |
| 108 | L, M or T; predominantly L | Q, $L^{(7)}$, R, P, E, K, S, T, M, A, H; preferably Q or $L^{(7)}$ |

Notes:
[1]In particular, but not exclusively, in combination with KERE or KQRE at positions 43-46.
[2]Usually as GLEW at positions 44-47.
[3]Usually as KERE or KQRE at positions 43-46, e.g. as KEREL, KEREF, KQREL, KQREF, KEREG, KQREW or KQREG at positions 43-47. Alternatively, also sequences such as TERE (for example TEREL), TQRE (for example TQREL), KECE (for example KECEL or KECER), KQCE (for example KQCEL), RERE (for example REREG), RQRE (for example RQREL, RQREF or RQREW), QERE (for example QEREG), QQRE, (for example QQREW, QQREI or QQREF), KGRE (for example KGREG), KDRE (for example KDREV) are possible. Some other possible, but less preferred sequences include for example DECKL and NVCEL.
[4]With both GLEW at positions 44-47 and KERE or KQRE at positions 43-46.
[5]Often as KP or EP at positions 83-84 of naturally occurring $V_{HH}$ domains.
[6]In particular, but not exclusively, in combination with GLEW at positions 44-47.
[7]With the proviso that when positions 44-47 are GLEW, position 108 is always Q in (non-humanized) $V_{HH}$ sequences that also contain a W at 103.
[8]The GLEW group also contains GLEW-like sequences at positions 44-47, such as for example GVEW, EPEW, GLER, DQEW, DLEW, GIEW, ELEW, GPEW, EWLP, GPER, GLER and ELEW.

Again, such immunoglobulin single variable domains may be derived in any suitable manner and from any suitable source, and may for example be naturally occurring $V_{HH}$ sequences (i.e. from a suitable species of Camelid, e.g. llama) or synthetic or semi-synthetic VHs or VLs (e.g. from human). Such immunoglobulin single variable domains may include "humanized" or otherwise "sequence optimized" VHHs, "camelized" immunoglobulin sequences (and in particular camelized heavy chain variable domain sequences, i.e. camelized VHs), as well as human VHs, human VLs, camelid VHHs that have been altered by techniques such as affinity maturation (for example, starting from synthetic, random or naturally occurring immunoglobulin sequences), CDR grafting, veneering, combining fragments derived from different immunoglobulin sequences, PCR assembly using overlapping primers, and similar techniques for engineering immunoglobulin sequences well known to the skilled person; or any suitable combination of any of the foregoing as further described herein.

function that these stretches of amino acid residues may have in a polypeptide of the invention, as long as these stretches of amino acid residues allow the polypeptide of the invention to bind to P2X7 with a certain affinity and potency (as defined herein). Thus, generally, the invention in its broadest sense provides monovalent polypeptides (also referred to herein as "monovalent polypeptide(s) of the invention") that are capable of binding to P2X7 with a certain specified affinity, avidity, efficacy and/or potency and that comprises one or more CDR sequences as described herein and, in particular a suitable combination of two or more such CDR sequences, that are suitably linked to each other via one or more further amino acid sequences, such that the entire polypeptide forms a binding domain and/or binding unit that is capable of binding to P2X7. It should however also be noted that the presence of only one such CDR sequence in a monovalent polypeptide of the invention may by itself already be sufficient to provide the monovalent polypeptide of the invention the capacity of binding to P2X7; reference is for example again made to the so-called "Expedite fragments" described in WO 03/050531.

Thus, in a specific, but non-limiting aspect, the monovalent polypeptide of the invention may comprise at least one stretch of amino acid residues that is chosen from the group consisting of:

CDR1 sequences:
a) SEQ ID NOs: 34-47;
b) stretches of amino acid sequences that have at least 80% amino and identity with at least one of the amino acid sequences of SEQ ID NOs: 34-47;
c) stretches of amino acid sequences that have 3, 2, or 1 amino acid difference with at least one of the amino acid sequences of SEQ ID NOs: 34-47;
and/or
CDR2 sequences:
d) SEQ ID NOs: 62-75;
e) stretches of amino acid sequences that have at least 80% amino acid identity with at least one of the amino acid sequences of SEQ ID NOs: 62-75;
f) stretches of amino acid sequences that have 3, 2, or 1 amino acid difference with at least one of the amino acid sequences of SEQ ID NOs: 62-75;
and/or
CDR3 sequences:
g) SEQ ID NOs: 90-103;
h) stretches of amino acid sequences that have at least 80% amino acid identity with at least one of the amino acid sequences of SEQ ID NOs: 90-103;
i) stretches of amino acid sequences that have 3, 2, or 1 amino acid difference with at least one of the amino acid sequences of SEQ ID NOs: 90-103.

Monovalent polypeptides comprising one or more of the above specified stretches of amino acid residues show improved properties such as e.g. improved binding characteristics (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein), improved affinity and/or improved avidity for P2X7 and/or improved efficacy and/or potency for modulating P2X7.

More in particular, the monovalent polypeptides of the invention comprising one or more of the above specified stretches of amino acid residues can bind to protein P2X7 with an affinity (suitably measured and/or expressed as a $K_D$-value (actual or apparent), a $K_A$-value (actual or apparent), a $k_{on}$-rate and/or a $k_{off}$-rate, or alternatively as an $IC_{50}$ value, as further described herein) preferably such that they:

bind to P2X7 with a dissociation constant ($K_D$) of 1000 nM to 1 nM or less, preferably 100 nM to 1 nM or less, more preferably 15 nM to 1 nM or even 10 nM to 1 nM or less;
and/or such that they;
bind to P2X7 with a $k_{on}$-rate of between $10^4$ $M^{-1}s^{-1}$ to about $10^7$ $M^{-1}s^{-1}$, preferably between $10^5$ $M^{-1}s^{-1}$ and $10^7$ $M^{-1}s^{-1}$, more preferably about $10^6$ $M^{-1}s^{-1}$ or more;
and/or such that they:
bind to P2X7 with a $k_{on}$-rate between $10^{-2}$ $s^{-1}$ ($t_{1/2}$=0.69 s) and $10^{-4}$ $s^{-1}$ (providing a near irreversible complex with a $t_{1/2}$ of multiple days), preferably between $10^{-3}$ $s^{-1}$ and $10^{-4}$ $s^{-1}$, or lower.

Some preferred $IC_{50}$ values for binding of the monovalent polypeptides of the invention to P2X7 become clear from the further description and examples herein. Assays to determine the $IC_{50}$ include binding in ELISA.

In particular, a monovalent polypeptide of the invention may be a monovalent polypeptide that comprises one antigen binding site, wherein said antigen binding site comprises at least one stretch of amino acid residues that is chosen from the group consisting of the CDR1 sequences, CDR2 sequences and CDR3 sequences as described above (or any suitable combination thereof). In a preferred aspect, however, the monovalent polypeptide of the invention comprises more than one, such as two or more stretches of amino acid residues chosen from the group consisting of the CDR1 sequences of the invention, the CDR2 sequences of the invention and/or the CDR3 sequences of the invention. Preferably, the monovalent polypeptide of the invention comprises three stretches of amino acid residues chosen from the group consisting of the CDR1 sequences of the invention, the CDR2 sequences of the invention and the CDR3 sequences of the invention, respectively. The combinations of CDR's that are mentioned herein as being preferred for the monovalent polypeptides of the invention are listed in Table B-1.

It should be noted that the invention is not limited as to the origin of the monovalent polypeptide of the invention (or of the nucleic acid of the invention used to express it), nor as to the way that the monovalent polypeptide or nucleic acid of the invention is (or has been) generated or obtained. Thus, the monovalent polypeptides of the invention may be naturally occurring monovalent polypeptides (from any suitable species) or synthetic or semi-synthetic monovalent polypeptides.

Furthermore, it will also be clear to the skilled person that it is possible to "graft" one or more of the CDR's mentioned above onto other "scaffolds", including but not limited to human scaffolds or non-immunoglobulin scaffolds. Suitable scaffolds and techniques for such CDR grafting will be clear to the skilled person and are well known in the art, see for example U.S. Pat. No. 7,180,370, WO 01/27160, EP 0605522, EP 0460167, U.S. Pat. No. 7,054,297, Nicaise et al, (Protein Science 13: 1882-1891, 2004), Ewert et al. (Methods 34: 184-199, 2004), Kettleborough et al. (Protein Eng. 4: 773-783, 1991), O'Brien and Jones (Methods Mol. Biol. 207: 81-100, 2003), Skerra (J. Mol. Recognit. 13: 167-187, 2000) and Saerens et al. (J. Mol. Biol. 352: 597-607, 2005) and the further references cited therein. For example, techniques known per se for grafting mouse or rat CDR's onto human frameworks and scaffolds can be used in an analogous manner to provide chimeric proteins comprising one or more of the CDR sequences defined herein for the monovalent polypeptides of the invention and one or more human framework regions or sequences. Suitable scaffolds for presenting amino acid sequences will be clear to the skilled person, and for example comprise, without limitation, to binding scaffolds based on or derived from immunoglobulins (i.e. other than the immunoglobulin sequences already described herein), protein scaffolds derived from protein A domains (such as Affibodies™), tendamistat, fibronectin, lipocalin, CTLA-4, T-cell receptors, designed ankyrin repeats, avimers and PDZ domains (Binz et al. Nat. Biotech., 23: 1257, 2005), and binding moieties based on DNA or RNA including but not limited to DNA or RNA aptamers (Ulrich et al. Comb. Chem. High Throughput Screen 9: 619-32, 2006).

In said monovalent polypeptides of the invention, the CDR's may be linked to further amino acid sequences and/or may be linked to each other via amino acid sequences, in which said amino acid sequences are preferably framework sequences or are amino acid sequences that act as framework sequences, or together form a scaffold for presenting the CDR's.

According to a preferred, but non-limiting embodiment, the monovalent polypeptides of the invention comprise at least three CDR sequences linked to at least two framework sequences, in which preferably at least one of the three CDR sequences is a CDR3 sequence, with the other two CDR sequences being CDR1 or CDR2 sequences, and preferably being one CDR1 sequence and one CDR2 sequence. According to one specifically preferred, but non-limiting embodiment, the monovalent polypeptides of the invention have the structure FR1-CDR1-FR2-CDR2-FR3-CDR3-FR4, in which CDR1, CDR2 and CDR3 are as defined herein for the monovalent polypeptides of the invention, and FR1, FR2, FR3 and FR4 are framework sequences. In such a monovalent polypeptide of the invention, the framework sequences may be any suitable framework sequences, and examples of suitable framework sequences will be clear to the skilled person, for example on the basis the standard handbooks and the further disclosure and prior art mentioned herein.

Accordingly, the present invention also relates to a monovalent polypeptide against P2X7 which essentially consists of 4 framework regions (FR1 to FR4, respectively) and 3 complementarity determining regions (CDR1 to CDR3, respectively), in which:

CDR1 is chosen from the group consisting of:
a) SEQ ID NOs: 34-47;
b) stretches of amino acid sequences that have at least 80% amino acid identity with at least one of the amino acid sequences of SEQ ID NOs: 34-47;
c) stretches of amino acid sequences that have 3, 2, or 1 amino acid difference with at least one of the amino acid sequences of SEQ ID NOs: 34-47;
and/or
CDR2 is chosen from the group consisting of:
d) SEQ ID NOs: 62-75;
e) stretches of amino acid sequences that have at least 80% amino acid identity with at least one of the amino acid sequences of SEQ ID NOs: 62-75;
f) stretches of amino acid sequences that have 3, 2, or 1 amino acid difference with at least one of the amino acid sequences of SEQ ID NOs: 62-75;
and/or
CDR3 is chosen from the group consisting of:
g) SEQ ID NOs: 90-103;
h) stretches of amino acid sequences that have at least 80% amino acid identity with at least one of the amino acid sequences of SEQ ID NOs: 90-103;
i) stretches of amino acid sequences that have 3, 2, or 1 amino acid difference with at least one of the amino acid sequences of SEQ ID NOs: 90-103.

In particular, according to this preferred but non-limiting aspect, the invention relates to a monovalent polypeptide against P2X7 which consists of 4 framework regions (FR1 to FR4 respectively) and 3 complementarity determining regions (CDR1 to CDR3 respectively), in which:

CDR1 is chosen from the group consisting of:
a) SEQ ID NOs: 34-47;
b) stretches of amino acid sequences that have at least 80% amino acid identity with at least one of the amino acid sequences of SEQ ID NOs: 34-47;
c) stretches of amino acid sequences that have 3, 2, or 1 amino acid difference with at least one of the amino acid sequences of SEQ ID NOs: 34-47;
and
CDR2 is chosen from the group consisting of:
d) SEQ ID NOs: 62-75;
e) stretches of amino acid sequences that have at least 80% amino acid identity with at least one of the amino acid sequences of SEQ ID NOs: 62-75;
f) stretches of amino acid sequences that have 3, 2, or 1 amino acid difference with at least one of the amino acid sequences of SEQ ID NOs: 62-75;
and
CDR3 is chosen from the group consisting of:
g) SEQ ID NOs: 90-103;
h) stretches of amino acid sequences that have at least 80% amino acid identity with at least one of the amino acid sequences of SEQ NOs: 90-103;
i) stretches of amino acid sequences that have 3, 2, or 1 amino acid difference with at least one of the amino acid sequences of SEQ ID NOs: 90-103.

The invention also relates to a monovalent polypeptide in which the CDR sequences have at least 70% amino acid identity, preferably at least 80% amino acid identity, more preferably at least 90% amino acid identity, such as 95% amino acid identity or more or even (essentially) 100% amino acid identity with the CDR sequences of at least one of the amino acid sequences of SEQ ID NOs: 6-19.

In one specific, but non-limiting aspect, the monovalent polypeptide of the invention may be a monovalent polypeptide that comprises an immunoglobulin fold or a monovalent polypeptide that under suitable conditions (such as physiological conditions) is capable of forming an immunoglobulin fold (i.e. by folding). Reference is inter alia made to the review by Halaby et al, (J. Protein Eng. 12: 563-71, 1999). Preferably, when properly folded so as to form an immunoglobulin fold, the stretches of amino acid residues may be capable of properly forming the antigen binding site for binding P2X7.

Accordingly, the framework sequences are preferably (a suitable combination of) immunoglobulin framework sequences or framework sequences that have been derived from immunoglobulin framework sequences (for example, by sequence optimization such as humanization or camelization). For example, the framework sequences may be framework sequences derived from an immunoglobulin single variable domain such as a light chain variable domain (e.g. a $V_L$-sequence) and/or from a heavy chain variable domain (e.g. a $V_H$-sequence). In one particularly preferred aspect, the framework sequences are either framework sequences that have been derived from a $V_{HH}$-sequence (in which said framework sequences may optionally have been partially or fully humanized) or are conventional $V_H$ sequences that have been camelized (as defined herein).

The framework sequences may preferably be such that the monovalent polypeptide of the invention is an immunoglobulin single variable domain such as a Domain antibody (or an amino acid sequence that is suitable for use as a domain antibody); is a single domain antibody (or an amino acid that is suitable for use as a single domain antibody); is a "dAb" (or an amino acid that is suitable for use as a dAb); or is a Nanobody® (including but not limited to $V_{HH}$) Again, suitable framework sequences will be clear to the skilled person, for example on the basis the standard handbooks and the further disclosure and prior art mentioned herein.

In particular, the framework sequences present in the monovalent polypeptides of the invention may contain one or more of Hallmark residues (as defined in WO 08/020079 (Tables A-3 to A-8)), such that the monovalent polypeptide of the invention is a Nanobody. Some preferred, but non-limiting examples of (suitable combinations of) such framework sequences will become clear from the further disclosure herein (see e.g. Table B-1). Generally, Nanobodies (in particular $V_{HH}$ sequences and partially humanized Nanobodies) can in particular be characterized by the presence of one or more "Hallmark residues" in one or more of the framework sequences (as e.g. further described in WO 08/020079, page 61, line 24 to page 98, line 3).

More in particular, a Nanobody can be an immunoglobulin single variable domain and/or polypeptide with the (general) structure

FR1-CDR1-FR2-CDR2-FR3-CDR3-FR4 in which FR1 to FR4 refer to framework regions 1 to 4, respectively, and in which CDR1 to CDR3 refer to the complementarity determining regions 1 to 3, respectively, and which:

i) have at least 80% amino acid identity with at least one of the amino acid sequences of SEQ ID NOs: 6-19 (see Table B-3), in which for the purposes of determining the degree of amino acid identity, the amino acid residues that form the CDR sequences are disregarded. In this respect, reference is also made to Table B-1, which lists the framework 1 sequences (SEQ ID NOs: 20-33), framework 2 sequences (SEQ ID NOs: 48-61), framework 3 sequences (SEQ ID NOs: 76-89) and framework 4 sequences (SEQ ID NOs: 104-117 of the immunoglobulin single variable domains of SEQ ID NOs: 6-19 (see Table B-3); or ii) combinations of framework sequences as depicted in Table B-1;

and in which:

iii) preferably one or more of the amino acid residues at positions 11, 37, 44, 45, 47, 83, 84, 103, 104 and 108 according to the Kabat numbering are chosen from the Hallmark residues mentioned in Table A-3 to Table A-8 of WO 08/020079.

In a preferred aspect, the present invention provides an immunoglobulin single variable domain or monovalent polypeptide that is selected from any of SEQ ID ND's: 6-19.

The present invention also provides monovalent polypeptides that belong to the same epitope bin as any one of the immunoglobulin single variable domains with SEQ ID NO's: 6-19. Accordingly, the present invention also relates to monovalent polypeptides directed against P2X7, that cross-blocks the binding to P2X7 of at least one of the immunoglobulin single variable domains with SEQ ID NO's: 6-19 and/or that are cross-blocked from binding to P2X7 by at least one of the immunoglobulin single variable domains with SEQ ID NO's: 6-19.

Again, such monovalent polypeptides may be an immunoglobulin single variable domain derived in any suitable manner and from any suitable source, and may for example be naturally occurring $V_{HH}$ sequences (i.e. from a suitable species of Camelid) or synthetic or semi-synthetic amino acid sequences, including but not limited to "humanized" (as defined herein) Nanobodies or VHH sequences, "camelized" (as defined herein) immunoglobulin sequences (and in particular camelized heavy chain variable domain sequences), as well as Nanobodies that have been obtained by techniques such as affinity maturation (for example, starting from synthetic, random or naturally occurring immunoglobulin sequences), CDR grafting, veneering, combining fragments derived from different immunoglobulin sequences. PCR assembly using overlapping primers, and similar techniques for engineering immunoglobulin sequences well known to the skilled person; or any suitable combination of any of the foregoing as further described herein. Also, when an immunoglobulin single variable domain comprises a $V_{HH}$ sequence, said immunoglobulin single variable domain may be suitably humanized, as further described herein, so as to provide one or more further (partially or fully) humanized immunoglobulin single variable domains of the invention. Similarly, when an immunoglobulin single variable domain comprises a synthetic or semi-synthetic sequence (such as a partially humanized sequence), said immunoglobulin single variable domain may optionally be further suitably humanized, again as described herein, again so as to provide one or more further (partially or fully) humanized immunoglobulin single variable domains of the invention.

These monovalent polypeptides of the invention, and in particular the immunoglobulin single variable domains comprising the CDR sequences of the invention are particularly suited for use as building block or binding unit for the preparation of multivalent polypeptides.

Accordingly, the monovalent polypeptides of the invention that bind P2X7 can be in essentially isolated form (as defined herein), or they may form part of a protein or polypeptide, which may comprise or essentially consist of one or more monovalent polypeptides that bind P2X7 and which may optionally further comprise one or more further amino acid sequences (all optionally linked via one or more suitable linkers). The present invention also relates to a protein or polypeptide that comprises or essentially consists of one or more monovalent polypeptides of the invention (or suitable fragments thereof).

The one or more monovalent polypeptides of the invention are thus used as a binding unit or building block in such a protein or polypeptide, so as to provide a monovalent, multivalent or multiparatopic polypeptide of the invention, respectively, all as described herein. The present invention thus also relates to a polypeptide which is a monovalent construct comprising or essentially consisting of one monovalent polypeptide of the invention. The present invention thus also relates to a polypeptide which is a multivalent polypeptide, such as e.g. a bivalent or trivalent polypeptide comprising or essentially consisting of two or more monovalent polypeptides of the invention (for multivalent and multispecific polypeptides containing one or more VHH domains and their preparation, reference is also made to Conrath et al., J. Biol. Chem. 276: 7346-735(1 2001, as well as to for example WO 96/34103, WO 99/23221 and WO 2010/115998).

As will be clear from the further description above and herein, the amino acid sequences (or ISV's) of the invention can be used as "building blocks" to form polypeptides of the invention, i.e. by suitably combining them with each other, one or more with other amino acid sequences of the invention and/or with one or more other groups, residues, moieties or binding units, in order to form compounds or constructs as described herein (such as, without limitations, the biparatopic, bi/multivalent and bi/multispecific polypeptides of the invention described herein) which combine within one molecule one or more desired properties or biological functions.

The blocking polypeptides or ISVs provided by the invention preferentially reduce inflammation, such as MS or nephritis.

Accordingly, the present invention provides polypeptides comprising or essentially consisting of two or more immunoglobulin single variable domains each of which specifically bind to P2X7, preferably human P2X7 (herein referred to as "P2X7"). Such polypeptides are also referred to herein as "multivalent polypeptide(s) of the invention". The two or more immunoglobulin single variable domains may optionally be linked via one or more peptidic linkers.

Preferably, the multivalent polypeptide comprises two or more immunoglobulin single variable domains directed against P2X7, wherein the "first" immunoglobulin single variable domain directed against P2X7 and the "second" immunoglobulin single variable domain directed against P2X7 have the same or a different paratope. The latter polypeptides are also referred to herein as "multiparatopic polypeptide(s) of the invention". Accordingly, the present invention relates to a polypeptide comprising or consisting of two or more immunoglobulin single variable domains that are directed against P2X7, wherein the "first" immunoglobulin single variable domain directed against P2X7 and the "second" immunoglobulin single variable domain directed against P2X7 have different paratopes. Such polypeptides comprise or consist of two or more immunoglobulin single variable domains that are directed against different epitopes on P2X7. More specifically, such polypeptides comprise at least one "first" immunoglobulin single variable domain that is directed against a first epitope on P2X7 and at least one "second" immunoglobulin single variable domain that is directed against a second epitope on P2X7 different from the first epitope on P2X7. Preferably, these multiparatopic polypeptides of the invention are biparatopic or triparatopic polypeptides (also referred to herein as "biparatopic polypeptide(s) of the invention" and "triparatopic polypeptide(s) of the invention"), as further defined herein. Particularly preferred biparatopic polypeptides in accordance with the invention are those shown in the Examples described herein and Table B-4.

Polypeptides of the invention that contain at least two Nanobodies, in which at least one Nanobody is directed against a first antigen (i.e. against P2X7) and at least one Nanobody is directed against a second antigen (i.e. different from P2X7), will also be referred to as "multispecific" polypeptides of the invention, and the Nanobodies present in such polypeptides will also be referred to herein as being in a "multispecific format". Thus, for example, a "bispecific" polypeptide of the invention is a polypeptide that comprises at least one Nanobody directed against a first antigen (i.e. P2X7) and at least one further Nanobody directed against a second antigen (i.e. different from P2X7), whereas a "trispecific" polypeptide of the invention is a polypeptide that comprises at least one Nanobody directed against a first antigen (i.e. P2X7), at least one further Nanobody directed against a second antigen (i.e. different from P2X7) and at least one further Nanobody directed against a third antigen (i.e. different from both P2X7, and the second antigen); etc.

Accordingly, in its simplest form, a bispecific polypeptide of the invention is a bivalent polypeptide of the invention (as defined herein), comprising a first Nanobody directed against P2X7, and a second Nanobody directed against a second antigen, in which said first and second Nanobody may optionally be linked via a linker sequence (as defined herein); whereas a trispecific polypeptide of the invention in its simplest form is a trivalent polypeptide of the invention (as defined herein), comprising a first Nanobody directed against P2X7, a second Nanobody directed against a second antigen and a third Nanobody directed against a third antigen, in which said first, second and third Nanobody may optionally be linked via one or more, and in particular one and more, in particular two, linker sequences.

Polypeptides of the invention that contain at least two Nanobodies which are directed against P2X7, wherein at least one "first" Nanobody is directed against a first antigenic determinant, epitope, part, domain, subunit or confirmation of P2X7 (e.g. hP2X7); and wherein at least one "second" Nanobody is directed against a second antigenic determinant, epitope, part, domain, subunit or confirmation of said P2X7 (e.g. hP2X74) different from the first, will also be referred to as "multiparatopic" polypeptides of the invention, and the Nanobodies present in such polypeptides will also be referred to herein as being in a "multiparatopic format". Thus, for example, a "biparatopic" polypeptide of the invention is a polypeptide that comprises at least one Nanobody directed against a first antigenic determinant, epitope, part, domain, subunit or confirmation of an antigen (i.e. P2X7) and at least one further Nanobody directed against a second antigenic determinant, epitope, part, domain, subunit or confirmation of said antigen (i.e. same P2X7) different from the first, whereas a "triparatopic" polypeptide of the invention is a polypeptide that comprises at least one Nanobody directed against a first antigenic determinant, epitope, part, domain, subunit or confirmation of an antigen (i.e. P2X7), at least one further Nanobody directed against a second antigenic determinant, epitope, part, domain, subunit or confirmation of said antigen (i.e. same P2X7) different from the first, and at least one further Nanobody directed against a third antigenic determinant, epitope, part, domain, subunit or confirmation of an antigen (i.e. same P2X7) but different from said first and said second antigenic determinant, epitope, part, domain, subunit or confirmation of said antigen; etc.

Accordingly, in its simplest form, a biparatopic polypeptide of the invention is a bivalent polypeptide of the invention (as defined herein), comprising a first Nanobody directed against a first antigenic determinant, epitope, part, domain, subunit or confirmation of P2X7, and a second Nanobody directed against a second antigenic determinant, epitope, part, domain, subunit or confirmation of said P2X7 different from the first, in which said first and said second Nanobody may optionally be linked via a linker sequence (as defined herein); whereas a triparatopic polypeptide of the invention in its simplest form is a trivalent polypeptide of the invention (as defined herein), comprising a first Nanobody directed against a first antigenic determinant, epitope, part, domain, subunit or confirmation of P2X7, a second Nanobody directed against a second antigenic determinant, epitope, part, domain, subunit or confirmation of said P2X7 different from the first, and a third Nanobody directed against a third antigenic determinant, epitope, part, domain, subunit or confirmation of the same P2X7 but different from said first and said second antigenic determinant, epitope, part, domain, subunit or confirmation, in which said first, second and third Nanobody may optionally be linked via one or more, and in particular one and more, in particular two, linker sequences.

However, as will be clear from the description hereinabove, the invention is not limited thereto, in the sense that a multispecific polypeptide of the invention may comprise at least one Nanobody against P2X7, and any number of Nanobodies directed against one or more antigens different from P2X7.

Furthermore, although it is encompassed within the scope of the invention that the specific order or arrangement of the various Nanobodies in the polypeptides of the invention may have some influence on the properties of the final polypeptide of the invention (including but not limited to the affinity, specificity or avidity for P2X7, or against the one or more other antigens), said order or arrangement is usually not critical and may be suitably chosen by the skilled person, optionally after some limited routine experiments based on the disclosure herein. Thus, when reference is made to a specific multivalent or multispecific polypeptide of the invention, it should be noted that this encompasses any order or arrangements of the relevant Nanobodies, unless explicitly indicated otherwise.

Finally, it is also within the scope of the invention that the polypeptides of the invention contain two or more Nanobodies and one or more further amino acid sequences (as mentioned herein).

For multivalent and multispecific polypeptides containing one or more $V_{HH}$ domains and their preparation, reference is also made to Conrath et al., J. Biol. Chem., Vol. 276, 7346-7350, 2001; Muyldermans, Reviews in Molecular Biotechnology 74 (2001), 277-302; as well as to for example WO 96/34103 and WO 99/23221. Some other examples of some specific multispecific and/or multivalent polypeptide of the invention can be found in the applications by Ablynx N. V. referred to herein.

The compounds or polypeptides of the invention can generally be prepared by a method which comprises at least one step of suitably linking the one or more amino acid sequences (or ISV's) of the invention to the one or more further groups, residues, moieties or binding units, optionally via the one or more suitable linkers, so as to provide the compound or polypeptide of the invention. Polypeptides of the invention can also be prepared by a method which generally comprises at least the steps of providing a nucleic acid that encodes a polypeptide of the invention, expressing said nucleic acid in a suitable manner, and recovering the expressed polypeptide of the invention. Such methods can be performed in a manner known per se, which will be clear to the skilled person, for example on the basis of the methods and techniques further described herein.

It will be clear to the skilled person that the Nanobodies (or ISV's) that are mentioned herein as "preferred" (or "more preferred", "even more preferred", etc.) are also preferred (or more preferred, or even more preferred, etc.) for use in the polypeptides described herein. Thus, polypeptides that comprise or essentially consist of one or more "preferred" Nanobodies (or ISV's) of the invention will generally be preferred, and polypeptides that comprise or essentially consist of one or more "more preferred" Nanobodies (or ISV's of the invention will generally be more preferred, etc.

In one specific aspect of the invention, a Nanobody (or ISV) of the invention or a compound, construct or polypeptide of the invention comprising at least one Nanobody (or ISV) of the invention may have an increased half-life, compared to the corresponding amino acid sequence of the invention. Some preferred, but non-limiting examples of such Nanobodies (or ISV's), compounds and polypeptides will become clear to the skilled person based on the further disclosure herein, and for example comprise Nanobodies (or ISV's) sequences or polypeptides of the invention that have been chemically modified to increase the half-life thereof (for example, by means of pegylation); amino acid sequences of the invention that comprise at least one additional binding site for binding to a serum protein (such as serum albumin, see for example EP 0 368 684 B1, page 4); or polypeptides of the invention that comprise at least one Nanobody (or ISV) of the invention that is linked to at least one moiety (and in particular at least one amino acid sequence) that increases the half-life of the Nanobody (or ISV) of the invention. Examples of polypeptides of the invention that comprise such half-life extending moieties or amino acid sequences will become clear to the skilled person based on the further disclosure herein; and for example include, without limitation, polypeptides in which the one or more Nanobodies (or ISV's) of the invention are suitable linked to one or more serum proteins or fragments thereof (such as serum albumin or suitable fragments thereof) or to one or more binding units that can bind to serum proteins (such as, for example, Nanobodies (or ISV's) or (single) domain antibodies that can bind to serum proteins such as serum albumin, serum immunoglobulins such as IgG, or transferrine); polypeptides in which a Nanobody (or ISV) of the invention is linked to an Fc portion (such as a human Fc) or a suitable part or fragment thereof; or polypeptides in which the one or more Nanobodies (or ISV's) of the invention are suitable linked to one or more small proteins or peptides that can bind to serum proteins (such as, without limitation, the proteins and peptides described in WO 91/01743, WO 01/45746, WO 02/076489 and to the US provisional application of Ablynx N. V. entitled "Peptides capable of binding to serum proteins" of Ablynx N. V. filed on Dec. 5, 2006 (see also PCT/EP/2007/063348).

Again, as will be clear to the skilled person, such Nanobodies (or ISV's), compounds, constructs or polypeptides may contain one or more additional groups, residues, moieties or binding units, such as one or more further amino acid sequences and in particular one or more additional Nanobodies (or ISV's) (i.e. not directed against P2X7), so as to provide a tri- of multispecific Nanobody (or ISV) construct.

Generally, the Nanobodies (or ISV's) of the invention (or compounds, constructs or polypeptides comprising the same) with increased half-life preferably have a half-life that is at least 1.5 times, preferably at least 2 times, such as at least 5 times, for example at least 10 times or more than 20 times, greater than the half-life of the corresponding amino acid sequence of the invention per se. For example, the Na nobodies (or ISV's), compounds, constructs or polypeptides of the invention with increased half-life may have a half-life that is increased with more than 1 hours, preferably more than 2 hours, more preferably more than 6 hours, such as more than 12 hours, or even more than 24, 48 or 72 hours, compared to the corresponding amino acid sequence of the invention per se.

In a preferred, but non-limiting aspect of the invention, such Nanobodies (or ISV's), compound, constructs or polypeptides of the invention exhibit a serum half-life in human of at least about 12 hours, preferably at least 24 hours, more preferably at least 48 hours, even more preferably at least 72 hours or more. For example, compounds or polypeptides of the invention may have a half-life of at least 5 days (such as about 5 to 10 days), preferably at least 9 days (such as about 9 to 14 days), more preferably at least about 10 days (such as about 10 to 15 days), or at least about 11 days (such as about 11 to 16 days), more preferably at least about 12 days (such as about 12 to 18 days or more), or more than 14 days (such as about 14 to 19 days).

In another one aspect of the invention, a polypeptide of the invention comprises one or more (such as two or preferably one) Nanobodies (or ISV's) of the invention linked (optionally via one or more suitable linker sequences) to one or more (such as two and preferably one) amino acid sequences that allow the resulting polypeptide of the invention to cross the blood brain barrier. In particular, said one or more amino acid sequences that allow the resulting polypeptides of the invention to cross the blood brain barrier may be one or more (such as two and preferably one) Nanobodies (or ISV's), such as the Nanobodies (or ISV's)

described in WO 02/057445, of which FC44 (SEQ ID NO: 189 of WO 06/040153) and FC5 (SEQ ID NO: 190 of WO 06/040154) are preferred examples.

Generally, for pharmaceutical use, the polypeptides of the invention may be formulated as a pharmaceutical preparation or composition comprising at least one polypeptide of the invention and at least one pharmaceutically acceptable carrier, diluent or excipient and/or adjuvant, and optionally one or more further pharmaceutically active polypeptides and/or compounds. By means of non-limiting examples, such a formulation may be in a form suitable for oral administration, for parenteral administration (such as by intravenous, intramuscular or subcutaneous injection or intravenous infusion), for topical administration, for administration by inhalation, by a skin patch, by an implant, by a suppository, etc, wherein the parenteral administration is preferred. Such suitable administration forms—which may be solid, semi-solid or liquid, depending on the manner of administration—as well as Methods and carriers for use in the preparation thereof, will be clear to the skilled person, and are further described herein. Such a pharmaceutical preparation or composition will generally be referred to herein as a "pharmaceutical composition". A pharmaceutical preparation or composition for use in a non-human organism will generally be referred to herein as a "veterinary composition".

Thus, in a further aspect, the invention relates to a pharmaceutical composition that contains at least one amino acid of the invention, at least one polypeptide of the invention or at least one polypeptide of the invention and at least one suitable carrier, diluent or excipient (i.e., suitable for pharmaceutical use), and optionally one or more further active substances.

Generally, the polypeptides of the invention can be formulated and administered in any suitable manner known per se. Reference is for example made to the general background art cited above (and in particular to WO 04/041862, WO 04/041863, WO 04/041865, WO 04/041867 and WO 08/020079) as well as to the standard handbooks, such as Remington's Pharmaceutical Sciences, 18$^{th}$ Ed., Mack Publishing Company, USA (1990), Remington, the Science and Practice of Pharmacy, 21st Edition, Lippincott Williams and Wilkins (2005); or the Handbook of Therapeutic Antibodies (S. Dubel, Ed.), Wiley, Weinheim, 2007 (see for example pages 252-255).

The polypeptides of the invention may be formulated and administered in any manner known per se for conventional antibodies and antibody fragments (including ScFv's and diabodies) and other pharmaceutically active proteins. Such formulations and Methods for preparing the same will be clear to the skilled person, and for example include preparations suitable for parenteral administration (e.g. intravenous, intraperitoneal, subcutaneous, intramuscular, intraluminal, intra-arterial or intrathecal administration) or for topical (i.e., transdermal or intradermal) administration.

Preparations for parenteral administration may for example be sterile solutions, suspensions, dispersions or emulsions that are suitable for infusion or injection. Suitable carriers or diluents for such preparations for example include, without limitation, those mentioned on page 143 of WO 08/020079. In one embodiment, the preparation is an aqueous solution or suspension.

The polypeptides of the invention can be administered using methods of delivery known from gene therapy, see, e.g., U.S. Pat. No. 5,399,346, which is incorporated by reference for its gene therapy delivery methods. Using a gene therapy Method of delivery, primary cells transfected with the gene encoding an amino acid sequence, polypeptide of the invention can additionally be transfected with tissue specific promoters to target specific organs, tissue, grafts, tumors, or cells and can additionally be transfected with signal and stabilization sequences for subcellularly localized expression.

Thus, the polypeptides of the invention may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the polypeptides of the invention may be combined with one or more excipients and used in the form of ingestible tablets, buccal tablets, troches, capsules, elixirs, suspensions, syrups, wafers, and the like. Such compositions and preparations should contain at least 0.1% of the polypeptide of the invention. Their percentage in the compositions and preparations may, of course, be varied and may conveniently be between about 2 to about 60% of the weight of a given unit dosage form. The amount of the polypeptide of the invention in such therapeutically useful compositions is such that an effective dosage level will be obtained.

For local administration at the site of tumor resection, the polypeptides of the invention may be used in biodegradable polymeric drug delivery systems, slow release poly(lactic-co-glycolic acid) formulations and the like (Hart et al., Cochrane Database Syst Rev. 2008 Jul. 16; (3); CD007294).

In a further preferred aspect of the invention, the polypeptides of the invention, such as a polypeptide consisting essentially of one monovalent anti-human P2X7 immunoglobulin single variable domain and of one monovalent anti-human serum albumin immunoglobulin single variable domain linked by a GS linker, may have a beneficial distribution and kinetics profile in solid tumors compared to conventional antibodies, such as, e.g. IgG.

The tablets, troches, pills, capsules, and the like may also contain binders, excipients, disintegrating agents, lubricants and sweetening or flavoring agents, for example those mentioned on pages 143-144 of WO 08/020079. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the polypeptides of the invention, sucrose or fructose as a sweetening agent, Methyl and propylparabens as preservatives, a dye and flavoring such as cherry or orange flavor. Of course, any material used in preparing any unit dosage form should be pharmaceutically acceptable and substantially non-toxic in the amounts employed. In addition, the polypeptides of the invention may be incorporated into sustained-release preparations and devices.

Preparations and formulations for oral administration may also be provided with an enteric coating that will allow the constructs of the invention to resist the gastric environment and pass into the intestines. More generally, preparations and formulations for oral administration may be suitably formulated for delivery into any desired part of the gastrointestinal tract. In addition, suitable suppositories may be used for delivery into the gastrointestinal tract.

The polypeptides of the invention may also be administered intravenously or intraperitoneally by infusion or injection. Particular examples are as further described on pages 144 and 145 of WO 08/020079 or in PCT/EP2010/062975 (entire document).

For topical administration, the polypeptides of the invention may be applied in pure form, i.e., when they are liquids. However, it will generally be desirable to administer them to the skin as compositions or formulations, in combination with a dermatologic acceptable carrier, which may be a solid or a liquid. Particular examples are as further described on page 145 of WO 08/020079.

Generally, the concentration of the polypeptides of the invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the polypeptides of the invention required for use in treatment will vary not only with the particular polypeptide selected but also with the route of administration, the nature of the condition being treated and the age and condition of the patient and will be ultimately at the discretion of the attendant physician or clinician. Also the dosage of the polypeptides of the invention varies depending on the target cell, tumor, tissue, graft, or organ.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

An administration regimen could include long-term, daily treatment. By "long-term" is meant at least two weeks and preferably, several weeks, months, or years of duration. Necessary modifications in this dosage range may be determined by one of ordinary skill in the art using only routine experimentation given the teachings herein. See Remington's Pharmaceutical Sciences (Martin, E. W., ed, 4), Mack Publishing Co., Easton, Pa. The dosage can also be adjusted by the individual physician in the event of any complication.

In another aspect, the invention relates to a method for the prevention and/or treatment of at least one disease or disorder associated with P2X7, said method comprising administering, to a subject in need thereof, a pharmaceutically active amount of a polypeptide of the invention, and/or of a pharmaceutical composition comprising the same.

In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The subject to be treated may be any warm-blooded animal, but is in particular a mammal, and more in particular a human being. As will be clear to the skilled person, the subject to be treated will in particular be a person suffering from, or at risk of, the diseases and disorders mentioned herein.

The invention relates to a method for the prevention and/or treatment of at least one disease or disorder that is associated with P2X7, with its biological or pharmacological activity, and/or with the biological pathways or signaling in which P2X7 is involved, said method comprising administering, to a subject in need thereof, a pharmaceutically active amount of an amino acid sequence of the invention, of a polypeptide of the invention and/or of a pharmaceutical composition comprising the same. In an embodiment, the invention relates to a method for the prevention and/or treatment of at least one disease or disorder that can be treated by modulating P2X7, its biological or pharmacological activity, and/or the biological pathways or signaling in which P2X7 is involved, said method comprising administering, to a subject in need thereof, a pharmaceutically active amount of a polypeptide of the invention, and/or of a pharmaceutical composition comprising the same. In an embodiment, said pharmaceutically effective amount may be an amount that is sufficient to modulate P2X7, its biological or pharmacological activity, and/or the biological pathways or signaling in which P2X7 is involved; and/or an amount that provides a level of the polypeptide of the invention in the circulation that is sufficient to modulate P2X7, its biological or pharmacological activity, and/or the biological pathways or signaling in which P2X7 is involved.

In an embodiment the invention relates to a method for the prevention and/or treatment of at least one disease or disorder that can be prevented and/or treated by administering a polypeptide of the invention, or a nucleotide construct of the invention encoding the same, and/or of a pharmaceutical composition comprising the same, to a patient. In an embodiment, the method comprises administering a pharmaceutically active amount of a polypeptide of the invention, or a nucleotide construct of the invention encoding the same, and/or of a pharmaceutical composition comprising the same to a subject in need thereof.

In an embodiment the invention relates to a method for the prevention and/or treatment of at least one disease or disorder that can be prevented and/or treated by inhibiting binding of ATP to P2X7 in specific cells or in a specific tissue of a subject to be treated (and in particular, by inhibiting binding of ATP to P2X7 in an MS patient), said method comprising administering a pharmaceutically active amount of a polypeptide of the invention, or a nucleotide construct of the invention encoding the same, and/or of a pharmaceutical composition comprising the same, to a subject in need thereof.

In an embodiment, the invention relates to a method for the prevention and/or treatment of at least one disease or disorder chosen from the group consisting of the diseases and disorders listed herein, said method comprising administering, to a subject in need thereof, a polypeptide of the invention, or a nucleotide construct of the invention encoding the same, and/or of a pharmaceutical composition comprising the same.

In an embodiment, the invention relates to a method for immunotherapy, and in particular for passive immunotherapy, which method comprises administering, to a subject suffering from or at risk of the diseases and disorders mentioned herein, a pharmaceutically active amount of a polypeptide of the invention, or a nucleotide construct of the invention encoding the same, and/or of a pharmaceutical composition comprising the same.

In the above methods, the amino acid sequences, polypeptides of the invention and/or the compositions comprising the same can be administered in any suitable manner, depending on the specific pharmaceutical formulation or composition to be used. Thus, the polypeptides of the invention and/or the compositions comprising the same can for example be administered orally, intraperitoneally (e.g.

intravenously, subcutaneously, intramuscularly, or via any other route of administration that circumvents the gastrointestinal tract), intranasally, transdermally, topically, by means of a suppository, by inhalation, again depending on the specific pharmaceutical formulation or composition to be used. The clinician will be able to select a suitable route of administration and a suitable pharmaceutical formulation or composition to be used in such administration, depending on the disease or disorder to be prevented or treated and other factors well known to the clinician.

The polypeptides of the invention and/or the compositions comprising the same are administered according to a regime of treatment that is suitable for preventing and/or treating the disease or disorder to be prevented or treated. The clinician will generally be able to determine a suitable treatment regimen, depending on factors such as the disease or disorder to be prevented or treated, the severity of the disease to be treated and/or the severity of the symptoms thereof, the polypeptide of the invention to be used, the specific route of administration and pharmaceutical formulation or composition to be used, the age, gender, weight, diet, general condition of the patient, and similar factors well known to the clinician.

Generally, the treatment regimen will comprise the administration of one or more polypeptides of the invention, or of one or more compositions comprising the same, in one or more pharmaceutically effective amounts or doses. The specific amount(s) or doses to be administered can be determined by the clinician, again based on the factors cited above.

Generally, for the prevention and/or treatment of the diseases and disorders mentioned herein and depending on the specific disease or disorder to be treated, the potency of the specific polypeptide of the invention to be used, the specific route of administration and the specific pharmaceutical formulation or composition used, the polypeptides of the invention will generally be administered in an amount between 1 gram and 0.01 microgram per kg body, weight per day, preferably between 0.1 gram and 0.1 microgram per kg body weight per day, such as about 1, 10, 100 or 1000 microgram per kg body weight per day, either continuously (e.g. by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment. Generally, some guidance on the amounts to be administered can be obtained from the amounts usually administered for comparable conventional antibodies or antibody fragments against the same target administered via essentially the same route, taking into account however differences in affinity/avidity, efficacy, biodistribution, half-life and similar factors well known to the skilled person.

In an embodiment, a single contiguous polypeptide of the invention will be used. In one embodiment two or more polypeptides of the invention are provided in combination.

The polypeptides of the invention may be used in combination with one or more further pharmaceutically active compounds or principles, i.e., as a combined treatment regimen, which may or may not lead to a synergistic effect. Again, the clinician will be able to select such further compounds or principles, as well as a suitable combined treatment regimen, based on the factors cited above and his expert judgment.

In particular, the polypeptides of the invention may be used in combination with other pharmaceutically active compounds or principles that are or can be used for the prevention and/or treatment of the diseases and disorders cited herein, as a result of which a synergistic effect may or may not be obtained. Examples of such compounds and principles, as well as routes, methods and pharmaceutical formulations or compositions for administering them will be clear to the clinician.

The effectiveness of the treatment regimen used according to the invention may be determined and/or followed in any manner known per se for the disease or disorder involved, as will be clear to the clinician. The clinician will also be able, where appropriate and on a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

In another aspect, the invention relates to the use of polypeptide of the invention in the preparation of a pharmaceutical composition for prevention and/or treatment of at least one disease and disorder associated with P2X7; and/or for use in one or more of the methods of treatment mentioned herein.

The subject to be treated may be any warm-blooded animal, but is in particular a mammal, and more in particular a human being. In veterinary applications, the subject to be treated includes any animal raised for commercial purposes or kept as a pet. As will be clear to the skilled person, the subject to be treated will in particular be a person suffering from, or at risk of, the diseases and disorders mentioned herein.

The invention relates to the use of a polypeptide of the invention, or a nucleotide encoding the same, in the preparation of a pharmaceutical composition for the prevention and/or treatment of at least one disease or disorder that can be prevented and/or treated by administering a polypeptide of the invention, or a nucleotide encoding the same, and/or a pharmaceutical composition of the same to a patient.

More in particular, the invention relates to the use of a polypeptide of the invention, or a nucleotide encoding the same, in the preparation of a pharmaceutical composition for the prevention and/or treatment of diseases and disorders associated with P2X7, and in particular for the prevention and treatment of one or more of the diseases and disorders listed herein.

Again, in such a pharmaceutical composition, the one or more polypeptide of the invention, or nucleotide encoding the same, and/or a pharmaceutical composition of the same, may also be suitably combined with one or more other active principles, such as those mentioned herein.

The invention also relates to a composition (such as, without limitation, a pharmaceutical composition or preparation as further described herein) for use, either in vitro (e.g. in an in vitro or cellular assay) or in vivo (e.g. in an a single cell or multi-cellular organism, and in particular in a mammal, and more in particular in a human being, such as in a human being that is at risk of or suffers from a disease or disorder of the invention).

The ISVs of the present invention ameliorate the effects of inflammation in a relevant experimental model of glomerulonephritis. Based on their mode of action, the ISVs and constructs of the present invention may be useful in the treatment of other P2X7 associated diseases, including but not limiting to MS, IBD, neuropathic pain, epilepsy, stroke, diabetes, hypertension and cancer.

It is believed that, as the ISVs of the invention modulate P2X7 receptor function and are capable of antagonizing the effects of ATP at the P2X7 receptor, these compounds may also be useful in the treatment P2X7 associated diseases, including neurodegenerative disease. Neurodegenerative diseases include dementia, particularly degenerative dementia (such as senile dementia, dementia with Lewy bodies, Alzheimer's disease, Pick's disease, Huntingdon's chorea, Parkinson's disease and Creutzfeldt-Jakob disease, ALS, or motor neuron disease; in particular Alzheimer's disease); vascular dementia (including multi-infarct dementia); as well as dementia associated with intracranial space occupying lesions; trauma; infections and related conditions (including HIV infection, meningitis and shingles); metabolism; toxins; anoxia and vitamin deficiency; and mild cognitive impairment e.g. associated with ageing, particularly age associated memory impairment. The neurodegenerative disease, e.g. to be treated by the ISVS or constructs of the invention, can for example be degenerative dementia (in particular Alzheimer's disease), vascular dementia (in particular multi-infarct dementia), or mild cognitive impairment (MCI) e.g. MCI associated with ageing such as age associated memory impairment.

The combinations of the present invention may also be useful as neuroprotectants and in the treatment of neurodegeneration following trauma such as stroke, cardiac arrest, pulmonary bypass, traumatic brain injury, spinal cord injury or the like.

It is believed that, as the ISVs of the invention modulate P2X7 receptor function and are capable of antagonizing the effects of ATP at the P2X7 receptor, these compounds may be useful in the treatment of pain, including acute pain, chronic pain, chronic articular pain, musculoskeletal pain, neuropathic pain, inflammatory pain, visceral pain, pain associated with cancer, pain associated with migraine, tension headache and cluster headaches, pain associated with functional bowel disorders, lower back and neck pain, pain associated with sprains and strains, sympathetically maintained pain; myositis, pain associated with influenza or other viral infections such as the common cold, pain associated with rheumatic fever, pain associated with myocardial ischemia, post-operative pain, cancer chemotherapy, headache, toothache and dysmenorrhea.

It is to be understood that reference to treatment includes both treatment of established symptoms and prophylactic treatment, unless explicitly stated otherwise.

According to a further aspect of the invention, we therefore provide a construct of ISV as defined herein for use in human or veterinary medicine and/or for use in therapy.

According to another aspect of the invention, we provide a combination as defined herein for use in the treatment or prevention (e.g. treatment) of a condition which is mediated by P2X7. The combination can be for use in the treatment or prevention (e.g. treatment of pain, inflammation (e.g. MS, rheumatoid arthritis or osteoarthritis) or a neurodegenerative disease, in particular for use in the treatment of inflammatory pain, neuropathic pain, visceral pain, rheumatoid arthritis or osteoarthritis; e.g. in a mammal such as a human.

According to a further aspect of the invention, we provide a method of treating a human or animal (e.g. rodent e.g. rat) subject, for example a human subject, suffering from a condition which is mediated by P2X7, for example a condition or disease disclosed herein (in particular pain, inflammation, MS, rheumatoid arthritis, osteoarthritis or a neurodegenerative disease, which comprises administering to said subject an effective amount of a combination as defined herein.

According to a further aspect of the invention we provide a method of treating a human or animal (e.g. rodent e.g. rat) subject, for example a human subject, suffering from pain, inflammation (e.g. MS, rheumatoid arthritis or osteoarthritis), or a neurodegenerative disease (more particularly rheumatoid arthritis or osteoarthritis, and/or pain such as inflammatory pain, neuropathic pain or visceral pain), which method comprises administering to said subject an effective amount of a construct or ISV as defined herein.

According to another aspect of the invention, we provide the use of a construct or an ISV as defined herein for the manufacture of a medicament for the treatment or prevention (e.g. treatment) of a condition which is mediated by the action of P2X7 receptors, for example a condition or disease disclosed herein, e.g. in a mammal such as a human or rodent e.g. human or rat e.g. human. According to another aspect of the invention we provide the use of a combination as defined herein for the manufacture of a medicament for the treatment or prevention (e.g. treatment) of pain (e.g. inflammatory pain, neuropathic pain or visceral pain), inflammation (e.g. MS, rheumatoid arthritis or osteoarthritis), or a neurodegenerative disease; e.g. in a mammal such as a human or rodent e.g. human or rat e.g. human.

In order to use a combination as defined herein for the treatment of humans and other mammals it can optionally be formulated in accordance with pharmaceutical practice as a pharmaceutical composition. Therefore in another aspect of the invention there is provided a pharmaceutical composition comprising a combination as defined herein, adapted for use in human or veterinary medicine.

In order to use a combination as defined herein in therapy, they it can optionally be formulated into a pharmaceutical composition in accordance with pharmaceutical practice. The present invention also provides a pharmaceutical composition, which comprises a combination as defined herein, or a pharmaceutically acceptable salt thereof, and optionally a pharmaceutically acceptable carrier.

The invention will now be further described by means of the following non-limiting preferred aspects, examples and figures.

Aspects

A1. A polypeptide comprising at least one immunoglobulin single variable domain that can bind P2X7 with a Kd of less than 50 nM for use in treating P2X7 associated diseases, wherein the binding of said immunoglobulin single variable domain to said P2X7 inhibits the activity of P2X7.

A2. The polypeptide according to aspect A1, wherein said P2X7 associated disease is selected from the group consisting of MS, IBD, neuropathic pain, epilepsy, stroke, diabetes, hypertension and cancer.

A3. The polypeptide according to aspect A1 or A2, wherein said P2X7 is human P2X7, A4. The polypeptide according to any one of aspects A1 to A3, wherein said immunoglobulin single variable domain binds SEQ ID NO: 1, SEQ ID NO: 2 and/or SEQ ID NO: 3.

A5. The polypeptide according to any one of aspects A1 to A4, wherein at least one immunoglobulin single variable domain comprises an amino acid sequence of formula 1: FR1-CDR1-FR2-CDR2-FR3-CDR3-FR4 (1); wherein FR1 to FR4 refer to framework regions 1 to 4 and are framework regions (FRs) of an immunoglobulin single variable domain; and wherein CDR1 is chosen from the group consisting of:
SEQ ID NOs: 34-47,
polypeptides that have at least 80% amino acid identity with SEQ ID NOs: 34-47, and
polypeptides that have 3, 2, or 1 amino acid difference with SEQ ID NOs: 34-47; and wherein CDR2 is chosen from the group consisting of:
SEQ ID NOs: 62-75;
polypeptides that have at least 80% amino acid identity with SEQ ID NOs: 62-75; and
polypeptides that have 3, 2, or 1 amino acid difference with SEQ ID NOs: 62-75; and wherein CDR3 is chosen from the group consisting of:
SEQ ID NOs: 90-103;
polypeptides that have at least 80% amino acid identity with SEQ ID NOs: 90-103; and
polypeptides that have 3, 2, or 1 amino acid difference with SEQ ID NOs: 90-103.

A6. The polypeptide according to aspects A5, wherein the framework regions (FRs) have a sequence identity of more than 80% with the FRs of SEQ ID NOs: 6-19.

A7. The polypeptide according to aspect A5 or A6, wherein at least one immunoglobulin single variable domain is chosen from the group of immunoglobulin single variable domains, wherein:
CDR1 is SEQ ID NO: 34, CDR2 is SEQ ID NO: 62; and CDR3 is SEQ ID NO: 90;
CDR1 is SEQ ID NO: 35, CDR2 is SEQ ID NO: 63; and CDR3 is SEQ ID NO: 91;
CDR1 is SEQ ID NO: 40, CDR2 is SEQ ID NO: 68; and CDR3 is SEQ ID NO: 96;
CDR1 is SEQ ID NO: 36, CDR2 is SEQ ID NO: 64; and CDR3 is SEQ ID NO: 92;
CDR1 is SEQ ID NO: 37, CDR2 is SEQ ID NO: 65; and CDR3 is SEQ ID NO: 93;
CDR1 is SEQ ID NO: 38, CDR2 is SEQ ID NO: 66; and CDR3 is SEQ ID NO: 94;
CDR1 is SEQ ID NO: 39, CDR2 is SEQ ID NO: 67; and CDR3 is SEQ ID NO: 95;
CDR1 is SEQ ID NO: 41, CDR2 is SEQ ID NO: 69; and CDR3 is SEQ ID NO: 97;
CDR1 is SEQ ID NO: 42, CDR2 is SEQ ID NO: 70; and CDR3 is SEQ ID NO: 98;
CDR1 is SEQ ID NO: 43, CDR2 is SEQ ID NO: 71; and CDR3 is SEQ ID NO: 99;
CDR1 is SEQ ID NO: 44, CDR2 is SEQ ID NO: 72; and CDR3 is SEQ ID NO: 100;
CDR1 is SEQ ID NO: 45, CDR2 is SEQ ID NO: 73; and CDR3 is SEQ ID NO: 101;
CDR1 is SEQ ID NO: 46, CDR2 is SEQ ID NO: 74; and CDR3 is SEQ ID NO: 102; and
CDR1 is SEQ ID NO: 47, CDR2 is SEQ ID NO: 75; and CDR3 is SEQ ID NO: 103;

A8. The polypeptide according to any one of aspects A5 to A7, wherein the polypeptide is selected from the group consisting of polypeptides comprising immunoglobulin single variable domains that have an amino acid sequence with a sequence identity of more than 80% with SEQ ID NOs: 6-19.

A9. The polypeptide according to any one of aspects A5 to A7, wherein the polypeptide is selected from the group consisting of polypeptides comprising immunoglobulin single variable domains that have an amino acid sequence with a sequence identity of more than 90% with SEQ ID NOs: 6-19.

A10. The polypeptide according to any one of aspects A1 to A9, comprising at least two immunoglobulin single variable domains that can bind P2X7, A11. The polypeptide according to aspect A10, wherein at least two immunoglobulin single variable domains comprise an amino acid sequence of formula 1: FR1-CDR1-FR2-CDR2-FR3-CDR3-FR4 (1);

wherein FR1 to FR4 refer to framework regions 1 to 4 and are framework regions (FRs) of an immunoglobulin single variable domain; and wherein CDR1 is chosen from the group consisting of:
SEQ ID NOs: 34-47,
polypeptides that have at least 80% amino acid identity with SEQ ID NOs: 34-47, and
polypeptides that have 3, 2, or 1 amino acid difference with SEQ ID NOs: 34-47; and wherein CDR2 is chosen from the group consisting of:
SEQ ID NOs: 62-75;
polypeptides that have at least 80% amino acid identity with SEQ ID NOs: 62-75; and
polypeptides that have 3, 2, or 1 amino acid difference with SEQ ID NOs: 62-75; and wherein CDR3 is chosen from the group consisting of:
SEQ ID NOs: 90-103;
polypeptides that have at least 80% amino acid identity with SEQ ID NOs: 90-103; and
polypeptides that have 3, 2, or 1 amino acid difference with SEQ ID NOs: 90-103.

A12. The polypeptide according to aspect A11, wherein the framework regions (FRs) have a sequence identity of more than 80% with the FRs of SEQ ID NOs: 6-19.

A13. The polypeptide according to aspect A11 or A12, wherein at least two immunoglobulin single variable domains are chosen from the group of immunoglobulin single variable domains, wherein:
CDR1 is SEQ ID NO: 34, CDR2 is SEQ ID NO: 62; and CDR3 is SEQ ID NO: 90;
CDR1 is SEQ ID NO: 35, CDR2 is SEQ ID NO: 63; and CDR3 is SEQ ID NO: 91;
CDR1 is SEQ ID NO: 40, CDR2 is SEQ ID NO: 68; and CDR3 is SEQ ID NO: 96;
CDR1 is SEQ ID NO: 36, CDR2 is SEQ ID NO: 64; and CDR3 is SEQ ID NO: 92;
CDR1 is SEQ ID NO: 37, CDR2 is SEQ ID NO: 65; and CDR3 is SEQ ID NO: 93;
CDR1 is SEQ ID NO: 38, CDR2 is SEQ ID NO: 66; and CDR3 is SEQ ID NO: 94;
CDR1 is SEQ ID NO: 39, CDR2 is SEQ ID NO: 67; and CDR3 is SEQ ID NO: 95;
CDR1 is SEQ ID NO: 41, CDR2 is SEQ ID NO: 69; and CDR3 is SEQ ID NO: 97;
CDR1 is SEQ ID NO: 42, CDR2 is SEQ ID NO: 70; and CDR3 is SEQ ID NO: 98;
CDR1 is SEQ ID NO: 43, CDR2 is SEQ ID NO: 71; and CDR3 is SEQ ID NO: 99;
CDR1 is SEQ ID NO: 44, CDR2 is SEQ ID NO: 72; and CDR3 is SEQ ID NO: 100;
CDR1 is SEQ ID NO: 45, CDR2 is SEQ ID NO: 73; and CDR3 is SEQ ID NO: 101;
CDR1 is SEQ ID NO: 46, CDR2 is SEQ ID NO: 74; and CDR3 is SEQ ID NO: 102; and
CDR1 is SEQ ID NO: 47, CDR2 is SEQ ID NO: 75; and CDR3 is SEQ ID NO: 103;

A14. The polypeptide according to any one of aspects A10 to A13, wherein the polypeptide is selected from the group consisting of polypeptides comprising at least two immunoglobulin single variable domains that each have an amino acid sequence with a sequence identity of more than 80% with SEQ ID NOs: 6-19.

A15. The polypeptide according to any one of aspects A10 to A13, wherein the polypeptide is selected from the group consisting of polypeptides comprising at least two immunoglobulin single variable domains that each have an amino acid sequence with a sequence identity of more than 90% with SEQ ID NOs: 6-19.

A16. The polypeptide according to any one of aspects A10 to A15, comprising at least two immunoglobulin single variable domains that can bind P2X7, wherein said at least two immunoglobulin single variable domains that can bind P2X7 can be the same or different.

A17. The polypeptide according to any of aspects A1 to A16 further comprising an immunoglobulin single variable domain binding human serum albumin such as e.g. Alb8 (SEQ ID NO: 126) or Alb11 (SEQ ID NO: 125).

A18. The polypeptide according to any one of aspects A1 to A17, wherein the polypeptide is selected from the group consisting of polypeptides that have an amino acid sequence with a sequence identity of more than 80% with SEQ ID NOs: 118-124.

A19. The polypeptide according to any one of aspects A1 to A18, wherein the polypeptide is selected from the group consisting of polypeptides that have an amino acid sequence with a sequence identity of more than 90% with SEQ NOs: 118-124.

A20. The polypeptide according to any one of aspects A1 to A19, wherein the polypeptide is selected from the group consisting of SEQ ID NOs: 118-124.

A21. A polypeptide comprising at least two immunoglobulin single variable domains which are directed against P2X7, wherein
a) at least one first immunoglobulin single variable domain is directed against a first antigenic determinant, epitope, part, domain, subunit or conformation of a P2X7; and wherein,
b) at least one second immunoglobulin single variable domain is directed against a second antigenic determinant, epitope, part, domain, subunit or conformation of said P2X7 different from the first antigenic determinant epitope, part, domain, subunit or conformation, respectively.

A22. The polypeptide according to any one of aspects A1 to A21, wherein said immunoglobulin single variable domain consists of a domain antibody, an amino acid sequence that is suitable for use as a domain antibody, a single domain antibody, an amino acid sequence that is suitable for use as a single domain antibody, a dAb, an amino acid sequence that is suitable for use as a dAb, a Nanobody, a VHH sequence, a humanized VHH sequence or a camelized VH sequence.

A23. The polypeptide according to any of aspects A1 to A22, wherein the IC50 in an Alphascreen assay is 30 nM or lower, A24. The polypeptide according to any of aspects A1 to A23, wherein the IC50 in an Alphascreen assay is 3 nM or lower.

A25. The polypeptide according to any of aspects A1 to A24, further comprising a pharmaceutically acceptable excipient.

A26. A method for producing a polypeptide according to any one of aspects A1 to A25, said method at least comprising the steps of:
a) expressing, in a suitable host cell or host organism or in another suitable expression system, a nucleic acid or nucleotide sequence encoding a polypeptide according to any one of aspects A1 to A25; optionally followed by:
b) isolating and/or purifying said immunoglobulin single variable domain or said polypeptide.

A27. Method for screening immunoglobulin single variable domains directed against P2X7 and in particular human P2X7 (SEQ ID NOs: 1-3) that comprises at least the steps of:
a) providing a set, collection or library of immunoglobulin single variable domains; and
b) screening said set, collection or library of immunoglobulin single variable domains for immunoglobulin single variable domains that can bind to and/or have affinity for P2X7 and in particular human P2X7 (SEQ ID NOs: 1-3); and
c) isolating the amino acid sequence(s) that can bind to and/or have affinity for P2X7 and in particular human P2X7 (SEQ ID NO: 1-3).

A28. An immunoglobulin single variable domain that can bind P2X7 with a Kd of less than 50 nM, wherein the binding of said immunoglobulin single variable domain to said P2X7 inhibits the activity of P2X7.

The entire contents of all of the references (including literature references, issued patents, published patent applications, and co-pending patent applications) cited throughout this application are hereby expressly incorporated by reference, in particular for the teaching that is referenced hereinabove.

TABLE B-1

Preferred combinations of CDR sequences, preferred combinations of framework sequences, and preferred combinations of framework and CDR sequences. ("ID" refers to the SEQ ID NO as used herein)

| ID | FR1 | ID | CDR1 | ID | FR2 | ID | CDR2 |
|----|-----|----|------|----|-----|----|------|
| 20 | EVQLVESGGKL VQAGGSLRLSC SASG | 34 | RTFSFSTSTMG | 48 | WFRQAPGKELEF VA | 62 | AIDWSDFN |
| 21 | EVQLVESGGGL VQPGGSLTLSC AASG | 35 | IAFNYYSMS | 49 | WHRQAPGKQRTL VA | 63 | DISPGGHT |
| 22 | EVQLVESGGGL VQPGGSLRLSC AASG | 36 | FTFRNYDMS | 50 | WVRQAPGKGPEW VS | 64 | YMNSGGGG |
| 23 | RGAAGGVWGRL GAGWGSLSLSC AASG | 37 | STFNNSVMG | 51 | WYRQAPGKQREL VA | 65 | DISGGGVT |

TABLE B-1-continued

Preferred combinations of CDR sequences, preferred combinations of framework sequences, and preferred combinations of framework and CDR sequences. ("ID" refers to the SEQ ID NO as used herein)

| ID | (FR1) | ID | (CDR1) | ID | (FR2) | ID | (CDR2) |
|---|---|---|---|---|---|---|---|
| 24 | EVQLVESGGKL VQAGGSLRLSC SASG | 38 | RTFSFSTSTMG | 52 | WFRQAPGKELEF VA | 66 | AIDWSDFN |
| 25 | EVQLVESGGKL VQAGGSLRLSC SASG | 39 | RTFSFSTSTMG | 53 | VWFQAPGKELEF VA | 67 | AIDWSDFN |
| 26 | EVQLVESGGGL VQAGGSLRLSC AASG | 40 | RTFRHYAMG | 54 | WFRQAPGKEREF VA | 68 | AISSYGST |
| 27 | EMQLVESGGGL VQAGGSLRLSC AASG | 41 | RTFRHYAMG | 55 | WFRQAPGKEREF VA | 69 | AISSYGST |
| 28 | EVQLVESGGGL VQPGGSLRLSC VVSG | 42 | FTVDDYAIG | 56 | WFRQAPGKEREG IS | 70 | CUTSSDGN |
| 29 | EVQLVESGGGL VQPGGSLELSC TVSG | 43 | SIFSTSAMA | 57 | WYRQVPGKPRWL VA | 71 | TITRDGTT |
| 30 | EVQLVESGGGL VQAGGSLRLSC AASG | 44 | ITFSSYAMG | 58 | WYQRAPGKQREL VA | 72 | EISDGGGT |
| 31 | AVQLVESGGGL VQAGGSLRLSC AASGNFFR | 45 | VNTMA | 59 | WYRQAPGKQREL VA | 73 | DITRGDRT NYADTVNG |
| 32 | KVQLVESGGGL VQAGGSLRLSC AASGSPIS | 46 | SYAMG | 60 | WYRQAPGKPREL VA | 74 | RIYTFFTA WYEDSVKG |
| 33 | EVQLVESGGGL VQPGESLRSLC TASRFMLD | 47 | YYDIG | 61 | WFRQAPGKEREG VS | 75 | CRFTNDGS TAYADSVK G |

| ID | FR3 | ID | CDR3 | ID | FR4 |
|---|---|---|---|---|---|
| 76 | TYYADSVKGRFTISRHNPR NSVYLQLNSLKPEDTAVYY CAA | 90 | HSETRGGTRYFD RPSLYNY | 104 | WGQGTQ VTVSSA |
| 77 | EYEDSVKGRFTISRDNFKN TMTLHMNSLKPEDTAVYFC AA | 91 | RLRFEVSSNY | 105 | WGQGTQ VTVSSA |
| 78 | TAYADSVKGRFTISRDNAK NTLCLQMNSLKPEDTAVYY CAT | 92 | EKPLGGA | 106 | WGQGTQ VTVSSA |
| 79 | NYADSVKGRFTISRDNAKN MVYLQMHILKPEDTAVYYC NV | 93 | KRRFPIWRDY | 107 | WGKGTL VTVSSA |
| 80 | TYYADSVKGRFTISRHNPR NSVLYLQLNLKPEDTAVYY CAA | 94 | HSETRDGTRTFD RPSLYNY | 108 | WGQGTQ VTVSSA |
| 81 | TYYADSVKGRFIISRHNPR NSVYLQLNSLKPEDTAVYY CAA | 95 | HSETRGGTRYFD RPSLYNY | 109 | WGQGTQ VTVSSA |
| 82 | DYGDSVKGRFTISRDDAKN TVPLQMNSLKPEDTAVYYC AAA | 96 | DETLGAVPNFRL HEKYEYEY | 110 | WGQGTQ VTVSSA |
| 83 | DYGDSVKGRFTISRDDAKN TVPLQMNSLKPEDTAVYC AAA | 97 | DETLGAVPNFRL HEKYEYEY | 111 | WGQGTQ VTVSSA |
| 84 | TYYALSVKGRFTASSDNAK NYVYLQMNSLNPEDTAVYY CAA | 98 | DPVRRGWGCRDH YKY | 112 | WGQGTQ VTVSSA |
| 85 | NYIDSVQGRFTISRDNAKN MIYLRMNSLKPEDTAVYYC VT | 99 | ILSGKKT | 113 | WGQGTQ VTVSSA |
| 86 | YSADSVKGRFTISRDNAKN TVYLQMTSLRPEDTAVYYC NA | 100 | LFTSDWFG | 114 | WGQGTQ VTVSSA |
| 87 | RFTISRDNVRNTVYLQMNG LRPEDTAAYYCYA | 101 | VIELGVLEPRDY | 115 | WGQGTQ VTVSS |
| 88 | RFTISRDNAQNTVYLQMNS LKSEDTAVYYCHG | 102 | RVRYDY | 116 | WGQGTQ VTVSS |
| 89 | RFTISRDIVKHTVYLQMNS LQPEDTAVYYCAA | 103 | GPLTKRRQCVPG DFSMDF | 117 | WGEGTL VTVSS |

TABLE B-2

P2X7 sequences from various species "ID" refers to the SEQ ID NO as used herein)

| Prot ID | spec | ID | Sequence |
|---|---|---|---|
| NP_002553.3 | Homo sapiens | 1 | MPACCSCSDVFQYETNKVTRIQSMNYGTIKWFFHVIIFSYVCFALVSDKLQRKEPVISSVHTKVKGIAEVKEE IVENGVKKLVHSVFDTADYTFPLQGNSFFVMTNFLKTEGQEQRLCPEYPTRRTLCSSDRGCKKGWMDPQSKGI QTGRCVVYEGNQKTCEVSAWCPIEAVEEAPRPALLNSAENFTVLIKNNIDFPGHNYTTRNILPGLNITCTFHK TQNPQCPIFRLGDIFRETGDNFSDVAIQGGIMGIEIYWDCNLDRWFHHCRPKYSFRRLDDKTTNVSLYPGYNF RYAKYYKENNVEKRTLIKVFGIRFDILVFGTGGKFDIIQLVVYIGSTLSYFGLAAVFIDFLIDTYSSNCCRSH IYPWCKCCQPCVVNEYYRKKVESIVEPKPTLKYVSFVDESHIRMVNQQLLGRSLQDVKGQEVPRPAMDFTDLS RLPLALHDTPPIPGQPEEIQLLRKEATPRSDSPVWCQCGSCLPSQLPESHRCLEELCCRKKPGACITTSELF RKLVLSRHVLQFLLLYQEPLLALDVDSTNSRLRHCAYRCYATWRFGSQDMADFAILPSCCRWIRKEFPKSEG QYSGFKSPY |
| AAH11913.1 H155Y, H270R | Homo sapiens | 2 | MPACCSCSDVFQYETNKVTRIQSMNYGTIKWFFHVIIFSYVCFALVSDKLYQRKEPVISSVHTKVKGIAEVKE EIVENGVKKLVHSVFDTADYTFPLQGNSFFVMTNFLKTEGQEQRLCPEYPTRRTLCSSDRGCKKGWMDPQSKG IQTGRCVVHEGNQKTCEVSAWCPIEAVEEAPRPALLNSAENFTVLIKNNIDFPGHNYTTRNILPGLNITCTFH KTQNPQCPIFRLGDIFRETGDNFSDVAIQGGIMGIEIYWDCNLDRWFHHCHPKYSFRRLDDKTTNVSLYPGYN FRYAKYYKENNVEKRTLIKVFGIRFDILVFGTGGKFDIIQLVVYIGSTLSYFGLAAVFIDFLIDTYSSNCCRS HIYPWCKCCQPCVVNEYYRKKCESIVEPKPTLKYVSFVDESHIRMVNQQLLGRSLQDVKGQEVPRPAMDFTDL SRLPLALHDTPPIPGQPEEIQLLRKEATPRSDSPVWCQCGSCLPSQLPESHRCLEELCCRKKPGACITTSEL FRKLVLSRHVLQFLLLYQEPLLALDVDSTNSRLRHCAYRCYATWRFGSQDMADFAILPSCCRWIRKEFPKSE GQYSGFKSPY |
| 20089_ H155Y_A348T | Homo sapiens | 3 | MPACCSCSDVFQYETNKVTRIQSMNYGTIKWFFHVIIFSYVCFALVSDKLYQRKEPVISSVHTKVKGIAEVKE EIVENGVKKLVHSVFDTADYTFPLQGNSFFVMTNFLKTEGQEQRLCPEYPTRRTLCSSDRGCKKGWMDPQSKG IQTGRCVVYEGNQKTCEVSAWCPIEAVEEAPRPALLNSAENFTVLIKNNIDFPGHNYTTRNILPGLNITCTFH KTQNPQCPIFRLGDIFRETGDNFSDVAIGQQIMGIEIYWDCNLDRWFHHCHPKYSFRRLDDKTTNVSLYPGYN FRYAKYYKENNVEKRTLIKVFGIRFDILVFGTGGKFDIIQLVVYIGSTLSYFGLATVFIDFLIDTYSSNCCRS HIYPWCKCCQPCVVNEYYYRKKCESIVEPKPTLKYVSFVDESHIRMVNQQLLGRSLQDVKGQEVPRPAMDFTD LSRLPLALHDTPPIPGQPEEIQLLRKEATPRSDSPVWCQCGSCLPSQLPESHRCLEELCCRKKPGACITTSE LFRKLVLSRHVQFLLLYQEPLLALDVDSTNSRLRHCAYRCYATWRFGSQDMADFAILPSCCRWIRKEFPKSE GQYSGFKSPY |
| CAA08853.1 | mus musculus | 4 | MPACCSWNDVFQYETNKVTRIQSTNYGTVKWVLHMIVFSYISFALVSDKLYQRKEPVISSVHTKVKGIAEVTE NVTEGGVTKLGHSIFDTADYTFPLQGNSFFVMTNYVKSEGQVQTLVPEYPRRGAQCSSDRRCKKGWMDPQSKG IQTGRCVPYDKTRKTCEVSAWCPTEEEKEAPRPALLRSAENFTVLIKNNIHFPGHNYTTRNILPTMNGSCTFH KAWDPQCSIFRLGDIFQEAGENFTEVAVQGGIMGIEIYWDCNLDSWSHHCRPRYSFRRLDDKNMDESVPGYNF RYAKYYKENNVEKRTLIKAFGIRFDILVFGTGGKFDIIQLVVYIGSTLSYFGLATVCIDLLINTYSSAFCRSG VYPYCKCCEPTCVNEYYRKKCESIMEPKPTLKYVSFVDEPHIRMVDQQLLGKSLQVVKGQEVPRPQMDFSDLS RLSLSLHDSPLTPGQSEEIQLLHEEVAPKSGDSPSWCQCGNCLPSRLPEQRRALEELCCRKKPGRCITTSKLF HKLVLSRDTLQLLLLLYQDPLLVLGEEATNSRLRHRAYRCYATWRFGSQDMADFAILPSCCRWIRKEFPTEGQ YSGFKYPY |
| CAA65131.1 | Rattus norvegicus | 5 | MPACCSWNDVFQYETNKVTRIQSVNYGTIKWILHMTVFSYVSFALMSDKLYQRKEPLISSVHTKVKGVAEVTE NVTEGGVTKLVHGIFDTADYTLPLQGNSFFVMTNYLKSEGQEQKLCPEYPSRGKQCHSDQGCIKGWMDPQSKG IQTGRCIPYDDKRKTCEIFAWCPAEEGKEAPRPALLRSAENFTVLIKNNIDFPGHNYTTRNILPGMNISCTFH KTWNPQCPIFRLGDIFQEIGENFTEVAVQGGIMGIEIYWDCNLDSWSHRCQPKYSFRRLDDKYTNESLFPGYN FRYAKYYKENGMEKRTLIKAFGVRFDILVFGTGGKFDIIQLVVYIGSTLSYFGLATVCIDLIINTYASTCCRS RVYPSCKCCEPCAVNEYYRKKCEPIVEPKPTLKYVSFVDEPHIWMVDQQLLGKSLQDVKGQEVPRPQTDFLE LSRLSLSHHSPPIPGQPEEMQLLQIEAVPRSDSPDWCQCGNCLPSQLPENRRALEELCCRKPGQCITTSEL FSKIVSREALQLLLLYQEPLLALEGEAINSKLRHCAYRSYATWRDVSQDMADFAILPSCCRWKIRKEFPKTQG QYSGFKYPY |

TABLE B-3

Amino acid sequences of monovalent anti P2X7 Nanobodies ("ID" refers to the SEQ ID NO as used herein)

| Nanobody ID | | SEQUENCE |
|---|---|---|
| 1c81 | 6 | EVQLVESGGKLVQAGGSLRLSCASASGRTFSFSTSTMGWFRQAPGKELEFVAAIDWSDFNTYYADSVKGRFTISRHNPRNSVYQ LNSLKPEDTAVYYCAAHSETRGGTRYFDRPSLYNYWGQGTQVTVSSA |
| 1c113 | 7 | EVQLVESGGGLVQPGGSLTLSCAASGIAFNYYSMSWHRQAPGKQRTLVADISPGGHTEYEDSVKGRFTISRDNFKNTMTLHMNS LKPEDTAVYFCAARLRFEVSSNYWGQGTQVTVSSA |
| 1c121 | 8 | EVQLVESGGGLVQPGGSLRLSCAASGFTFRNYDMSWVRQAPGKGPEWVSYMNSGGGGTAYADSVKGRFTISRDNAKNTLCLQMN SLKPEDTAVYYCATEKPLGGAWGQGTQVTVSSA |
| 1c126 | 9 | RGAAGGVWGRLGAGSWGLSLSCAASGSTFNNSVMGWYRQAPGKQRELVADISGGGVTNYADSVKGRFTISRDNAKNMVYLQMHI LKPEDTAVYYCNVKRRFPIWRDYWGKGTLVTVSSA |
| 3c22 | 10 | EVQLVESGGGLVQAGGSLRLSCASASGRTFSFSTSTMGWFRQAPGKELEFVAAIDWSDFNTYYADSVKGRFTISRHNPRNSVYLQ LNSLKPEDTAVYYCAASHSETRDGTRTFDRPSLYNYWGQGTQVTVSSA |

TABLE B-3-continued

Amino acid sequences of monovalent anti P2X7 Nanobodies
("ID" refers to the SEQ ID NO as used herein)

| Nanobody | ID | SEQUENCE |
|---|---|---|
| 3c29 | 11 | EVQLVESGGKLVQAGGSLRLSCSASGRTFSFSTSTMGWFRQAPGKELEFVAAIDWSDFNTYYADSVKGRFIISRHNPRNSVYLQLNSLKPEDTAVYYCAAHSETRGGTRYFDRPSLYNYWGQGTQVTVSSA |
| 3c23 | 12 | EVQLVESGGGLVQAGGSLRLSCAASGRTFRHYAMGWFRQAPGKEREFVAAISSYGSTDYGDSVKGRFTISRDDAKNTVPLQMNSLKPEDTAVYYCAAADETLGAVPNFRLHEKYEYEYWGQGTQVTVSSA |
| 3x28 | 13 | EMQLVESGGGLVQAGGSLRLSCAASGRTFRHYAMGWFRQAPGKEREFVAAISSYGSTDYGDSVKGRFTISRDDAKNTVPLQMNSLKPEDTAVYYCAAADETLGAVPNFRLHEKYEYEYWGQGTQVTVSSA |
| 3c31 | 14 | EVQLVESGGGLVQPGGSLRLSCVVSGFTVDDYAIGWFRQAPGKEREGISCITSSDGNTYYALSVKGRFTASSDNAKNTVYLQMNSLNPEDTAVYYCAADPVRRGWGCRDHYKYWGQGTQVTVSSA |
| 3c34 | 15 | EVQLVESGGGLVQPGGSLELSCTVSGSIFSTSAMAWYRQVPGKPRWLVATITRDGTTNYIDSVQGRFTISRDNAKNMIYLRMNSLKPEDTAVYYCVTILSGKKTWGQGTQVTVSSA |
| 3c39 | 16 | EVQLVESGGGLVQAGGSLRLSCAASGITFSSYAMGWYRQAPGKQRELVAEISDGGGTYSADSVKGRFTISRDNAKNTVYLQMTSLRPEDTAVYYCNALFTSDWFGWGQGTQVTVSSA |
| 8G11 | 17 | AVQLVESGGGLVQAGGSLRLSCAASGNFFRVNTMAWYRQAPGKQRELVADITRGDRTNYADTVNGRFTISRDNVRNTVYLQMNGLRPEDTAAYYCYAVIELGVLEPRDYWGQGTQVTVSS |
| 14D5 | 18 | KVQLVESGGGLVQAGGSLRLSCAASGSPISSYAMGWYRQAPGKPRELVARIYTGGTAWYEDSVKGRFTISRDNAQNTVYLQMNSLKSEDTAVYYCHGRVRYDYWGQGTQVTVSS |
| 13A7 | 19 | EVQLVESGGGLVQPGESLRLSCTASRFMLDYYDIGWFRQAPGKEREGVSCRFTNDGSTAYADSVKGRFTISRDIVKHTVYLQMNSLQPEDTAVYYCAAGPLTKRRQCVPGDFSMDFWGEGTLVTVSS |

TABLE B-4

Multivalent polypeptides ("ID" refers to the SEQ ID NO as used herein)

| Name | ID | Amino acid sequence |
|---|---|---|
| pME1c113-mIgG1Fc_LSF | 118 | MALPVTALLLPLALLLHAARPDYKDDDDKRSMAEVQLVESGGGLVQPGGSLTLSCAASGIAFNYYSMSWHRQAPGKQRTLVADISPGGHTEYEDSVKGRFTISRDNFKNTMTLHMNSLKPEDTAVYFCAARLRFEVSSNYWGQGTQVTVSSLEPRDCGCKPCICTVPEVSSEVSSVFIFPPKPKDVLLISLFPKVTCVVVDISKDDPEVQFSWFVDDVEVHTAQTQPREEQFNSTFRSVSELPIMHQDWLNGKEFKCRVNSAAFPAPIETISKTKGRPKAPQVYTIPPPKEQMAKDKVSLTCMITDFFPEDITVEWQWNGQPAENYKNTQPIMDTDGSYFVYSKLNVQKSNWEAGNTFTCSVLHEGHNHHTEKSLSHSPGKGK |
| 14D5-14D5 | 119 | EVQLVESGGGLVQAGGSLRLSCAASGSPISSYAMGWYRQAPGKPRELVARIYTGGTAWYEDSVKGRFTISRDNAQNTVYLQMNSLKSEDTAVYYCHGRVRYDYWGQGTQVTVSSGGGGSGGGGSGGGGSGGGGSGGGGSGGGGSGGGGSEVQLVESGGGLVQAGGSLRLSCAASGSPISSYAMGWYRQAPGKPRELVARIYTGGTAWYEDSVKGRFTISRDNAQNTVYLQMNSLKSEDTAVYYCHGRVRYDYWGQGTQVTVSS |
| 14D5-14D5-Alb8 | 120 | EVQLVESGGGLVQAGGSLRLSCAASGSPISSYAMGWYRQAPGKPRELVARIYTGGTAWYEDSVKGRFTISRDNAQNTVYLQMNSLKSEDTAVYYCHGRVRYDYWGQGTQVTVSSGGGGSGGGGSGGGGSGGGGSGGGGSGGGGSGGGGSEVQLVESGGGLVQAGGSLRLSCAASGSPISSYAMGWRYQAPGKPRELVARIYTGGTAWYEDSVKGRFTISRDNAQNTVYLQMNSLKSEDTAVYYCHGRVRYDYWGQGTQVTVSSGGGGSGGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSAAAEQKLISEEDLNGAAHHHHHH |
| 13A7-13A7 | 121 | EVQLVESGGGLVQPGESLRLSCTASRFMLDYYDIGWFRQAPGKEREGVSCRFTNDGSTAYADSVKGRFTISRDIVKHTVYLQMNSLQPEDTAVYYCAAGPLTKRRQCVPGDFSMDFWGEGTLVTVSSGGGGSGGGGSGGGGSGGGGSGGGGSGGGGSGGGGSEVQLVESGGGLVQPGESLRLSCTASRFMLDYYDIGWFRQAPGKEREGVSCRFTNDGSTAYADSVKGRFTISRDIVKHTVYLQMNSLQPEDTAVYYCAAGPLTKRRQCVPGDFSMDFWGEGTLVTVSS |
| 13A7-13A7-Alb8 | 122 | EVQLVESGGGLVQPGESLRLSCTASRFMLDYYDIGWFRQAPGKEREGVSCRFTNDGSTAYADSVKGRFTISRDIVKHTVYLQMNSLQPEDTAVYYCAAGPLTKRRQCVPGDFSMDFWGEGTLVTVSSGGGGSGGGGSGGGGSGGGGSGGGGSGGGGSGGGGSEVQLVESGGGLVQPGESLRLSCTASRFMLDYYDIGWFRQAPGKEREGVSCRFTNDGSTAYADSVKGRFTISRDIVKHTVYLQMNSLQPEDTAVYYCAAGPLTKRRQCVPGDFSMDFWGEGTLVTVSSGGGGSGGGSEVQLVESGGGLVQPGNSLRLSCAASGFTFSSFGMSWVRQAPGKGLEWVSSISGSGSDTLYADSVKGRFTISRDNAKTTLYLQMNSLRPEDTAVYYCTIGGSLSRSSQGTLVTVSSAAAEQKLISEEDLNGAAHHHHHH |
| 8G11-8G11 | 123 | EVQLVESGGGLVQAGGSLRLSCAASGNFFRVNTMAWYRQAPGKWRELVADITRGDRTNYADTVNGRFTISRDNVRNTVYLQMNGLRPEDTAAYYCYAVIELGVLEPRDYWGQGTQVTVSSGGGGSGGGGSGGGGSGGGGSGGGGSGGGGSGGGGSEVQLVESGGGLVQAGGSLRLSCAASGNFFRVNTMAWYRQAPGKQRELVADITRGDRTNYADTVNGRFTISRDNVRNTVYLQMNGLRPEDTAAYYCYAVIELGVLEPRDYWGQGTQVTVSS |
| 8G11-8G11-Alb8 | 124 | EVQLVESGGGLVQAGGSLRLSCAASGNFFRVNTMAWYRQAPGKQRELVADITRGDRTNYADTVNGRFTISRDNVRNTVYLQMNGLRPEDTAAYYCYAVIELGVLEPRDYWGQGTQVTVSSGGGGSGGGGSGGGGSGGGGSGGGGSGGGGSGGGGSEVQLVESGGGLVQAGGSLRLSCAASGNFFRVNTMAWYRQAPGKQRELVADITRGDRTNYADTVNGRFTISRDNVRNTVYLQMNGLRPE |

TABLE B-4-continued

Multivalent polypeptides ("ID" refers to the SEQ ID NO as used herein)

| Name | ID | Amino acid sequence |
|---|---|---|
| | | DTAAYYCYAVIELGVLEPRDYWGQGTQVTVSSGGGGSGGGSEVQLVESGGGLVQPGNSLRLSCAASGFTFSSFGMSWVRQA PGKGLEWVSSISGSGSDTLYADSVKGRFTISRDNAKTTLYLQMNSLRPEDTAVYYCTIGGSLSRSSQGTLVTVSSAAAEQK LISEEDLNGAAHHHHHH |

TABLE B-5 various amino acid sequences ("ID" to the SEQ ID NO as used herein)

| Name | ID | Amino acid sequence |
|---|---|---|
| Alb-11 | 125 | EVQLVESGGGLVQPGNSLRLSCAASGFTFSSFGMSWVRQAPGKGLEWVSSISGSGSDTLYADSVKGRFTISRDNAK TTLYLQMNSLRPEDTAVYYCTIGGSLSRSSQGTLVTVSS |
| Alb-8 | 126 | EVQLVESGGGLVQPGNSLRLSCAASGFTFSSFGMSWVRQAPGKGLEWVSSISGSGSDTLYADSVKGRFTISRDNAK TTLYLQMNSLRPEDTAVYYCTIGGSLSRSSQGTLVTVSSAAAEQKLISEEDLNGAAHHHHHH |
| Tag-1 or 3xFLAG-His$_6$ | 127 | GAADYKDHKDGDYKDHDIDYKDDDDKGAAHHHHHH |
| 5GS | 128 | GGGGS |
| 6GS | 129 | SGGSGGS |
| 9GS | 130 | GGGGSGGGS |
| 10GS | 131 | GGGGSGGGGS |
| 15GS | 132 | GGGGSGGGGSGGGGS |
| 18GS | 133 | GGGGSGGGGSGGGGGGGS |
| 20GS | 134 | GGGGSGGGGSGGGGSGGGGS |
| 25GS | 135 | GGGGSGGGGSGGGGSGGGGSGGGGS |
| 30GS | 136 | GGGGSGGGGSGGGGSGGGGSGGGGSGGGGS |
| 35GS | 137 | GGGGSGGGGSGGGGSGGGGSGGGGSGGGGSGGGGS |
| VHH1 consensus | 138 | QVQLVESGGGLVQPGGSLRLSCAASGFTLDYYAIGWFRQAPGKERGVSCISSSDGSTYYADSVKGRFTISRDNAKN TVYLQMNSLKPEDTAVYYCAA |

EXAMPLES

Example 1.1

Immunization of Llamas 405 and 418 and Construction of Phage Display Libraries

Llamas were immunized by a DNA-prime>protein boost strategy (Koch-Nolte et al. 2007 Faseb J 21:3490-3499). Llamas were immunized per gene gun (Biorad) on shaved left and right flanks with cDNA constructs for mouse P2X7 (mP2X7) and human P2X7 (hP2X7) adsorbed on gold particles (1 µm, 12 shots each with 1 µg DNA/mg gold) and boosted with the same, 3 times in 2-week intervals (FIG. 1). Three and 9 days post final DNA immunization, 100 ml peripheral blood each was collected. Total RNA was prepared from blood lymphocytes, the VHH repertoire was amplified by RT-PCR and cloned into the pAX50 in phagemid, generating phage libraries PRL1 and PBL2. Llamas were further boosted once with HEK cells transfected to stably express mP2X7 or hP2X7 (Adriouch et al., 2008 FASEB J. 22, 861-869) ($2 \times 10^7$ HEK_mP2X7 and $3 \times 10^7$ HEK_hP2X7 cells, pretreated for 15 min with 1 mM ATP and then fixed in 2% paraformaldehyde for 10 min on ice). Four and 8 days later, peripheral blood was collected and phage libraries PBL3 and PBL4 were generated. A final boost was performed with purified bead-bound recombinant mP2X7 (5 µg/50 µl beads) immunoprecipitated with agarose-coupled mAbs HANO43 and HANO44 (Adriouch et al. 2005, Möller et al. 2007) from HEK_mP2X7 cell lysates. Four and 10 days later phage libraries PBL5 and P8L6 were generated. RNA was reverse transcribed into cDNA, the VHH repertoire was amplified by PCR and cloned into the pAX50 phagemid vector. Phages were amplified in TG1 *E. coli*.

Example 1.2

Selection, Sequencing and Initial Characterization of Human P2X7-Specific Nbs

Selections of anti-hP2X7 Nanobodies (Nbs) were carried out with combined phage libraries PBL5 and PBL6. Two selections were carried out each comprising two rounds of panning on hP2X7-expressing cells. In selection 1, phage libraries PBL5+6 (200 µl) were panned on mouse Yac-1 lymphoma cells transfected to stably express human P2X7 (2.5×10$^7$ cells). Cell bound phages were eluted by trypsinization (15 min RT) and supernatants were used to amplify phage per re-infection in TG1 *E. coll*. Rescued phages from the first round of selection (200 µl) were further panned on HEK cells stably transfected to express hP2X7 (2×10$^7$ cells). For each llama, clones were picked from round 2 (R2) only. Phagemids were prepared from each clone and sequenced with pAX50 sequencing primers. For expression of Nbs as single domain antibodies, pAX50 phagemid vectors were individually transformed into HB2151 *E. coli*. Monovalent Nbs were expressed as soluble His6x tagged proteins and purified from periplasma lysates by immobilized metal affinity chromatography.

Sequencing results revealed 34 identical clones from the R2 selection of libraries PBL5+6 of llama 405 (family a) (Table 1). 41 clones were sequenced from the R2 selection of libraries PBL5+6 of llama 418, consisting of 3 different families (Table 1) of which 39 were identical (family b, 1c113). Test expression and binding analyses on HEK_hP2X7 cells showed that 1c81 (family a) and 1c113 (family b) bind hP2X7 specifically, whereas 2 other selected clones (1c121 and 1c126) were non-binders (FIG. 2A).

Hence, the identified clones were llama-specific. Nonetheless, even after two elaborated rounds of panning, non-binders were selected. Moreover, the results were severely skewed by the presence of apparently dominant phages,

TABLE 1 grouping of individual clones into families

| family | clone | # in R2 | Lama |
|---|---|---|---|
| Selection I | | | |
| a | 1c81 | 34x | 405 |
| b | 1c113 | 39x | 418 |
|  | 1c121 | 1x |  |
|  | 1c126 | 1x |  |
| Selection II | | | |
| a | 3c22 | 4x | 405 |
| a | 3c29 | 1x |  |
| c | 3c23 | 1x |  |
| c | 3c28 | 2x |  |
|  | 3c31 | 1x |  |
|  | 3c34 | 4x | 418 |
|  | 3c39 | 4x |  |

To increase the number and diversity of selected clones, a second selection was carried out using the same cells as above: Yac-1_hP2X7 in R1, and HEK_hP2X7 in R2. In order to prevent re-selection of the apparently dominant phages, binding sites were saturated by pre-incubation of Yac-1 cells in R1 with excess of purified 1c81 and 1c113 Nbs (0.7 µg per 2×10$^7$ cells) prior to panning.

Although dominant phages were counter-selected for, the second selection procedure did not reveal any other moderate to strong binders, in particular, sequencing of 8 clones from R2 of llama 418 library revealed clones belonging to 2 different families, each with 4 clones of identical sequences. Test expression and binding analyses on HEK_hP2X7 cells showed no (3c34) or only very weak binding (3c39) to HEK_hP2X7 cells.

Sequencing of 10 clones from R2 of llama 405 library revealed clones belonging to 3 different families, 5 of the 10 clones belonged to family a, i.e., the same family as 1c81, albeit with slightly different amino acid sequences. Four of these had identical amino acid sequences. A further 3 clones consisting of 2 distinct sequences belonged to a new family (family c, 3c23 and 3c28). Test expression and binding analyses on HEK_hP2X7 cells showed that 3c23 (family c) bound hP2X7 specifically, whereas one other selected clone (3c31) was a non-binder (FIG. 2B).

These results corroborate the previous findings, that identifying any P2X7 binder is not straight forward.

Example 1.3

Reformatting of Nbs into Bivalent Molecules and Production of Recombinant Proteins Homomeric and heteromeric dimers of Nbs 1c81, 1c113 and 3c23 were constructed by PCR, so as to insert a 35-GS linker (Sfil-Nb1-20G5-BamH1-15GS-Nb2-Notl) using long flanking primers. The VHH domains were also recloned as fusion proteins to the Fc-domain of mouse IgG1 by PCR amplification with primers flanked by suitable restriction enzyme sites (5' BamH1, and 3' Xhol), into the eukaryotic expression vector pME (Scheuplein et al., 2010).

Monovalent and bivalent Nbs were expressed as soluble His6x tagged proteins in HB2151 *E. coli* and purified from *E. coli* periplasma lysates by immobilized metal affinity chromatography. Bivalent Nbs were expressed as N-terminally FLAG-tagged Nb-Fc fusion proteins in transiently transfected HEK cells. Five days after transfection. Nb-Fc fusion proteins were purified from cell supernatants by affinity chromatography on M2-anti-FLAG immobilized on agarose beads. Nbs and Nb-Fc fusion proteins were conjugated to Alexa647 according to the manufacturer's instructions (Pierce, Invitrogen).

Example 1.4

FACS Analyses of Transfected HEX Cells Confirm Specificity of P2X7 Nbs

In order to verify the specificity of the selected Nbs and to determine whether the Nbs would bind also to mouse P2X7 or rat P2X7, HEK cells were co-transfected with expression constructs for GFP and either hP2X7, mP2X7, or rP2X7. Twenty four hours post transfection cells were stained with Nb-Fc fusion proteins or mAb L4 before FACS analyses (FIG. 3). The results show that Nbs 3c23 (designated as WD3c23Fc in the figure) and 1c113 (designated as WD1c113Fc in the figure) recognize hP2X7, but not rP2X7 or mP2X7, whereas Nb 1c81 (designated as WD1c81Fc in the figure) specifically reacts with cells transfected with hP2X7, rP2X7, and mP2X7. By comparison, previously described Nbs 13A7 and 14D5 (WO 2010/070145) recognize mP2X7, but not hP2X7 or rP2X7, mAb L4 recognizes hP2X7 and rP2X7, but not mP2X7.

Unexpectedly, clones with different species specificity and cross-reactivity were identified and selected, although derived from the same immunisation and boosting strategy using mouse and human P2X7 DNA in and P2X7 cells.

Example 1.5

Cross-Blockade Binding Analyses Show that Nbs 1c81 (Family a) and 1c113 (Family b) Share an Overlapping Binding Site with the Anti-hP2X7 mAb L4

Primary lymphocytes express low levels of P2X7. Combining antibodies recognizing different epitopes or using conformation independent antibodies would be of advantage for visualization of the purine receptor. To investigate whether the selected Nbs recognize overlapping epitopes, cross-blocking analyses were performed with un-conjugated Nb-Fc fusion proteins and Alexa647-conjugated mAb L4 and Nbs 1c113-Fc and 3c23-Fc (FIG. 4). HEK cells transfected to stably express high levels of hP2X7 were pre-incubated with saturating levels of either un-conjugated mAb L4, Nb 1c81-Fc, Nb 1c113-Fc, Nb 3c23-Fc, a control Nb (1067-Fc, anti-hCD38), or medium only (vehicle). Without washing, cells were stained with the indicated conjugated antibodies in amounts 10 times less than un-conjugated antibodies.

In all cases the control Nb, 1067-Fc, did not affect staining by the Alexa647-conjugated P2X7 mAb/Nbs. Staining with Alexa647-conjugated 1c113-Fc was completely blocked by unlabeled 1c113-Fc, 1c81-Fc and mAb L4 but not by 3c23-Fc. Concurrently, 3c23-Fc Alexa647 staining was completely abrogated by un' conjugated 3c23-Fc but was unaffected by the other antibodies. Finally, whereas binding of mAb L4 AF647 was unaffected by 3c23-Fc, staining was abrogated in the presence of un-conjugated L4 and 1c113-Fc. 1c81-Fc also blocked L4 AF647 staining, albeit incompletely.

In order to further assess the utility of Nb-Fc fusion proteins of Nbs 13A7 and 14D5, lymphocytes from lymph nodes, spleen or liver of wild type and P2X7$^{-/-}$ mice were co-stained with fluorochrome-conjugated mouse P2X7-specific 13A7-Fc, 14D5-Fc or human P2X7-specific 3c23-Fc (negative control) and with antibodies against CD4, CD25, and NK1.1 before flow cytometry. FIG. 13 demonstrates that Nb-Fc fusion proteins of Nbs 13A7 and 14D5 detect P2X7 on lymphocytes from lymph nodes, spleen and liver.

Hence, these Nbs are useful tools for monitoring expression of P2X7 on primary cells from lymph node, spleen and liver.

Example 1.6

Combination of Epitope-Independent Nbs Permits Visualization of P2X7 on Human Peripheral Blood Lymphocytes and Monocytes Detection of the surface expression of P2X7 on primary lymphocytes is limited by the availability of suitable tools and the inherent low expression of the purine receptor on lymphocyte subsets (Buell et al. 1998). Having shown that 3c23-Fc binds independently of 1c81-Fc and 1c113-Fc, we tested whether a combination of the fluorochrome-labelled Nb-Fc fusion proteins would improve detection of P2X7 on lymphocyte and monocyte populations in human peripheral blood (FIG. 5). To this end, comparative staining of PBL from a single donor was performed with mAb L4 vs. 1c113-Fc, 3c23-Fc, or a combination of the latter two Nb-Fc fusion proteins. The results demonstrate that the combination of Nb-Fc fusion proteins yields improved detection sensitivity as compared to staining with mAb L4 alone (MFI 21 vs. 11 for CD4$^+$ cells and MFI of 17 vs. 10 for CD4$^-$ cells) (FIG. 5A). In order to verify the specificity of the observed staining, blocking analyses were performed with a 10 fold excess of a combination of the same unlabeled Nb-Fc fusion proteins used for staining or a control In order to validate the utility of combining 1c113-Fc and 3c23-Fc for detection of P2X7 in different donors, aliquots of full blood from three separate donors were stained by the same procedure (FIG. 5B). Monocytes, granulocytes, and lymphocytes were gated by FSC vs. SSC. CD4$^+$ T cells, CD8$^+$ T cells and CD4$^-$/CD8$^-$ lymphocytes (corresponding mainly to B cells) were gated on the basis of CD4 and CD8 expression. Results are shown in a concatenate representation. The extent of specific staining was calculated as the fold increase in MFI of unblocked (−) vs. blocked (+) staining (Table 1.2). The results show specific staining of cell surface P2X7 in monocytes and all lymphocyte subsets, but not in granulocytes. The level of P2X7 expression can be ordered qualitatively as monocytes >CD4>CD8>CD4−/CD8−.

TABLE 1.2

Signal-to-background ratio for the expression of P2X7 on human peripheral blood leukocytes. Mean fluorescence intensities were determined for each population of cells shown in FIG. 5. Respective unblocked (−) versus blocked (+) quotients were calculated as fold increase of signal over background.

| | Quotient MFI AF647 unblocked/blocked | | |
|---|---|---|---|
| | donor 1 | donor 2 | donor 3 |
| CD4 T cells | 3.1 | 4.2 | 4.5 |
| CD8 T cells | 2.7 | 4.5 | 6.4 |
| CD4−/CD8− lymphocytes | 2.1 | 1.3 | 1.1 |
| monocytes | 5.1 | 6.3 | 5.3 |
| granulocytes | 0.78 | 1.7 | 0.8 |

Example 1.7

Nbs 1c81 and 3c23 Block ATP-Induced Shedding of CD62L in Transfected HEK Cells

We have previously shown that treatment of HEK cells co-transfected with P2X7 and CD62L (L-selectin) with ATP results in the P2X7-dependent shedding of CD62L (via P2X7-dependent activation of an endogenous metalloprotease). To determine whether the selected Nbs could block P2X7 function, CD62L shedding analyses were carried out with transfected HEK cells (FIG. 6). Cells were transfected with a cDNA expression construct for CD62L only, or co-transfected with constructs for CD62L and hP2X7 (Y155_T348). 24 h post transfection, cells were harvested and shedding of CD62L was induced by incubation with ATP.

In HEK cells transfected with CD62L only, incubation with 4 mM ATP showed no effect on cell surface levels of CD62L (FIG. 6A). In HEK cells co-transfected with CD62L and hP2X7, in contrast, treatment with ATP induced shedding of CD62L in a dose-dependent manner (EC-50 1.5 mM; FIG. 6B). Pre-incubation of the cells with Fc-fusion constructs of the Nbs 1c81 or 3c23 prior to treatment with 2 mM or 4 mM ATP abrogated shedding of CD62L. A control Fc fusion protein, 1067-Fc (anti-hCD38), did not affect shedding (FIG. 6B).

Example 1.8

Nbs 1c81 and 3c23 Block Shedding of CD62L in Transfected HEK Cells

The mouse mAb L4 has been reported to block P2X7 activation on human monocytes (Buell et al. 1998). In order to compare the blocking potencies of the selected Nbs, Nb-Fc fusion proteins, and mAb L4, comparative dose response assays were performed with transfected HEK cells (FIG. 7). To this end, HEK cells were co-transfected with GFP, CD62L and hP2X7. 24 h post transfection, cells were harvested by gentle trypsinization and incubated for 15 min at RT with the indicated amounts of Nb, Nb-Fc fusion protein, or mAb L4. Cells were further incubated for 60 min at 37° C. in the absence or presence of 4 mM ATP before staining for cell surface CD62L and FACS analyses.

The results show complete blockade of CD62L shedding by a saturating dose of Nbs 1c81 and 3c23, a partial blockade by a saturating dose of Nb 1c113 and mAb L4, and no blockade by a control Nb and Nb-Fc fusion protein. Titration analyses revealed that the bivalent Nb-Fc fusion proteins have improved molar inhibition potencies over their single domain counterparts: 3c23-Fc showed a 4-fold increase over 3c23 whereas 1c81-Fc was 20-fold more potent than 1c81. Hence, based on the potency to block or potentiate ATP-induced shedding of CD62L, the anti-hP2X7 antibodies could be ordered as 3c23-Fc>3c23>1c81-Fc>1c81>1c113-Fc>1c113, mAb L4 in descending order of potency (Table 1.3).

TABLE 1.3

Calculated $IC_{50}$ values of anti-hP2X7 antibodies in the blockade of L-selectin shedding in transfected HEK cells. $IC_{50}$ values were calculated from curves in FIG. 7 with 700 fluorescent units of anti-CD62L marked as point of half maximal blockade (dotted red line). $IC_{50}$ values could not be estimated for curves with maximal inhibition below threshold. $IC_{50}$ values in nM were calculated taking respective average molecular weights into consideration.

|  | 3c23 | 3c23Fc | 1c81 | 1c81Fc | 1c113 | 1c113Fc | L4 | 2145 | 1067Fc |
|---|---|---|---|---|---|---|---|---|---|
| $IC_{50}$ [ng/ml] | 40 | 50 | 1500 | 400 | 2800 | >2800 | >2800 | >2800 | >2800 |
| Mw (kDa) | 15 | 80 | 15 | 80 | 15 | 80 | 150 | 15 | 80 |
| $IC_{50}$ [nM] | 2.7 | 0.6 | 100 | 5 | >185 | >35 | >19 | n/a | n/a | n/a = not applicable.

Example 1.9

Nbs 3c23 and 1c81 Block ATP-Mediated Externalization of Phosphatidylserine and Cell Death by RPMI 8226 Lymphoma Cells RPMI 8226 is a human B-cell myeloma cell line which endogenously expresses P2X7 (FIG. 8A) This cell line responds to ATP treatment with the externalization of phosphatidylserine (PS) and cell death (irreversible uptake of propidium iodide) (Farrell et al, 2010 Biochimica et Biophysica Acta 1800 pp 1173 FACS analyses confirmed an ATP-dose dependent externalization of PS by RPMI 8226 cells ($EC_{50}$ 1.8 mM) (FIG. 8B). To test whether the selected NbS could block ATP-induced activation of endogenously expressed P2X7, the capacity of Nbs to block the ATP-mediated PS-externalization by RPMI 8226 cells was investigated (FIG. 8C). To this end, RPMI 8226 cells were pre-incubated with the mAb L4, anti-hP2X7 Nb-Fc fusion proteins 1c113-Fc, 1c81-Fc, 3c23-Fc or with a control Nb-Fc fusion protein 1067-Fc for 15 min at RT and then further incubated for 60 min at 37° C. with 4 mM ATP. The extent of P2X7 activation was assayed by visualization of externalized phosphatidylserine with fluorochrome-labeled Annexin V (FIG. 8C). The results show nearly complete blockade of ATP-induced PS-externalization by 1c81-Fc and 3c23-Fc, whereas mAb L4 and the 1c113-Fc both only partially prevented PS-externalization, and complete lack of blockade by the control Nb-Fc fusion protein 1067-Fc.

Example 1.10

Nbs 1c81 and 3c23 Prevent P2X7-Mediated Cell Death of RPMI 8226 Cells

It has previously been demonstrated that prolonged activation of P2X7 on RPMI 8226 cells by ATP results in cell death, as detected by irreversible uptake of propidium iodide (Farrell et al, 2010). It was next investigated whether P2X7 specific Nbs would prevent cell death. To this end, RPMI 8226 cells were pre-incubated with respective antibodies prior to treatment with ATP for 60 min or 24 h. Cells were then washed and stained with Annexin V and propidium iodide to assess externalization of phosphatidylserine and cell death (FIG. 9).

During the 60-min incubation with 2 mM ATP, mAb L4 and Nb 1c113-Fc, both partially prevented exposition of phosphatidylserine as compared to the controls (FIG. 9, upper panels). This partial blockade did not suffice to prevent cell death during an overnight incubation with ATP (FIG. 9, lower panels). In contrast, Nb-Fc fusion proteins 1c81-Fc and 3c23-Fc both completely blocked P2X7-mediated exposition of phosphatidylserine and cell death irrespective of the duration of ATP treatment (FIG. 9 upper and lower panels).

Example 1.11

Nbs 1c81 and 3c23 Block ATP-Induced Externalization of PS and Shedding of CD62L by Human T Cells Having demonstrated that Nbs 1c81 and 3c23 effectively block ATP-induced externalization of PS by RPMI8226 lymphoma cells that endogenously express P2X7, we next investigated whether these Nbs could also block ATP-induced externalization of PS and shedding of CD62L by CD4+ T cells and CD8+ T cells (FIG. 10). To this end, aliquots of full blood were pre-incubated for 30 min at RT with respective Nb-Fc fusion proteins or with mAb L4 prior to treatment with 4 mM ATP for 30 min at 37° C. Subsequently, cells were stained for CD62L expression and externalization of PS (Annexin V) as readouts for P2X7 activation.

T cells from the three donors responded ATP by CD62L shedding and Annexin V staining to different extents (FIG. 10). Whereas T cells from donors 1 and 2 showed weaker responses to ATP, cells from donor 3 responded strongly to P2X7 activation. In magnitude of P2X7 sensitivity, the donors can be ordered as donor 3>donor 2>donor 1. Response to ATP by CD4+ T cells was comparable to CD8+

T cells in respective donors. Both mAb L4 and 1c113-Fc showed partial blockade of CD62L shedding and exposition of PS; the control antibody 1067-Fc did not affect ATP-mediated activation of P2X7. Nb-Fc proteins 1c81-Fc and 3c23-Fc completely prevented ATP-mediated activation of P2X7.

Example 1.12

Nb 3c23 Blocks ATP-Induced Calcium Influx in Human RPMI 8226 Lymphoma Cells

RPMI 8226 cells were loaded with the $Ca^{2+}$ indicator Fluo-4. Real time flow cytometry analyses were performed (BD FACS Canto). Cells were washed and resuspended in PBS supplemented with $Ca^{2+}$ and $Mg^{2+}$ (Invitrogen) in the absence (solvent) or presence of the human P2X7-specific Nb 3c23-3c23 or mouse P2X7-specific Nb 13A7-13A7 (negative control) and analyzed by flow cytometry (BD FACS-Canto). An infrared lamp was used to maintain a constant sample temperature of 37° C. After equilibration for 100 sec, ATP was added to a final concentration of 2 mM and incubation was continued for 100 sec before addition of ionomycin to a final concentration of 5 µM. FIG. 14 demonstrates that Nb 3c23 blocks ATP-induced Calcium influx in human RPMI 8226 lymphoma cells.

Example 1.13

Nb 3c23 Blocks ATP-Induced Release of IL-1β from Human Blood Cells

Aliquots of heparinized whole blood from four donors were incubated in the absence or presence of Nb 3c233c23 for 2 h with LPS (1 µg/ml) before addition of ATP to a final concentration of 5 mM and further incubation for 1 h at 37° C. Plasma was prepared by centrifugation of cells and IL-1β levels in plasma were determined by ELISA (R&D Systems). *P<0.001 (One-way ANOVA). FIG. 15** demonstrates that Nb 3c23 blocks ATP-induced release of IL-1β from human blood cells.

Example 1.14

Dose Response Analysis of Nb 3c23 Blocking ATP-Induced Release of IL-1β from Human Blood Cells Aliquots of heparinized whole blood were incubated in the absence or presence of the indicated concentrations of Nb 3c23, 3c23-3c23, and 3c23Fc for 2 h with LPS (1 µg/ml) before addition of ATP to a final concentration of 2 mM and further incubation for 1 h at 37° C. Plasma was prepared by centrifugation of cells and IL-1β levels in plasma were determined by ELISA (R&D Systems). Mouse P2X7-specific Nb 13A7 was used as a negative control. FIG. 16 depicts a dose response analysis of Nb 3c23 blocking ATP-induced release of IL-1β from human blood cells.

Example 1.15

Mouse Nb 13A7 Blocks and Nb 14D5 Potentiates NAD+ and ATP-Induced Shedding of CD62L by the lymphoma cell line Yac-1

The functional effects of mouse P2X7-specific Nbs were further evaluated using P2X7-expressing murine cells. The lymphoma cell line Yac-1 endogenously expresses mouse P2X7 and the toxin related ecto-ADP-ribosyltransferase ART2.2. On these cells, P2X7 can be activated by extracellular ATP as well as by NAD+-dependent ADP-ribosylation of R125 catalyzed by ART2.2 (Adriouch et al., 2008). Nb 13A7 blocked both NAD+-induced and ATP-induced shedding of CD62L by these cells; conversion into a bivalent format markedly enhanced the blocking potency of this Nb (FIG. 21). In contrast, Nb 14D5 potentiated ATP- and NAD+-induced shedding of CD62L by Yac-1 cells. Again, conversion into a bivalent format markedly enhanced the potency of this Nb (FIG. 1000b). Although binding of Nb 14D5 by itself did not induce gating of mouse P2X7, it lowered the threshold of gating for both ATP and NAD+ (WO 2010/070145). Similarly, Nb 13A7 effectively blocked and Nb 14D5 potentiated NAD+ and ATP-induced shedding of CD62L from primary T cells (FIG. 22). Nb 13A7 also effectively blocked ATP induced Ca2+ influx as well as ATP-induced processing and secretion of IL-1β by peritoneal macrophages (see example 1.18 and 1.19 below).

Example 1.16

Nb 13A7 Blocks, Nb 14D5 Potentiates ATP-Induced Calcium Influx in HEK Cells Stably Transfected with Mouse P2X7

Real time flow cytometry analyses of mouse-P2X7 transfected HEK cells loaded with the $Ca^{2+}$ indicator Fluo-4 in the presence of the mouse P2X7-specific Nb 14D5-14D5, Nb 13A7-13A7 or human P2X7-specific Nb 3c23-3c23 (negative control). Cells were exposed to extracellular ATP to a final concentration of 250 µM or 1 mM and, two minutes later, to the $Ca^{2+}$ ionophore ionomycin at a concentration of 5 µM. As demonstrated in FIG. 17, Nb 13A7 blocks, Nb 14D5 potentiates ATP-induced calcium influx in HEK cells stably transfected with mouse P2X7.

Example 1.17

Nb 13A7 Reverses, Nb 14D5 Induces and Potentiates ATP-Mediated Calcium Influx in HEK Cells Stably Transfected with Mouse P2X7

Real time flow cytometry analyses of mouse-P2X7 transfected HEK cells loaded with the $Ca^{2+}$ indicator Fluo-4. Cells were incubated with indicated concentrations of ATP for two minutes before treatment with mouse P2X7-specific Nb 14D5-14D5, Nb 13A7-13A7 or the human P2X7-specific Nb 3c23-3c23. As demonstrated in FIG. 18, Nb 13A7 reverses, Nb 14D5 induces and potentiates ATP-mediated calcium influx in HEK cells stably transfected with mouse P2X7.

Example 1.18

Nb 13A7 Blocks, Nb 14D5 Potentiates ATP-Induced Calcium Influx in Mouse Peritoneal Macrophages Mouse peritoneal macrophages were loaded with the $Ca^{2+}$ indicator Fluo-4. Real time flow cytometry analyses were performed (BD FACS Canto). Cells were washed and resuspended in PBS supplemented with $Ca^{2+}$ and $Mg^{2+}$ (Invitrogen) in the absence (solvent) or presence of the P2X7-potentiating Nb 14D5 or the P2X7-antagonizing Nb 13A7 (1 µg/500 µl). An infrared lamp was used to maintain a constant sample temperature of 37° C. After equilibration for 120 sec, cells were exposed to the indicated concentrations of extracellular ATP and two minutes later to the Ca$^{2+}$ ionophore ionomycin to a final concentration of 1 µM. As shown in FIG. 19, Nb 13A7 blocks, Nb 14D5 potentiates ATP-induced Calcium influx in mouse peritoneal macrophages.

Example 1.19

Nb 13A7 Blocks, Nb 14D5 Potentiates the Processing and Secretion of IL-1β by Peritoneal Macrophages Heparinized blood from wildtype or P2X7$^{-/-}$ mice was incubated in the presence of monovalent Nbs (1 µg/200 µl) 14D5, 13A7, or solvent for 2 h with LPS (1 µg/ml) before addition of ATP to the indicated final concentrations and further incubation for 30 min at 37° C. a) Samples were centrifuged and IL-1β levels in plasma were analyzed by ELISA (Biolegend). b) Erythrocytes were lysed and blood leukocytes were stained in two steps, first with fluorochrome-conjugated mAbs specific for CD11b, Ly-6C, and Ly-6G. Cells were then fixed (2% PFA) and permeabilized (PBS containing 0.3% saponin and 0.1% BSA) before staining for pro-IL-1β (e-Bioscience). Flow cytometry analyses were performed (BD FACS Canto) and gating was performed on CD11b$^+$Ly-6C$^{hi}$ monocytes. As demonstrated in FIG. 20, Nb 13A7 blocks, Nb 14D5 potentiates the processing and secretion of IL-1β by peritoneal macrophages.

Example 1.20

Conclusion

Three different families of Nbs were selected from two llamas by panning on cells expressing human P2X7 (hP2X7) and confirmed for hP2X7 specificity. Families a (1c81, llama 418) and b (1c113, llama 405) were selected by panning phage library on hP2X7-transfected Yac-1 and HEK cells sequentially. Family c (3c23, llama 405) was selected by masking 1c81 and 1c113 epitopes with purified Nbs and repeating panning. Nbs were reformatted into bivalent constructs and Nb-Fc fusion proteins. Monovalent and bivalent His-tagged Nbs were expressed in *E. coli* and purified from periplasma lysates by immobilized metal affinity chromatography. FLAG-tagged Nb-Fc fusion proteins were expressed in HEK cells and were purified from HEK cell supernatants by affinity chromatography on immobilized anti-FLAG mAb M2. Specificity of Nbs was verified on HEK cells transfected with human P2X7, mouse P2X7, or rat P2X7, Epitope-specificity was tested by cross-blocking analyses with the selected Nbs and the anti-hP2X7 mAb L4. Nbs 1c81 and 1c113 recognized an epitope shared with L4, Nb 3c23 recognizes a distinct, non-overlapping epitope. Combining Nbs with different epitopes permitted improved staining of cell surface P2X7 on human peripheral blood lymphocytes and monocytes. In particular, Nbs 1c113-Fc and 3c23-Fc are useful for monitoring expression of P2X7 on primary human blood cells. Potency of Nbs to block P2X7-dependent, ATP-induced shedding of L-selectin (C062L) and externalization of phosphatidylserine (PS) was tested on transfected HEK cells, human RPMI-8226 lymphoma cells, and primary human peripheral blood leukocytes. Nbs 1c81 and 3c23 blocked ATP-induced activation of P2X7 more efficiently than mAb L4. Reformatted bivalent Nb-Fc fusion proteins of 1c81 and 3c23 showed 5-20 fold enhanced potency to block activation of P2X7 than their monovalent counterparts. Examples 1.15- to 1.19 show functional effects of the mouse specific Nbs on ATP-induced Calcium influx and ATP-induced release of IL-1β, which mirror the results with the human P2X7-specific Nbs (Examples 1.12 to 1.14). Example 1.20 shows that Nbs 13A7 and 14D5 are useful tools for monitoring expression of P2X7 on primary cells from lymph node, spleen and liver.

Example 2

Ex-Vivo and In-Vivo Blockade and Activation of Anti-Mouse P2X7 Nanobodies

In order to assess the capacity of the Nanobodies to modulate P2X7 after systemic injection in vivo, two regulatory T cell subsets previously shown to display high sensitivity to NAD$^+$- and ATP-mediated gating of P2X7: CD4$^+$CD25$^+$ Tregs and iNKT cells were further elaborated (Hubert et al, 2010 J. Exp. Med. 207 pp 2561-2568; Scheuplein et al., 2010).

Example 2.1

Methodology

Nanobodies were injected intravenously by the tail vein of mice. Mice were sacrificed 1.5 h and 24 h later and analyzed for blockade or enhancement of P2X7 activation both in vivo and ex vivo.

Protocol set up: Wildtype C57bl/6 mice were injected with respective amounts of the Nanobody either by i.v. into tail vein. 1.5 h or 24 h post injection (p.i.), mice were sacrificed and splenocytes and liver lymphocytes prepared as described in previous experiments. 200 µl of splenocyte or liver leukocyte suspension were pelleted by centrifugation. Pellet was resuspended in 100 µl RPMI only, 25 µM NAD or 250 µM ATP in RPMI and incubated at 37° C. for 15 min to induce P2X7 activation and compared with sample kept on ice without ex vivo P2X7 activation (4° C.). After incubation, cells were washed in annexin V binding buffer and stained in annexin binding buffer.

Staining of primary cells from spleen and liver with fluorochrome-conjugated Nb 13A7 confirmed prominent expression of P2X7 by Tregs and iNKT cells (see Example 1.5, FIG. 13). Intravenous injection of these Nbs into mice resulted in effective staining of these regulatory T cells in lymph nodes, spleen and liver within 30 minutes after injection (data not shown).

Example 2.2

In Viva Activation of P2X7 by Enhancing HLE-Nanobody 14D5 (14D5-14D5-Alb8)

Injections of the 14D5-14D5-Alb8 Nb, remarkably resulted in a twofold reduction in the fraction of Tregs recovered from the spleen and an even more dramatic reduction of iNKT cells recovered from the liver 2 h after injection (FIG. 11a). Tregs numbers (as percentage of CD4+ cells) were down to 4% in mice injected with 14D5-14D5-Alb8 (n=3) vs, 9% in mice injected with the 13A7-13A7-Alb8 (n=3) and 12% in the mouse injected with the Dummy-Nb (n=1) iNKT cell numbers (as percentage of CD3 positive cells) were down to 10% vs. 45% in mice treated with 13A7-13A7-Alb8 and 14D5-14D5-Alb8, respectively, and to 55% in the mouse treated with the Dummy-Nb. 24 h after injection, numbers of Tregs and iNKT cells showed partial recovery in mice injected with 14D5-14D5-Alb8, but were still below those of mice injected with 13A7-13A7-Alb8 or Dum-Alb8-Dum (Dummy-Nb). In a separate experiment, mice injected with the 8G11-8G11-Alb8 showed numbers of Tregs and iNKT cells comparable to those of the Dummy-Nb injected mouse (FIG. 11c). The T cells recovered from the spleens of 14D5-14D5-Alb8 injected mice showed enhanced shedding of CD27 in response to a 15 min incubation at 37° C. with exogenous NAD as compared to mice injected with the Dummy-Nb (FIG. 11b).

Thus, 14D5-14D5-Alb8 Nb potentiates mouse P2X7.

Example 2.3

In Vivo Blockade of P2X7 by Antagonistic HLE-Nanobodies 8G11 and 13A7 (8G11-8G11-Alb8 and 13A7-13A7-Alb8, Respectively)

The results of functional assays performed on spleen and liver cells prepared 2 h after intraperitoneal injection of HLE-Nbs reveal blocking effects of both 8G11-8G11-Alb8 and 13A7-13A7-Alb8 on P2X7 (FIG. 11c).

Injection of 13A7-13A7-Alb8 completely prevented the shedding of CD27 by splenic Tregs and partially on blocked shedding of CD27 by liver iNKT cells in response to exogenous NAD added ex vivo (FIG. 11b). Injection of 13A7-13A7-A1138 also effectively blocked the externalization of phosphatidylserine by splenic Tregs and liver iNKT cells in response to exogenous NAD added ex vivo (FIG. 11c). In line with the in vitro results on Yac-1 lymphoma cells (see Example 1.15), 13A7-13A7-Alb8 was more effective in blocking P2X7 than 8G11-8G11-Alb8, despite the lower staining levels seen for 13A7 than for 8G11 with anti-myc. The results indicate that at 2 h after injection, the lowest dose of 13A7-13A7-Alb8 (15 µg) was still more effective than the highest dose of 8G11-8G11-Alb8 (200 µg) and only slightly less effective than the highest dose of 13A7-13A7-Alb8 (200 µg). The results of kinetic analyses indicate similar functional effects of the blocking HLE-Nbs at 24 h after injection as compared to 2 h after injection (FIG. 11b).

Example 3

Assessment of Anti-P2X7 Nanobodies in an Inflammatory Model

Example 3.1

Methodology

The reformatted Nbs were tested for therapeutic potential in a mouse model of experimentally induced inflammation: anti-podocyte antibody induced glomerulonephritis. Previous studies had shown that P2X7-deficient mice develop milder forms of these diseases, leading to the hypothesis that pharmacological inhibition of P2X7 in wildtype mice might mimic the beneficial effects of the genetic deletion of P2X7: Conversely, pharmacological activation of P2X7 might potentiate these inflammatory responses.

Example 3.2

Antibody-Induced Nephritis

Systemic injections of serum from animals immunized with mouse podocytes cause a slowly progressing inflammation of the kidney: Appearance of albumin in the urine (albuminuria) can be used as a read-out of damage to the glomerular filtration apparatus. Since the volume of urine can vary widely, depending mainly on the amount of fluid intake, it is common to normalize the concentration of albumin in urine to the concentration of creatinine: Disease progression is much slower than that of ConA-induced hepatitis. In wildtype mice, albuminuria usually is detectable from day 7-9 after serum injection. Animals usually succumb to disease and must be sacrificed at day 14-15 after serum injection.

To assess the potential therapeutic and/or proinflammatory effects of anti-P2X7 HLE-Nbs in the nephritis model, groups of 6 week old C57BL6 mice (n 6) received 5 injections of HLE-Nbs (an initial dose of 50 µg 2 h before injection of anti-podocyte serum (APN) and 25 µg each on days 3, 6, 9, and 12): Control mice received injections of pre-immune serum (PI). Groups of 5-6 mice received injections with Dummy-Nb, 13A7-13A7-ALB8, or 14D5-14D5-ALB8, 24 h urine was collected in metabolic cages on day 3, 6, 9, 12, 15 and 21. Animals were sacrificed on day 15 or 21, kidneys and blood samples were collected and subjected to further analyses including determination of serum cholesterol, triglycerides, and creatinine.

Example 3.3

Nb 14D5 Enhances, Nb 1307 Decreases Disease Parameters in a Nephritis Model

Albumin in urine was quantified by ELISA, creatinine levels were determined by automated measurement (FIG. 12A). On the day of sacrifice, blood urea nitrogen, serum triglycerides and serum cholesterol levels were determined by automated measurement; IL-6 in serum and MCP-1 in urine were quantified by ELISA. Significance was assessed with the Mann Whitney U test (FIG. 12B). The results of urine analyses show detectable proteinuria in animals treated with antipodocyte serum and the Dummy-Nb beginning at day 9 with steadily increasing urine albumin levels until the end of the experiment at day 15 or 21 (FIG. 12A). Mice treated with the P2X7 antagonistic 13A7-13A7-ALB8 showed much lower urine albumin levels at the time of sacrifice than mice treated with the Dummy-Nb (FIG. 12). These differences were statistically significant ($p<0.05$). In contrast, mice treated with the P2X7 enhancing 14D5-14D5-ALBS developed detectable albuminuria already on clay 3 after serum injection and continued to display significantly higher urine albumin levels than Dummy-Nb or 13A7-13A7-ALB8 treated mice throughout the course of the experiment. Consistent with a more severe nephritic syndrome in mice receiving the enhancing 14D5-14D5-ALB8, these mice also showed markedly higher levels of serum triglycerides, cholesterol and creatinine on day 15 and 21, while mice treated with 13A7-13A7-ALB8 showed normal levels of these serum parameters.

Example 3.4

Nb 13A7 Resists, Nb 14D5 Induces and Potentiates NAD$^+$ Induced Shedding of CD27$^+$ T Cells On the day of sacrifice (21 d after injection of antipodocyte antibodies, 3 d after the last injection of Nanbodies), splenocytes were incubated in the absence (PBS) or presence of NAD' for 30 min and then stained for CD4, CD25, and CD27 before FACS analyses. Gating was performed on CD4$^+$CD25$^+$ Tregs. Tregs from mice treated with the P2X7 agonistic Nb 14D5 contained a lower proportion of CD27$^+$ T cells, all of which were sensitive to NAD$^+$-induced loss of CD27; Tregs from mice treated with the P2X7 antagonistic Nb 13A7 were resistant to NAD$^+$-induced shedding of CD27. These results indicate that splenic Tregs were still coated with P2X7-specific Nbs on the day of sacrifice.

Example 3.5

Nb 14D5 Enhances, Nb 13D7 Decreases Inflammatory Kidney Damage

Figure 12C:
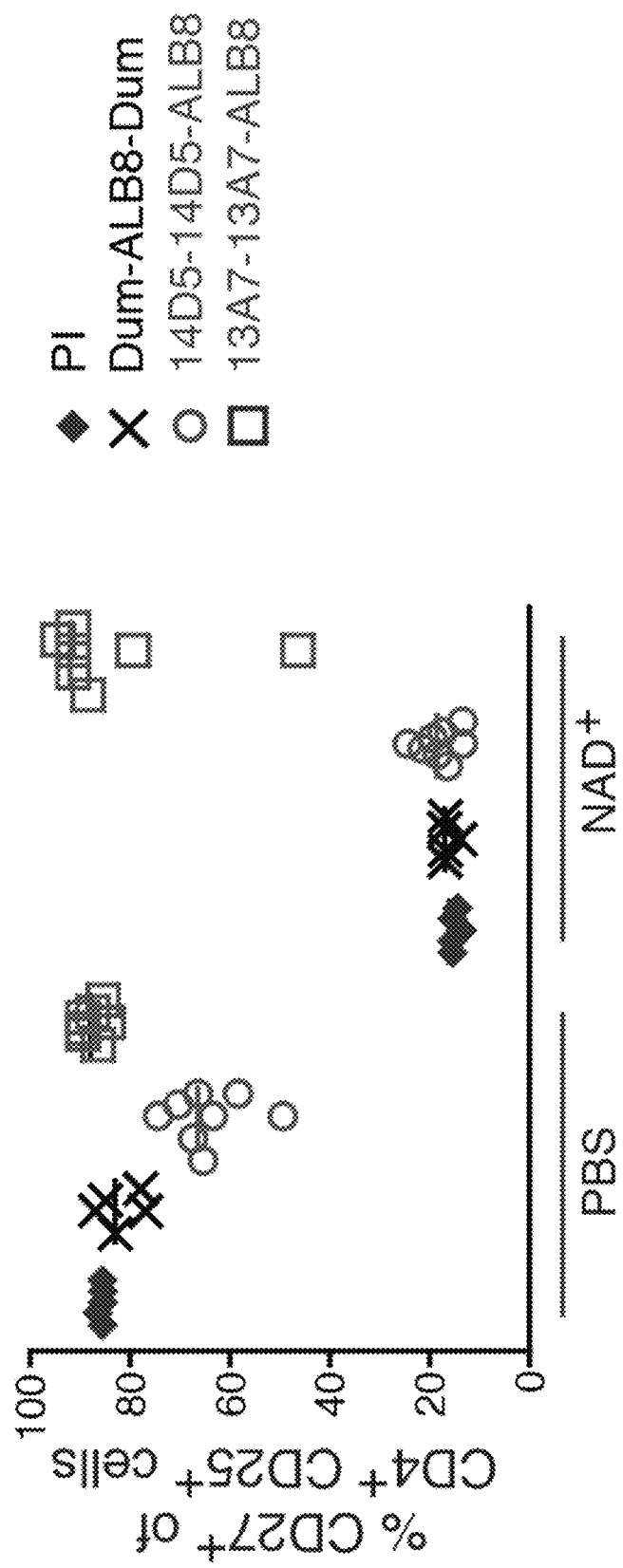
Figure 12D:
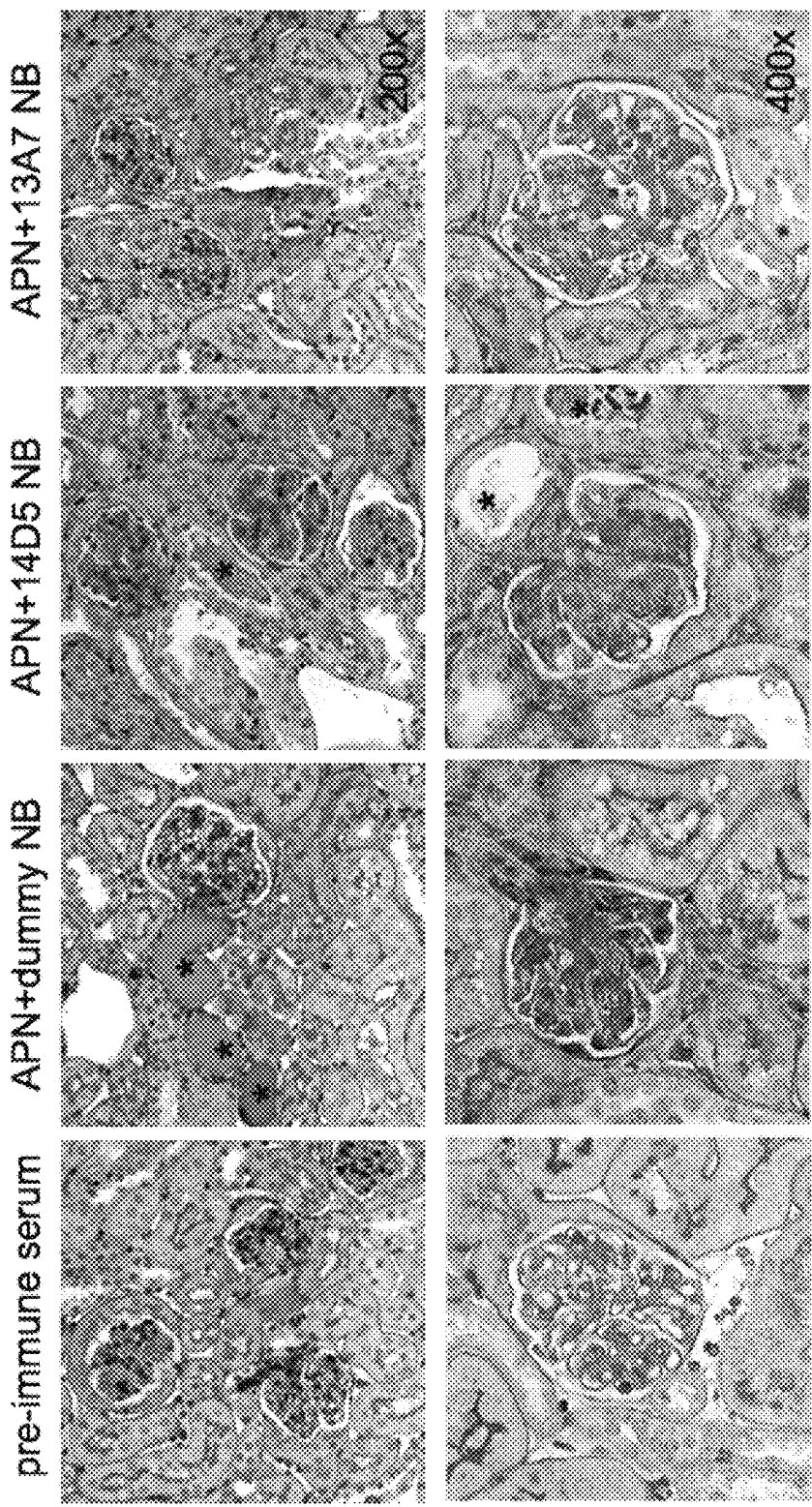
Figure 12E:
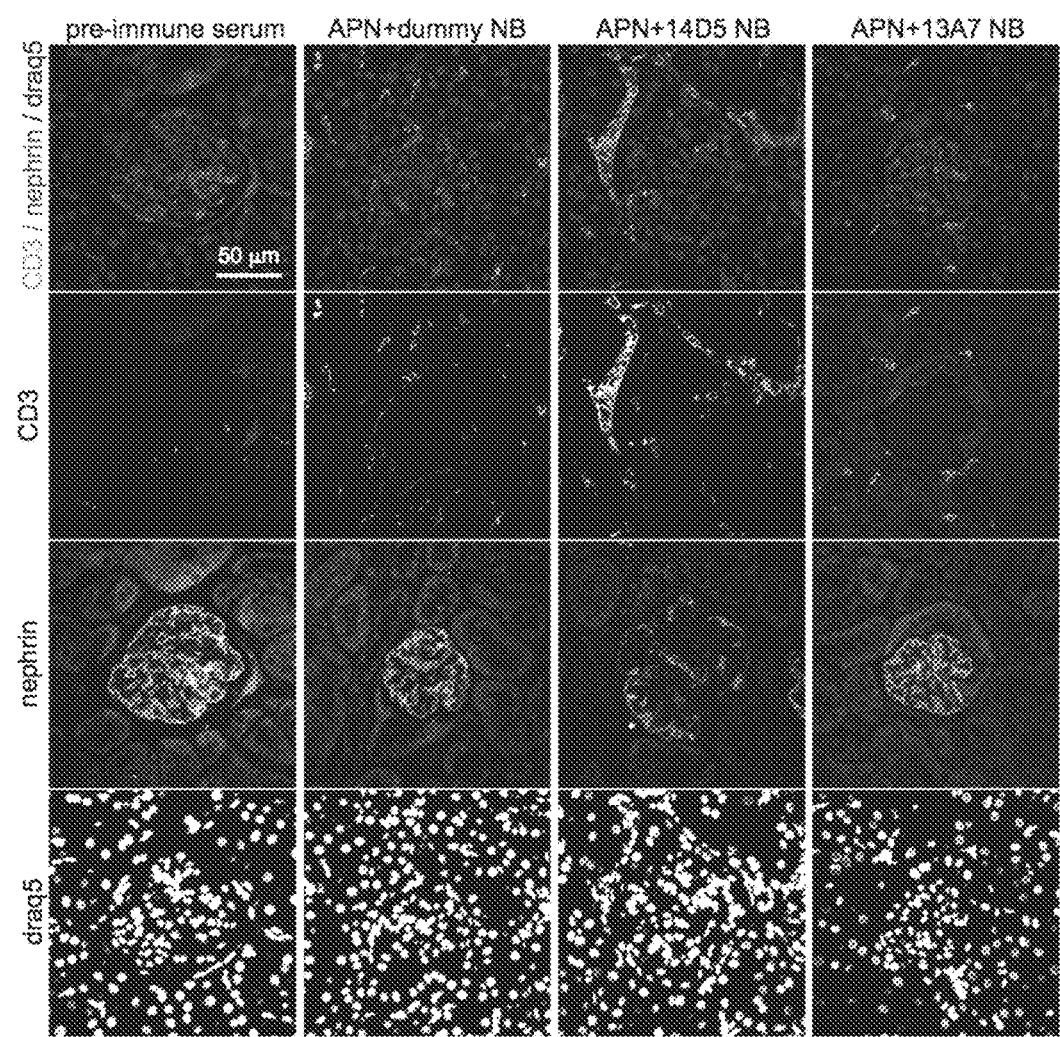

On the day of sacrifice (21 d after injection of anti-podocyte antibodies) Kidney sections were stained with Periodic Acid Schiff stain (PAS) (FIG. 12D top). Tubular protein casts are marked by asterisks. Kidney sections were stained with the DNA-staining dye draq5, a fluorochrome-conjugated mAb against the T cell marker CD3, and a fluorochrome-conjugated mAb against nephrin, a podocyte membrane protein at the renal filtration barrier (FIG. 12E, bottom). Podocyte nuclei are marked by asterisks. Kidney sections from mice treated with Nb 14D5 show stronger periglomerular infiltration of CD3$^+$ T cells and disrupted staining for nephrin than mice treated with Nb 13A7 or the control Nb.

Figure 12F:
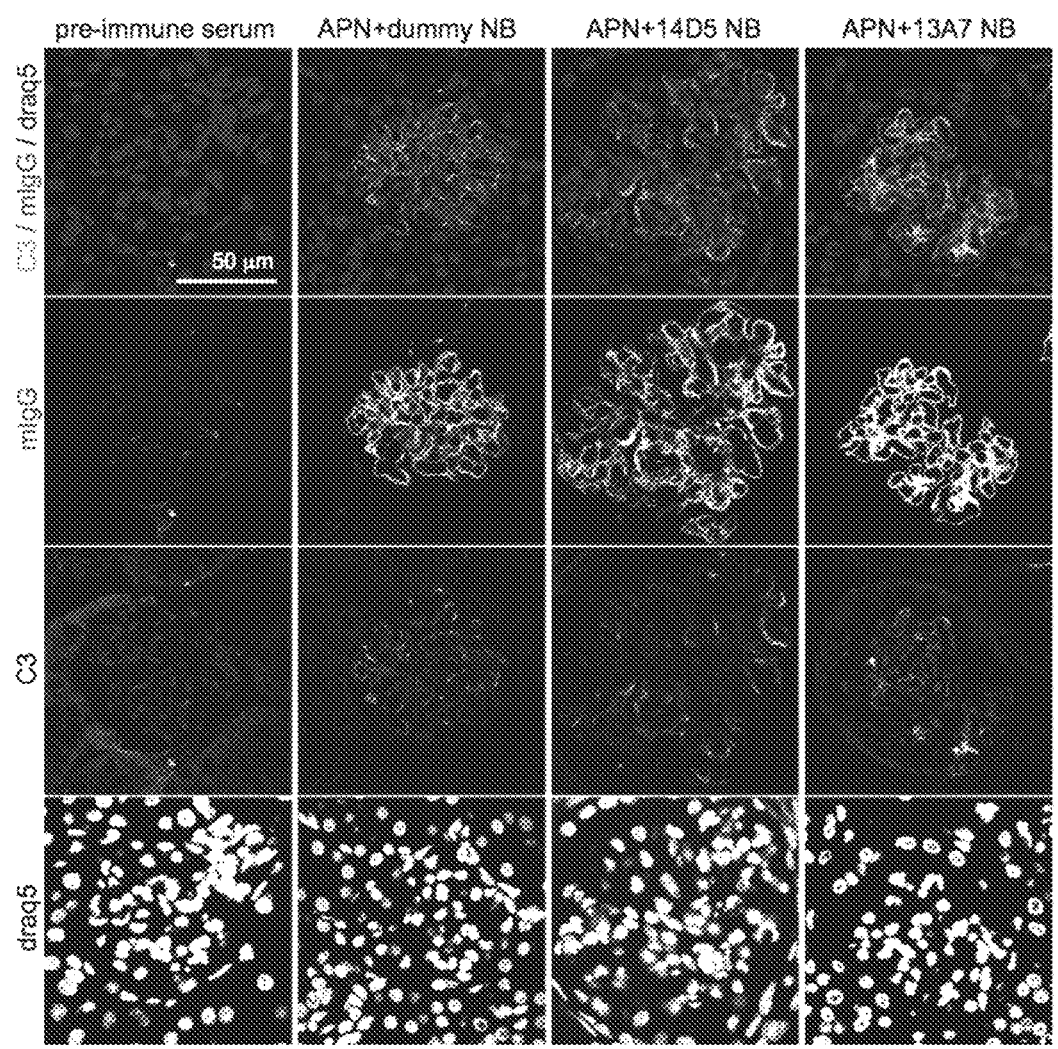

Kidney sections were stained with draq5 and fluorochrome conjugated mAbs against nephrin, the complement factor 3 (C3), and IgG before immunofluorescence microscopy (FIG. 12F). Sections from mice treated with AP serum (but not from mice treated with PI serum) show glomerular deposits of IgG and 3. The pattern of IgG deposits is regular in mice treated with Nb 13A7, but is partially disrupted in mice treated with the control Nb and strongly disrupted in mice treated with Nb 14D5.

Hence, animals treated with the P2X7-blocking Nb 13A7 showed little if any signs of kidney damage or of inflammation, whereas animals treated with the P2X7-potentiating Nb 14D5 showed aggravated inflammation and kidney damage: Albuminuria was significantly augmented in animals treated with Nb 14D5 or the control Nb but remained low in animals treated with Nb 13A7. Moreover, the former but not the latter showed clear histopathological signs of kidney damage consistent with a nephrotic syndrome, i.e. tubular protein casts, glomerular capillary occlusion, swelling of podocytes, disrupted nephrin staining at the filtration barrier and peritubular and periglomerular infiltration of inflammatory cells. Consistently, animals treated with the control Nb or with the P2X7-potentiating Nb 14D5 showed elevated concentrations of blood urea nitrogen, serum triglycerides, and cholesterol. Conversely, animals treated with the P2X7-blocking Nb 13A7 showed lower levels of the pro-inflammatory cytokines IL-6 in serum and MCP-1 in urine than animals treated with the P2X7-potentiating Nb 14D5. These results indicate that P2X7-blocking Nbs can ameliorate and that P2X7-potentiating Nbs can aggravate inflammatory kidney damage.

Example 3.4

Discussion and Conclusions

The results of in vitro analyses with nucleotide-induced activation of P2X7 on the Yac-1 lymphoma cell line revealed similar functional potencies of bivalent and HLE-Nbs. The two P2X7-antagonistic HLE-Nbs 13A7 and 8G11 both showed more efficient blockade of NAD (ADP-ribosylation)-induced activation of P2X7 than of ATP-induced activation, with 13A7 consistently showing better blocking effectiveness than 8G11. In case of the P2X7-enhancing 14D5 Nb, increasing the valency from monovalent to bivalent was accompanied by a markedly enhanced potency, while a further valency increase showed only a marginal further increase in potency.

Following systemic injections of HLE-Nbs at high doses (100 µg per mouse, corresponding to 5 mg/kg), the three P2X7-specific HLE-Nbs showed clearly detectable effects on P2X7 function on T cells in spleen and liver, faithfully recapitulating the effects observed with in vitro treatments of lymphoma cells, i.e., more efficient blockade by 13A7 than by 8G11 and a marked enhancement of P2X7 function by 14D5.

Using anti-myc antibody, Nbs could be detected on the surface of splenic and liver T cells, with most prominent staining of the two subpopulations known to express highest levels of P2X7: Tregs (CD4+CD25+) in the spleen.

In the spleen, 13A7 completely blocked P2X7-induced shedding of CD27 in response to low levels of NAD released during cell preparation, on both subpopulations of CD4+ helper T cells: the highly sensitive CD25+ population of Tregs as well as the less sensitive subpopulation of CD25- negative, naive CD4+ T cells (FIG. 11). 13A7 also completely protected both subpopulations against P2X7-induced shedding of CD27 in response to addition of higher concentrations of exogenous NAD. 13A7 further completely protected naive T cells, but only partially protected Tregs against P2X7-induced shedding of CD27 in response to addition of high concentrations of exogenous ATP. Time course analyses showed similar blocking activity at 24 h vs. 1.5 h after injection of 13A7. Titration analyses revealed little if any reduction of blocking activity of 13A7 when the dose was reduced from 200 µg to 15 µg per mouse.

An in vivo experiment revealed detectable effects of P2X7-specific HLE-Nbs also on P2X7 function and disease progression in a mouse model of experimentally induced nephritis. Effects were clearly evident in this nephritis model. The potent P2X7-antagonistic 13A7 HLE-Nb showed beneficial effects in this model, achieving statistical significance. The P2X7-enhancing 14D5 HLE-Nb significantly promoted disease progression in the nephritis model. In the nephritis model, mice treated with the potent antagonist 13A7 HLE-Nb showed much lower levels of albumin in urine at the time of sacrifice (day 15 after injection of anti-podocyte serum) than mice treated with the Dummy-Nb, with albumin serving as an indicator of damage to the glomerular filtration apparatus. These differences were statistically significant ($p<0.05$). In striking contrast, mice treated with the P2X7-enhancing 14D5 HLE Nb had much higher levels of albuminuria, and higher levels of serum cholesterol and creatinine than mice treated with the Dummy-Nb, consistent with a more severe nephritic syndrome. These differences also were statistically significant ($p<0.05$).

Hence, systemic administration of antagonistic ISVs such as Nb 13A7 alleviates, and of agonistic ISVs such as Nb 14D5 potentiates disease parameters in antibody-induced glomerulonephritis.

Example 3.5

Perspectives

Taken together, the results of this project extension underscore the feasibility of using HLE Nbs to manipulate the function of the P2X7 ion channel on T cells in vivo. The experiments with the mouse model of nephritis show that P2X7-blocking Nbs have therapeutically beneficial effects in dampening excessive inflammatory reactions in this and other diseases.

The finding that the P2X7 enhancing 14D5 HLE-Nb exacerbated the inflammatory response in the nephritis model shows that the Nbs can be used for enhancing desired inflammatory responses, e.g., in chronic infections with intracellular parasites such as Chlamydia and Toxoplasma, in which activation of P2X7 has been shown to have a beneficial effect.

Nbs in general provide numerous advantages over small molecule inhibitors, and these pertain also to Nbs directed against the P2X7 ion channel: low toxicity, biodegradability, high specificity for an individual member of a larger protein family, and a variety of reformatting options.

Example 4

Assessment of Anti-P2X7 Nanobodies in an MS Model

The animal model of MS, experimental autoimmune encephalomyelitis (EAE) using myelin oligodendrocyte glycoprotein (MOG) peptide residues 35-55 is induced in wildtype C57BL6 mice. The diseased mice receive anti-P2X7 Nbs or Dummy-Nb. Disease progression is monitored by appearance of clinical signs, immunocytochemical staining to assess brain inflammation and neuronal damage, and by measurement of Tcell cytokine production.

Example 4.1

Induction of EAE

EAE is actively induced in C57BL6 mice using synthetic myelin oligodendrocyte glycoprotein peptide 35-55 (MOG35-55) as described (Matute et al., 2007). Mice are injected subcutaneously (two 100 µL injections into adjacent areas in one hind limb) with an emulsion of 300 µg MOG35-55 dissolved in 100 µL PBS, mixed with 100 µL CFA containing 500 µg of Mycobacterium tuberculosis. Immediately after MOG35-55 injection, the animals receive an i.p. injection of pertussis toxin (PT, 200 ng in 200 µL PBS). Two days later the mice receive a second PT injection, and 1 week later they receive a booster injection of MOG35-55. Clinical signs are scored on a 5 point scale: grade 0, no clinical signs; 1, limp tail and/or impaired righting; 2; paresis of one hind limb; 3; paresis of two hind limbs; 4; moribund; 5, death. Scoring is done at the same time each day by a blinded investigator.

Example 42

Injection of Anti-P2X7 Nanobodies

Nanobodies are injected intravenously by the tail vein concurrently with the MOG35-55 immunisation protocol.

Groups of 5-6 mice receive injections with Dummy-Nb, 13A7-13A7-ALB8, or 14D5-14D5-ALB8 as described in Example 2.

Example 4.3

T-Cell Isolation and Cytokine Measurements

Splenocytes are isolated from MOG35-55 immunized EAE mice at 4 days or 21 days after the booster MOG injection/Nb-injection. After lysis of red blood cells, splenocytes are plated into 24 well plates at a density of $2\times10^5$ cells per well in 400 µl RPMI media, and incubated with immunogen (0 or 25 µg/ml MOG 35-55 peptide). After 1 day, aliquots of the media are assayed for levels of IL-17 or IFNγ by ELISA following recommended procedures. Each sample is assayed at least in triplicate, calculation of ng/ml cytokine is determined from standard curves, and the increase due to the presence of MOG peptide is determined. A semiquantitative analysis of 64 inflammatory molecules produced by activated splenocytes is carried out using the mouse cytokine antibody array III (e.g. RayBiotech) according to the manufacturer's protocols.

Example 4.4

Analysis for Infiltrating Cells

Mouse brains are perfused with saline and post fixed in 4% paraformaldehyde overnight. Dehydration of hemispheres, washes, drying and solidifying are according to standard protocols. Tissue is cut 8 µm thick. Sagital sections (8 or 10 µM) are cut beginning from midline, and are mounted. Further preparation of the sections is according to standard protocols. Four serial sections from each animal are analyzed for the number of infiltrating cells present in the region extending from the olfactory bulb to the dorsal third ventricle. Black and white images of all stained sections are obtained using the same exposure time with a 10× objective. Specific fields containing small round hematoxylinophyllic nuclei are defined, and contrast is adjusted so as to not count larger round cells presumably oligodendrocyte. Data is presented as number of cells per mm2.

Immunohistochemistry is used to detect T-cells. For this, frozen sections are stained using an anti-CD8 antibody. Sections are incubated in 3% BSA in PBS plus antibody overnight at 4° C., washed, and then developed with a secondary antibody labeled with FITC.

Equivalents

The foregoing written specification is considered to be sufficient to enable one skilled in the art to practice the invention. The present invention is not to be limited in scope by examples provided, since the examples are intended as an illustration of certain aspects and embodiments of the invention. Other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A polypeptide comprising at least one immunoglobulin single variable domain that binds human P2X7, wherein the at least one immunoglobulin single variable domain comprises an amino acid sequence of formula 1: FR1-CDR1-FR2-CDR2-FR 3-CDR3-FR4 (1); wherein FR1 to FR4 refer to framework regions 1 to 4 and are framework regions (FRs) of an immunoglobulin single variable domain; wherein CDR1 to CDR3 refer to complementarity determining regions 1 to 3 and are complementarity determining regions (CDRs) of an immunoglobulin single variable domain; and
   wherein CDR1 is chosen from the group consisting of:
      SEQ ID NO: 40 and, polypeptides that have 1 amino acid difference with SEQ ID NO: 40; and
   wherein CDR2 is chosen from the group consisting of:
      SEQ ID NO: 68 and; polypeptides that have 1 amino acid difference with SEQ ID NO: 68; and
   wherein CDR3 is chosen from the group consisting of:
      SEQ ID NO: 96 and; polypeptides that have 1 amino acid difference with SEQ ID NO: 96.

2. The polypeptide according to claim 1, wherein in the at least one immunoglobulin single variable domain
   CDR1 is SEQ ID NO: 40, CDR2 is SEQ ID NO: 68; and CDR3 is SEQ ID NO: 96.

3. The polypeptide according to claim 1, wherein the polypeptide is selected from the group consisting of polypeptides comprising immunoglobulin single variable domains that have framework sequences comprising an amino acid sequence with a sequence identity of more than 80% with framework sequences of SEQ ID NOs: 6-19.

4. The polypeptide according to claim 3, wherein the polypeptide is selected from the group consisting of polypeptides comprising immunoglobulin single variable domains that have framework sequences comprising an amino acid sequence with a sequence identity of more than 90% with framework sequences of SEQ ID NOs: 6-19.

5. The polypeptide according to claim 1, comprising at least two immunoglobulin single variable domains that bind P2X7.

6. The polypeptide according to claim 5, wherein one of the at least two immunoglobulin single variable domains that bind P2X7 comprises an amino acid sequence
   wherein CDR1 is SEQ ID NO: 40 or a polypeptide that has 1 amino acid difference with SEQ ID NO: 40; and
   wherein CDR2 is SEQ ID NO: 68 or a polypeptide that has 1 amino acid difference with SEQ ID NO: 68; and
   wherein CDR3 is SEQ ID NO: 96 or a polypeptide that has 1 amino acid difference with SEQ ID NO: 96, and
   wherein the other of the at least two immunoglobulin single variable domains that bind P2X7 comprises an amino acid sequence:
      wherein CDR1 is SEQ ID NO: 34 or a polypeptide that has 1 amino acid difference with SEQ ID NO: 34; CDR2 is SEQ ID NO: 62 or a polypeptide that has 1 amino acid difference with SEQ ID NO: 62; and CDR3 is SEQ ID NO: 90 or a polypeptide that has 1 acid difference with SEQ ID NO: 90; or
      wherein CDR1 is SEQ ID NO: 35 or a polypeptide that has 1 acid difference with SEQ ID NO: 35; CDR2 is SEQ ID NO: 63 or a polypeptide that has 1 acid difference with SEQ ID NO: 63; and CDR3 is SEQ ID NO: 91 or a polypeptide that has 1 acid difference with SEQ ID NO: 91; or
      wherein CDR1 is SEQ ID NO: 40 or a polypeptide that has 1 acid difference with SEQ ID NO: 40; CDR2 is SEQ ID NO: 68 or a polypeptide that has 1 acid difference with SEQ ID NO: 68; and CDR3 is SEQ ID NO: 96 or a polypeptide that has 1 acid difference with SEQ ID NO: 96; or
      wherein CDR1 is SEQ ID NO: 36 or a polypeptide that has 1 acid difference with SEQ ID NO: 36; CDR2 is SEQ ID NO: 64 or a polypeptide that has 1 acid difference with SEQ ID NO: 64; and CDR3 is SEQ ID NO: 92 or a polypeptide that has 1 acid difference with SEQ ID NO: 92; or
      wherein CDR1 is SEQ ID NO: 37 or a polypeptide that has 1 acid difference with SEQ ID NO: 37; CDR2 is SEQ ID NO: 65 or a polypeptide that has 1 acid difference with SEQ ID NO: 65; and CDR3 is SEQ ID NO: 93 or a polypeptide that has 1 acid difference with SEQ ID NO: 93; or
      wherein CDR1 is SEQ ID NO: 38 or a polypeptide that has 1 acid difference with SEQ ID NO: 38; CDR2 is SEQ ID NO: 66 or a polypeptide that has 1 acid difference with SEQ ID NO: 66; and CDR3 is SEQ ID NO: 94 or a polypeptide that has 1 acid difference with SEQ ID NO: 94; or
      wherein CDR1 is SEQ ID NO: 39 or a polypeptide that has 1 acid difference with SEQ ID NO: 39; CDR2 is SEQ ID NO: 67 or a polypeptide that has 1 acid difference with SEQ ID NO: 67; and CDR3 is SEQ ID NO: 95 or a polypeptide that has 1 acid difference with SEQ ID NO: 95; or
      wherein CDR1 is SEQ ID NO: 41 or a polypeptide that has 1 acid difference with SEQ ID NO: 41; CDR2 is SEQ ID NO: 69 or a polypeptide that has 1 acid difference with SEQ ID NO: 69; and CDR3 is SEQ ID NO: 97 or a polypeptide that has 1 acid difference with SEQ ID NO: 97; or
      wherein CDR1 is SEQ ID NO: 42 or a polypeptide that has 1 acid difference with SEQ ID NO: 42; CDR2 is SEQ ID NO: 70 or a polypeptide that has 1 acid difference with SEQ ID NO: 70; and CDR3 is SEQ ID NO: 98 or a polypeptide that has 1 acid difference with SEQ ID NO: 98; or
      wherein CDR1 is SEQ ID NO: 43 or a polypeptide that has 1 acid difference with SEQ ID NO: 43; CDR2 is SEQ ID NO: 71 or a polypeptide that has 1 acid difference with SEQ ID NO: 71; and CDR3 is SEQ ID NO: 99 or a polypeptide that has 1 acid difference with SEQ ID NO: 99; or
      wherein CDR1 is SEQ ID NO: 44 or a polypeptide that has 1 acid difference with SEQ ID NO: 44; CDR2 is SEQ ID NO: 72 or a polypeptide that has 1 acid difference with SEQ ID NO: 72; and CDR3 is SEQ ID NO: 100 or a polypeptide that has 1 acid difference with SEQ ID NO: 100; or wherein CDR1 is SEQ ID NO: 45 or a polypeptide that has 1 acid difference with SEQ ID NO: 45; CDR2 is SEQ ID NO: 73 or a polypeptide that has 1 acid difference with SEQ ID NO: 73; and CDR3 is SEQ ID NO: 101 or a polypeptide that has 1 acid difference with SEQ ID NO: 101; or wherein CDR1 is SEQ ID NO: 46 or a polypeptide that has 1 acid difference with SEQ ID NO: 46; CDR2 is SEQ ID NO: 74 or a polypeptide that has 1 acid difference with SEQ ID NO: 74; and CDR3 is SEQ ID NO: 102 or a polypeptide that has 1 acid difference with SEQ ID NO: 102; or wherein CDR1 is SEQ ID NO:47 or a polypeptide that has 1 acid difference with SEQ ID NO: 47; CDR2 is SEQ ID NO: 75 or a polypeptide that has 1 acid difference with SEQ ID NO: 75; and CDR3 is SEQ ID NO: 103 or a polypeptide that has 1 acid difference with SEQ ID NO: 103.

7. The polypeptide according to claim 6, wherein one of the at least two immunoglobulin single variable domains comprises an amino acid sequence wherein CDR1 is SEQ ID NO: 40, CDR2 is SEQ ID NO: 68; and CDR3 is SEQ ID NO: 96, and wherein the other of the at least two immunoglobulin single variable domains comprises an amino acid sequence wherein:

CDR1 is SEQ ID NO: 34, CDR2 is SEQ ID NO: 62; and CDR3 is SEQ ID NO: 90; or
CDR1 is SEQ ID NO: 35, CDR2 is SEQ ID NO: 63; and CDR3 is SEQ ID NO: 91; or
CDR1 is SEQ ID NO: 40, CDR2 is SEQ ID NO: 68; and CDR3 is SEQ ID NO: 96; or
CDR1 is SEQ ID NO: 36, CDR2 is SEQ ID NO: 64; and CDR3 is SEQ ID NO: 92; or
CDR1 is SEQ ID NO: 37, CDR2 is SEQ ID NO: 65; and CDR3 is SEQ ID NO: 93; or
CDR1 is SEQ ID NO: 38, CDR2 is SEQ ID NO: 66; and CDR3 is SEQ ID NO: 94; or
CDR1 is SEQ ID NO: 39, CDR2 is SEQ ID NO: 67; and CDR3 is SEQ ID NO: 95; or
CDR1 is SEQ ID NO: 41, CDR2 is SEQ ID NO: 69; and CDR3 is SEQ ID NO: 97; or
CDR1 is SEQ ID NO: 42, CDR2 is SEQ ID NO: 70; and CDR3 is SEQ ID NO: 98; or
CDR1 is SEQ ID NO: 43, CDR2 is SEQ ID NO: 71; and CDR3 is SEQ ID NO: 99; or
CDR1 is SEQ ID NO: 44, CDR2 is SEQ ID NO: 72; and CDR3 is SEQ ID NO: 100; or
CDR1 is SEQ ID NO: 45, CDR2 is SEQ ID NO: 73; and CDR3 is SEQ ID NO: 101; or
CDR1 is SEQ ID NO: 46, CDR2 is SEQ ID NO: 74; and CDR3 is SEQ ID NO: 102; or
CDR1 is SEQ ID NO: 47, CDR2 is SEQ ID NO: 75; and CDR3 is SEQ ID NO: 103.

8. The polypeptide according to claim 5, wherein the polypeptide is selected from the group consisting of polypeptides comprising at least two immunoglobulin single variable domains that each have framework sequences comprising an amino acid sequence with a sequence identity of more than 80% with framework sequences of SEQ ID NOs: 6-19.

9. The polypeptide according to claim 8, wherein the polypeptide is selected from the group consisting of polypeptides comprising at least two immunoglobulin single variable domains that each have framework sequences comprising an amino acid sequence with identity of more than 90% with framework sequences of SEQ ID NOs: 6-19.

10. The polypeptide according to claim 5, wherein said at least two immunoglobulin single variable domains that can bind human P2X7 are the same.

11. The polypeptide according to claim 5, further comprising an immunoglobulin single variable domain that binds human serum albumin.

12. The polypeptide according to claim 11, wherein the immunoglobulin single variable domain that binds human serum albumin comprises SEQ ID NO: 126 or SEQ ID NO: 125.

13. The polypeptide according to claim 1, further comprising an immunoglobulin single variable domain that binds human serum albumin.

14. The polypeptide according to claim 13, wherein the immunoglobulin single variable domain that binds human serum albumin comprises SEQ ID NO: 126 or SEQ ID NO: 125.

15. The polypeptide according to claim 1, wherein said immunoglobulin single variable domain consists of a domain antibody, an amino acid sequence that is suitable for use as a domain antibody, a single domain antibody, an amino acid sequence that is suitable for use as a single domain antibody, a dAb, an amino acid sequence that is suitable for use as a dAb, a Nanobody, a VHH sequence, a humanized VHH sequence or a camelized VH sequence.

16. A method for producing a polypeptide, said method at least comprising the steps of:
   a) expressing, in a suitable host cell or in another suitable expression system, a nucleic acid encoding a polypeptide according to claim 1; optionally followed by:
   b) isolating and/or purifying said polypeptide.

* * * * *

UNITED STATES PATENT AND TRADEMARK OFFICE
CERTIFICATE OF CORRECTION

PATENT NO. : 9,908,935 B2  
APPLICATION NO. : 14/403754  
DATED : March 6, 2018  
INVENTOR(S) : Welbeck Owusu Danquah et al.

Page 1 of 2

It is certified that error appears in the above-identified patent and that said Letters Patent is hereby corrected as shown below:

In the Claims

Claim 6, beginning at Column 193, Line 50, should read:
6. The polypeptide according to claim 5, wherein one of the at least two immunoglobulin single variable domains that bind P2X7 comprises an amino acid sequence
    wherein CDR1 is SEQ ID NO: 40 or a polypeptide that has 1 amino acid difference with SEQ ID NO: 40; and
    wherein CDR2 is SEQ ID NO: 68 or a polypeptide that has 1 amino acid difference with SEQ ID NO: 68; and
    wherein CDR3 is SEQ ID NO: 96 or a polypeptide that has 1 amino acid difference with SEQ ID NO: 96, and
    wherein the other of the at least two immunoglobulin single variable domains that bind P2X7 comprises an amino acid sequence:
    wherein CDR1 is SEQ ID NO: 34 or a polypeptide that has 1 amino acid difference with SEQ ID NO: 34; CDR2 is SEQ ID NO: 62 or a polypeptide that has 1 amino acid difference with SEQ ID NO: 62; and CDR3 is SEQ ID NO: 90 or a polypeptide that has 1 amino acid difference with SEQ ID NO: 90; or
    wherein CDR1 is SEQ ID NO: 35 or a polypeptide that has 1 amino acid difference with SEQ ID NO: 35; CDR2 is SEQ ID NO: 63 or a polypeptide that has 1 amino acid difference with SEQ ID NO: 63; and CDR3 is SEQ ID NO: 91 or a polypeptide that has 1 amino acid difference with SEQ ID NO: 91; or
    wherein CDR1 is SEQ ID NO: 40 or a polypeptide that has 1 amino acid difference with SEQ ID NO: 40; CDR2 is SEQ ID NO: 68 or a polypeptide that has 1 amino acid difference with SEQ ID NO: 68; and CDR3 is SEQ ID NO: 96 or a polypeptide that has 1 amino acid difference with SEQ ID NO: 96; or
    wherein CDR1 is SEQ ID NO: 36 or a polypeptide that has 1 amino acid difference with SEQ ID NO: 36; CDR2 is SEQ ID NO: 64 or a polypeptide that has 1 amino acid difference with SEQ ID NO: 64; and CDR3 is SEQ ID NO: 92 or a polypeptide that has 1 amino acid difference with SEQ ID NO: 92; or Signed and Sealed this  
Eighth Day of May, 2018

Andrei Iancu  
*Director of the United States Patent and Trademark Office* wherein CDR1 is SEQ ID NO: 37 or a polypeptide that has 1 amino acid difference with SEQ ID NO: 37; CDR2 is SEQ ID NO: 65 or a polypeptide that has 1 amino acid difference with SEQ ID NO: 65; and CDR3 is SEQ ID NO: 93 or a polypeptide that has 1 amino acid difference with SEQ ID NO: 93; or wherein CDR1 is SEQ ID NO: 38 or a polypeptide that has 1 amino acid difference with SEQ ID NO: 38; CDR2 is SEQ ID NO: 66 or a polypeptide that has 1 amino acid difference with SEQ ID NO: 66; and CDR3 is SEQ ID NO: 94 or a polypeptide that has 1 amino acid difference with SEQ ID NO: 94; or wherein CDR1 is SEQ ID NO: 39 or a polypeptide that has 1 amino acid difference with SEQ ID NO: 39; CDR2 is SEQ ID NO: 67 or a polypeptide that has 1 amino acid difference with SEQ ID NO: 67; and CDR3 is SEQ ID NO: 95 or a polypeptide that has 1 amino acid difference with SEQ ID NO: 95; or wherein CDR1 is SEQ ID NO: 41 or a polypeptide that has 1 amino acid difference with SEQ ID NO: 41; CDR2 is SEQ ID NO: 69 or a polypeptide that has 1 amino acid difference with SEQ ID NO: 69; and CDR3 is SEQ ID NO: 97 or a polypeptide that has 1 amino acid difference with SEQ ID NO: 97; or wherein CDR1 is SEQ ID NO: 42 or a polypeptide that has 1 amino acid difference with SEQ ID NO: 42; CDR2 is SEQ ID NO: 70 or a polypeptide that has 1 amino acid difference with SEQ ID NO: 70; and CDR3 is SEQ ID NO: 98 or a polypeptide that has 1 amino acid difference with SEQ ID NO: 98; or wherein CDR1 is SEQ ID NO: 43 or a polypeptide that has 1 amino acid difference with SEQ ID NO: 43; CDR2 is SEQ ID NO: 71 or a polypeptide that has 1 amino acid difference with SEQ ID NO: 71; and CDR3 is SEQ ID NO: 99 or a polypeptide that has 1 amino acid difference with SEQ ID NO: 99; or wherein CDR1 is SEQ ID NO: 44 or a polypeptide that has 1 amino acid difference with SEQ ID NO: 44; CDR2 is SEQ ID NO: 72 or a polypeptide that has 1 amino acid difference with SEQ ID NO: 72; and CDR3 is SEQ ID NO: 100 or a polypeptide that has 1 amino acid difference with SEQ ID NO: 100; or wherein CDR1 is SEQ ID NO: 45 or a polypeptide that has 1 amino acid difference with SEQ ID NO: 45; CDR2 is SEQ ID NO: 73 or a polypeptide that has 1 amino acid difference with SEQ ID NO: 73; and CDR3 is SEQ ID NO: 101 or a polypeptide that has 1 amino acid difference with SEQ ID NO: 101; or wherein CDR1 is SEQ ID NO: 46 or a polypeptide that has 1 amino acid difference with SEQ ID NO: 46; CDR2 is SEQ ID NO: 74 or a polypeptide that has 1 amino acid difference with SEQ ID NO: 74; and CDR3 is SEQ ID NO: 102 or a polypeptide that has 1 amino acid difference with SEQ ID NO: 102; or wherein CDR1 is SEQ ID NO: 47 or a polypeptide that has 1 amino acid difference with SEQ ID NO: 47; CDR2 is SEQ ID NO: 75 or a polypeptide that has 1 amino acid difference with SEQ ID NO: 75; and CDR3 is SEQ ID NO: 103 or a polypeptide that has 1 amino acid difference with SEQ ID NO: 103.